United States Patent
Fischer et al.

(10) Patent No.: US 11,530,193 B2
(45) Date of Patent: Dec. 20, 2022

(54) KINASE INHIBITORS

(71) Applicant: The University of Manchester

(72) Inventors: Peter Fischer, Manchester (GB); Christophe Fromont, Manchester (GB); Brett Stevenson, Manchester (GB); Sam Butterworth, Manchester (GB); Greg Iacobini, Manchester (GB); Graziella Greco, Manchester (GB); Miguel Garzon Sanz, Manchester (GB); Heulyn Jones, Manchester (GB); Divneet Kaur, Manchester (GB)

(73) Assignee: The University of Manchester, Manchester (GB)

( * ) Notice: Subject to any disclaimer, the term of this patent is extended or adjusted under 35 U.S.C. 154(b) by 13 days.

(21) Appl. No.: 17/055,239

(22) PCT Filed: May 15, 2019

(86) PCT No.: PCT/GB2019/051321
§ 371 (c)(1),
(2) Date: Nov. 13, 2020

(87) PCT Pub. No.: WO2019/220101
PCT Pub. Date: Nov. 21, 2019

(65) Prior Publication Data
US 2021/0269417 A1   Sep. 2, 2021

(30) Foreign Application Priority Data
May 15, 2018 (GB) ...................................... 1807845

(51) Int. Cl.
*C07D 401/14* (2006.01)
*A61P 3/10* (2006.01)
*C07D 401/04* (2006.01)
*C07D 405/14* (2006.01)
*C07D 413/14* (2006.01)
*C07D 417/14* (2006.01)
*C07D 487/04* (2006.01)

(52) U.S. Cl.
CPC .............. *C07D 401/14* (2013.01); *A61P 3/10* (2018.01); *C07D 401/04* (2013.01); *C07D 405/14* (2013.01); *C07D 413/14* (2013.01); *C07D 417/14* (2013.01); *C07D 487/04* (2013.01)

(58) Field of Classification Search
CPC .. C07D 401/14; C07D 487/04; C07D 413/14; C07D 405/14; C07D 417/14; C07D 401/04; A61P 3/10
USPC ...................................................... 514/210.18
See application file for complete search history.

(56) References Cited

FOREIGN PATENT DOCUMENTS

EP   1 054 004 A1   11/2000

OTHER PUBLICATIONS

International Search Report and Written Opinion in PCT/GB2019/051321 dated Aug. 7, 2019.
Liddle et al.; "Discovery of GSK143, a highly potent, selective and orally efficacious spleen tyrosine kinase inhibitor", Bioorganic & Medicinal Chemistry Letters, Pergamon, Amsterdam, NL, vol. 21, No. 20, Jul. 22, 2011, pp. 6188-6194.

*Primary Examiner* — Kahsay Habte
(74) *Attorney, Agent, or Firm* — Foley & Lardner LLP

(57) ABSTRACT

The present invention relates to certain 4-(substituted aniline)-2-(substituted piperidin-1-yl)pyrimidine-5-carboxamide compounds which may be useful in the treatment or prevention of a disease or medical condition mediated through signaling of CaMK1 isoforms. For example, such compounds and salts thereof may be useful in the treatment or prevention of a number of different cancers, metabolic diseases including type-2 diabetes, and/or immune-mediated disorders.

38 Claims, 1 Drawing Sheet

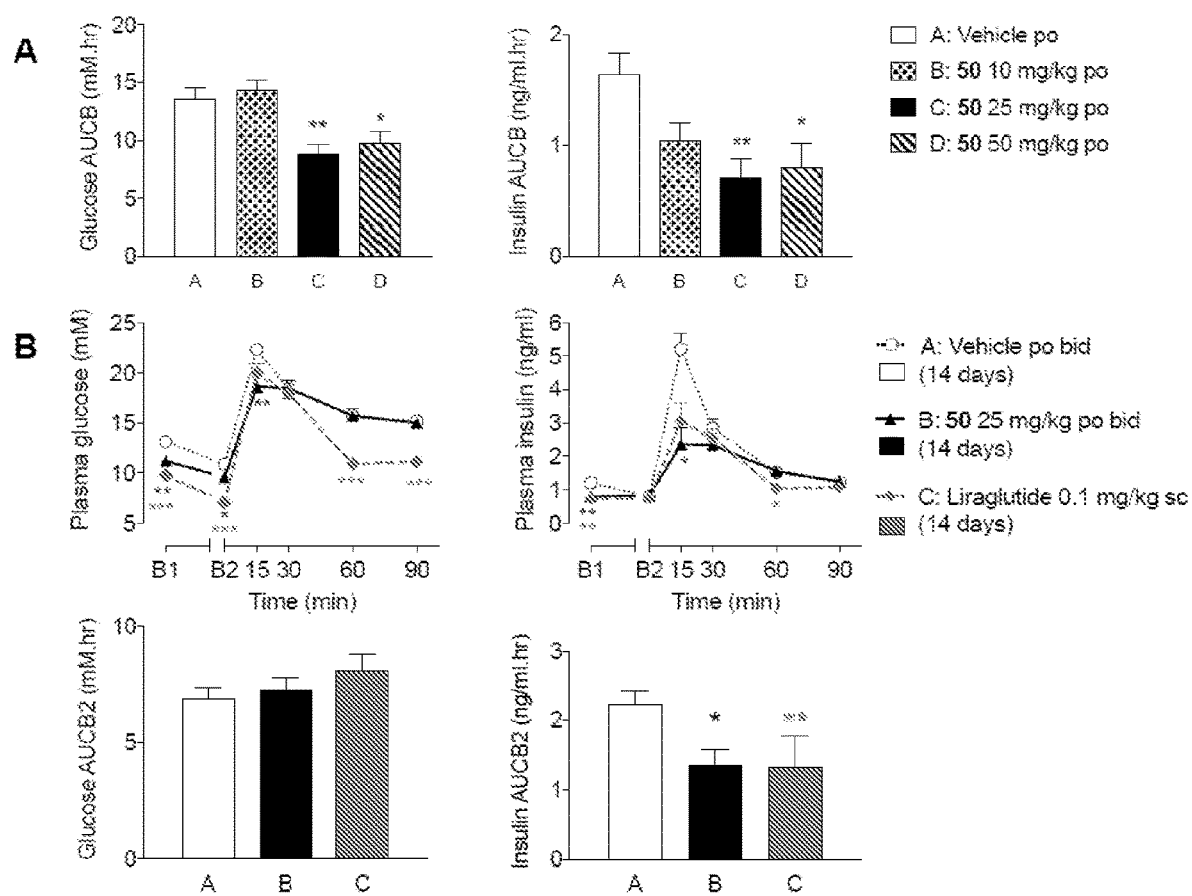

KINASE INHIBITORS

FIELD OF INVENTION

This invention relates to compounds. More specifically, the invention relates to compounds useful as inhibitors of calmodulin dependent kinases of the CaMK1 family (comprising CaMK1A (CaMK1), CaMK1B (PNCK), CaMK1D (CKLIK) and/or CaMK1G). Specifically, inhibitors of CaMK1A (CaMK1), CaMK1B (PNCK), CaMK1D (CKLIK) and/or CaMK1G are contemplated by the invention. In addition the invention contemplates pharmaceutical compositions comprising the compounds, processes to prepare the compounds and uses of the compounds.

BACKGROUND

The CaMK1 family kinases play a key role in the propagation of cellular calcium signaling to regulate cellular processes including transcription activator activity, cell cycle, hormone production, cell differentiation, actin filament organization and calcium-mediated granulocyte function including respiratory burst. CaMK1 signaling is consequently implicated in a range of human diseases including cancer, diabetes and inflammatory conditions.

The CaMK1 family of kinases may be activated by several calcium-dependent mechanisms. For example, under normal conditions CaMK1D signalling is controlled by at least two mechanisms; (1) a calcium/calmodulin complex activates the upstream CaMKK2 kinase, resulting in phosphorylation of the CaMK1D activation loop, whereby the protein assumes a basal kinase activity even in the absence of calcium/calmodulin, (2) calcium/calmodulin can also directly activate CaMK1 D, forming a complex that further increases the catalytic activity of the enzyme. Active CaMK1D directly or indirectly controls the activation of downstream proteins, including the transcription factors CREB and AFT1, and the transcription regulator CDK9. Activation of other CAMK1 family members also results in activation of CREB and AFT1, as well as other proteins involved in transcriptional regulation including eIF4G3/eIF4GII.

Aberrant over-expression of CaMK1D has been implicated in tumour initiation and progression in patients suffering from a range of cancers, in particular breast cancer. CaMK1B and CaMK1D expression has been implicated in mediating resistance to established breast cancer chemotherapeutics targeting ERBB2 (HER2) signaling in HER2-positive breast cancer. Examples of such therapies include trastuzumab (Herceptin™) and lapatinib (Tykerb/Tyverb™).

Activating polymorphisms in the CaMK1D gene loci have been linked to type-2 diabetes in multiple genome-wide association studies. The most highly-validated polymorph results in increased transcriptional enhancer activity when introduced into hepatocytes and siRNA experiments demonstrate that reduction of CaMK1D expression in hepatocytes leads to altered CRCT2 signalling and increased glycogen formation in the absence of insulin exposure.

AIMS OF THE INVENTION

It is an aim of certain embodiments of this invention to provide compounds that exhibit enhanced activity for inhibition of the family of CaMK1 kinases relative to prior art compounds.

It is an aim of certain embodiments of this invention to provide compounds that exhibit enhanced activity for inhibition of the family of CaMK1 kinases relative to prior art compounds, and improved selectivity for inhibition CaMK1 family kinases relative to non-CaMK1 family kinases, in particular with respect to inhibition of spleen tyrosine kinase (SYK).

A particular aim of certain embodiments of this invention is to provide compounds that exhibit enhanced activity for inhibition of CaMK1D kinases relative to prior art compounds.

Another particular aim of certain embodiments of this invention is to provide compounds that exhibit enhanced activity for inhibition of CaMK1D kinases relative to prior art compounds, and improved selectivity for inhibition CaMK1 D kinases relative to non-CaMK1 family kinases, in particular with respect to inhibition of SYK kinase.

Certain embodiments of the present invention satisfy some or all of the above aims.

BRIEF SUMMARY OF THE DISCLOSURE

According to a first aspect, the present invention provides a compound of Formula I or a pharmaceutically acceptable salt thereof:

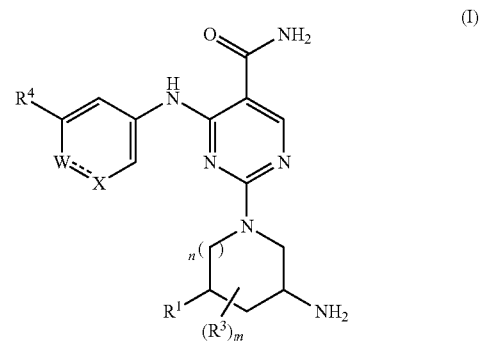

wherein:

$R^1$ is selected from the group consisting of: H, $C_{1-3}$ alkyl, $C_{1-3}$ haloalkyl, halo, —$OR^2$, —$NR^2R^2$, $C_3$ cycloalkyl and $C_3$ halocycloalkyl;

each $R^2$ is independently selected from the group consisting of: H, $C_{1-3}$ alkyl and $C_{1-3}$ haloalkyl;

each $R^3$ is independently selected from the group consisting of: $C_{1-3}$ alkyl, $C_{1-3}$ haloalkyl, halo, —$OR^2$, —$NR^2R^2$, $C_3$ cycloalkyl and $C_3$ halocycloalkyl;

n is 1 or 2;

m is 0 to 3;

W is

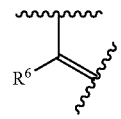

and X is

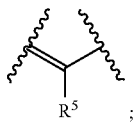

or W is

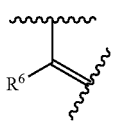

and X is

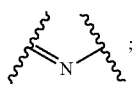

or W is

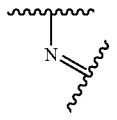

and X is

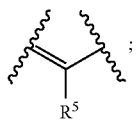

or W is

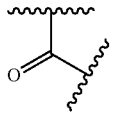

and X is

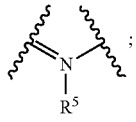

$R^4$ is selected from the group consisting of: $C_{3-6}$ alkyl, $C_{3-6}$ heteroalkyl, $C_{3-6}$ haloalkyl, $C_{3-6}$ heterohaloalkyl, $C_{3-6}$ alkenyl wherein (i) the carbon atom beta to the ring to which the alkene is bonded is cis-substituted with carbon; and (ii) the carbon atom alpha to the ring to which the alkene is bonded substituted with carbon, $C_{3-6}$ cycloalkyl, $C_{4-6}$ cycloalkenyl, 4- to 6-membered heterocycloalkyl including 1, 2 or 3 heteroatoms selected from N, O or S, 4- to 6-membered heterocycloalkenyl including 1, 2 or 3 heteroatoms selected from N, O or S, aryl, heteroaryl including 1, 2 or 3 heteroatoms selected from N, O or S, $-NR^{B1a}R^{B2a}$, $-NR^{B3a}C(O)R^{B2a}$, $-C(O)NR^{B2a}R^{B2a}$, $-C(O)$-(4- to 12-membered non-aromatic saturated or partially saturated monocyclic or fused, bridged, or spiro bicyclic heterocyclic ring system including 1, 2 or 3 heteroatoms selected from N, O or S), $-NR^{B3a}C(O)OR^{B2a}$, $-NR^{B3a}C(O)NR^{B3a}R^{B3a}$, $-NR^{B3a}SO_2R^{B2a}$, $-SO_2NR^{B3a}R^{B3a}$, $-SO_2R^{B2a}$ and $-S(O)(=NR^{B3a})R^{B2a}$;

$R^5$ is selected from the group consisting of: H, $C_{1-6}$ alkyl, $C_{1-6}$ heteroalkyl, $C_{1-6}$ haloalkyl, $C_{1-6}$ heterohaloalkyl, $C_{2-6}$ alkenyl, $C_{2-6}$ alkynyl, $C_{3-6}$ cycloalkyl, $C_{4-6}$ cycloalkenyl, 4- to 6-membered heterocycloalkyl including 1, 2 or 3 heteroatoms selected from N, O or S, 4- to 6-membered heterocycloalkenyl including 1, 2 or 3 heteroatoms selected from N, O or S, aryl, heteroaryl including 1, 2 or 3 heteroatoms selected from N, O or S, —O-aryl, —O-heteroaryl, halo, $-OR^{B2a}$, $-NR^{B3a}R^{B3a}$, $-SR^{B2a}$, $-CN$, $-NR^{B3a}C(O)R^{B2a}$, $-C(O)NR^{B2a}R^{B2a}$, $-CR^{B3a}(=NR^{B3a})$, $-NR^{B3a}C(O)OR^{B2a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NR^{B3a}R^{B3a}$, $-SO_2R^{B2a}$, $-S(O)(=NR^{B3a})R^{B2a}$ and $-C(O)OR^{B2a}$;

$R^6$ is selected from the group consisting of: H, $C_{1-6}$ alkyl, $C_{1-6}$ heteroalkyl, $C_{1-6}$ haloalkyl, $C_{1-6}$ heterohaloalkyl, $C_{2-6}$ alkenyl, $C_{2-6}$ alkynyl, $C_{3-6}$ cycloalkyl, $C_{4-6}$ cycloalkenyl, 4- to 6-membered heterocycloalkyl including 1, 2 or 3 heteroatoms selected from N, O or S, 4- to 6-membered heterocycloalkenyl including 1, 2 or 3 heteroatoms selected from N, O or S, aryl, heteroaryl including 1, 2 or 3 heteroatoms selected from N, O or S, —O-aryl, —O-heteroaryl, halo, $-OR^{B3a}$, $-NR^{B3a}R^{B3a}$, $-CR^{B3a}(=NR^{B3a})$, $-SR^{B3a}$, $-CN$, $-NR^{B3a}C(O)R^{B2a}$, $-C(O)NR^{B2a}R^{B2a}$, $-NR^{B3a}C(O)OR^{B2a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NR^{B3a}R^{B3a}$, $-SO_2R^{B2a}$, $-S(O)(=NR^{B3a})R^{B2a}$ and $-C(O)OR^{B2a}$ wherein $R^{B1a}$ is selected from the group consisting of: $C_{3-4}$ alkyl, $C_{3-4}$ heteroalkyl, $C_{3-4}$ haloalkyl, $C_{3-4}$ haloheteroalkyl, $C_{3-6}$ cycloalkyl, $C_{1-4}$ alkyl $C_{3-6}$ cycloalkyl, 4- to 12-membered non-aromatic saturated or partially saturated monocyclic or fused, bridged, or spiro bicyclic heterocyclic ring system including 1, 2 or 3 heteroatoms selected from N, O or S;

wherein $R^{B2a}$ is selected from the group consisting of: $C_{1-4}$ alkyl, $C_{1-4}$ heteroalkyl, $C_{1-4}$ haloalkyl, $C_{1-4}$ haloheteroalkyl, $C_{3-6}$ cycloalkyl, $C_{1-4}$ alkyl $C_{3-6}$ cycloalkyl, 4- to 12-membered non-aromatic saturated or partially saturated monocyclic or fused, bridged, or spiro bicyclic heterocyclic ring system including 1, 2 or 3 heteroatoms selected from N, O or S;

wherein $R^{B3a}$ is selected from the group consisting of: H, $C_{1-4}$ alkyl, $C_{1-4}$ heteroalkyl, $C_{1-4}$ haloalkyl, $C_{1-4}$ haloheteroalkyl, $C_{3-6}$ cycloalkyl, $C_{1-4}$ alkyl $C_{3-6}$ cycloalkyl, 4- to 12-membered non-aromatic saturated or partially saturated monocyclic or fused, bridged, or spiro bicyclic heterocyclic ring system including 1, 2 or 3 heteroatoms selected from N, O or S;

wherein the $C_{3-4}$ alkyl, $C_{3-4}$ heteroalkyl, $C_{3-4}$ haloalkyl, $C_{3-4}$ haloheteroalkyl, $C_{1-4}$ alkyl, $C_{1-4}$ heteroalkyl, $C_{1-4}$ haloalkyl, $C_{1-4}$ haloheteroalkyl, $C_{3-6}$ cycloalkyl, $C_{1-4}$ alkyl $C_{3-6}$ cycloalkyl and 4- to 12-membered non-aromatic saturated or partially saturated monocyclic or fused, bridged, or spiro bicyclic heterocyclic ring system including 1, 2 or 3 heteroatoms selected from N, O or S can be optionally substituted with $C_{1-4}$ alkyl, $C_{1-4}$ heteroalkyl, $C_{1-4}$ haloalkyl, $C_{1-4}$ haloheteroalkyl, $C_{3-6}$ cycloalkyl, $C_{1-4}$ alkyl $C_{3-6}$ cycloalkyl, aryl, heteroaryl including 1, 2 or 3 heteroatoms selected from N, O or S, —OH, —O($C_{1-3}$ alkyl), —($C_{1-3}$ alkyl)-OH, —($C_{1-3}$ alkyl)-O($C_{1-3}$ alkyl), =O, —NH$_2$, —NH($C_{1-3}$ alkyl), —N($C_{1-3}$ alkyl)$_2$ or ($C_{1-3}$ alkyl)-NH$_2$, —($C_{1-3}$ alkyl)-NH($C_{1-3}$ alkyl) or —($C_{1-3}$ alkyl)-N($C_{1-3}$ alkyl)$_2$;

wherein in the specific groups —NR$^{B1a}$R$^{B2a}$, —NR$^{B3a}$R$^{B3a}$, —C(O)NR$^{B2a}$R$^{B2a}$, —OC(O)NR$^{B3a}$R$^{B3a}$, —NR$^{B3a}$C(O)NR$^{B3a}$R$^{B3a}$, —NR$^{B3a}$C(NR$^{B3a}$)NR$^{B3a}$R$^{B3a}$ and —SO$_2$NR$_{B3a}$R$^{B3a}$ the pairs R$^{B1a}$/R$^{B2a}$, R$^{B3a}$/R$^{B3a}$ and R$^{B2a}$/R$^{B2a}$, together with the nitrogen atom to which they are bonded, can form a 4- to 12-membered monocyclic or fused, bridged, or spiro bicyclic ring system optionally including 1, 2 or 3 heteroatoms selected from N, O or S;

or wherein R$^4$ is $C_{1-6}$ alkyl or $C_{3-6}$ cycloalkyl and R$^6$ is —NR$^{B3a}$C(O)R$^{B2a}$, wherein the terminal R$^{B2a}$ is absent and R$^4$ and R$^6$ are joined via the carbonyl carbon, so that, together with the carbon atoms to which they are bonded, R$^4$ and R$^6$ form a 5- or 6-membered ring;

or wherein R$^5$ is —NR$^{B3a}$R$^{B3a}$ and R$^6$ is —CR$^{B3a}$(=NR$^{B3a}$), wherein the terminal R$^{B3a}$ of —CR$^{B3a}$(=NR$^{B3a}$) is absent and one R$^{B3a}$ of —NR$^{B3a}$R$^{B3a}$ is absent and R$^5$ and R$^6$ are joined via the imine nitrogen atom, so that, together with the carbon atoms to which they are bonded, R$^5$ and R$^6$ form a 5-membered ring;

provided that, when R$^4$ is aryl or heteroaryl including 1, 2 or 3 heteroatoms selected from N, O or S and R$^5$ is absent or H, one or both of the following is true: (i) the aryl or heteroaryl including 1, 2 or 3 heteroatoms selected from N, O or S is ortho-substituted with an R$^{sub}$ moiety; or (ii) R$^6$ is not H;

wherein each of the aforementioned $C_{3-6}$ alkyl, $C_{1-6}$ alkyl, $C_{3-6}$ heteroalkyl, $C_{3-6}$ haloalkyl, $C_{1-6}$ haloalkyl, $C_{3-6}$ heterohaloalkyl, $C_{1-6}$ heterohaloalkyl, $C_{3-6}$ alkenyl, $C_{2-6}$ alkenyl, $C_{3-6}$ cycloalkyl, $C_{4-6}$ cycloalkenyl, 4- to 6-membered heterocycloalkyl including 1, 2 or 3 heteroatoms selected from N, O or S, 4- to 6-membered heterocycloalkenyl including 1, 2 or 3 heteroatoms selected from N, O or S, aryl, heteroaryl, 4- to 12-membered non-aromatic saturated or partially saturated monocyclic or fused, bridged, or spiro bicyclic heterocyclic ring system including 1, 2 or 3 heteroatoms selected from N, O or S and $C_{2-6}$ alkynyl can be optionally substituted with 1, 2 or 3 R$^{sub}$ moieties, wherein each R$^{sub}$ moiety is independently selected from the group consisting of: $C_{1-6}$ alkyl, $C_{1-6}$ heteroalkyl, $C_{1-6}$ haloalkyl, $C_{1-6}$ heterohaloalkyl, $C_{2-6}$ alkenyl, $C_{2-6}$ alkynyl, $C_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —OR$^{B3a}$, =O, —NR$^{B3a}$R$^{B3a}$, —SR$^{B3a}$, —CN, —NO$_2$, —NR$^{B3a}$C(O)R$^{B3a}$, —C(O)NR$^{B3a}$R$^{B3a}$, —NR$^{B3a}$C(O)OR$^{B3a}$, —OC(O)NR$^{B3a}$R$^{B3a}$, —NR$^{B3a}$C(O)NR$^{B3a}$R$^{B3a}$, —NR$^{B3a}$C(NR$^{B3a}$)NR$^{B3a}$R$^{B3a}$, —NR$^{B3a}$SO$_2$R$^{B3a}$, —SO$_2$NR$^{B3a}$R$^{B3a}$, —SO$_2$R$^{B3a}$, —C(O)R$^{B3a}$ and —C(O)OR$^{B3a}$.

According to a second aspect, the present invention provides a compound for use in the treatment of a condition treatable by modulating or inhibiting CaMK1 family kinases, the compound being a compound of Formula I or a pharmaceutically acceptable salt thereof as defined in the first aspect.

According to a third aspect, the present invention provides a method of treating conditions modulated by CaMK1 family kinases, the method comprising administering to a subject in need of treatment a therapeutically beneficial amount of a compound of Formula I or a pharmaceutically acceptable salt thereof as defined in the first aspect.

The invention provides compounds capable of inhibiting CaMK1 family signaling, specifically by inhibition of CaMK1A, CaMK1B, CaMK1D and/or CaMK1G kinase activity.

In an embodiment, the compounds of the invention exhibit enhanced activity for inhibition of the family of CaMK1 kinases relative to prior art compounds and improved selectivity for inhibition CaMK1 family kinases relative to non-CaMK1 family kinases, in particular with respect to inhibition of SYK kinase.

In an embodiment, the compounds of the invention exhibit enhanced activity for inhibition of CaMK1 D kinases relative to prior art compounds.

In an embodiment, the compounds of the invention exhibit enhanced activity for inhibition of CaMK1D kinases relative to prior art compounds and improved selectivity for inhibition CaMK1D kinases relative to non-CaMK1 family kinases, in particular with respect to inhibition of SYK kinase.

In another aspect, the present invention provides a pharmaceutical formulation comprising a compound of the invention, or a pharmaceutically acceptable salt thereof, and a pharmaceutically acceptable excipient.

In another aspect, the present invention provides a compound of the invention, or a pharmaceutically acceptable salt thereof, for use as a medicament.

In another aspect, the present invention provides a method of synthesising a compound of the invention, or a pharmaceutically acceptable salt thereof.

In another aspect, the present invention provides novel intermediates as defined herein which are suitable for use in any one of the synthetic methods as set out herein.

SUMMARY OF THE FIGURES

FIG. 1—Results from the oral glucose tolerance test (OGTT) after acute and chronic (14 day) dosing as described in Example 143. A: Glucose and Insulin AUC (baseline) from OGTT following single dose, B: Glucose and Insulin AUC (baseline from B2) from OGTT following 14 days dosing. Significant differences are denoted by *$p<0.05$, $p<0.01$ and *$p<0.001$.

DETAILED DESCRIPTION

The following embodiments are generally applicable to all aspects of the invention. Preferred, suitable, and optional features of any one particular aspect of the present invention are also preferred, suitable, and optional features of any other aspect.

In an embodiment, R$^1$ is H.

In an embodiment, R$^1$ is selected from the group consisting of: $C_{1-3}$ alkyl, $C_{1-3}$ haloalkyl, halo, —OR$^2$ and —NR$^2$R$^2$. Preferably, R$^2$ is selected from the group consisting of H and $C_{1-3}$ alkyl. More preferably, R$^2$ is selected from the group consisting of H and Me.

In an embodiment, R$^1$ is selected from the group consisting of: $C_{1-3}$ alkyl, halo, —OR$^2$ and —NR$^2$R$^2$. Preferably, R$^2$ is selected from the group consisting of H and $C_{1-3}$ alkyl. More preferably, R$^2$ is selected from the group consisting of H and Me.

In an embodiment, R$^1$ is selected from the group consisting of: $C_{1-3}$ alkyl, F, C$_1$, —OR$^2$ and —NR$^2$R$^2$. Preferably, R$^2$ is selected from the group consisting of H and $C_{1-3}$ alkyl. More preferably, $R^2$ is selected from the group consisting of H and Me.

In an embodiment, $R^1$ is selected from the group consisting of: Me, F, $C_1$, —OH and —$NH_2$.

In an embodiment, m is 0 or 1.

In an embodiment, $R^3$ is selected from the group consisting of: $C_{1-3}$ alkyl, $C_{1-3}$ haloalkyl, halo, —$OR^2$ and —$NR^2R^2$. Preferably, $R^2$ is selected from the group consisting of H and $C_{1-3}$ alkyl. More preferably, $R^2$ is selected from the group consisting of H and Me.

In an embodiment, $R^3$ is selected from the group consisting of: $C_{1-3}$ alkyl, halo, —$OR^2$ and —$NR^2R^2$. Preferably, $R^2$ is selected from the group consisting of H and $C_{1-3}$ alkyl. More preferably, $R^2$ is selected from the group consisting of H and Me.

In an embodiment, $R^3$ is selected from the group consisting of: $C_{1-3}$ alkyl, F, $C_1$, —$OR^2$ and —$NR^2R^2$. Preferably, $R^2$ is selected from the group consisting of H and $C_{1-3}$ alkyl. More preferably, $R^2$ is selected from the group consisting of H and Me.

In an embodiment, $R^3$ is selected from the group consisting of: Me, F, $C_1$, —OH and —$NH_2$.

In a preferred embodiment, m is 0 (i.e. $R^3$ is absent).

In an embodiment, n is 2. In a preferred embodiment, n is 1.

In an embodiment, m is 0, n is 1 and $R^1$ is H.

In an embodiment, m is 0, n is 1 and $R^1$ is selected from the group consisting of: $C_{1-3}$ alkyl, $C_{1-3}$ haloalkyl, halo, —$OR^2$ and —$NR^2R^2$. Preferably, $R^2$ is selected from the group consisting of H and $C_{1-3}$ alkyl. More preferably, $R^2$ is selected from the group consisting of H and Me.

In an embodiment, m is 0, n is 1 and $R^1$ is selected from the group consisting of: $C_{1-3}$ alkyl, halo, —$OR^2$ and —$NR^2R^2$. Preferably, $R^2$ is selected from the group consisting of H and $C_{1-3}$ alkyl. More preferably, $R^2$ is selected from the group consisting of H and Me.

In an embodiment, m is 0, n is 1 and $R^1$ is selected from the group consisting of: $C_{1-3}$ alkyl, F, $C_1$, —$OR^2$ and —$NR^2R^2$. Preferably, $R^2$ is selected from the group consisting of H and $C_{1-3}$ alkyl. More preferably, $R^2$ is selected from the group consisting of H and Me.

In an embodiment, m is 0, n is 1 and $R^1$ is selected from the group consisting of: Me, F, $C_1$, —OH and —$NH_2$.

In an embodiment, m is 0, n is 2 and $R^1$ is H.

In an embodiment, m is 0, n is 2 and $R^1$ is selected from the group consisting of: $C_{1-3}$ alkyl, $C_{1-3}$ haloalkyl, halo, —$OR^2$ and —$NR^2R^2$. Preferably, $R^2$ is selected from the group consisting of H and $C_{1-3}$ alkyl. More preferably, $R^2$ is selected from the group consisting of H and Me.

In an embodiment, m is 0, n is 2 and $R^1$ is selected from the group consisting of: $C_{1-3}$ alkyl, halo, —$OR^2$ and —$NR^2R^2$. Preferably, $R^2$ is selected from the group consisting of H and $C_{1-3}$ alkyl. More preferably, $R^2$ is selected from the group consisting of H and Me.

In an embodiment, m is 0, n is 2 and $R^1$ is selected from the group consisting of: $C_{1-3}$ alkyl, F, $C_1$, —$OR^2$ and —$NR^2R^2$. Preferably, $R^2$ is selected from the group consisting of H and $C_{1-3}$ alkyl. More preferably, $R^2$ is selected from the group consisting of H and Me.

In an embodiment, m is 0, n is 2 and $R^1$ is selected from the group consisting of: Me, F, $C_1$, —OH and —$NH_2$.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereo centres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%.

The compounds of this invention may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess the desired activity.

In an embodiment, the compound of Formula I is represented by Formula II below, in which the carbon atoms depicted by the * are in the R-configuration or the S-configuration:

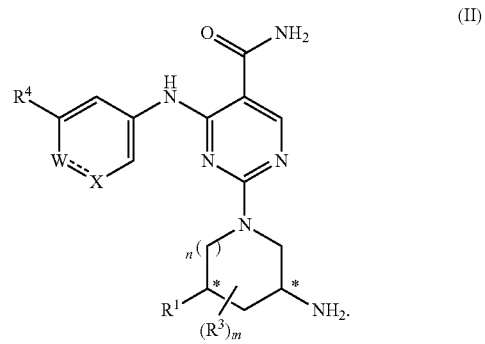

(II)

In a preferred embodiment, the compound of Formula I is represented by Formula IIA below, in which the carbon atom depicted by the * is in the R-configuration or the S-configuration:

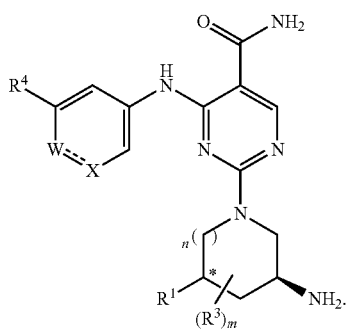
(IIA)

In an embodiment, the compound of Formula II has a structure of Formula IIB, IIC, IID or IIE:

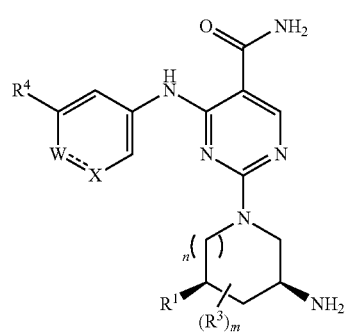
(IIB)

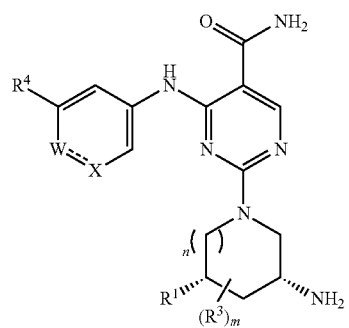
(IIC)

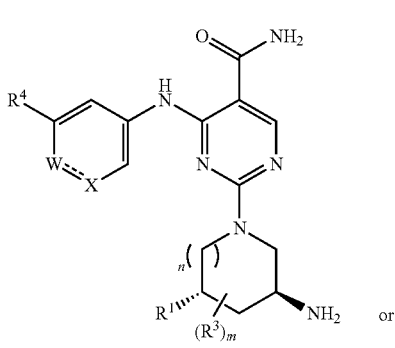
(IID) or

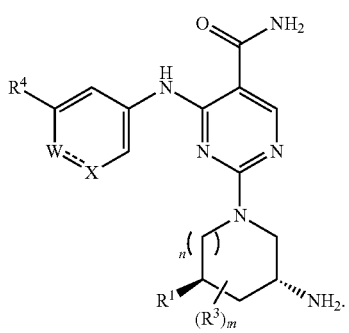
(IIE)

The following embodiments are applicable to compounds having a structure according to any of Formulae I, II, IIA, IIB, IIC, IIC, IID or IIE as defined above:

In an embodiment, W is

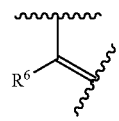

and X is

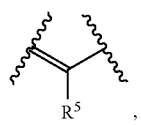

such that the compound has the Formula IIIA:

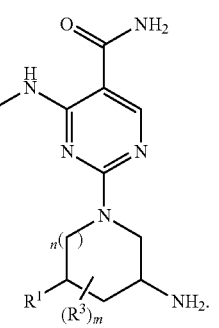
(IIIA)

In an embodiment, W is and X is

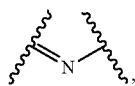

such that the compound has the Formula IIIB:

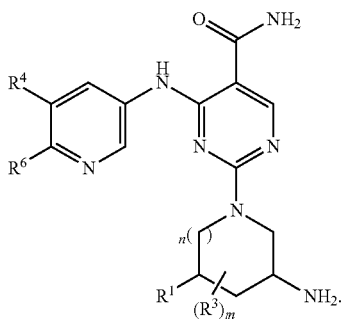
(IIIB)

In an embodiment, W is

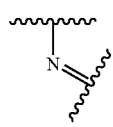 [SMILES: *N=*]

and X is

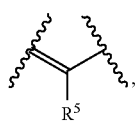

such that the compound has the Formula IIIC:

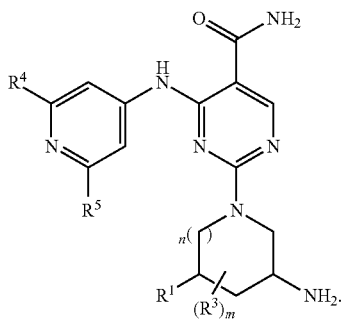
(IIIC)

In an embodiment, W is

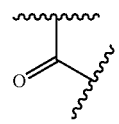

and X is

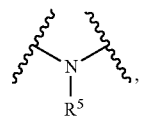

such that the compound has the Formula IIID:

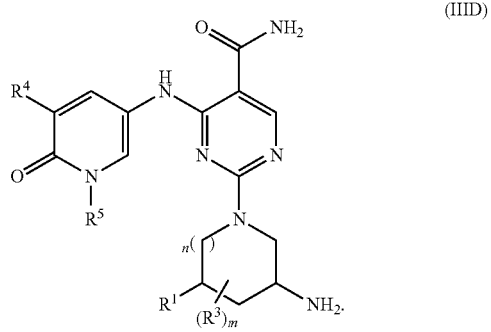
(IIID)

$R^4$:

In an embodiment, $R^4$ is selected from the group consisting of: $C_{3-6}$ alkyl, $C_{3-6}$ haloalkyl, $C_{3-6}$ alkenyl wherein (i) the carbon atom beta to the ring to which the alkene is bonded is cis-substituted with carbon; and (ii) the carbon atom alpha to the ring to which the alkene is bonded substituted with carbon, $C_{3-6}$ cycloalkyl, $C_{4-6}$ cycloalkenyl, 4- to 6-membered heterocycloalkyl including 1, 2 or 3 heteroatoms selected from N, O or S, aryl, heteroaryl including 1, 2 or 3 heteroatoms selected from N, O or S, $-NR^{B3a}C(O)R^{B2a}$, $-C(O)NR^{B2a}R^{B2a}$, $-C(O)$-(4- to 12-membered non-aromatic saturated or partially saturated monocyclic or fused, bridged, or spiro bicyclic heterocyclic ring system including 1, 2 or 3 heteroatoms selected from N, O or S), $-SO_2NR^{B3a}R^{B3a}$, $-SO_2R^{B2a}$ and $-S(O)(=NR^{B3a})R^{B2a}$; wherein the $R^{B2a}$ and $R^{B3a}$ groups are as defined in the first aspect; and wherein each of the aforementioned $C_{3-6}$ alkyl, $C_{3-6}$ haloalkyl, $C_{3-6}$ alkenyl, $C_{3-6}$ cycloalkyl, $C_{4-6}$ cycloalkenyl, 4- to 6-membered heterocycloalkyl including 1, 2 or 3 heteroatoms selected from N, O or S, aryl, heteroaryl and 4- to 12-membered non-aromatic saturated or partially saturated monocyclic or fused, bridged, or spiro bicyclic heterocyclic ring system including 1, 2 or 3 heteroatoms selected from N, O or S can be optionally substituted as per the first aspect.

In an embodiment, $R^4$ is $C_{3-6}$ alkyl (e.g. $C_3$, $C_4$, $C_5$ or $C_6$ alkyl). Preferably $R^4$ is selected from the group consisting of iso-propyl and t-butyl. Optional substituents for the $C_{3-6}$ alkyl groups are selected from the group consisting of: $-OR^{B3a}$, $=O$, $-NR^{B3a}R^{B3a}$, $-SR^{B3a}$, $-CN$, $-NO_2$, $-NR^{B3a}C(O)R^{B3a}$, $-C(O)NR^{B3a}R^{B3a}$, $-NR^{B3a}C(O)OR^{B3a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NRBaR^{B3a}$, $-SO_2R^{B3a}$, $-C(O)R^{B3a}$ and $-C(O)$ OR$^{B3a}$. Preferably, the optional substituents for the C$_{3-6}$ alkyl groups are selected from the group consisting of: —OR$^{B3a}$, —NR$^{B3a}$R$^{B3a}$, —SR$^{B3a}$, —CN and —NR$^{B3a}$C(O)R$^{B3a}$. More preferably, the optional substituents for the C$_{3-6}$ alkyl groups are selected from the group consisting of: —OR$^{B3a}$, —NR$^{B3a}$R$^{B3a}$, —CN and —NR$^{B3a}$C(O)R$^{B3a}$. Most preferably, the optional substituents for the C$_{3-6}$ alkyl groups are selected from the group consisting of: —OR$^{B3a}$ and —CN. In an embodiment, R$^{B3a}$ is selected from the group consisting of H, C$_{1-4}$ alkyl, C$_{1-4}$ haloalkyl and C$_{3-6}$ cycloalkyl.

In an embodiment, R$^4$ is —C(O)NR$^{B2a}$R$^{B2a}$, wherein each R$^{B2a}$ is independently selected from the group consisting of: C$_{1-4}$ alkyl, C$_{1-4}$ heteroalkyl, 4- to 12-membered non-aromatic saturated or partially saturated monocyclic or fused, bridged, or spiro bicyclic heterocyclic ring system including 1, 2 or 3 heteroatoms selected from N, O or S. In an embodiment, each R$^{B2a}$ is independently selected from the group consisting of: C$_1$ and C$_2$ alkyl. Optional substituents for the C$_{1-4}$ alkyl and C$_{1-4}$ heteroalkyl are selected from the group consisting of: —OH, —O(C$_{1-3}$ alkyl), —(C$_{1-3}$ alkyl)-OH, —(C$_{1-3}$ alkyl)-O(C$_{1-3}$ alkyl), =O, —NH$_2$, —NH(C$_{1-3}$ alkyl), —N(C$_{1-3}$ alkyl)$_2$ or (C$_{1-3}$ alkyl)-NH$_2$, —(C$_{1-3}$ alkyl)-NH(C$_{1-3}$ alkyl) or —(C$_{1-3}$ alkyl)-N(C$_{1-3}$ alkyl)$_2$. Preferably, the optional substituents for the C$_{1-4}$ alkyl and C$_{1-4}$ heteroalkyl are selected from the group consisting of: —OH, —O(C$_{1-3}$ alkyl), —NH$_2$, —NH(C$_{1-3}$ alkyl) or —N(C$_{1-3}$ alkyl)$_2$.

In an embodiment, R$^4$ is —C(O)NR$^{B2a}$R$^{B2a}$, wherein each R$^{B2a}$ is independently selected from the group consisting of: C$_{1-4}$ alkyl and C$_{1-4}$ heteroalkyl, wherein the R$^{B2a}$ moieties, together with the nitrogen atom to which they are bonded, form a 4- to 7-membered ring system optionally including 1, 2 or 3 additional heteroatoms selected from N, O and S as depicted in the following structure wherein Ring A is a 4- to 7-membered ring system optionally including 1, 2 or 3 additional heteroatoms selected from N, O and S:

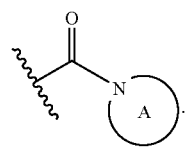

Optional substituents for the C$_{1-4}$ alkyl and C$_{1-4}$ heteroalkyl groups include: C$_{1-4}$ alkyl, C$_{1-4}$ haloalkyl, C$_{3-6}$ cycloalkyl, —OH, —O(C$_{1-3}$ alkyl), —(C$_{1-3}$ alkyl)-OH, —(C$_{1-3}$ alkyl)-O(C$_{1-3}$ alkyl), =O, —NH$_2$, —NH(C$_{1-3}$ alkyl), —N(C$_{1-3}$ alkyl)$_2$ or (C$_{1-3}$ alkyl)-NH$_2$, —(C$_{1-3}$ alkyl)-NH(C$_{1-3}$ alkyl) or —(C$_{1-3}$ alkyl)-N(C$_{1-3}$ alkyl)$_2$. Preferably, the optional substituents for the C$_{1-4}$ alkyl and C$_{1-4}$ heteroalkyl are selected from the group consisting of: C$_{1-4}$ alkyl, C$_{1-4}$ haloalkyl, —OH, —O(C$_{1-3}$ alkyl), —(C$_{1-3}$ alkyl)-OH, —(C$_{1-3}$ alkyl)-O(C$_{1-3}$ alkyl) and =O. Exemplary structures include:

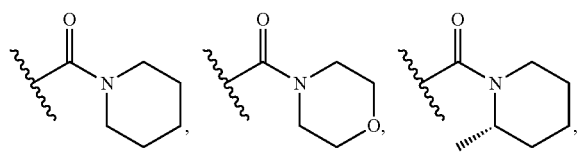

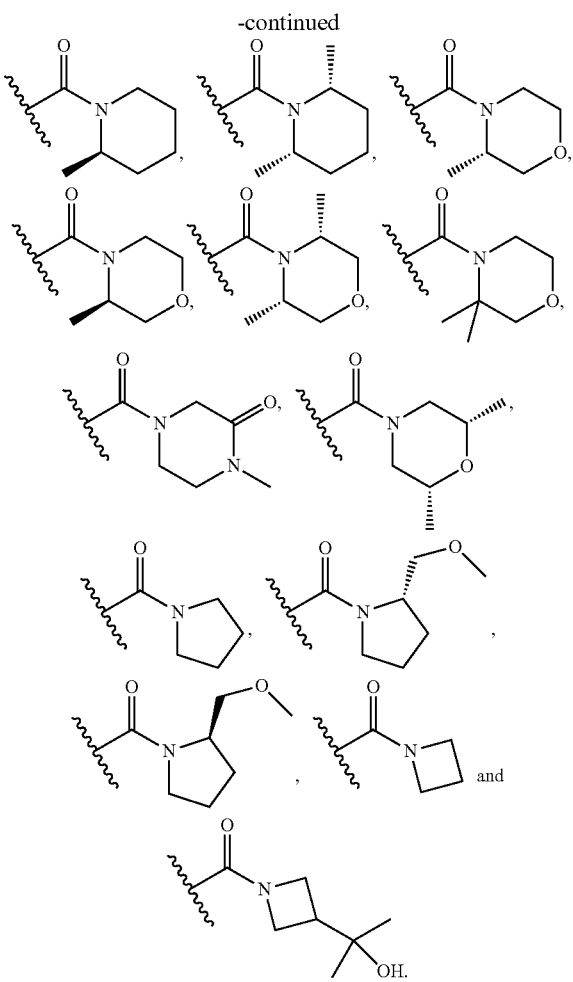

In an embodiment, R$^4$ is C$_{3-6}$ cycloalkyl (e.g. C$_3$ cycloalkyl, C$_4$ cycloalkyl, C$_5$ cycloalkyl or C$_6$ cycloalkyl). Optional substituents for the C$_{3-6}$ cycloalkyl group are selected from the group consisting of: C$_{1-6}$ alkyl, C$_{1-6}$ haloalkyl, halo, —OR$^{B3a}$, —NR$^{B3a}$R$^{B3a}$, —SR$^{B3a}$, —CN, —NO$_2$, —NR$^{B3a}$C(O)R$^{B3a}$ and —C(O)NR$^{B3a}$R$^{B3a}$. Preferably, the optional substituents for the C$_{3-6}$ cycloalkyl group are selected from the group consisting of: halo, —OR$^{B3a}$ and —CN. In an embodiment, R$^{B3a}$ is selected from the group consisting of: H, C$_{1-4}$ alkyl and C$_{1-4}$ haloalkyl. The substituent can be bonded to any atom of the C$_{3-6}$ cycloalkyl moiety, including the atom that bonds the C$_{3-6}$ cycloalkyl group to the remainder of the compound. Exemplary C$_{3-6}$ cycloalkyl groups include:

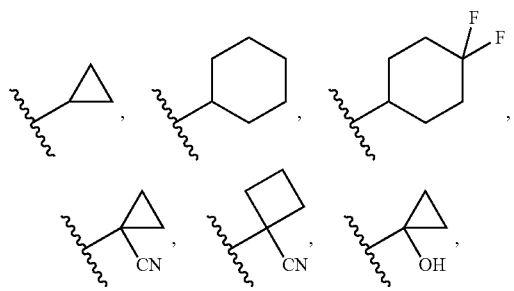

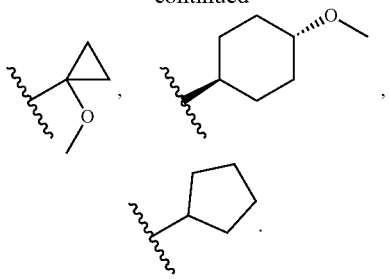

In an embodiment, $R^4$ is —$SO_2R^{B2a}$, wherein $R^{B2a}$ is $C_{1-4}$ alkyl (e.g. $C_1$, $C_2$, $C_3$ or $C_4$ alkyl).

In an embodiment, $R^4$ is —$SO_2NR^{B3a}R^{B3a}$, wherein each $R^{B3a}$ is independently selected from the group consisting of: H, $C_{1-4}$ alkyl and $C_{1-4}$ heteroalkyl. In an embodiment, each $R^{B3a}$ is independently selected from the group consisting of: H and $C_{1-4}$ alkyl (e.g. $C_1$, $C_2$, $C_3$ or $C_4$) alkyl. Optional substituents for the $C_{1-4}$ alkyl and $C_{1-4}$ heteroalkyl are selected from the group consisting of: —OH, —O($C_{1-3}$ alkyl), —($C_{1-3}$ alkyl)-OH, —($C_{1-3}$ alkyl)-O($C_{1-3}$ alkyl), =O, —$NH_2$, —NH($C_{1-3}$ alkyl), —N($C_{1-3}$ alkyl)$_2$ or ($C_{1-3}$ alkyl)-$NH_2$, —($C_{1-3}$ alkyl)-NH($C_{1-3}$ alkyl) or —($C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: —OH, —O($C_{1-3}$ alkyl), —$NH_2$, —NH($C_{1-3}$ alkyl) or —N($C_{1-3}$ alkyl)$_2$.

In an embodiment, $R^4$ is —$SO_2NR^{B3a}R^{B3a}$, wherein each $R^{B3a}$ is independently selected from the group consisting of: $C_{1-4}$ alkyl and $C_{1-4}$ heteroalkyl wherein the $R^{B3a}$ moieties, together with the nitrogen atom to which they are bonded, can form a 4- to 7-membered ring system optionally including 1, 2 or 3 additional heteroatoms selected from N, O and S as depicted in the following structure wherein Ring B is a 4- to 7-membered ring system optionally including 1, 2 or 3 additional heteroatoms selected from N, O and S:

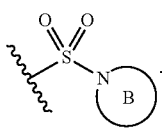

In an embodiment, each $R^{B3a}$ is independently $C_{1-4}$ alkyl (e.g. $C_1$, $C_2$, $C_3$ or $C_4$) alkyl. Optional substituents for the $C_{1-4}$ alkyl and $C_{1-4}$ heteroalkyl are selected from the group consisting of: —OH, —O($C_{1-3}$ alkyl), —($C_{1-3}$ alkyl)-OH, —($C_{1-3}$ alkyl)-O($C_{1-3}$ alkyl), =O, —$NH_2$, —NH($C_{1-3}$ alkyl), —N($C_{1-3}$ alkyl)$_2$ or ($C_{1-3}$ alkyl)-$NH_2$, —($C_{1-3}$ alkyl)-NH($C_{1-3}$ alkyl) or —($C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: —OH, —O($C_{1-3}$ alkyl), —$NH_2$, —NH($C_{1-3}$ alkyl) or —N($C_{1-3}$ alkyl)$_2$. In an embodiment,

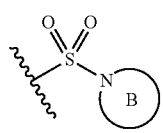

is selected from the group consisting of:

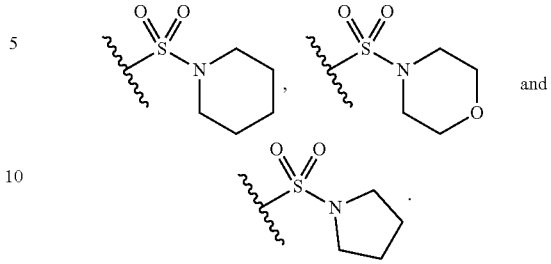

In an embodiment, $R^4$ is aryl or heteroaryl including 1, 2 or 3 heteroatoms selected from N, O or S. Optional substituents for the aryl or heteroaryl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —$OR^{B3a}$, —$NR^{B3a}R^{B3a}$, —$SR^{B3a}$, —CN, —$NO_2$, —$NR^{B3a}C(O)R^{B3a}$, —$C(O)NR^{B3a}R^{B3a}$, $NR^{B3a}C(O)OR^{B3a}$, —$OC(O)NR^{B3a}R^{B3a}$, —$NR^{B3a}C(O)NR^{B3a}R^{B3a}$, —$NR^{B3a}C(NR^{B3a})NR^{B3a}R^{B3a}$, —$NR^{B3a}SO_2R^{B3a}$, —$SO_2NR^{B3a}R^{B3a}$, —$SO_2R^{B3a}$, —$C(O)R^{B3a}$ and —$C(O)OR^{B3a}$. Preferably, the optional substituents for the aryl or heteroaryl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, halo, —$OR^{B3a}$, —$NR^{B3a}R^{B3a}$, —$SR^{B3a}$, —$NR^{B3a}C(O)R^{B3a}$, —$C(O)NR^{B3a}R^{B3a}$, —$SO_2R^{B3a}$, —$C(O)R^{B3a}$ and —$C(O)OR^{B3a}$. More preferably, the optional substituents for the aryl or heteroaryl moiety are selected from the group consisting of: $C_{1-6}$ alkyl (e.g. $C_1$, $C_2$, $C_3$ or $C_4$ alkyl), $C_{1-6}$ haloalkyl (e.g. $C_1$, $C_2$, $C_3$ or $C_4$ haloalkyl, such as $CF_3$), halo and —$OR^{B3a}$ (e.g. —O—$C_{1-4}$ alkyl, such as —O—$CH_3$, or —O—$C_{1-4}$ haloalkyl, such as —O—$CF_3$).

In an embodiment, $R^4$ is a $C_{3-6}$ alkenyl moiety wherein (i) the carbon atom beta to the ring to which the alkene is bonded is cis-substituted with carbon; and (ii) the carbon atom alpha to the ring to which the alkene is bonded substituted with carbon. Preferably, $R^4$ is a $C_{3-4}$ alkenyl moiety. Exemplary $C_{3-6}$ alkenyl moieties include:

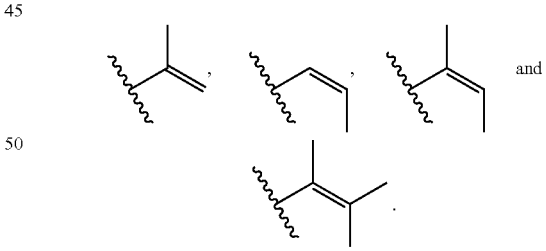

In an embodiment, $R^4$ is a 4- to 6-membered heterocycloalkyl including 1, 2 or 3 heteroatoms selected from N, O or S. The 4- to 6-membered heterocycloalkyl may be joined to the remainder of the molecule via a carbon atom or via a heteroatom. Optional substituents for the 4- to 6-membered heterocycloalkyl are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —$OR^{B3a}$, =O, —$NR^{B3a}R^{B3a}$, —$SR^{B3a}$, —CN, —$NO_2$, —$NR^{B3a}C(O)R^{B3a}$, —$C(O)R^{B3a}$, and —$C(O)NR^{B3a}R^{B3a}$. Preferably, the optional substituents for the 4- to 6-membered heterocycloalkyl are selected from the group consisting of: 4- to 6-membered heterocycloalkyl including 1, 2 or 3 heteroatoms selected from N, O or S, aryl, heteroaryl including 1, 2 or 3 heteroatoms selected from N, O or S, halo, —OR$^{B3a}$, =O, —NR$^{B3a}$R$^{B3a}$, —NR$^{B3a}$C(O)R$^{B3a}$, —C(O)R$^{B3a}$, and —C(O)NR$^{B3a}$R$^{B3a}$. More preferably, the optional substituents for the 4- to 6-membered heterocycloalkyl are selected from the group consisting of: aryl, =O, —NR$^{B3a}$R$^{B3a}$ and —C(O)R$^{B3a}$. In an embodiment, R$^{B3a}$ is selected from the group consisting of H, C$_{1-4}$ alkyl, C$_{1-4}$ haloalkyl and C$_{3-6}$ cycloalkyl. Exemplary structures include:

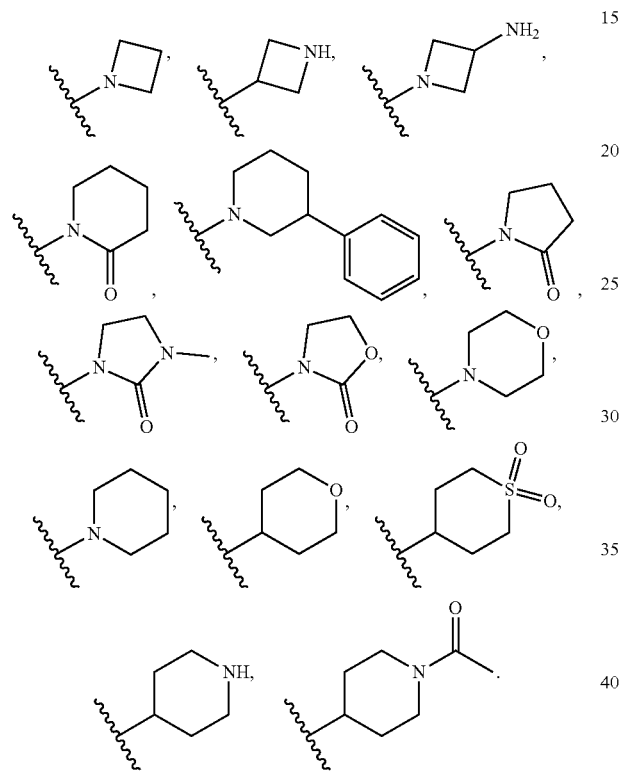

In an embodiment, R$^4$ is a —C(O)-(4- to 12-membered non-aromatic saturated or partially saturated monocyclic or fused, bridged, or spiro bicyclic heterocyclic ring system including 1, 2 or 3 heteroatoms selected from N, O or S). Optional substituents for this moiety are selected from the group consisting of: C$_{1-6}$ alkyl, C$_{1-6}$ haloalkyl, C$_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —OR$^{B3a}$, —NR$^{B3a}$R$^{B3a}$, —SR$^{B3a}$, NR$^{B3a}$C(O)R$^{B3a}$ and —C(O)NR$^{B3a}$R$^{B3a}$. Preferably, optional substituents for this moiety are selected from the group consisting of: aryl, heteroaryl including 1, 2 or 3 heteroatoms selected from N, O or S, halo, —OR$^{B3a}$, NR$^{B3a}$R$^{B3a}$, —SR$^{B3a}$, —NR$^{B3a}$C(O)R$^{B3a}$ and —C(O)NR$^{B3a}$R$^{B3a}$. More preferably, the optional substituents for this moiety are selected from the group consisting of: aryl, heteroaryl including 1, 2 or 3 heteroatoms selected from N, O or S and —OR$^{B3a}$. In an embodiment, R$^{B3a}$ is selected from the group consisting of H, C$_{1-4}$ alkyl, C$_{1-4}$ haloalkyl and C$_{3-6}$ cycloalkyl, preferably C$_{1-4}$ alkyl. Exemplary R$^4$ moieties include:

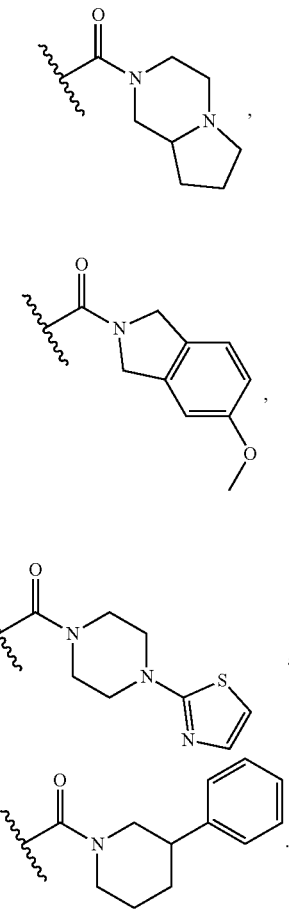

In an embodiment, R$^4$ is —S(O)(=NR$^{B3a}$)R$^{B2a}$, wherein R$^{B3a}$ is selected from the group consisting of: H, C$_{1-4}$ alkyl and C$_{1-4}$ haloalkyl, and R$^{B2a}$ is selected from the group consisting of: C$_{1-4}$ alkyl and C$_{1-4}$ haloalkyl. Preferably, R$^{B3a}$ is selected from the group consisting of: H and C$_{1-4}$ alkyl (e.g. C$_1$, C$_2$, C$_3$ or C$_4$ alkyl). Preferably, R$^{B3a}$ is C$_{1-4}$ alkyl (e.g. C$_1$, C$_2$, C$_3$ or C$_4$ alkyl).

In an embodiment, R$^4$ is —NR$^{B3a}$C(O)R$^{B2a}$, wherein R$^{B3a}$ is selected from the group consisting of: C$_{1-4}$ alkyl, C$_{1-4}$ heteroalkyl and C$_{1-4}$ haloalkyl, and R$^{B2a}$ is selected from the group consisting of: C$_{1-4}$ alkyl and C$_{1-4}$ haloalkyl. Preferably, R$^{B3a}$ is selected from the group consisting of: C$_{1-4}$ alkyl (e.g. C$_1$, C$_2$, C$_3$ or C$_4$ alkyl) and C$_{1-4}$ haloalkyl (e.g. C$_1$, C$_2$, C$_3$ or C$_4$ haloalkyl). Preferably, R$^{B2a}$ is selected from the group consisting of: (e.g. C$_1$, C$_2$, C$_3$ or C$_4$ alkyl) and C$_{1-4}$ haloalkyl (e.g. C$_1$, C$_2$, C$_3$ or C$_4$ haloalkyl).

In an embodiment, R$^4$ is C$_{4-6}$ cycloalkenyl. Optional substituents for the C$_{4-6}$ cycloalkenyl moiety are selected from the group consisting of: C$_{1-6}$ alkyl, C$_{1-6}$ haloalkyl, C$_{3-6}$ cycloalkyl, 4- to 6-membered heterocycloalkyl including 1, 2 or 3 heteroatoms selected from N, O or S, halo, —OR$^{B3a}$, —NR$^{B3a}$R$^{B3a}$, —SR$^{B3a}$, —NR$^{B3a}$C(O)R$^{B3a}$ and —C(O)NR$^{B3a}$R$^{B3a}$. Preferably, optional substituents for the C$_{4-6}$ cycloalkenyl moiety are selected from the group consisting of: halo, —OR$^{B3a}$, —NR$^{B3a}$R$^{B3a}$, —SR$^{B3a}$, —NR$^{B3a}$C(O)R$^{B3a}$ and —C(O)NR$^{B3a}$R$^{B3a}$. More preferably, optional substituents for the C$_{4-6}$ cycloalkenyl moiety are halo Exemplary R$^4$ moieties include:

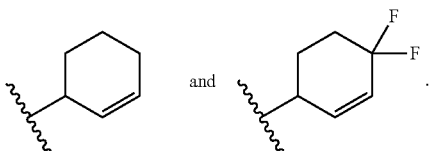 [SMILES: *C1C=CCCC1 ; *C1C=CC(F)(F)CC1]
and

In an embodiment, $R^4$ is $C_{3-6}$ haloalkyl. Preferably $R^4$ is selected from the group consisting of $C_3$ and $C_4$ haloalkyl. Optional substituents for the $C_{3-6}$ haloalkyl groups are selected from the group consisting of: $-OR^{B3a}$, $=O$, $-NR^{B3a}R^{B3a}$, $-SR^{B3a}$, $-CN$, $-NO_2$, $-NR^{B3a}C(O)R^{B3a}$, $-C(O)NR^{B3a}R^{B3a}$, $-NR^{B3a}C(O)OR^{B3a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2RB^{3a}$, $-SO_2NR^{B3a}R^{B3a}$, $-SO_2R^{B3a}$, $-C(O)R^{B3a}$ and $-C(O)OR^{B3a}$. Preferably, the optional substituents for the $C_{3-6}$ haloalkyl groups are selected from the group consisting of: $-OR^{B3a}$, $-NR^{B3a}R^{B3a}$, $-SR^{B3a}$, $-CN$ and $-NR^{B3a}C(O)R^{B3a}$. More preferably, the optional substituents for the $C_{3-6}$ haloalkyl groups are selected from the group consisting of: $-OR^{B3a}$, $-NR^{B3a}R^{B3a}$, $-CN$ and $-NR^{B3a}C(O)R^{B3a}$. In an embodiment, $R^{B3a}$ is selected from the group consisting of H, $C_{1-4}$ alkyl, $C_{1-4}$ haloalkyl and $C_{3-6}$ cycloalkyl.

In an embodiment, $R^5$ is H.

In an embodiment, $R^5$ is $R^4$ (i.e. $R^5$ is as defined in any of the above embodiments relating to $R^4$).

In an embodiment, $R^5$ is selected from the group consisting of: $C_{1-6}$ alkyl, $C_{1-6}$ heteroalkyl, $C_{1-6}$ haloalkyl, $C_{1-6}$ heterohaloalkyl, $C_{2-6}$ alkenyl, $C_{2-6}$ alkynyl, $-O$-aryl, $-O$-heteroaryl, halo, $-OR^{B2a}$, $-NR^{B3a}R^{B3a}$, $-SR^{B2a}$, $-CN$, $-CR^{B3a}(=NR^{B3a})$, $-OC(O)NR^{B3a}R^{B3a}$, $-NR^{B3a}C(NR^{B3a})NR^{B3a}R^{B3a}$ and $-C(O)OR^{B2a}$. Preferably, $R^5$ is selected from the group consisting of: $C_{1-6}$ alkyl, $C_{1-6}$ haloalkyl, $C_{2-6}$ alkenyl, $C_{2-6}$ alkynyl, $-O$-aryl, $-O$-heteroaryl, halo, $-OR^{B2a}$, $-NR^{B3a}R^{B3a}$, $-SR^{B2a}$, $-CN$, $-CR^{B3a}(=NR^{B3a})$, $-OC(O)NR^{B3a}R^{B3a}$, $-NR^{B3a}C(NR^{B3a})NR^{B3a}R^{B3a}$ and $-C(O)OR^{B2a}$. More preferably, $R^5$ is selected from the group consisting of: $C_{1-6}$ alkyl, $C_{1-6}$ haloalkyl, $C_{2-6}$ alkenyl, halo and $-C(O)OR^{B2a}$.

In an embodiment, $R^5$ is $C_{1-6}$ alkyl (e.g. $C_1$, $C_2$, $C_3$, $C_4$, $C_5$ or $C_6$ alkyl). Preferably $R^5$ is selected from the group consisting of methyl, ethyl, n-propyl, iso-propyl, n-butyl, s-butyl, i-butyl and t-butyl. Preferably $R^5$ is selected from the group consisting of methyl, ethyl, n-propyl, iso-propyl, n-butyl, s-butyl, i-butyl and t-butyl. Optional substituents for the $C_{1-6}$ alkyl groups are selected from the group consisting of: $-OR^{B3a}$, $=O$, $-NR^{B3a}R^{B3a}$, $-SR^{B3a}$, $-CN$, $-NO_2$, $-NR^{B3a}C(O)R^{B3a}$, $-C(O)NR^{B3a}R^{B3a}$, $-NR^{B3a}C(O)OR^{B3a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NR^{B3a}R^{B3a}$, $-SO_2R^{B3a}$, $-C(O)R^{B3a}$ and $-C(O)OR^{B3a}$. Preferably, the optional substituents for the $C_{1-6}$ alkyl groups are selected from the group consisting of: $-OR^{B3a}$, $-NR^{B3a}R^{B3a}$, $-SR^{B3a}$, $-CN$ and $-NR^{B3a}C(O)R^{B3a}$. More preferably, the optional substituents for the $C_{1-6}$ alkyl groups are selected from the group consisting of: $-OR^{B3a}$, $-NR^{B3a}R^{B3a}$, $-CN$ and $-NR^{B3a}C(O)R^{B3a}$. In an embodiment, $R^{B3a}$ is selected from the group consisting of H, $C_{1-4}$ alkyl, $C_{1-4}$ haloalkyl and $C_{3-6}$ cycloalkyl.

In an embodiment, $R^5$ is $C_{1-6}$ haloalkyl (e.g. $C_1$, $C_2$, $C_3$, $C_4$, $C_5$ or $C_6$ haloalkyl). Preferably $R^5$ is selected from the group consisting of methyl, ethyl, n-propyl, iso-propyl, n-butyl, s-butyl, i-butyl and t-butyl substituted with a halogen atom. More preferably, $R^5$ is selected from the group consisting of $-CF_3$ and $-CF(CH_3)_2$. Optional substituents for the $C_{1-6}$ haloalkyl groups are selected from the group consisting of: $-OR^{B3a}$, $=O$, $-NR^{B3a}R^{B3a}$, $-SR^{B3a}$, $-CN$, $-NO_2$, $-NR^{B3a}C(O)R^{B3a}$, $-C(O)NR^{B3a}R^{B3a}$, $-NR^{B3a}C(O)OR^{B3a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NR^{B3a}R^{B3a}$, $-SO_2R^{B3a}$, $-C(O)R^{B3a}$ and $-C(O)OR^{B3a}$. Preferably, the optional substituents for the $C_{1-6}$ haloalkyl groups are selected from the group consisting of: $-OR^{B3a}$, $-NR^{B3a}R^{B3a}$, $-SR^{B3a}$, $-CN$ and $-NR^{B3a}C(O)R^{B3a}$. More preferably, the optional substituents for the $C_{1-6}$ haloalkyl groups are selected from the group consisting of: $-OR^{B3a}$, $-NR^{B3a}R^{B3a}$, $-CN$ and $-NR^{B3a}C(O)R^{B3a}$. In an embodiment, $R^{B3a}$ is selected from the group consisting of H, $C_{1-4}$ alkyl, $C_{1-4}$ haloalkyl and $C_{3-5}$ cycloalkyl.

In an embodiment, $R^5$ is $-C(O)OR^{B2a}$, wherein $R^{B2a}$ is selected from the group consisting of: $C_{1-4}$ alkyl and $C_{1-4}$ haloalkyl. Preferably, $R^{B2a}$ is $C_{1-4}$ alkyl (e.g. $C_1$, $C_2$, $C_3$ or $C_4$ alkyl).

In an embodiment, $R^5$ is a $C_{2-6}$ alkenyl moiety. Optionally, (i) the carbon atom beta to the ring to which the alkene is bonded is cis-substituted with carbon; and/or (ii) the carbon atom alpha to the ring to which the alkene is bonded substituted with carbon. Preferably, $R^4$ is a $C_{3-4}$ alkenyl moiety. Exemplary $C_{3-6}$ alkenyl moieties include:

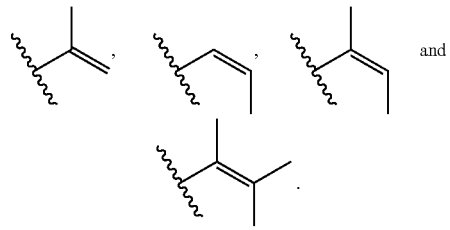
, , and .

In an embodiment, $R^6$ is halo (e.g. F, Cl or Br).
$R^6$;

In an embodiment, $R^6$ is H.

In an embodiment, $R^6$ is $R^4$ (i.e. $R^6$ is as defined in any of the above embodiments relating to $R^4$).

In an embodiment, $R^6$ is selected from the group consisting of: $C_{1-6}$ alkyl, $C_{1-6}$ heteroalkyl, $C_{1-6}$ haloalkyl, $C_1$-heterohaloalkyl, $C_{2-6}$ alkenyl, $C_{2-6}$ alkynyl, $-O$-aryl, $-O$-heteroaryl, halo, $-OR^{B3a}$, $-NR^{B3a}R^{B3a}$, $-SR^{B2a}$, $-CN$, $-CR^{B3a}(=NR^{B3a})$, $-OC(O)NR^{B3a}R^{B3a}$, $-NR^{B3a}C(NR^{B3a})NR^{B3a}R^{B3a}$ and $-C(O)OR^{B2a}$. Preferably, $R^6$ is selected from the group consisting of: $C_{1-6}$ alkyl, $C_{1-6}$ haloalkyl, $C_{2-6}$ alkenyl, $C_{2-6}$ alkynyl, $-O$-aryl, $-O$-heteroaryl, halo, $-OR^{B3a}$, $-NR^{B3a}R^{B3a}$, $-SR^{B2a}$, $-CN$, $-CR^{B3a}(=NR^{B3a})$, $-OC(O)NR^{B3a}R^{B3a}$, $-NR^{B3a}C(NR^{B3a})NR^{B3a}R^{B3a}$ and $-C(O)OR^{B2a}$. More preferably, $R^6$ is selected from the group consisting of: $C_{1-6}$ alkyl, $C_{1-6}$ haloalkyl, halo, $-OR^{B3a}$ and $-CN$.

In an embodiment, $R^6$ is $C_{1-6}$ alkyl (e.g. $C_1$, $C_2$, $C_3$, $C_4$, $C_5$ or $C_6$ alkyl). Preferably $R^6$ is selected from the group consisting of methyl, ethyl, n-propyl, iso-propyl, n-butyl, s-butyl, i-butyl and t-butyl. Optional substituents for the $C_{1-6}$ alkyl groups are selected from the group consisting of: $-OR^{B3a}$, $=O$, $-NR^{B3a}R^{B3a}$, $-SR^{B3a}$, $-CN$, $-NO_2$, $-NR^{B3a}C(O)R^{B3a}$, $-C(O)NR^{B3a}R^{B3a}$, $-NR^{B3a}C(O)OR^{B3a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $NR^{B3a}SO_2R^{B3a}$, $-SO_2NR^{B3a}R^{B3a}$, $-SO_2R^{B3a}$, $-C(O)R^{B3a}$ and $-C(O)OR^{B3a}$. Preferably, the optional substituents for the $C_{1-6}$ alkyl groups are selected from the group consisting of: —$OR^{B3a}$, —$NR^{B3a}R^{B3a}$, —$SR^{B3a}$, —CN and —$NR^{B3a}C(O)R^{B3a}$. More preferably, the optional substituents for the $C_{1-6}$ alkyl groups are selected from the group consisting of: —$OR^{B3a}$, —$NR^{B3a}R^{B3a}$, —CN and —$NR^{B3a}C(O)R^{B3a}$. In an embodiment, $R^{B3a}$ is selected from the group consisting of H, $C_{1-4}$ alkyl, $C_{1-4}$ haloalkyl and $C_{3-6}$ cycloalkyl.

In an embodiment, $R^6$ is $C_{1-6}$ haloalkyl (e.g. $C_1$, $C_2$, $C_3$, $C_4$, $C_5$ or $C_6$ haloalkyl). Preferably $R^6$ is selected from the group consisting of methyl, ethyl, n-propyl, iso-propyl, n-butyl, s-butyl, i-butyl and t-butyl substituted with a halogen atom. More preferably, $R^6$ is selected from the group consisting of —$CF_3$ and —$CF(CH_3)_2$. Optional substituents for the $C_{1-6}$ haloalkyl groups are selected from the group consisting of: —$OR^{B3a}$, =O, —$NR^{B3a}R^{B3a}$, —$SR^{B3a}$, —CN, —$NO_2$, —$NR^{B3a}C(O)R^{B3a}$, —$C(O)NR^{B3a}R^{B3a}$, —$NR^{B3a}C(O)OR^{B3a}$, —$OC(O)NR^{B3a}R^{B3a}$, —$NR^{B3a}C(O)NR^{B3a}R^{B3a}$, —$NR^{B3a}C(NR^{B3a})NR^{B3a}R^{B3a}$, —$NR^{B3a}SO_2R^{B3a}$, —$SO_2NR^{B3a}R^{B3a}$, —$SO_2R^{B3a}$, —$C(O)R^{B3a}$ and —$C(O)OR^{B3a}$. Preferably, the optional substituents for the $C_{1-6}$ haloalkyl groups are selected from the group consisting of: —$OR^{B3a}$, —$NR^{B3a}R^{B3a}$, —$SR^{B3a}$, —CN and —$NR^{B3a}C(O)R^{B3a}$. More preferably, the optional substituents for the $C_{1-6}$ haloalkyl groups are selected from the group consisting of: —$OR^{B3a}$, —$NR^{B3a}R^{B3a}$, —CN and —$NR^{B3a}C(O)R^{B3a}$. In an embodiment, $R^{B3a}$ is selected from the group consisting of H, $C_{1-4}$ alkyl, $C_{1-4}$ haloalkyl and $C_{3-6}$ cycloalkyl.

In an embodiment, $R^6$ is halo (e.g. F, Cl or Br).

In an embodiment, $R^6$ is —$OR^{B3a}$, wherein $R^{B3a}$ is selected from the group consisting of: H, $C_{1-4}$ alkyl and $C_{1-4}$ haloalkyl. Preferably, $R^{B3a}$ is selected from the group consisting of: H and $C_{1-4}$ alkyl (e.g. $C_1$, $C_2$, $C_3$ or $C_4$ alkyl).

In an embodiment, $R^6$ is —CN.

$R^4$ and $R^6$:

In an embodiment, $R^4$ is $C_{1-6}$ alkyl or $C_{3-6}$ cycloalkyl and $R^6$ is —$NR^{B3a}C(O)R^{B2a}$, wherein the terminal $R^{B2a}$ is absent and $R^4$ and $R^6$ are joined via the carbonyl carbon, so that, together with the carbon atoms to which they are bonded, $R^4$ and $R^6$ form a 5- or 6-membered ring and the structure is:

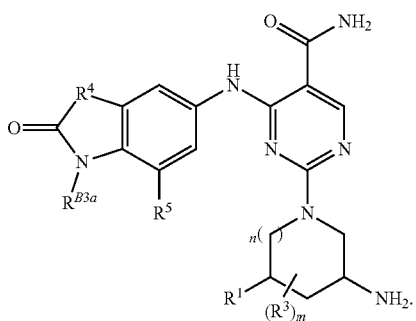

Preferably, $R^{B3a}$ is H, $C_{1-4}$ alkyl, $C_{1-4}$ haloalkyl, $C_{3-6}$ cycloalkyl, $C_{1-4}$ alkyl $C_{3-6}$ cycloalkyl, 4- to 12-membered non-aromatic saturated or partially saturated monocyclic or fused, bridged, or spiro bicyclic heterocyclic ring system including 1, 2 or 3 heteroatoms selected from N, O or S. More preferably, $R^{B3a}$ is H, $C_{1-4}$ alkyl, $C_{1-4}$ haloalkyl and $C_{3-6}$ cycloalkyl. Exemplary structures include:

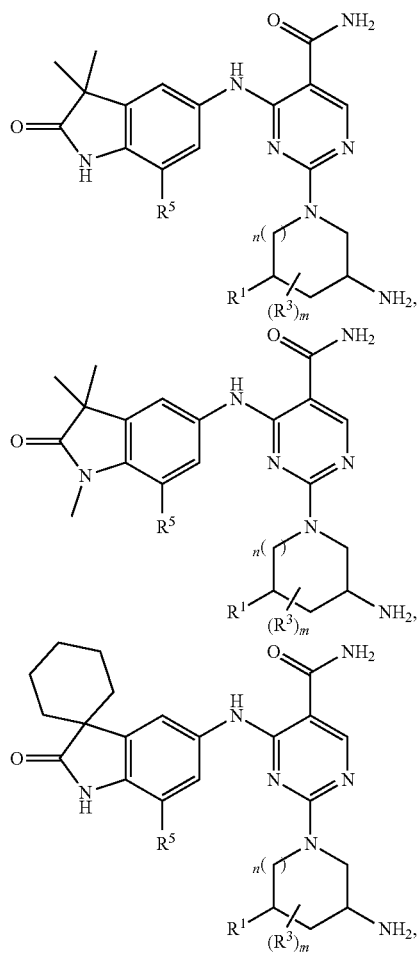

$R^5$ and $R^6$:

In an embodiment, $R^5$ is —$NR^{B3a}R^{B3a}$ and $R^6$ is —$CR^{B3a}$ (=$NR^{B3a}$), wherein the terminal $R^{B3a}$ of —$CR^{B3a}$ (=$NR^{B3a}$) is absent and one $R^{B3a}$ of —$NR^{B3a}R^{B3a}$ is absent and $R^5$ and $R^6$ are joined via the imine nitrogen atom, so that, together with the carbon atoms to which they are bonded, $R^5$ and $R^6$ form a 5-membered ring and the structure is:

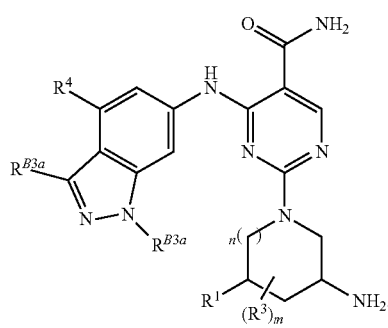

Preferably, $R^{B3a}$ is H, $C_{1-4}$ alkyl, $C_{1-4}$ haloalkyl, $C_{3-6}$ cycloalkyl, $C_{1-4}$ alkyl $C_{3-6}$ cycloalkyl, 4- to 12-membered non-aromatic saturated or partially saturated monocyclic or fused, bridged, or spiro bicyclic heterocyclic ring system including 1, 2 or 3 heteroatoms selected from N, O or S. More preferably, $R^{B3a}$ is H, $C_{1-4}$ alkyl, $C_{1-4}$ haloalkyl and $C_{3-6}$ cycloalkyl. Exemplary structures include:

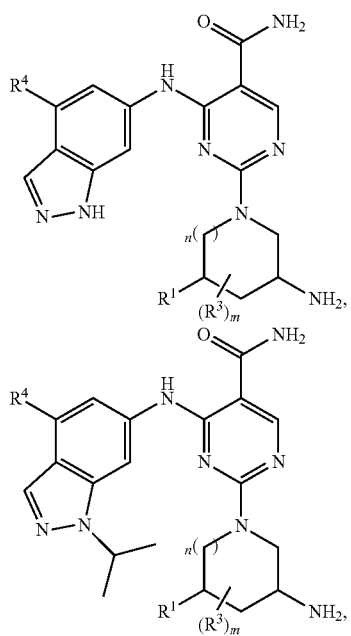

R⁴/R⁵/R⁶:

Any embodiment of R⁴ described herein, any embodiment of R⁵ described herein, and any embodiment of R⁶ described herein may be combined in any combination.

In particular, the following embodiments are particularly preferred embodiments:

In an embodiment, R⁴ is any embodiment of R⁴ described herein, R⁵ is H and R⁶ is H.

In an embodiment, R⁴ is $C_{3-6}$ alkyl (e.g. $C_3$, $C_4$, $C_5$ or $C_6$ alkyl) and R⁵ is $C_{1-6}$ alkyl (e.g. $C_1$, $C_2$, $C_3$, $C_4$, $C_5$ or $C_6$ alkyl). Preferably R⁴ is selected from the group consisting of iso-propyl and t-butyl and R⁵ is selected from the group consisting of methyl, ethyl, n-propyl, iso-propyl, n-butyl, s-butyl, i-butyl and t-butyl. Optional substituents for the alkyl groups are selected from the group consisting of: $—OR^{B3a}$, $=O$, $—NR^{B3a}R^{B3a}$, $—SR^{B3a}$, $—CN$, $—NO_2$, $—NR^{B3a}C(O)R^{B3a}$, $—C(O)NR^{B3a}R^{B3a}$, $—NR^{B3a}C(O)OR^{B3a}$, $—OC(O)NR^{B3a}R^{B3a}$, $—NR^{B3a}C(O)NR^{B3a}R^{B3a}$, $—NR^{B3a}C(NR^{B3a})NR^{B3a}R^{B3a}$, $—NR^{B3a}SO_2R^{B3a}$, $—SO_2NR^{B3a}R^{B3a}$, $—SO_2R^{B3a}$, $—C(O)R^{B3a}$ and $—C(O)OR^{B3a}$. Preferably, the optional substituents for the alkyl groups are selected from the group consisting of: $—OR^{B3a}$, $—NR^{B3a}R^{B3a}$, $—SR^{B3a}$, $—CN$ and $—NR^{B3a}C(O)R^{B3a}$. More preferably, the optional substituents for the alkyl groups are selected from the group consisting of: $—OR^{B3a}$, $—NR^{B3a}R^{B3a}$, $—CN$ and $—NR^{B3a}C(O)R^{B3a}$. Most preferably, the optional substituents for the $C_{3-6}$ alkyl groups are selected from the group consisting of: $—OR^{B3a}$ and $—CN$. In an embodiment, $R^{B3a}$ is selected from the group consisting of H, $C_{1-4}$ alkyl, $C_{1-4}$ haloalkyl and $C_{3-6}$ cycloalkyl.

In an embodiment, R⁴ is $—C(O)NR^{B2a}R^{B2a}$, wherein each $R^{B2a}$ is independently selected from the group consisting of: $C_{1-4}$ alkyl, $C_{1-4}$ heteroalkyl, 4- to 12-membered non-aromatic saturated or partially saturated monocyclic or fused, bridged, or spiro bicyclic heterocyclic ring system including 1, 2 or 3 heteroatoms selected from N, O or S and R⁵ is selected from the group consisting of methyl, ethyl, n-propyl, iso-propyl, n-butyl, s-butyl, i-butyl and t-butyl substituted with a halogen atom. In an embodiment, each $R^{B2a}$ is independently selected from the group consisting of: $C_1$ and $C_2$ alkyl and R⁵ is selected from the group consisting of $—CF_3$ and $—CF(CH_3)_2$. Optional substituents for the $C_{1-4}$ alkyl and $C_{1-4}$ heteroalkyl are selected from the group consisting of: $—OH$, $—O(C_{1-3}$ alkyl), $—(C_{1-3}$ alkyl)-OH, $—(C_{1-3}$ alkyl)-O($C_{1-3}$ alkyl), $=O$, $—NH_2$, $—NH(C_{1-3}$ alkyl), $—N(C_{1-3}$ alkyl)$_2$ or $(C_{1-3}$ alkyl)-NH$_2$, $—(C_{1-3}$ alkyl)-NH($C_{1-3}$ alkyl) or $—(C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: $—OH$, $—O(C_{1-3}$ alkyl), $—NH_2$, $—NH(C_{1-3}$ alkyl) or $—N(C_{1-3}$ alkyl)$_2$.

In an embodiment, R⁴ is $—C(O)NR^{B2a}R^{B2a}$, wherein each $R^{B2a}$ is independently selected from the group consisting of: $C_{1-4}$ alkyl and $C_{1-4}$ heteroalkyl, wherein the $R^{B2a}$ moieties, together with the nitrogen atom to which they are bonded, form a 4- to 7-membered ring system optionally including 1, 2 or 3 additional heteroatoms selected from N, O and S as depicted in the following structure wherein Ring A is a 4- to 7-membered ring system optionally including 1, 2 or 3 additional heteroatoms selected from N, O and S:

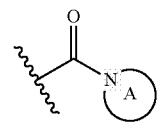

and R⁵ is selected from the group consisting of methyl, ethyl, n-propyl, iso-propyl, n-butyl, s-butyl, i-butyl and t-butyl substituted with a halogen atom. Optional substituents for the $C_{1-4}$ alkyl and $C_{1-4}$ heteroalkyl groups include: $C_{1-4}$ alkyl, $C_{1-4}$ haloalkyl, $C_{3-6}$ cycloalkyl, $—OH$, $—O(C_{1-3}$ alkyl), $—(C_{1-3}$ alkyl)-OH, $—(C_{1-3}$ alkyl)-O($C_{1-3}$ alkyl), $=O$, $—NH_2$, $—NH(C_{1-3}$ alkyl), $—N(C_{1-3}$ alkyl)$_2$ or $(C_{1-3}$ alkyl)-NH$_2$, $—(C_{1-3}$ alkyl)-NH($C_{1-3}$ alkyl) or $—(C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: $C_{1-4}$ alkyl, $C_{1-4}$ haloalkyl, $—OH$, $—O(C_{1-3}$ alkyl), $—(C_{1-3}$ alkyl)-OH, $—(C_{1-3}$ alkyl)-O($C_{1-3}$ alkyl) and $=O$. Exemplary structures for

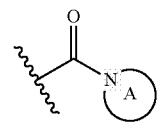

include:

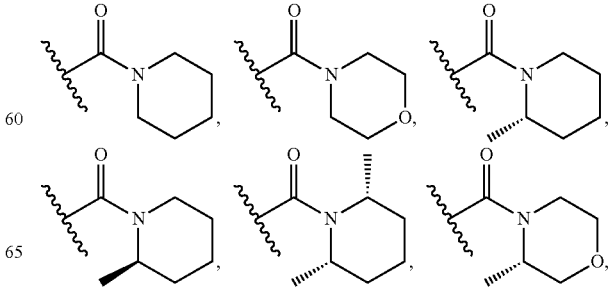

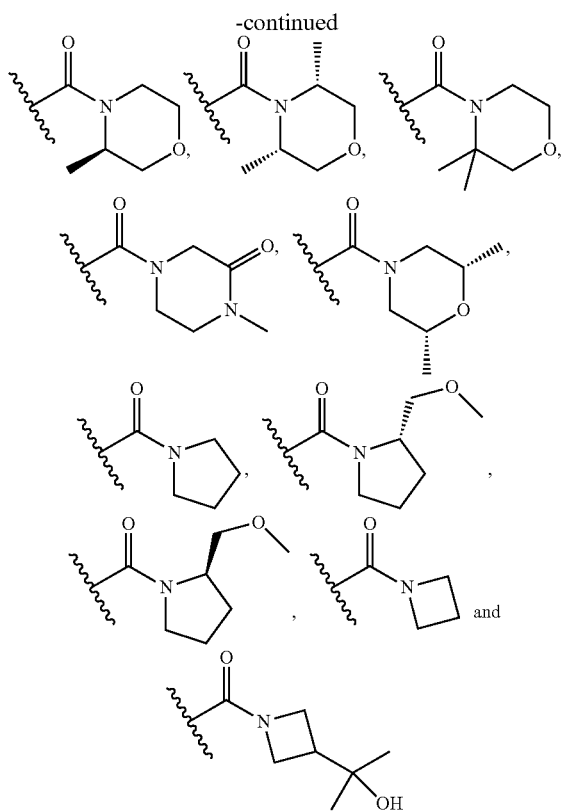

and R⁵ is preferably selected from the group consisting of —CF₃ and —CF(CH₃)₂.

In an embodiment, R⁴ and R⁵ are each independently $C_{3-6}$ cycloalkyl (e.g. $C_3$ cycloalkyl, $C_4$ cycloalkyl, $C_5$ cycloalkyl or $C_6$ cycloalkyl). Optional substituents for the $C_{3-6}$ cycloalkyl group are selected from the group consisting of: $C_{1-6}$ alkyl, $C_{1-6}$ haloalkyl, halo, —OR$^{B3a}$, —NR$^{B3a}$R$^{B3a}$, —SR$^{B3a}$, —CN, —NO₂, —NR$^{B3a}$C(O)R$^{B3a}$ and —C(O)NR$^{B3a}$R$^{B3a}$. Preferably, the optional substituents for the $C_{3-6}$ cycloalkyl group are selected from the group consisting of: halo, —OR$^{B3a}$ and —CN. In an embodiment, R$^{B3a}$ is selected from the group consisting of: H, $C_{1-4}$ alkyl and $C_{1-4}$ haloalkyl. The substituent can be bonded to any atom of the $C_{3-6}$ cycloalkyl moiety, including the atom that bonds the $C_{3-6}$ cycloalkyl group to the remainder of the compound. Exemplary $C_{3-6}$ cycloalkyl groups for each of R⁴ and R⁵ include:

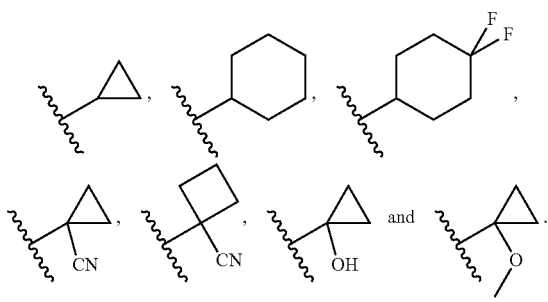

In an embodiment, R⁴ is —SO₂NR$^{B3a}$R$^{B3a}$, wherein each R$^{B3a}$ is independently selected from the group consisting of: $C_{1-4}$ alkyl and $C_{1-4}$ heteroalkyl wherein the R$^{B3a}$ moieties, together with the nitrogen atom to which they are bonded, can form a 4- to 7-membered ring system optionally including 1, 2 or 3 additional heteroatoms selected from N, O and S as depicted in the following structure wherein Ring B is a 4- to 7-membered ring system optionally including 1, 2 or 3 additional heteroatoms selected from N, O and S:

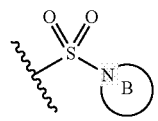

and R⁶ is selected from the group consisting of methyl, ethyl, n-propyl, iso-propyl, n-butyl, s-butyl, i-butyl and t-butyl. In an embodiment, each R$^{B3a}$ is independently $C_{1-4}$ alkyl (e.g. $C_1$, $C_2$, $C_3$ or $C_4$) alkyl. Optional substituents for the $C_{1-4}$ alkyl and $C_{1-4}$ heteroalkyl are selected from the group consisting of: —OH, —O($C_{1-3}$ alkyl), —($C_{1-3}$ alkyl)-OH, —($C_{1-3}$ alkyl)-O($C_{1-3}$ alkyl), =O, —NH₂, —NH($C_{1-3}$ alkyl), —N($C_{1-3}$ alkyl)₂ or ($C_{1-3}$ alkyl)-NH₂, —($C_{1-3}$ alkyl)-NH($C_{1-3}$ alkyl) or —($C_{1-3}$ alkyl)-N($C_{1-3}$ alkyl)₂. Preferably, the optional substituents for the $C_{1-4}$ alkyl and $C_{1-4}$ heteroalkyl are selected from the group consisting of: —OH, —O($C_{1-3}$ alkyl), —NH₂, —NH($C_{1-3}$ alkyl) or —N($C_{1-3}$ alkyl)₂. In an embodiment,

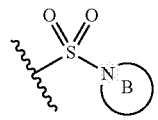

is selected from the group consisting of:

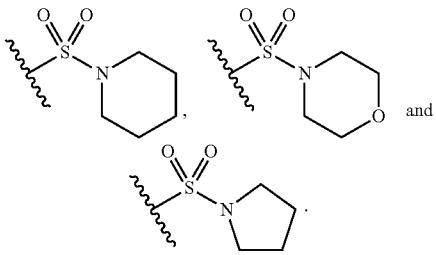

In an embodiment, R⁴ is —SO₂NR$^{B3a}$R$^{B3a}$, wherein each R$^{B3a}$ is independently selected from the group consisting of: $C_{1-4}$ alkyl and $C_{1-4}$ heteroalkyl wherein the R$^{B3a}$ moieties, together with the nitrogen atom to which they are bonded, can form a 4- to 7-membered ring system optionally including 1, 2 or 3 additional heteroatoms selected from N, O and S as depicted in the following structure wherein Ring B is a 4- to 7-membered ring system optionally including 1, 2 or 3 additional heteroatoms selected from N, O and S:

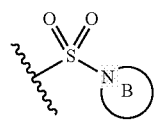

and R⁵ is selected from the group consisting of methyl, ethyl, n-propyl, iso-propyl, n-butyl, s-butyl, i-butyl and t-butyl. In an embodiment, each $R^{B3a}$ is independently $C_{1-4}$ alkyl (e.g. $C_1$, $C_2$, $C_3$ or $C_4$) alkyl. Optional substituents for the $C_{1-4}$ alkyl and $C_{1-4}$ heteroalkyl are selected from the group consisting of: —OH, —O($C_{1-3}$ alkyl), —($C_{1-3}$ alkyl)-OH, —($C_{1-3}$ alkyl)-O($C_{1-3}$ alkyl), =O, —$NH_2$, —NH($C_{1-3}$ alkyl), —N($C_{1-3}$ alkyl)$_2$ or ($C_{1-3}$ alkyl)-$NH_2$, —($C_{1-3}$ alkyl)-NH($C_{1-3}$ alkyl) or —($C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: —OH, —O($C_{1-3}$ alkyl), —$NH_2$, —NH($C_{1-3}$ alkyl) or —N($C_{1-3}$ alkyl)$_2$. In an embodiment,

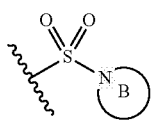

is selected from the group consisting of:

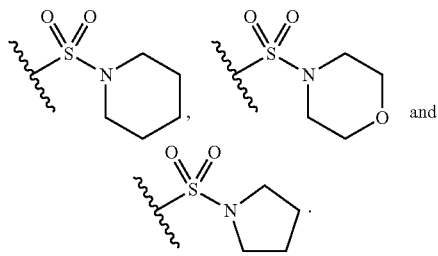

In an embodiment, $R^4$ is —$SO_2NR^{B3a}R^{B3a}$, wherein each $R^{B3a}$ is independently selected from the group consisting of: H, $C_{1-4}$ alkyl and $C_{1-4}$ heteroalkyl and $R^5$ is selected from the group consisting of methyl, ethyl, n-propyl, iso-propyl, n-butyl, s-butyl, i-butyl and t-butyl. In an embodiment, each $R^{B3a}$ is independently selected from the group consisting of: H and $C_{1-4}$ alkyl (e.g. $C_1$, $C_2$, $C_3$ or $C_4$) alkyl. Optional substituents for the $C_{1-4}$ alkyl and $C_{1-4}$ heteroalkyl are selected from the group consisting of: —OH, —O($C_{1-3}$ alkyl), —($C_{1-3}$ alkyl)-OH, —($C_{1-3}$ alkyl)-O($C_{1-3}$ alkyl), =O, —$NH_2$, —NH($C_{1-3}$ alkyl), —N($C_{1-3}$ alkyl)$_2$ or ($C_{1-3}$ alkyl)-$NH_2$, —($C_{1-3}$ alkyl)-NH($C_{1-3}$ alkyl) or —($C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: —OH, —O($C_{1-3}$ alkyl), —$NH_2$, —NH($C_{1-3}$ alkyl) or —N($C_{1-3}$ alkyl)$_2$.

In an embodiment, $R^4$ is —C(O)$NR^{B2a}R^{B2a}$, wherein each $R^{B2a}$ is independently selected from the group consisting of: $C_{1-4}$ alkyl, $C_{1-4}$ heteroalkyl, 4- to 12-membered non-aromatic saturated or partially saturated monocyclic or fused, bridged, or spiro bicyclic heterocyclic ring system including 1, 2 or 3 heteroatoms selected from N, O or S and $R^5$ is selected from the group consisting of methyl, ethyl, n-propyl, iso-propyl, n-butyl, s-butyl, i-butyl and t-butyl. In an embodiment, each $R^{B2a}$ is independently selected from the group consisting of: $C_1$ and $C_2$ alkyl. Optional substituents for the $C_{1-4}$ alkyl and $C_{1-4}$ heteroalkyl are selected from the group consisting of: —OH, —O($C_{1-3}$ alkyl), —($C_{1-3}$ alkyl)-OH, —($C_{1-3}$ alkyl)-O($C_{1-3}$ alkyl), =O, —$NH_2$, —NH($C_{1-3}$ alkyl), —N($C_{1-3}$ alkyl)$_2$ or ($C_{1-3}$ alkyl)-$NH_2$, —($C_{1-3}$ alkyl)-NH($C_{1-3}$ alkyl) or —($C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: —OH, —O($C_{1-3}$ alkyl), —$NH_2$, —NH($C_{1-3}$ alkyl) or —N($C_{1-3}$ alkyl)$_2$.

In an embodiment, $R^4$ is —C(O)$NR^{B2a}R^{B2a}$, wherein each $R^{B2a}$ is independently selected from the group consisting of: $C_{1-4}$ alkyl and $C_{1-4}$ heteroalkyl, wherein the $R^{B2a}$ moieties, together with the nitrogen atom to which they are bonded, form a 4- to 7-membered ring system optionally including 1, 2 or 3 additional heteroatoms selected from N, O and S as depicted in the following structure wherein Ring A is a 4- to 7-membered ring system optionally including 1, 2 or 3 additional heteroatoms selected from N, O and S:

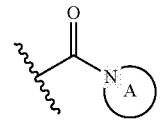

and $R^5$ is selected from the group consisting of methyl, ethyl, n-propyl, iso-propyl, n-butyl, s-butyl, i-butyl and t-butyl. Optional substituents for the $C_{1-4}$ alkyl and $C_{1-4}$ heteroalkyl groups include: $C_{1-4}$ alkyl, $C_{1-4}$ haloalkyl, $C_{3-6}$ cycloalkyl, —OH, —O($C_{1-3}$ alkyl), —($C_{1-3}$ alkyl)-OH, —($C_{1-3}$ alkyl)-O($C_{1-3}$ alkyl), =O, —$NH_2$, —NH($C_{1-3}$ alkyl), —N($C_{1-3}$ alkyl)$_2$ or ($C_{1-3}$ alkyl)-$NH_2$, —($C_{1-3}$ alkyl)-NH($C_{1-3}$ alkyl) or —($C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: $C_{1-4}$ alkyl, $C_{1-4}$ haloalkyl, —OH, —O($C_{1-3}$ alkyl), —($C_{1-3}$ alkyl)-OH, —($C_{1-3}$ alkyl)-O($C_{1-3}$ alkyl) and =O. Exemplary structures for

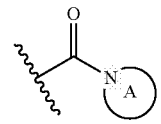

include:

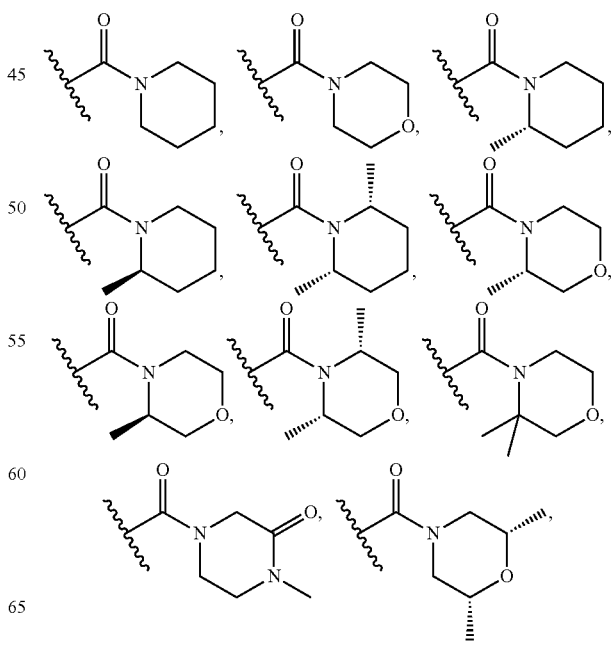

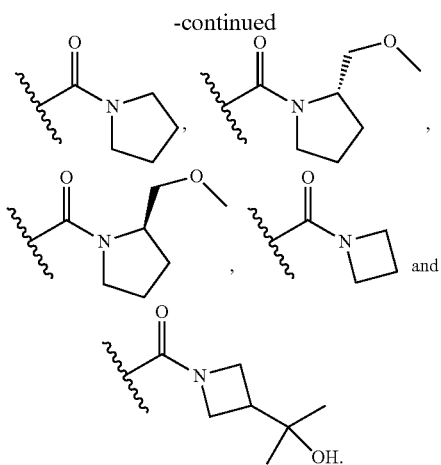

and

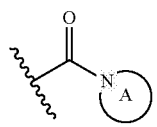

In an embodiment, $R^4$ is $-SO_2R^{B2a}$, wherein $R^{B2a}$ is $C_{1-4}$ alkyl (e.g. $C_1$, $C_2$, $C_3$ or $C_4$ alkyl) and $R^5$ is selected from the group consisting of methyl, ethyl, n-propyl, iso-propyl, n-butyl, s-butyl, i-butyl and t-butyl.

In an embodiment, $R^4$ and $R^5$ are each independently a $-SO_2R^{B2a}$, wherein $R^{B2a}$ is $C_{1-4}$ alkyl (e.g. $C_1$, $C_2$, $C_3$ or $C_4$ alkyl).

In an embodiment, $R^4$ is $C_{3-6}$ alkyl (e.g. $C_3$, $C_4$, $C_5$ or $C_6$ alkyl) and $R^5$ is $-C(O)OR^{B2a}$, wherein $R^{B2a}$ is selected from the group consisting of: $C_{1-4}$ alkyl and $C_{1-4}$ haloalkyl. Preferably, $R^{B2a}$ is $C_{1-4}$ alkyl (e.g. $C_1$, $C_2$, $C_3$ or $C_4$ alkyl). Optional substituents for the $C_{3-6}$ alkyl groups are selected from the group consisting of: $-OR^{B3a}$, $=O$, $-NR^{B3a}R^{B3a}$, $-SR^{B3a}$, $-CN$, $-NO_2$, $-NR^{B3a}C(O)R^{B3a}$, $-C(O)NR^{B3a}R^{B3a}$, $-NR^{B3a}C(O)OR^{B3a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $NR^{B3a}SO_2R^{B3a}$, $-SO_2NR^{B3a}R^{B3a}$, $-SO_2R^{B3a}$, $-C(O)R^{B3a}$ and $-C(O)OR^{B3a}$. Preferably, the optional substituents for the $C_{3-6}$ alkyl groups are selected from the group consisting of: $-OR^{B3a}$, $-NR^{B3a}R^{B3a}$, $-SR^{B3a}$, $-CN$ and $-NR^{B3a}C(O)R^{B3a}$. More preferably, the optional substituents for the $C_{3-6}$ alkyl groups are selected from the group consisting of: $-OR^{B3a}$, $-NR^{B3a}R^{B3a}$, $-CN$ and $-NR^{B3a}C(O)R^{B3a}$. In an embodiment, $R^{B3a}$ is selected from the group consisting of H, $C_{1-4}$ alkyl, $C_{1-4}$ haloalkyl and $C_{3-6}$ cycloalkyl.

In an embodiment, $R^4$ is $-C(O)NR^{B2a}R^{B2a}$, wherein each $R^{B2a}$ is independently selected from the group consisting of: $C_{1-4}$ alkyl and $C_{1-4}$ heteroalkyl, wherein the $R^{B2a}$ moieties, together with the nitrogen atom to which they are bonded, form a 4- to 7-membered ring system optionally including 1, 2 or 3 additional heteroatoms selected from N, O and S as depicted in the following structure wherein Ring A is a 4- to 7-membered ring system optionally including 1, 2 or 3 additional heteroatoms selected from N, O and S:

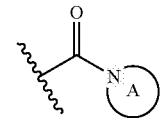

and $R^5$ is aryl or heteroaryl including 1, 2 or 3 heteroatoms selected from N, O or S. Optional substituents for the $C_{1-4}$ alkyl and $C_{1-4}$ heteroalkyl groups include: $C_{1-4}$ alkyl, $C_{1-4}$ haloalkyl, $C_{3-6}$ cycloalkyl, $-OH$, $-O(C_{1-3}$ alkyl), $-(C_{1-3}$ alkyl)-OH, $-(C_{1-3}$ alkyl)-O($C_{1-3}$ alkyl), $=O$, $-NH_2$, $-NH(C_{1-3}$ alkyl), $-N(C_{1-3}$ alkyl)$_2$ or $(C_{1-3}$ alkyl)-$NH_2$, $-(C_{1-3}$ alkyl)-NH($C_{1-3}$ alkyl) or $-(C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: $C_{1-4}$ alkyl, $C_{1-4}$ haloalkyl, $-OH$, $-O(C_{1-3}$ alkyl), $-(C_{1-3}$ alkyl)-OH, $-(C_{1-3}$ alkyl)-O($C_{1-3}$ alkyl) and $=O$. Optional substituents for the aryl or heteroaryl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, $-OR^{B3a}$, $-NR^{B3a}R^{B3a}$, $-SR^{B3a}$, $-CN$, $-NO_2$, $-NR^{B3a}C(O)R^{B3a}$, $-C(O)NR^{B3a}R^{B3a}$, $-NR^{B3a}C(O)OR^{B3a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NR^{B3a}R^{B3a}$, $-SO_2R^{B3a}$, $-C(O)R^{B3a}$ and $-C(O)OR^{B3a}$. Preferably, the optional substituents for the aryl or heteroaryl moiety are selected from the group consisting of: $C_{1-6}$ alkyl, $C_{1-6}$ haloalkyl, $C_{3-e}$ cycloalkyl, 4- to 6-membered heterocycloalkyl including 1, 2 or 3 heteroatoms selected from N, O or S, halo, $-OR^{B3a}$, $-NR^{B3a}R^{B3a}$, $-SR^{B3a}$, $-NR^{B3a}C(O)R^{B3a}$, $-C(O)NR^{B3a}R^{B3a}$, $-SO_2R^{B3a}$, $-C(O)R^{B3a}$ and $-C(O)OR^{83a}$. More preferably, the optional substituents for the aryl or heteroaryl moiety are selected from the group consisting of: Cie alkyl (e.g. $C_1$, $C_2$, $C_3$ or $C_4$ alkyl), $C_{1-6}$ haloalkyl (e.g. $C_1$, $C_2$, $C_3$ or $C_4$ haloalkyl), halo and $-OR^{B3a}$ (e.g. $-O-C_{1-4}$ alkyl, such as $-O-CH_3$, or $-O-C_4$ haloalkyl, such as $-O-CF_3$). Exemplary structures for include:

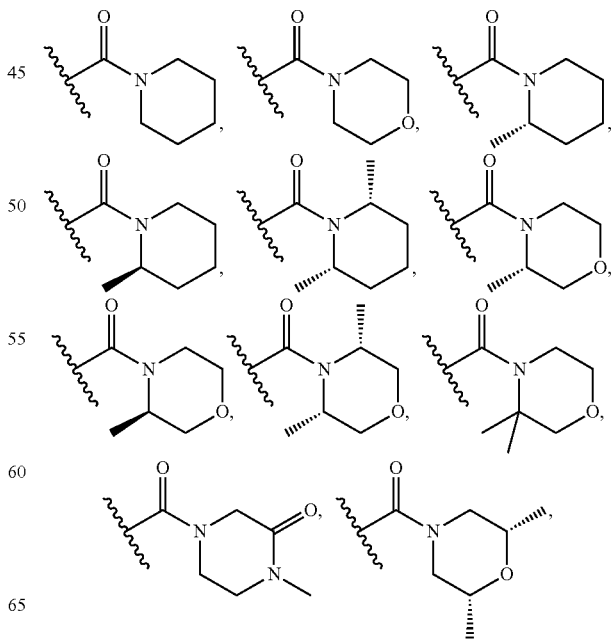

-continued

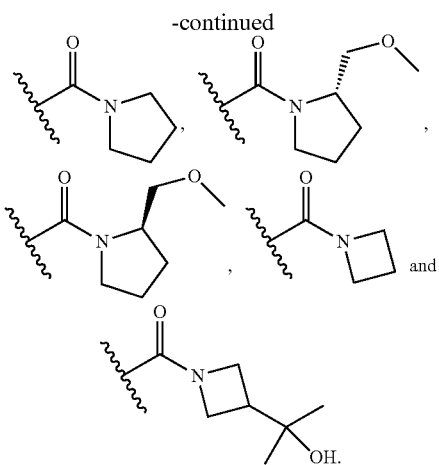

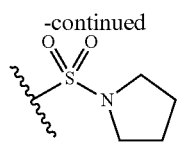

and $R^5$ is preferably selected from the group consisting of —$CF_3$ and —$CF(CH_3)_2$.

In an embodiment, $R^4$ is —$SO_2NR^{B3a}R^{B3a}$, wherein each $R^{B3a}$ is independently selected from the group consisting of: H, $C_{1-4}$ alkyl and $C_{1-4}$ heteroalkyl and $R^5$ is selected from the group consisting of methyl, ethyl, n-propyl, iso-propyl, n-butyl, s-butyl, i-butyl and t-butyl substituted with a halogen atom. In an embodiment, each $R^{B3a}$ is independently selected from the group consisting of: H and $C_{1-4}$ alkyl (e.g. $C_1$, $C_2$, $C_3$ or $C_4$) alkyl and $R^5$ is preferably selected from the group consisting of —$CF_3$ and —$CF(CH_3)_2$.

In an embodiment, $R^4$ is —$SO_2NR^{B3a}R^{B3a}$, wherein each $R^{B3a}$ is independently selected from the group consisting of: $C_{1-4}$ alkyl and $C_{1-4}$ heteroalkyl wherein the $R^{B3a}$ moieties, together with the nitrogen atom to which they are bonded, can form a 4- to 7-membered ring system optionally including 1, 2 or 3 additional heteroatoms selected from N, O and S as depicted in the following structure wherein Ring B is a 4- to 7-membered ring system optionally including 1, 2 or 3 additional heteroatoms selected from N, O and S:

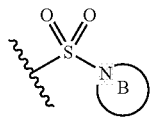

$R^5$ is selected from the group consisting of methyl, ethyl, n-propyl, iso-propyl, n-butyl, s-butyl, i-butyl and t-butyl substituted with a halogen atom. In an embodiment, each $R^{B3a}$ is independently $C_{1-4}$ alkyl (e.g. $C_1$, $C_2$, $C_3$ or $C_4$) alkyl. Optional substituents for the $C_{1-4}$ alkyl and $C_{1-4}$ heteroalkyl are selected from the group consisting of: —OH, —O($C_{1-3}$ alkyl), —($C_{1-3}$ alkyl)-OH, —($C_{1-3}$ alkyl)-O($C_{1-3}$ alkyl), =O, —$NH_2$, —NH($C_{1-3}$ alkyl), —N($C_{1-3}$ alkyl)$_2$ or ($C_{1-3}$ alkyl)-$NH_2$, —($C_{1-3}$ alkyl)-NH($C_{1-3}$ alkyl) or —($C_{1-3}$ alkyl)-N($C_{1-3}$ alkyl)$_2$. Preferably, the optional substituents for the $C_{1-4}$ alkyl and $C_{1-4}$ heteroalkyl are selected from the group consisting of: —OH, —O($C_{1-3}$ alkyl), —$NH_2$, —NH($C_{1-3}$ alkyl) or —N($C_{1-3}$ alkyl)$_2$. In an embodiment,

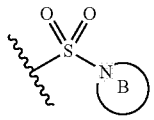

is selected from the group consisting of:

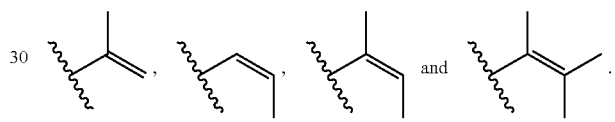

In an embodiment, $R^4$ and $R^5$ are each independently a $C_{3-6}$ alkenyl moiety wherein (i) the carbon atom beta to the ring to which the alkene is bonded is cis-substituted with carbon; and (ii) the carbon atom alpha to the ring to which the alkene is bonded substituted with carbon. Preferably, $R^4$ and $R^5$ are each independently a $C_{3-4}$ alkenyl moiety. Exemplary $C_{3-6}$ alkenyl moieties include:

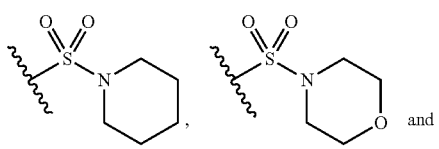

In an embodiment, $R^4$ is —$SO_2R^{B2a}$, wherein $R^{B2a}$ is $C_{1-4}$ alkyl (e.g. $C_1$, $C_2$, $C_3$ or $C_4$ alkyl) and $R^5$ is selected from the group consisting of methyl, ethyl, n-propyl, iso-propyl, n-butyl, s-butyl, i-butyl and t-butyl substituted with a halogen atom. $R^5$ is preferably selected from the group consisting of —$CF_3$ and —$CF(CH_3)_2$.

In an embodiment, $R^4$ is a 4- to 6-membered heterocycloalkyl including 1, 2 or 3 heteroatoms selected from N, O or S and $R^5$ is selected from the group consisting of methyl, ethyl, n-propyl, iso-propyl, n-butyl, s-butyl, i-butyl and t-butyl substituted with a halogen atom. The 4- to 6-membered heterocycloalkyl may be joined to the remainder of the molecule via a carbon atom or via a heteroatom. Optional substituents for the 4- to 6-membered heterocycloalkyl are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —$OR^{B3a}$, =O, —$NR^{B3a}R^{B3a}$, —$SB^{3a}$, —CN, —$NO_2$, —$NR^{B3a}C(O)R^{B3a}$ and —$C(O)NR^{B3a}R^{B3a}$. Preferably, the optional substituents for the 4- to 6-membered heterocycloalkyl are selected from the group consisting of: 4- to 6-membered heterocycloalkyl including 1, 2 or 3 heteroatoms selected from N, O or S, aryl, heteroaryl including 1, 2 or 3 heteroatoms selected from N, O or S, halo, —$OR^{B3a}$, =O, —$NR^{B3a}R^{B3a}$, —$NR^{B3a}C(O)R^{B3a}$ and —$C(O)NR^{B3a}R^{B3a}$. More preferably, the optional substituents for the 4- to 6-membered heterocycloalkyl are selected from the group consisting of: aryl, =O and —$NR^{B3a}R^{B3a}$. In an embodiment, $R^{B3a}$ is selected from the group consisting of H, $C_{1-4}$ alkyl, $C_{1-4}$ haloalkyl and $C_{3-6}$ cycloalkyl. Exemplary structures include:

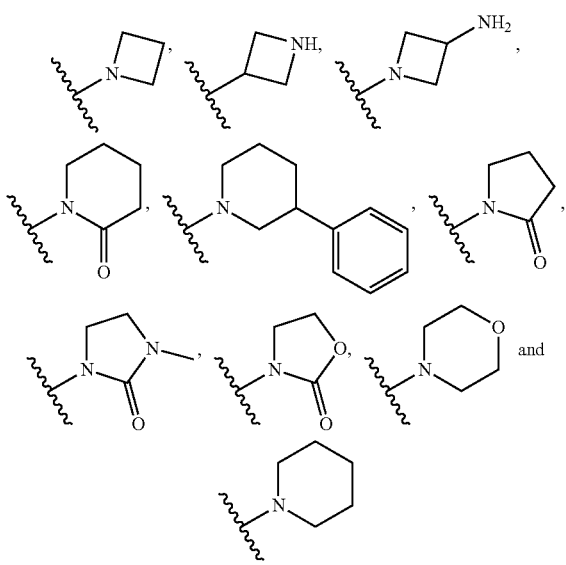

and $R^5$ is preferably selected from the group consisting of —$CF_3$ and —$CF(CH_3)_2$.

In an embodiment, $R^4$ is a 4- to 6-membered heterocycloalkyl including 1, 2 or 3 heteroatoms selected from N, O or S and $R^5$ is selected from the group consisting of methyl, ethyl, n-propyl, iso-propyl, n-butyl, s-butyl, i-butyl and t-butyl. The 4- to 6-membered heterocycloalkyl may be joined to the remainder of the molecule via a carbon atom or via a heteroatom. Optional substituents for the 4- to 6-membered heterocycloalkyl are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —$OR^{B3a}$, =O, —$NR^{B3a}R^{B3a}$, —$SR^{B3a}$, —CN, —$NO_2$, —$NR^{B3a}C(O)R^{B3a}$, —$C(O)R^{B3a}$, and —$C(O)NR^{B3a}R^{B3a}$. Preferably, the optional substituents for the 4- to 6-membered heterocycloalkyl are selected from the group consisting of: 4- to 6-membered heterocycloalkyl including 1, 2 or 3 heteroatoms selected from N, O or S, aryl, heteroaryl including 1, 2 or 3 heteroatoms selected from N, O or S, halo, —$OR^{B3a}$, =O, —$NR^{B3a}R^{B3a}$, —$NR^{B3a}C(O)R^{B3a}$, —$C(O)R^{B3a}$, and —$C(O)NR^{B3a}R^{B3a}$. More preferably, the optional substituents for the 4- to 6-membered heterocycloalkyl are selected from the group consisting of: aryl, =O, —$NR^{B3a}R^{B3a}$ and —$C(O)R^{B3a}$. In an embodiment, $R^{B3a}$ is selected from the group consisting of H, $C_{1-4}$ alkyl, $C_{1-4}$ haloalkyl and $C_{3-6}$ cycloalkyl. Exemplary structures include:

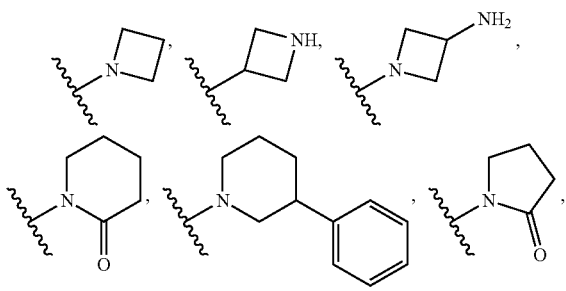

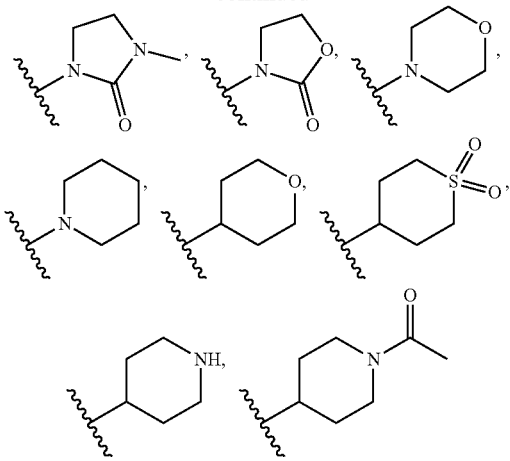

and $R^5$ is preferably selected from the group consisting of iso-propyl, s-butyl, i-butyl and t-butyl, most preferably iso-propyl.

In an embodiment, $R^4$ is $C_{3-6}$ alkyl (e.g. $C_3$, $C_4$, $C_5$ or $C_6$ alkyl) and $R^5$ is selected from the group consisting of methyl, ethyl, n-propyl, iso-propyl, n-butyl, s-butyl, i-butyl and t-butyl substituted with a halogen atom. Optional substituents for the $C_{3-6}$ alkyl groups are selected from the group consisting of: —$OR^{B3a}$, =O, —$NR^{B3a}R^{B3a}$, —$SR^{B3a}$, —CN, —$NO_2$, —$NR^{B3a}C(O)R^{B3a}$, —$C(O)NR^{B3a}R^{B3a}$, —$NR^{B3a}C(O)OR^{B3a}$, —$OC(O)NR^{B3a}R^{B3a}$, —$NR^{B3a}C(O)NR^{B3a}R^{B3a}$, —$NR^{B3a}C(NR^{B3a})NR^{B3a}R^{B3a}$, —$NR^{B3a}SO_2R^{B3a}$, —$SO_2NR^{B3a}R^{B3a}$, —$SO_2R^{B3a}$, —$C(O)R^{B3a}$ and —$C(O)OR^{B3a}$. Preferably, the optional substituents for the $C_{3-6}$ alkyl groups are selected from the group consisting of: —$OR^{B3a}$, —$NR^{B3a}R^{B3a}$, —$SR^{B3a}$, —CN and —$NR^{B3a}C(O)R^{B3a}$. More preferably, the optional substituents for the $C_{3-6}$ alkyl groups are selected from the group consisting of: —$OR^{B3a}$, —$NR^{B3a}R^{B3a}$, —CN and —$NR^{B3a}C(O)R^{B3a}$. In an embodiment, $R^{B3a}$ is selected from the group consisting of H, $C_{1-4}$ alkyl, $C_{1-4}$ haloalkyl and $C_{3-6}$ cycloalkyl. $R^5$ is preferably selected from the group consisting of —$CF_3$ and —$CF(CH_3)_2$.

In an embodiment, $R^4$ is —$C(O)NR^{B2a}R^{B2a}$, wherein each $R^{B2a}$ is independently selected from the group consisting of: $C_{1-4}$ alkyl and $C_{1-4}$ heteroalkyl, wherein the $R^{B2a}$ moieties, together with the nitrogen atom to which they are bonded, form a 4- to 7-membered ring system optionally including 1, 2 or 3 additional heteroatoms selected from N, O and S as depicted in the following structure wherein Ring A is a 4- to 7-membered ring system optionally including 1, 2 or 3 additional heteroatoms selected from N, O and S:

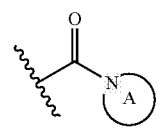

and $R^5$ is halo. Optional substituents for the $C_{1-4}$ alkyl and $C_{1-4}$ heteroalkyl groups include: $C_{1-4}$ alkyl, $C_{1-4}$ haloalkyl, $C_{3-6}$ cycloalkyl, —OH, —$O(C_{1-3}$ alkyl), —$(C_{1-3}$ alkyl)-OH, —$(C_{1-3}$ alkyl)-$O(C_{1-3}$ alkyl), =O, —$NH_2$, —$NH(C_{1-3}$ alkyl), —$N(C_{1-3}$ alkyl$)_2$ or $(C_{1-3}$ alkyl)-$NH_2$, —$(C_{1-3}$ alkyl)-$NH(C_{1-3}$ alkyl) or —$(C_{1-3}$ alkyl)-$N(C_{1-3}$ alkyl$)_2$. Preferably, the optional substituents for the $C_{1-4}$ alkyl and $C_{1-4}$ heteroalkyl are selected from the group consisting of: $C_{1-4}$ alkyl, $C_{1-4}$ haloalkyl, —OH, —O($C_{1-3}$ alkyl), —($C_{1-3}$ alkyl)-OH, —($C_{1-3}$ alkyl)-O($C_{1-3}$ alkyl) and =O. Exemplary structures for

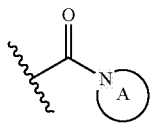

include:

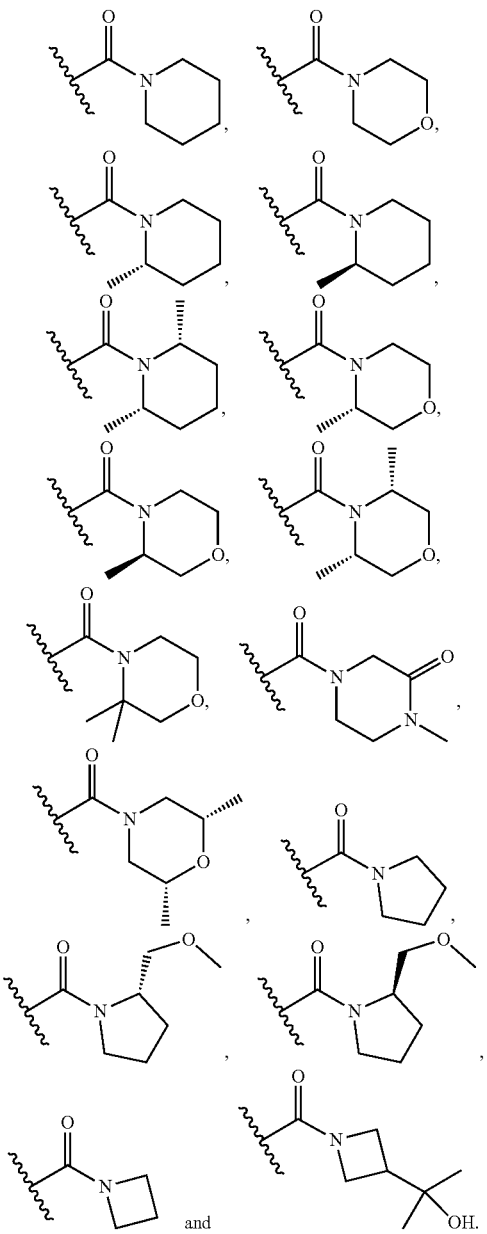

In an embodiment, $R^4$ is $C_{4-6}$ cycloalkenyl and $R^6$ is halo (e.g. F, $C_1$ or Br). Optional substituents for the $C_{4-6}$ cycloalkenyl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, halo, —OR$^{B3a}$, —NR$^{B3a}$R$^{B3a}$, —SR$^{B3a}$, —NR$^{B3a}$C(O)R$^{B3a}$ and —C(O)NR$^{B3a}$R$^{B3a}$. Preferably, optional substituents for the $C_{4-6}$ cycloalkenyl moiety are selected from the group consisting of: halo, —OR$^{B3a}$, —NR$^{B3a}$R$^{B3a}$, —SR$^{B3a}$, —NR$^{B3a}$C(O)R$^{B3a}$ and —C(O)NR$^{B3a}$R$^{B3a}$. More preferably, optional substituents for the $C_{4-6}$ cycloalkenyl moiety are halo. Exemplary $R^4$ moieties include:

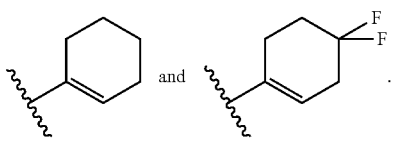 [SMILES: *C1=CCCCC1 ; *C1=CCC(F)(F)CC1]

In an embodiment, $R^4$ is $C_{3-6}$ cycloalkyl (e.g. $C_3$ cycloalkyl, $C_4$ cycloalkyl, $C_5$ cycloalkyl or $C_6$ cycloalkyl) and $R^5$ is halo. Optional substituents for the $C_{3-6}$ cycloalkyl group are selected from the group consisting of: $C_{1-6}$ alkyl, $C_{1-6}$ haloalkyl, halo, —OR$^{B3a}$, —NR$^{B3a}$R$^{B3a}$, —SR$^{B3a}$, —CN, —NO$_2$, —NR$^{B3a}$C(O)R$^{B3a}$ and —C(O)NR$^{B3a}$R$^{B3a}$. Preferably, the optional substituents for the $C_{3-6}$ cycloalkyl group are selected from the group consisting of: halo, —OR$^{B3a}$ and —CN. In an embodiment, R$^{B3a}$ is selected from the group consisting of: H, $C_{1-4}$ alkyl and $C_{1-4}$ haloalkyl. The substituent can be bonded to any atom of the $C_{3-6}$ cycloalkyl moiety, including the atom that bonds the $C_{3-6}$ cycloalkyl group to the remainder of the compound. Exemplary $C_{3-6}$ cycloalkyl groups include:

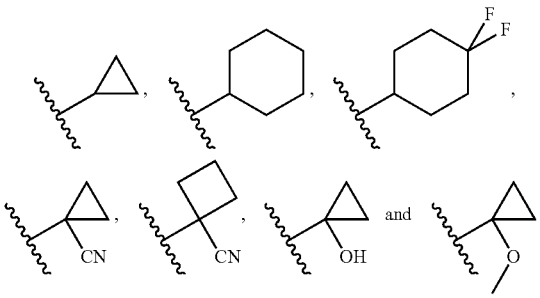

In an embodiment, $R^4$ is aryl or heteroaryl including 1, 2 or 3 heteroatoms selected from N, O or S and $R^6$ is not H. Preferably, $R^6$ is —OR$^{B3a}$, wherein R$^{B3a}$ is selected from the group consisting of: H, $C_{1-4}$ alkyl and $C_{1-4}$ haloalkyl. Preferably, R$^{B3a}$ is selected from the group consisting of: H and $C_{1-4}$ alkyl (e.g. $C_1$, $C_2$, $C_3$ or $C_4$ alkyl). Optional substituents for the aryl or heteroaryl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —OR$^{B3a}$, —NR$^{B3a}$R$^{B3a}$, —SR$^{B3a}$, —CN, —NO$_2$, —NR$^{B3a}$C(O)R$^{B3a}$, —C(O)NR$^{B3a}$R$^{B3a}$, —NR$^{B3a}$C(O)OR$^{B3a}$, —OC(O)NR$^{B3a}$R$^{B3a}$, —NR$^{B3a}$C(O)NR$^{B3a}$R$^{B3a}$, —NR$^{B3a}$C(NR$^{B3a}$)NR$^{B3a}$R$^{B3a}$, —NR$^{B3a}$SO$_2$R$^{B3a}$, —SO$_2$NR$^{B3a}$R$^{B3a}$, —SO$_2$R$^{B3a}$, —C(O)R$^{B3a}$ and —C(O)OR$^{B3a}$ Preferably, the optional substituents for the aryl or heteroaryl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, halo, —OR$^{B3a}$, —NR$^{B3a}$R$^{B3a}$, —SR$^{B3a}$, —NR$^{B3a}$C(O)

$R^{B3a}$, —C(O)NR$^{B3a}$R$^{B3a}$, —SO$_2$R$^{B3a}$, —C(O)R$^{B3a}$ and —C(O)OR$^{B3a}$. More preferably, the optional substituents for the aryl or heteroaryl moiety are selected from the group consisting of: C$^{1-6}$ alkyl (e.g. C$_1$, C$_2$, C$_3$ or C$_4$ alkyl), C$_{1-6}$ haloalkyl (e.g. C$_1$, C$_2$, C$_3$ or C$_4$ haloalkyl, such as CF$_3$), halo and —OR$^{B3a}$ (e.g. —O—C$_{1-4}$ alkyl, such as —O—CH$_3$, or —O—C$_{1-4}$ haloalkyl, such as —O—CF$_3$).

In an embodiment, R$^4$ is C$_{3-6}$ cycloalkyl (e.g. C$_3$ cycloalkyl, C$_4$ cycloalkyl, C$_5$ cycloalkyl or C$_6$ cycloalkyl) and R$^5$ is selected from the group consisting of methyl, ethyl, n-propyl, iso-propyl, n-butyl, s-butyl, i-butyl and t-butyl. Optional substituents for the C$_{3-6}$ cycloalkyl group are selected from the group consisting of: C$_{1-6}$ alkyl, C$_{1-6}$ haloalkyl, halo, —OR$^{B3a}$, —NR$^{B3a}$R$^{B3a}$, —SR$^{B3a}$, —CN, —NO$_2$, —NR$^{B3a}$C(O)R$^{B3a}$ and —C(O)NR$^{B3a}$R$^{B3a}$. Preferably, the optional substituents for the O3-6 cycloalkyl group are selected from the group consisting of: halo, —OR$^{B3a}$ and —CN. In an embodiment, R$^{B3a}$ is selected from the group consisting of: H, C$_{1-4}$ alkyl and C$_{1-4}$ haloalkyl. The substituent can be bonded to any atom of the C$_{3-6}$ cycloalkyl moiety, including the atom that bonds the C$_{3-6}$ cycloalkyl group to the remainder of the compound. Exemplary C$_{3-6}$ cycloalkyl groups include:

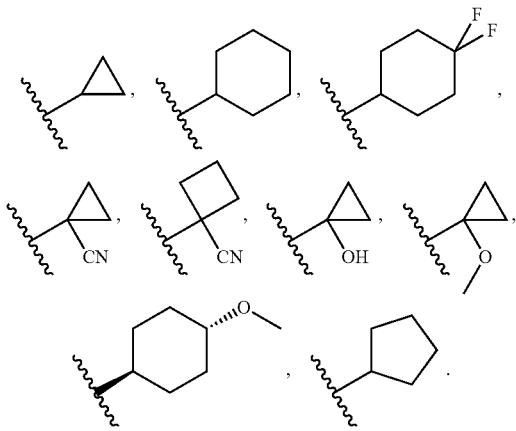

Preferably, R$^5$ is selected from the group consisting of iso-propyl, s-butyl, i-butyl and t-butyl.

In an embodiment, R$^4$ is C$_{3-6}$ alkyl (e.g. C$_3$, C$_4$, C$_5$ or C$_6$ alkyl), R$^5$ is C$_{1-6}$ alkyl (e.g. C$_1$, C$_2$, C$_3$, C$_4$, C$_5$ or C$_6$ alkyl) and R$^6$ is —OR$^{B3a}$, wherein R$^{B3a}$ is selected from the group consisting of: H, C$_{1-4}$ alkyl and C$_{1-4}$ haloalkyl. Optional substituents for the alkyl groups are selected from the group consisting of: —OR$^{B3a}$, =O, —NR$^{B3a}$R$^{B3a}$, —SR$^{B3a}$, —CN, —NO$_2$, —NR$^{B3a}$C(O)R$^{B3a}$, —C(O)NR$^{B3a}$R$^{B3a}$, —NR$^{B3a}$C(O)OR$^{B3a}$, —OC(O)NR$^{B3a}$R$^{B3a}$, —NR$^{B3a}$C(O) NR$^{B3a}$R$^{B3a}$, —NR$^{B3a}$C(NR$^{B3a}$)NR$^{B3a}$R$^{B3a}$, NR$^{B3a}$SO$_2$R$^{B3a}$, —SO$_2$NR$^{B3a}$R$^{B3a}$, —SO$_2$R$^{B3a}$, —C(O)R$^{B3a}$ and —C(O)OR$^{B3a}$. Preferably, the optional substituents for the alkyl groups are selected from the group consisting of: —OR$^{B3a}$, —NR$^{B3a}$R$^{B3a}$, —SR$^{B3a}$, —CN and —NR$^{B3a}$C(O)R$^{B3a}$. More preferably, the optional substituents for the alkyl groups are selected from the group consisting of: —OR$^{B3a}$, —NR$^{B3a}$R$^{B3a}$, —CN and —NR$^{B3a}$C(O)R$^{B3a}$. In an embodiment, R$^{B3a}$ is selected from the group consisting of H, C$_{1-4}$ alkyl, C$_{1-4}$ haloalkyl and C$_3$e cycloalkyl. Preferably R$^4$ is selected from the group consisting of iso-propyl and t-butyl, R$^5$ is selected from the group consisting of methyl, ethyl, n-propyl, iso-propyl, n-butyl, s-butyl, i-butyl and t-butyl and R$^{B3a}$ is selected from the group consisting of: H and C$_{1-4}$ alkyl (e.g. C$_1$, C$_2$, C$_3$ or C$_4$ alkyl).

In an embodiment, R$^4$ is C$_{3-6}$ alkyl (e.g. C$_3$, C$_4$, C$_5$ or C$_6$ alkyl) and R$^5$ is selected from the group consisting of aryl and heteroaryl including 1, 2 or 3 heteroatoms selected from N, O or S. Optional substituents for the alkyl groups are selected from the group consisting of: —OR$^{B3a}$, =O, —NR$^{B3a}$R$^{B3a}$, —SR$^{B3a}$, —CN, —NO$_2$, —NR$^{B3a}$C(O)R$^{B3a}$, —C(O)NR$^{B3a}$R$^{B3a}$, —NR$^{B3a}$C(O)OR$^{B3a}$, —OC(O) NR$^{B3a}$R$^{B3a}$, —NR$^{B3a}$C(O)NR$^{B3a}$R$^{B3a}$, —NR$^{B3a}$C(NR$^{B3a}$) NR$^{B3a}$R$^{B3a}$, —NR$^{B3a}$SO$_2$R$^{B3a}$, —SO$_2$NR$^{B3a}$R$^{B3a}$, —SO$_2$R$^{B3a}$, —C(O)R$^{B3a}$ and —C(O)OR$^{B3a}$. Preferably, the optional substituents for the alkyl groups are selected from the group consisting of: —OR$^{B3a}$, —NR$^{B3a}$R$^{B3a}$, —SR$^{B3a}$, —CN and —NR$^{B3a}$C(O)R$^{B3a}$. More preferably, the optional substituents for the alkyl groups are selected from the group consisting of: —OR$^{B3a}$, —NR$^{B3a}$R$^{B3a}$, —CN and —NR$^{B3a}$C(O)R$^{B3a}$. Most preferably, the optional substituents for the C$_{3-6}$ alkyl groups are selected from the group consisting of: —OR$^{B3a}$ and —CN. In an embodiment, R$^{B3a}$ is selected from the group consisting of H, C$_{1-4}$ alkyl, C$_{1-4}$ haloalkyl and C$_{3-6}$ cycloalkyl. Optional substituents for the aryl or heteroaryl moiety are selected from the group consisting of: C$_{1-6}$ alkyl, C$_{1-6}$ haloalkyl, C$_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —OR$^{B3a}$, —NR$^{B3a}$R$^{B3a}$, —SR$^{B3a}$, —CN, —NO$_2$, —NR$^{B3a}$C(O)R$^{B3a}$, —C(O)NR$^{B3a}$R$^{B3a}$, —NR$^{B3a}$C(O)OR$^{B3a}$, —OC(O) NR$^{B3a}$R$^{B3a}$, —NR$^{B3a}$C(O)NR$^{B3a}$R$^{B3a}$, —NR$^{B3a}$C(NR$^{B3a}$) NR$^{B3a}$R$^{B3a}$, —NR$^{B3a}$SO$_2$R$^{B3a}$, —SO$_2$NR$^{B3a}$R$^{B3a}$, —SO$_2$R$^{B3a}$, —C(O)R$^{B3a}$ and —C(O)OR$^{B3a}$ Preferably, the optional substituents for the aryl or heteroaryl moiety are selected from the group consisting of: C$_{1-6}$ alkyl, C$_{1-6}$ haloalkyl, C$_{3-6}$ cycloalkyl, 4- to 6-membered heterocycloalkyl including 1, 2 or 3 heteroatoms selected from N, O or S, halo, —OR$^{B3a}$, —NR$^{B3a}$R$^{B3a}$, —SR$^{B3a}$, —NR$^{B3a}$C(O) R$^{B3a}$, —C(O)NR$^{B3a}$R$^{B3a}$, —SO$_2$R$^{B3a}$, —C(O)R$^{B3a}$ and —C(O)OR$^{B3a}$. More preferably, the optional substituents for the aryl or heteroaryl moiety are selected from the group consisting of: C$_{1-6}$ alkyl (e.g. C$_1$, C$_2$, C$_3$ or C$_4$ alkyl), C$_{1-6}$ haloalkyl (e.g. C$_1$, C$_2$, C$_3$ or C$_4$ haloalkyl, such as CF$_3$), halo and —OR$^{B3a}$ (e.g. —O—C$_{1-4}$ alkyl, such as —O—CH$_3$, or —O—C$_{1-4}$ haloalkyl, such as —O—CF$_3$).

In an embodiment, R$^4$ is C$_{3-6}$ cycloalkyl (e.g. C$_3$ cycloalkyl, C$_4$ cycloalkyl, C$_5$ cycloalkyl or Ce cycloalkyl) and R$^5$ is selected from the group consisting of methyl, ethyl, n-propyl, iso-propyl, n-butyl, s-butyl, i-butyl and t-butyl substituted with a halogen atom. Optional substituents for the C$_{3-6}$ cycloalkyl group are selected from the group consisting of: C$_{1-6}$ alkyl, C$_{1-6}$ haloalkyl, halo, —OR$^{B3a}$, —NR$^{B3a}$R$^{B3a}$, —SR$^{B3a}$, —CN, —NO$_2$, —NR$^{B3a}$C(O)R$^{B3a}$ and —C(O)NR$^{B3a}$R$^{B3a}$. Preferably, the optional substituents for the C$_{3-6}$ cycloalkyl group are selected from the group consisting of: halo, —OR$^{B3a}$ and —CN. In an embodiment, R$^{B3a}$ is selected from the group consisting of: H, C$_{1-4}$ alkyl and C$_{1-4}$ haloalkyl. The substituent can be bonded to any atom of the C$_{3-6}$ cycloalkyl moiety, including the atom that bonds the C$_{3-6}$ cycloalkyl group to the remainder of the compound. Exemplary C$_{3-6}$ cycloalkyl groups include:

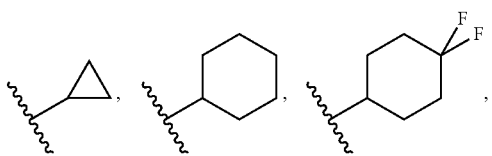

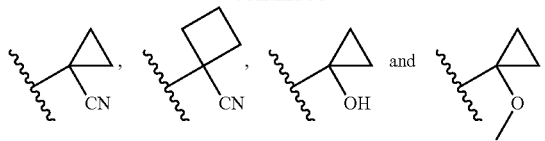

and $R^5$ is preferably selected from the group consisting of —$CF_3$ and —$CF(CH_3)_2$.

In an embodiment, $R^4$ is $C_{3-6}$ haloalkyl and $R^5$ is selected from the group consisting of methyl, ethyl, n-propyl, iso-propyl, n-butyl, s-butyl, i-butyl and t-butyl substituted with a halogen atom. In an embodiment, each of $R^4$ and $R^5$ are independently $C_{3-6}$ haloalkyl. Preferably, each of $R^4$ and $R^5$ are —$CF(CH_3)_2$.

In an embodiment, $R^4$ and $R^5$ are each independently aryl or heteroaryl including 1, 2 or 3 heteroatoms selected from N, O or S and $R^6$ is not H. Optional substituents for the aryl or heteroaryl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —$OR^{B3a}$, —$NR^{B3a}R^{B3a}$, —$SR^{B3a}$, —CN, —$NO_2$, —$NR^{B3a}C(O)R^{B3a}$, —$C(O)NR^{B3a}R^{B3a}$, —$NR^{B3a}C(O)OR^{B3a}$, —$OC(O)NR^{B3a}R^{B3a}$, —$NR^{B3a}C(O)NR^{B3a}R^{B3a}$, —$NR^{B3a}C(NR^{B3a})NR^{B3a}R^{B3a}$, —$NR^{B3a}SO_2R^{B3a}$, —$SO_2NR^{B3a}R^{B3a}$, —$SO_2R^{B3a}$, —$C(O)R^{B3a}$ and —$C(O)OR^{B3a}$. Preferably, the optional substituents for the aryl or heteroaryl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, halo, —$OR^{B3a}$, —$NR^{B3a}R^{B3a}$, —$SR^{B3a}$, —$NR^{B3a}C(O)R^{B3a}$, —$C(O)NR^{B3a}R^{B3a}$, —$SO_2R^{B3a}$, —$C(O)R^{B3a}$ and —$C(O)OR^{B3a}$. More preferably, the optional substituents for the aryl or heteroaryl moiety are selected from the group consisting of: $C_{1-6}$ alkyl (e.g. $C_1$, $C_2$, $C_3$ or $C_4$ alkyl), $C_{1-6}$ haloalkyl (e.g. $C_1$, $C_2$, $C_3$ or $C_4$ haloalkyl), halo and —$OR^{B3a}$ (e.g. —O—$C_{1-4}$ alkyl, such as —O—$CH_3$, or —O—$C_{1-4}$ haloalkyl, such as —O—$CF_3$).

In an embodiment, $R^4$ is $C_{4-6}$ cycloalkenyl and $R^5$ is $C_{1-6}$ alkyl (e.g. $C_1$, $C_2$, $C_3$, $C_4$, $C_5$ or $C_6$ alkyl). Optional substituents for the $C_{4-6}$ cycloalkenyl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, halo, —$OR^{B3a}$, —$NR^{B3a}R^{B3a}$, —$SR^{B3a}$, —$NR^{B3a}C(O)R^{B3a}$ and —$C(O)NR^{B3a}R^{B3a}$. Preferably, optional substituents for the $C_{4-6}$ cycloalkenyl moiety are selected from the group consisting of: halo, —$OR^{B3a}$, —$NR^{B3a}R^{B3a}$, —$SR^{B3a}$, —$NR^{B3a}C(O)R^{B3a}$ and —$C(O)NR^{B3a}R^{B3a}$. More preferably, optional substituents for the $C_{4-6}$ cycloalkenyl moiety are halo. Exemplary $R^4$ moieties include:

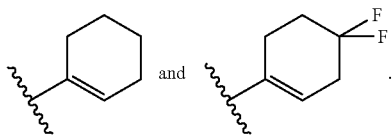 [SMILES: *C1=CCCCC1 ; *C1=CCC(F)(F)CC1]

Preferably $R^5$ is selected from the group consisting of methyl, ethyl, n-propyl, iso-propyl, n-butyl, s-butyl, i-butyl and t-butyl. Optional substituents for the alkyl groups are selected from the group consisting of: —$OR^{B3a}$, =O, —$NR^{B3a}R^{B3a}$, —$SR^{B3a}$, —CN, —$NO_2$, —$NR^{B3a}C(O)R^{B3a}$, —$C(O)NR^{B3a}R^{B3a}$, —$NR^{B3a}C(O)OR^{B3a}$, —$OC(O)NR^{B3a}R^{B3a}$, —$NR^{B3a}C(O)NR^{B3a}R^{B3a}$, —$NR^{B3a}C(NR^{B3a})NR^{B3a}R^{B3a}$, —$NR^{B3a}SO_2R^{B3a}$, —$SO_2NR^{B3a}R^{B3a}$, —$SO_2R^{B3a}$, —$C(O)R^{B3a}$ and —$C(O)OR^{B3a}$. Preferably, the optional substituents for the alkyl groups are selected from the group consisting of: —$OR^{B3a}$, —$NR^{B3a}R^{B3a}$, —$SR^{B3a}$, —CN and —$NR^{B3a}C(O)R^{B3a}$. More preferably, the optional substituents for the alkyl groups are selected from the group consisting of: —$OR^{B3a}$, —$NR^{B3a}R^{B3a}$, —CN and —$NR^{B3a}C(O)R^{B3a}$. In an embodiment, $R^{B3a}$ is selected from the group consisting of H, $C_{1-4}$ alkyl, $C_{1-4}$ haloalkyl and $C_{3-6}$ cycloalkyl.

In an embodiment, $R^4$ is a $C_{3-6}$ alkenyl moiety wherein (i) the carbon atom beta to the ring to which the alkene is bonded is cis-substituted with carbon; and (ii) the carbon atom alpha to the ring to which the alkene is bonded substituted with carbon and $R^5$ is selected from the group consisting of methyl, ethyl, n-propyl, iso-propyl, n-butyl, s-butyl, i-butyl and t-butyl substituted with a halogen atom. Preferably, $R^4$ is a $C_{3-4}$ alkenyl moiety. Exemplary $C_{3-6}$ alkenyl moieties include:

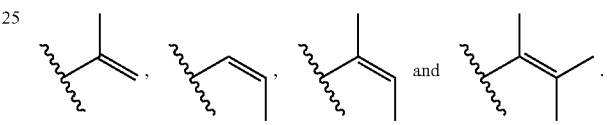

$R^5$ is preferably selected from the group consisting of —$CF_3$ and —$CF(CH_3)_2$.

In an embodiment, $R^4$ is aryl or heteroaryl including 1, 2 or 3 heteroatoms selected from N, O or S and $R^5$ is selected from the group consisting of methyl, ethyl, n-propyl, iso-propyl, n-butyl, s-butyl, i-butyl and t-butyl substituted with a halogen atom. Optional substituents for the aryl or heteroaryl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —$OR^{B3a}$, —$NR^{B3a}R^{B3a}$, —$SR^{B3a}$, —CN, —$NO_2$, —$NR^{B3a}C(O)R^{B3a}$, —$C(O)NR^{B3a}R^{B3a}$, —$NR^{B3a}C(O)OR^{B3a}$, —$OC(O)NR^{B3a}R^{B3a}$, —$NR^{B3a}C(O)NR^{B3a}R^{B3a}$, —$NR^{B3a}C(NR^{B3a})NR^{B3a}R^{B3a}$, —$NR^{B3a}SO_2R^{B3a}$, —$SO_2NR^{B3a}R^{B3a}$, —$SO_2R^{B3a}$, —$C(O)R^{B3a}$ and —$C(O)OR^{B3a}$. Preferably, the optional substituents for the aryl or heteroaryl moiety are selected from the group consisting of: $C_{1-6}$ alkyl, $C_{1-6}$ haloalkyl, $C_{3-6}$ cycloalkyl, 4- to 6-membered heterocycloalkyl including 1, 2 or 3 heteroatoms selected from N, O or S, halo, —$OR^{B3a}$, —$NR^{B3a}R^{B3a}$, —$SR^{B3a}$, —$NR^{B3a}$ $C(O)R^{B3a}$, —$C(O)NR^{B3a}R^{B3a}$, —$SO_2R^{B3a}$, —$C(O)R^{B3a}$ and —$C(O)OR^{B3a}$. More preferably, the optional substituents for the aryl or heteroaryl moiety are selected from the group consisting of: $C_{1-6}$ alkyl (e.g. $C_1$, $C_2$, $C_3$ or $C_4$ alkyl), $C_{1-6}$ haloalkyl (e.g. $C_1$, $C_2$, $C_3$ or $C_4$ haloalkyl), halo and —$OR^{B3a}$ (e.g. —O—$C_{1-4}$ alkyl, such as —O—$CH_3$, or —O—$C_{1-4}$ haloalkyl, such as —O—$CF_3$). $R^5$ is preferably selected from the group consisting of —$CF_3$ and —$CF(CH_3)_2$.

In an embodiment, $R^4$ and $R^5$ are each independently $C_{3-6}$ alkyl (e.g. $C_3$, $C_4$, $C_5$ or $C_6$ alkyl), and $R^6$ is halo. Optional substituents for the alkyl groups are selected from the group consisting of: —$OR^{B3a}$, =O, —$NR^{B3a}R^{B3a}$, —$SR^{B3a}$, —CN, —$NO_2$, —$NR^{B3a}C(O)R^{B3a}$, —$C(O)NR^{B3a}R^{B3a}$, —$NR^{B3a}C(O)OR^{B3a}$, —$OC(O)NR^{B3a}R^{B3a}$, —$NR^{B3a}C(O)$ NRB³UR$^{B3a}$, —NR$^{B3a}$C(NR$^{B3a}$)NR$^{B3a}$R$^{B3a}$, —NR$^{B3a}$SO$_2$R$^{B3a}$, —SO$_2$NR$^{B3a}$R$^{B3a}$, —SO$_2$R$^{B3a}$, —C(O)R$^{B3a}$ and —C(O)OR$^{B3a}$. Preferably, the optional substituents for the alkyl groups are selected from the group consisting of: —OR$^{B3a}$, —NR$^{B3a}$R$^{B3a}$, —SR$^{B3a}$, —CN and —NR$^{B3a}$C(O)R$^{B3a}$. More preferably, the optional substituents for the alkyl groups are selected from the group consisting of: —OR$^{B3a}$, —NR$^{B3a}$R$^{B3a}$, —CN and —NR$^{B3a}$C(O)R$^{B3a}$. In an embodiment, R$^{B3a}$ is selected from the group consisting of H, C$_{1-4}$ alkyl, C$_{1-4}$ haloalkyl and C$_{3-6}$ cycloalkyl. Preferably R$^4$ and R$^5$ are each independently selected from the group consisting of iso-propyl and t-butyl and R$^6$ is selected from the group consisting of F, C$_1$ or Br.

In an embodiment, R$^4$ and R$^5$ are each independently C$_{3-6}$ alkyl (e.g. C$_3$, C$_4$, C$_5$ or C$_6$ alkyl), and R$^6$ is CN. Optional substituents for the alkyl groups are selected from the group consisting of: —OR$^{B3a}$, =O, —NR$^{B3a}$R$^{B3a}$, —SR$^{B3a}$, —CN, —NO$_2$, —NR$^{B3a}$C(O)R$^{B3a}$, —C(O)NR$^{B3a}$R$^{B3a}$, —NR$^{B3a}$C(O)OR$^{B3a}$, —OC(O)NR$^{B3a}$R$^{B3a}$, —NR$^{B3a}$C(O)NR$^{B3a}$R$^{B3a}$, —NR$^{B3a}$C(NR$^{B3a}$)NR$^{B3a}$R$^{B3a}$, —NR$^{B3a}$SO$_2$R$^{B3a}$, —SO$_2$NR$^{B3a}$R$^{B3a}$, —SO$_2$R$^{B3a}$, —C(O)R$^{B3a}$ and —C(O)OR$^{B3a}$. Preferably, the optional substituents for the alkyl groups are selected from the group consisting of: —OR$^{B3a}$, —NR$^{B3a}$R$^{B3a}$, —SR$^{B3a}$, —CN and —NR$^{B3a}$C(O)R$^{B3a}$. More preferably, the optional substituents for the alkyl groups are selected from the group consisting of: —OR$^{B3a}$, —NR$^{B3a}$R$^{B3a}$, —CN and —NR$^{B3a}$C(O)R$^{B3a}$. In an embodiment, R$^{B3a}$ is selected from the group consisting of H, C$_{1-4}$ alkyl, C$_{1-4}$ haloalkyl and C$_{3-6}$ cycloalkyl. Preferably R$^4$ and R$^5$ are each independently selected from the group consisting of iso-propyl and t-butyl and R$^6$ is CN.

Also provided is a compound selected from the compounds recited in the examples below or a pharmaceutically acceptable salt thereof.

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "halo" or "halogen" includes to one of the halogens, group 17 of the periodic table. In particular the term includes fluorine, chlorine, bromine and iodine.

The term C$_{m-n}$ refers to a group with m to n carbon atoms.

The term "C$_{1-6}$ alkyl" includes a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. The term "C$_{1-4}$ alkyl" includes such groups containing up to 4 carbon atoms. Alkylene groups include divalent alkyl groups and may likewise be linear or branched and have two points of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, C$_1$-C$_4$ alkoxy. Other substituents for the alkyl group may alternatively be used.

The term "C$_{1-6}$ haloalkyl", e.g. "C$_{1-4}$ haloalkyl", includes a hydrocarbon chain substituted with at least one halogen atom independently chosen at each occurrence, for example, from fluorine, chlorine, bromine and iodine. The halogen atom may be present at any position on the hydrocarbon chain. For example, C$_{1-6}$ haloalkyl may refer to chloromethyl, fluoromethyl, trifluoromethyl, chloroethyl e.g. 1-chloromethyl and 2-chloromethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl or trifluoropropyl.

The term "heteroalkyl", includes an alkyl group in which the hydrocarbon chain has at least one heteroatom selected from nitrogen, oxygen and/or sulfur atom interrupting the hydrocarbon chain. The heteroatom may be present at any position in the hydrocarbon chain. For example, C$_{1-6}$ heteroalkyl may refer to an ether, thioether or amine compound such as CH$_3$CH$_2$OCH$_2$CH$_3$, CH$_3$NHCH$_2$CH$_3$ or CH$_3$SCH$_3$. A heteroalkylene group includes divalent heteroalkyl group having two points of attachment to the remainder of the molecule. The groups —CH$_2$CH$_2$OCH$_2$CH$_2$—, —CH$_2$NHCH$_2$CH$_2$— or —CH$_2$SCH$_2$— are examples of heteroalkylene groups. The heteroalkyl and heteroalkylene groups may be unsubstituted or substituted by one or more substituents. Possible substituents are described below. Substituents for the alkyl group may be halogen, e.g. fluorine, chlorine, bromine and iodine, OH, C$_1$-C$_4$ alkoxy. Other substituents for the heteroalkyl group may alternatively be used.

The term "C$_{2-6}$ alkenyl" includes a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "C$_{2-6}$ alkenyl" may be ethenyl, propenyl, butenyl, butadienyl, pentenyl, pentadienyl, hexenyl and hexadienyl.

The term "C$_{2-6}$ alkynyl" includes a branched or linear hydrocarbon chain containing at least one triple bond and having 2, 3, 4, 5 or 6 carbon atoms. The triple bond may be at any possible position of the hydrocarbon chain. For example, the "C$_{2-6}$ alkynyl" may be ethynyl, propynyl, butynyl, pentynyl and hexynyl.

The term "C$_{3-6}$ cycloalkyl" includes a saturated hydrocarbon ring system containing 3, 4, 5 or 6 carbon atoms. For example, the "C$_3$-C$_6$ cycloalkyl" may be cyclopropyl, cyclobutyl, cyclopentyl, cyclohexyl, bicycle[2.1.1]hexane or bicycle[1.1.1]pentane.

The term "heterocyclyl", "heterocyclic" or "heterocycle" includes a non-aromatic saturated or partially saturated monocyclic or fused, bridged, or spiro bicyclic heterocyclic ring system(s). Monocyclic heterocyclic rings may contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles may contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles comprising at least one nitrogen in a ring position include, for example, azetidinyl, pyrrolidinyl, piperidinyl, piperazinyl, morpholinyl, thiomorpholinyl, tetrahydrotriazinyl, tetrahydropyrazolyl, tetrahydropyridinyl, homopiperidinyl, homopiperazinyl, 3,8-diaza-bicyclo[3.2.1]octanyl, 8-aza-bicyclo[3.2.1]octanyl, 2,5-Diaza-bicyclo[2.2.1]heptanyl and the like. Typical sulfur containing heterocycles include tetrahydrothienyl, dihydro-1,3-dithiol, tetrahydro-2H-thiopyran, and hexahydrothiepine. Other heterocycles include dihydro oxathiolyl, tetrahydro oxazolyl, tetrahydro-oxadiazolyl, tetrahydrodioxazolyl, tetrahydrooxathiazolyl, hexahydrotriazinyl, tetrahydro oxazinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O), for example, 2 oxopyrrolidinyl, 2-oxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. For example, the term "piperidino" or "morpholino" refers to a piperidin-1-yl or morpholin-4-yl ring that is linked via the ring nitrogen.

The term "bridged ring systems" includes ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane, and quinuclidine.

The term "spiro bi-cyclic ring systems" includes ring systems in which two ring systems share one common spiro carbon atom, i.e. the heterocyclic ring is linked to a further carbocyclic or heterocyclic ring through a single common spiro carbon atom. Examples of spiro ring systems include 3,8-diaza-bicyclo[3.2.1]octane, 2,5-Diaza-bicyclo[2.2.1]heptane, 6-azaspiro[3.4]octane, 2-oxa-6-azaspiro[3.4]octane, 2-azaspiro[3.3]heptane, 2-oxa-6-azaspiro[3.3]heptane, 6-oxa-2-azaspiro[3.4]octane, 2,7-diaza-spiro[4.4]nonane, 2-azaspiro[3.5]nonane, 2-oxa-7-azaspiro[3.5]nonane and 2-oxa-6-azaspiro[3.5]nonane.

"Heterocyclyl-Cm-n alkyl" includes a heterocyclyl group covalently attached to a Cm-n alkylene group, both of which are defined herein.

The term "aromatic" when applied to a substituent as a whole includes a single ring or polycyclic ring system with 4n+2 electrons in a conjugated π (pi) system within the ring or ring system where all atoms contributing to the conjugated π (pi) system are in the same plane.

The term "aryl" includes an aromatic hydrocarbon ring system. The ring system has 4n+2 electrons in a conjugated π (pi) system within a ring where all atoms contributing to the conjugated r (pi) system are in the same plane. For example, the "aryl" may be phenyl and naphthyl. The aryl system itself may be substituted with other groups.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π (pi) system where all atoms contributing to the conjugated π (pi) system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzthiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl and imidazo[1,2-b][1,2,4]triazinyl. Examples of heteroaryl groups comprising at least one nitrogen in a ring position include pyrrolyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, indolyl, isoindolyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl and pteridinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl-Cm-n alkyl-" includes a heteroaryl group covalently attached to a Cm-n alkylene group, both of which are defined herein. Examples of heteroaralkyl groups include pyridin-3-ylmethyl and the like.

The term "optionally substituted" includes either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

A bond terminating in a " ⌇ " represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in " ⌇ ".

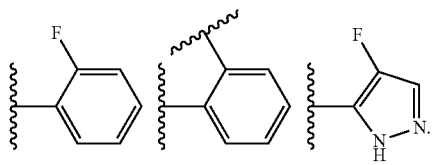

"Meta" substitution is a substitution pattern where two substituents are on carbons one carbon removed from each other, i.e. with a single carbon atom between the substituted carbons. In other words there is a substituent on the second atom away from the atom with another substituent. For example the groups below are meta substituted.

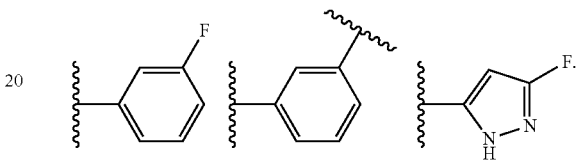

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted.

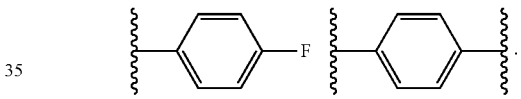

The term "acyl" includes an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, e.g. R is H or $C_{1-3}$ alkyl. In one embodiment acyl is alkyl-carbonyl. Examples of acyl groups include, but are not limited to, formyl, acetyl, propionyl and butyryl. A particular acyl group is acetyl (also represented as Ac).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525.

Suitable or preferred features of any compounds of the present invention may also be suitable features of any other aspect.

Methods and Uses of the Compounds:

In an embodiment, the condition treatable by modulating or inhibiting CaMK1 family kinase signaling is selected from the group consisting of: cancer, sarcoma, carcinoma, blastoma, lymphoma and leukemia. More specifically the condition modulated by CaMK1D may be selected from the group consisting of: cancer, sarcoma, carcinoma, blastoma, lymphoma and leukemia. Specific conditions treatable by the inhibition of CaMK1 family kinase signaling may be selected from the group consisting of: basal cell carcinoma, medulloblastoma, rhabdomyosarcoma, chondrosarcoma, melanoma, small-cell lung cancer, non-small-cell lung cancer, B-cell lymphoma, multiple myeloma, brain cancer, esophagus cancer, breast cancer, ovarian cancer, stomach cancer, colorectal cancer, liver cancer, kidney cancer, head and neck cancer, mesothelioma, soft tissue sarcomas, bone sarcomas, testicular cancer, prostate cancer, pancreatic cancer, bone cancer, bone metastasis, acute leukemia, chronic leukemia, glioma, Hodgkin's disease, cutaneous melanoma, bladder cancer, endocrine system cancer, parathyroid gland cancer, thyroid gland cancer, cervical cancer, endometrium cancer, ovarian cancer, skin cancer, renal cell carcinoma, pituitary adenoma, spinal axis tumours, uterine cancer, gastric cancer and biliary tract cancer. Breast cancer is an example of a particular, specific condition treatable by the inhibition of CaMK1 family kinase signaling. Specific examples of breast cancer that are treatable by the inhibition of CaMK1 family kinase signaling are HER2-positive breast cancer and triple-negative breast cancer.

Further conditions also treatable by the inhibition of CaMK1 family kinase signaling may be selected from the group consisting of: acute and chronic inflammatory conditions or conditions otherwise mediated by the immune system (for example rheumatoid arthritis, chronic obstructive pulmonary disease, acute respiratory distress syndrome, hepatic cirrhosis, lung fibrosis, glomerulonephritis, multiple sclerosis, psoriasis, benign prostatic hypertrophy (BPH), hypersensitivity reactions of the skin, atherosclerosis and restenosis, allergic asthma, diabetic retinopathy and diabetic nephropathy) and conditions associated with acute or chronic hyperglycemia (for example insulin-dependent/type-1 diabetes, insulin-independent/type-2 diabetes, stress-induced hyperglycemia).

The embodiments relating to the first aspect are also applicable to all other aspects of the invention, including the second and third aspects above.

Pharmaceutical compositions:

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier.

Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w/w compounds of the invention, more preferably from 0.05 to 80% w/w compounds of the invention, still more preferably from 0.10 to 70% w/w compounds of the invention, and even more preferably from 0.10 to 50% w/w compounds of the invention (all percentages by weight being based on total composition).

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories or enemas; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient.

For the above-mentioned compounds of the invention the dosage administered will, of course, vary with the compound employed, the mode of administration, the treatment desired and the disorder indicated. In using a compound of the invention for therapeutic or prophylactic purposes it will generally be administered so that a daily dose in the range, for example, a daily dose selected from 0.1 mg/kg to 100 mg/kg, 1 mg/kg to 75 mg/kg, 1 mg/kg to 50 mg/kg, 1 mg/kg to 20 mg/kg or 5 mg/kg to 10 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Suitably the compound of the invention is adminstered orally, for example in the form of a tablet, or capsule dosage form. The daily dose administered orally may be, for example a total daily dose selected from 1 mg to 1000 mg, 5 mg to 1000 mg, 10 mg to 750 mg or 25 mg to 500 mg. Typically, unit dosage forms will contain about 0.5 mg to 0.5 g of a compound of this invention.

Pharmaceutically acceptable salts, solvates, hydrates, complexes, polymorphs, tautomers, prodrugs, isomers, isotopically labelled compounds, metabolites, enantiomers, intermediates etc:

The invention contemplates pharmaceutically acceptable salts of the compounds of the invention. These may include the acid addition and base salts of the compounds.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see "Handbook of Pharmaceutical Salts: Properties, Selection, and Use" by Stahl and Wermuth (Wiley-VCH, Weinheim, Germany, 2002).

Preferably the salt is an acid addition salt. The salts may be formate or hydrochloride.

Pharmaceutically acceptable salts of compounds of the invention may be prepared by one or more of three methods:

(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water. It is to be understood that the invention encompasses all such solvated forms that possess CaMK1 family inhibitory activity.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The compounds of the invention include compounds of a number of formula as herein defined, including all polymorphs and crystal habits thereof, prodrugs and isomers thereof (including optical, geometric and tautomeric isomers) as hereinafter defined and isotopically-labeled compounds of the invention.

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{15}$O, $^{17}$O, $^{18}$O, $^{18}$F and the like. The radionuclide that is used will depend on the specific application of that radio-labelled derivative. For example, for in vitro competition assays, $^3$H or $^{14}$C are often useful. For radio-imaging applications, $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

It is also to be understood that certain compounds of the invention may exhibit polymorphism, and that the invention encompasses all such forms that possess CaMK1 family inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

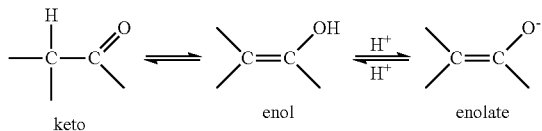

keto    enol    enolate

The in vivo effects of a compound of the invention may be exerted in part by one or more metabolites that are formed within the human or animal body after administration of a compound of the invention.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

Also, the compounds of the present invention as well as intermediates for the preparation thereof can be purified according to various well-known methods, such as for example crystallization or chromatography.

Combination therapies:

The methods of treatment according to the invention or the compound for use in the treatment of condition treatable by modulating or inhibiting CaMK1 family kinases as defined herein may be applied as a sole therapy or be a combination therapy with an additional active agent.

The methods of treatment according to the invention or the compound for use in the treatment of condition treatable by modulating or inhibiting CaMK1 family kinases as defined herein may involve, in addition to the compound of the invention, conventional surgery or radiotherapy or chemotherapy. Such chemotherapy may include one or more of the following specific anti-tumour agents listed below or anti-tumour agents from one or more of the categories of listed below:

(i) antiproliferative/antineoplastic drugs and combinations thereof, such as alkylating agents (for example cis-platin, oxaliplatin, carboplatin, cyclophosphamide, nitrogen mustard, bendamustin, melphalan, chlorambucil, busulphan, capecitabine temozolamide, ifosamide, mitobronitol, carboquone, thiotepa, ranimustine, nimustine, AMD-473, altretamine, AP-5280, apaziquone, brostallicin, carmustine, estramustine, fotemustine, gulfosfamide, KW-2170, mafosfamide, mitolactol, etaplatin, lobaplatin, nedaplatin, satraplatin and nitrosoureas); antimetabolites (for example gemcitabine and antifolates such as fluoropyrimidines like 5-fluorouracil and tegafur, raltitrexed, methotrexate, pemetrexed, cytosine arabinoside, 6-mercaptopurine riboside, leucovarin, UFT, doxifluridine, carmoflur, cytarabine, enocitabine S-1,5-azacitidine, cepecitabine, clofarabine, decitabine, eflornithine, ethynlcytidine, TS-1, nelarabine, nolatrexed, ocosfate, pelitrexol, triapine, trimetrexate, vidarabine, and hydroxyurea); antibiotics (for example anthracyclines like adriamycin, bleomycin, doxorubicin, daunomycin, epirubicin, idarubicin, mitomycin-C, dactinomycin, mithramycin, aclarubicin, actinomycin D, amrubicin, annamycin, elsamitrucin, galarubicin, nemorubicin, neocarzinostatin, peplomycin, piarubicin, rebeccamycin, stimalamer, streptozocin, valrubicin and zinostatin); antimitotic agents (for example vinca alkaloids like vincristine, vinblastine, vindesine and vinorelbine and taxoids like taxol, docetaxol (Taxotere), and paclitaxel and polokinase inhibitors); proteasome inhibitors, for example carfilzomib and bortezomib; interferon therapy; and topoisomerase inhibitors (for example epipodophyllotoxins like etoposide and teniposide, aclarubicin, amonafide, belotecan, 10-hydroxycamptothecin, 9-aminocamptothecin, diflomotecan, edotecarin, exatecan, gimatecan, lurtotecan, pirarubicin, pixantrone, rubitecan, sobuzoxane, SN-38, tafluposide, amsacrine, topotecan, mitoxantrone and camptothecin) and adjuvants used in combination with these therapies, for example folinic acid;

(ii) cytostatic agents such as antioestrogens (for example tamoxifen, fulvestrant, toremifene, raloxifene, droloxifene, lasofoxifeneand iodoxyfene), antiandrogens (for example bicalutamide, mifepristone, flutamide, nilutamide, casodex and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5oc-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-A/-(3-chloro-4-fluorophenyl)-7-(3-morpholinopropoxy)-quinazolin-4-amine (CI 1033), erbB2 tyrosine kinase inhibitors (such as lapatinib/GW-572016); ErbB2 inhibitors (for example GW-28297, $2C_4$, pertuzumab, TAK-165, AR-209, and 2B-1); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, P13 kinase inhibitors, Plt3 kinase inhibitors, CSF-1 R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, for example the anti-vascular endothelial cell growth factor antibody bevacizumab (Avastin™); *COXII* inhibitors (for example Arcoxia (etoricoxib), Bextra (valdecoxib), Celebrex (celecoxib), Paracoxib Vioxx (rofecoxib)); MMP inhibitors (for example MMP-2 inhibitors, MMP-9 inhibitors, AG-3340, RO 32-3555, and RS 13-0830); thalidomide; lenalidomide; and for example, a VEGF receptor (for example SU-1 1248, SU-5416, SU-6668, and angiozyme), tyrosine kinase inhibitors (such as vandetanib, vatalanib, sunitinib, axitinib and pazopanib); acitretin; fenretinide; zoledronic acid; angiostatin; aplidine; cilengtide; A-4; endostatin; halofuginome; rebimastat; removab; revlimid; squalamine; ukrain; and vitaxincombretastatin;

(yI) gene therapy approaches, including for example approaches to replace aberrant genes such as aberrant p53 or aberrant BRCA1 or BRCA2;
(vii) immunotherapy approaches, including for example antibody therapy such as alemtuzumab, rituximab, ibritumomab tiuxetan (Zevalin®) and ofatumumab; interferons such as interferon a; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); interferons, such as interferon alpha, interferon alpha-2a, interferon alpha-2b, interferon beta, interferon gamma-1 a, and interferon gamma-n; PF3512676; Filgrastim (Neupogen); lentinan; sizofilan; TheraCys; ubenimex; WF-10; BAM-002; dacarbazine; daclizumab; denileukin; gemtuzumab; ozogamicin; imiquimod; lenograstim; melanoma vaccine (Corixa); molgramostim; OncoVAX-CL; sargramostim; tasonermin; tecleukin; thymalasin; tositumomab; Virulizin; Z-100; epratuzumab; mitumomab; oregovomab; pemtumomab; and toll-like receptor modulators for example TLR-7 or TLR-9 agonists; and
(viii) cytotoxic agents for example fludaribine (fludara), cladribine, pentostatin (Nipent™), edotecarin, SU-1 1248, paclitaxel, Erbitux, and irinotecan;
(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;
(x) targeted therapies, for example PI3Kd inhibitors, for example idelalisib and perifosine; (xi) agents that modulate DNA damage response, for example inhibitors of PARP, DNAPK, ATM, ATR, for example olaparib, niraparib, iniparib, talazoparib and veliparib.
(xii) and additional active agents such as estramustine phosphate, fludarabine phosphate, farnesyl transferase inhibitors, PDGFr, streptozocin, strontium-89, suramin, hormonal therapies (for example Lupron, doxercalciferol, fadrozole, formestane and trelstar), supportive care products (for example, Filgrastim (Neupogen), ondansetron (Zofran), Fragmin, Procrit, Aloxi and Emend), biological response modifiers (e.g. Krestin, lentinan, sizofiran, picibanil and ubenimex), alitretinoin, ampligen, atrasenten, bexarotene, bosentan, calcitriol, exisulind, fotemustine, ibandronic acid, miltefosine, I-asparaginase, procarbazine, dacarbazine, hydroxycarbamide, pegaspargase, tazarotne, TLK-286, Velcade, Tarceva, tretinoin.

The combination therapies defined herein may be achieved by way of the simultaneous, sequential or separate dosing of the individual components of the treatment. Such combination products employ the compounds of this invention within a therapeutically effective dosage range described herein and the other pharmaceutically-active agent within its approved dosage range.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

In some embodiments in which a combination treatment is used, the amount of the compound of the invention and the amount of the other pharmaceutically active agent(s) are, when combined, therapeutically effective to treat a targeted disorder in the patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound of the invention and an approved or otherwise published dosage range(s) of the other pharmaceutically active compound(s).

According to a further aspect of the invention there is provided a pharmaceutical product comprising a compound of the invention, or a pharmaceutically acceptable salt thereof as defined herein and an additional active agent for the treatment of a condition which is modulated by CaMK1 family kinase signaling. The additional active agent may be an anti-tumour agent as defined herein.

In an embodiment there is provided a pharmaceutical product comprising a compound of the invention, or a pharmaceutically acceptable salt thereof as defined herein and an additional active agent for the treatment of a condition which is modulated by CaMK1D kinase signaling. The additional active agent may be an anti-tumour agent as defined herein.

According to a further aspect of the invention there is provided a method of treatment of a condition modulated by CaMK1 family kinase signaling comprising administering a therapeutically effective amount of a compound of the invention, or a pharmaceutically acceptable salt thereof simultaneously, sequentially or separately with an additional anti-tumour agent, as defined herein, to a patient in need thereof.

In an embodiment the condition is a condition modulated by CaMK1 D.

According to a further aspect of the invention there is provided a compound of the invention, or a pharmaceutically acceptable salt thereof for use simultaneously, sequentially or separately with an additional anti-tumour agent as defined herein, in the treatment of a condition modulated by CaMK1 family kinase signaling. In an embodiment the condition is a condition modulated by CaMK1D.

According to another aspect of the invention there is provided a use of the compound of the invention in combination with an anti-tumour agent as herein described. The compound of the invention may be used simultaneously, sequentially or separately with the additional anti-tumour agent. The use may be in a single combination product comprising the compound of the invention and the anti-tumour agent.

According to a further aspect there is provided a method of providing a combination product, wherein the method comprises providing a compound of the invention simultaneously, sequentially or separately with an anti-tumour agent, as defined herein. The method may comprise combining the compound of the invention and the anti-tumour agent in a single dosage form. Alternatively the method may comprise providing the anti-tumour agent as separate dosage forms.

The compound of the invention may also be used be used in combination with radiotherapy. Suitable radiotherapy treatments include, for example X-ray therapy, proton beam therapy or electron beam therapies. Radiotherapy may also encompase the use of radionuclide agents, for example $^{131}$I, $^{32}$P, $^{90}$Y, $^{89}$Sr, $^{153}$Sm or $^{223}$Ra. Such radionuclide therapies are well known and commercially available.

According to a further aspect of the invention there is provided a compound of the invention, or a pharmaceutically acceptable salt thereof as defined hereinbefore for use in the treatment of cancer conjointly with radiotherapy.

According to a further aspect of the invention there is provided a method of treatment of a human or animal subject suffering from a cancer comprising administering to the subject a therapeutically effective amount of a compound of the invention, or a pharmaceutically acceptable salt thereof simultaneously, sequentially or separately with radiotherapy.

Synthesis

In the description of the synthetic methods described herein and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

All of the reactions described herein and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl or trifluoroacetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

EXAMPLES

HPLC Method 1

Performed on a Shimadzu UFLCXR system coupled to an Applied Biosystems AP12000. Column maintained at 40° C. Column: Phenomenex Gemini-NX 3 m-110A C18, 50×2 mm. Total flow rate 0.5 mL/min. UV detection at 220 nm (channel 2) and 254 nm (channel 1). Gradient: Pre-equilibration run for one min at 5% B; then method run: 5 to 98% solvent B in 2 min, 98% B for 2 min, 98 to 5% B in 0.5 min then 5% for one min. Acid method: Solvent A=0.1% Formic Acid in water; solvent B=0.1% Formic Acid in MeCN.

HPLC Method 2

Performed on an Agilent HPLC. Column: Waters X-Select C18 2.5 μm, 4.6×30 mm, using standard acidic (0.1% Formic acid) 4 min method, 5-95% MeCN/water, UV detection at 254 nm).

HPLC Method 3

Performed on a Waters ACQUITY UPLC with PDA detector scanning between 210-400 nm. Mass spectral data was obtained using a Waters ACQUITY QDa detector scanning in the positive (ES+) and negative (ES−) modes between m/z 100-650. Samples were passed through a Waters ACQUITY UPLC BEH C18 1.7 μm 2.1×50 mm column coupled to a Waters ACQUITY UPLC BEH C18 VanGuard precolumn 2.1×5 mm. Gradient: Pre-equilibration run for 30 s at 5% B; then method run: 5 to 95% solvent B in 2 min, 95% B for 30 s, 95 to 5% B in 6 s then 5% B for 54 s. The column was maintained at 40° C. Acid method: Solvent A=0.1% Formic Acid in water; solvent B=MeCN. Base method: Solvent A=0.1% ammonium hydroxide in water; solvent B=MeCN.

HPLC Method 4

Performed on an Agilent HPLC. Column: Waters X-Bridge C18 2.5 μm, 4.6×30 mm, using standard basic (0.1% ammonium bicarbonate) 4 min method, 5-95% MeCN/water, UV detection at 254 nm).

Example 1: 2-(3-aminopiperidin-1-yl)-4-((3-(tert-butyl)phenyl)amino)pyrimidine-5-carboxamide Step 1-1: 2-chloro-4-(2,3,5,6-tetrafluorophenoxy)pyrimidine-5-carboxamide. 2,3,5,6-tetrafluorophenol (2.42 g, 14.58 mmol) was added to a solution of 2,4-dichloropyrimidine-5-carboxamide (3.11 g, 16.20 mmol) and DIPEA (3.39 mL, 19.44 mmol) in DMF (20 mL). The reaction was stirred at ambient temperature (hereafter referred to as RT). Upon complete consumption of starting material (After 1 h the reaction was complete) the reaction was diluted with water (30 mL) and EtOAc (30 mL); The layers were partitioned and the aqueous layer was extracted again with EtOAc (2×30 mL). The combined organic layers were washed with brine (100 mL), dried ($Na_2SO_4$) and concentrated under reduced pressure. No further purification was required. (5.21 g, 95%). m/z (ES+) (M+H)+ 322; $t_R$=1.82 min. HPLC Method 2.

Step 1-2: 2-(3-aminopiperidin-1-yl)-4-(2,3,5,6-tetrafluorophenoxy)pyrimidine-5-carboxamide. Piperidin-3-amine, 2HCl (0.220 g, 1.271 mmol) was added to a solution of 2-chloro-4-(2,3,5,6-tetrafluorophenoxy)pyrimidine-5-carboxamide (0.389 g, 1.211 mmol) in $CH_2Cl_2$ (hereafter referred to as DCM, 100 mL). The reaction was stirred at RT for 1 h and filtered, washing with DCM (100 mL) to give 2-(3-aminopiperidin-1-yl)-4-(2,3,5,6-tetrafluorophenoxy)pyrimidine-5-carboxamide (0.300 g, 61.1%). m/z (ES+) (M+H)+ 386.2; $t_R$=1.06 min. HPLC Method 2.

Step 1-3: 2-(3-aminopiperidin-1-yl)-4-((3-(tert-butyl)phenyl)amino)pyrimidine-5-carboxamide. 3-(tert-butyl)aniline (0.058 g, 0.389 mmol) was charged into microwave vessle containing 2-(3-aminopiperidin-1-yl)-4-(2,3,5,6-tetrafluorophenoxy) pyrimidine-5-carboxamide (0.06 g, 0.156 mmol) in dioxane (1 mL) and 1M HCl (aq) (0.5 mL). The reaction mixture was heated in the microwave (CEM, 150° C., full W) for 45 min. The crude mixture was loaded onto an SCX cartridge, washed with MeOH (4 column volumes) and eluted with 1% $NH_3$ in MeOH (4 column volumes). The ammonical MeOH layer was concentrated under reduced pressure. The residue was purified by silica gel chromatography ((10% 0.7 M Ammonia/MeOH)/DCM) to afford the title compound. (3 mg, 5%). 1H NMR (400 MHz, MeOD) δ 8.54 (s, 1H), 7.72 (s, 1H), 7.41 (d, J=7.8 Hz, 1H), 7.28 (t, J=7.9 Hz, 1H), 7.14 (dd, J=7.8, 2.0 Hz, 1H), 4.62 (dd, J=12.6, 3.9 Hz, 1H), 4.53 (d, J=13.2 Hz, 1H), 3.18-3.12 (m, 1H), 2.96 (dd, J=12.7, 9.4 Hz, 1H), 2.85-2.78 (m, 1H), 2.07-1.99 (m, 1H), 1.84-1.77 (m, 1H), 1.63-1.39 (m, 2H), 1.36 (s, 9H); m/z (ES+) (M+H)+ 369; $t_R$=2.01 min. HPLC Method 2.

Example 2: 2-(3-aminopiperidin-1-yl)-4-((3,5-di-tert-butylphenyl)amino)pyrimidine-5-carboxamide Prepared from 2-((2-aminoethyl)(methyl)amino)-4-(2,3,5,6-tetrafluorophenoxy)pyrimidine-5-carboxamide by an analogous method to example 1 (3 mg, 4%). $^1$H NMR (400 MHz, MeOD) δ 8.53 (s, 1H), 7.50 (d, J=1.7 Hz, 2H), 7.20 (t, J=1.7 Hz, 1H), 4.66-4.51 (m, 2H), 3.19-3.12 (m, 1H), 2.97 (dd, J=12.7, 9.3 Hz, 1H), 2.86-2.78 (m, 1H), 2.09-1.98 (m, 1H), 1.84-1.78 (m, 1H), 1.59-1.41 (m, 2H), 1.36 (s, 18H); m/z (ES+) (M+H)+ 425; $t_R$=2.47 min. HPLC Method 2.

Example 3: (S)-2-(3-aminopiperidin-1-yl)-4-((3,5-di-tert-butylphenyl)amino)pyrimidine-5-carboxamide Step 3-1: 2-chloro-4-((3,5-di-tert-butylphenyl)amino)pyrimidine-5-carboxamide. To a solution of 2,4-dichloropyrimidine-5-carboxamide (2 mmol, 384 mg) in THF (10 mL) was added 3,5-di-tert-butylaniline (2.2 mmol, 452 mg) followed by DIPEA (2.2 mmol, 385 uL) and the suspension heated at 50° C. for 24 h. Saturated $NH_4Cl$ was added and the crude extracted with EtOAc (3×). The organic phases were combined, washed with brine and dried on $Na_2SO_4$. The organic phase was filtered and the solvents evaporated under vacuum. The crude material was purified by chromatography on silica, using a gradient DCM/THF to provide the title compound as a white solid. $^1$H NMR (300 MHz, DMSO-d6) 11.39 (s, 1H), 8.76 (s, 1H), 8.42 (s, 1H), 7.92 (s, 1H), 7.48 (d, J=1.6 Hz, 2H), 7.18 (br t, J=1.5 Hz, 1H), 1.29 (s, 9H). m/z (ES+) (M+H)+ 361.2/363.3; $t_R$=3.27 min. HPLC Method 1.

Step 3-2: Tert-butyl (S)-(1-(5-carbamoyl-4-((3,5-di-tert-butylphenyl)amino)pyrimidin-2-yl)piperidin-3-yl)carbamate To a suspension of 2-chloro-4-((3,5-di-tert-butylphenyl)amino)pyrimidine-5-carboxamide (0.5 mmol) in THF (8 mL) was added DIPEA (0.55 mmol, 100 uL) followed by tert-butyl (S)-piperidin-3-ylcarbamate (0.5 mmol, 100 mg). The suspension formed was stirred at RT for 60 h. Saturated $NH_4Cl$ was added and the crude was extracted with EtOAc (3×). The organic phases were combined, washed with brine and dried on Na$_2$SO$_4$. The organic phase was filtered and the solvents evaporated under vacuum to provide the title compound, which was directly used in step 3-3. m/z (ES$^+$) (M+H)$^+$ 525.3; t$_R$=3.22 min. HPLC Method 1.

Step 3-3: (S)-2-(3-aminopiperidin-1-yl)-4-((3,5-di-tert-butylphenyl)amino)pyrimidine-5-carboxamide. Tert-butyl (S)-(1-(5-carbamoyl-4-((3,5-di-tert-butylphenyl)amino)pyrimidin-2-yl)piperidin-3-yl)carbamate was dissolved in DCM (1 mL) and an excess of HCl in dioxane (4M, 5 mL) was added. After 1 h Et$_2$O (excess) was added to precipitate the product as the HCl salt. The solid was centrifuged and the supernatant discarded. The solid was re-suspended in pure Et$_2$O and centrifuged again (2×). The solid was dried under vacuum to give the hydrochloride salt of the title compound as a white solid (0.032 g, 63%). $^1$H NMR (400 MHz, MeOD) δ 8.54 (s, 1H), 7.50 (d, J=1.7 Hz, 2H), 7.20 (t, J=1.7 Hz, 1H), 4.67-4.54 (m, 2H), 3.19-3.14 (m, 1H), 3.00-2.96 (m, 1H), 2.86-2.80 (m, 1H), 2.08-1.99 (m, 1H), 1.83-1.78 (m, 1H), 1.63-1.41 (m, 2H), 1.36 (s, 18H). m/z (ES$^+$) (M+H)$^+$ 425; t$_R$=1.81 min. HPLC Method 2.

Examples 4-10 were prepared by an analogous method to example 3.

Example 4: (S)-2-(3-aminopiperidin-1-yl)-4-((3-(2-cyanopropan-2-yl)phenyl)amino)pyrimidine-5-carboxamide (0.040 g, 73.3%). $^1$H NMR (400 MHz, MeOD) 8.56 (s, 1H), 8.08 (t, J=2.0 Hz, 1H), 7.47-7.36 (m, 2H), 7.21 (ddd, J=7.4, 2.0, 1.3 Hz, 1H), 4.67-4.60 (m, 1H), 4.54 (d, J=13.2 Hz, 1H), 3.19-3.09 (m, 1H), 2.96 (dd, J=12.7, 9.4 Hz, 1H), 2.81-2.79 (m, 1H), 2.03 (br s, 1H), 1.84 (br s, 1H), 1.77 (s, 6H), 1.64-1.52 (m, 1H), 1.49-1.36 (m, 1H); m/z (ES$^+$) (M+H)$^+$ 380; t$_R$=1.66 min. HPLC Method 2.

Example 5: (S)-2-(3-aminopiperidin-1-yl)-4-((3-(methylsulfonyl)phenyl)amino)pyrimidine-5-carboxamide (5 mg, 45.1%). $^1$H NMR (400 MHz, MeOD) δ 9.08 (s, 1H), 8.61 (s, 1H), 7.67-7.55 (m, 2H), 7.49 (s, 1H), 4.78 (s, 1H), 4.62 (s, 1H), 3.16-3.10 (m, 4H), 2.99-2.92 (m, 2H), 2.09 (br s, 1H), 1.89-1.86 (m, 1H), 1.65-1.59 (m, 1H), 1.53-1.44 (m, 1H); m/z (ES+) (M+H)$^+$ 391; t$_R$=1.30 min. HPLC Method 2.

Example 6: (S)-2-(3-aminopiperidin-1-yl)-4-((4-methyl-3-(piperidin-1-ylsulfonyl)phenyl)amino)pyrimidine-5-carboxamide (0.025 g, 19.2%). $^1$H NMR (400 MHz, MeOD) δ 8.99 (s, 1H), 8.57 (s, 1H), 7.39-7.22 (m, 2H), 4.80 (s, 1H), 4.63 (d, J=13.3 Hz, 1H), 3.25-2.96 (m, 6H), 2.87-2.83 (m, 2H), 2.59 (s, 3H), 2.07-2.03 (m, 1H), 1.89-1.82 (m, 1H), 1.65-1.52 (m, 6H), 1.46-1.38 (m, 1H); m/z (ES+) (M+H)$^+$ 474; t$_R$=1.89 min. HPLC Method 2.

Example 7: (R)-2-(3-aminopiperidin-1-yl)-4-((3,5-di-tert-butylphenyl)amino)pyrimidine-5-carboxamide hydrochloride Step 1: THF, DIPEA, 50° C., 24 h; Step 2: THF, DIPEA, 16 h, RT; Step 3: HCl in dioxane (4M), RT. m/z (ES$^+$) (M+H)$^+$ 425.3; t$_R$=2.44 min. HPLC Method 1.

Example 8: (S)-2-(3-aminopiperidin-1-yl)-4-((2-(tert-butyl)pyridin-4-yl)amino)pyrimidine-5-carboxamide Step 1: THF, DIPEA, 12 h, RT (48 mg, 43%). $^1$H NMR (300 MHz, MeOD) δ 8.59 (s, 1H), 8.32 (d, J=5.4 Hz, 1H), 7.74 (s, 1H), 7.49 (s, 1H), 4.63 (d, J=11.6 Hz, 2H), 4.50 (d, J=13.3 Hz, 1H), 3.19 (t, J=10.9 Hz, 1H), 3.08-2.95 (m, 1H), 2.86 (s, 1H), 2.06 (d, J=10.6 Hz, 1H), 1.82 (s, 1H), 1.67-1.43 (m, 3H), 1.38 (s, 9H); m/z (ES HRMS) C$_{19}$H$_{28}$N$_7$O calc 370.2355, found [MH]$^+$ 370.2354.

Example 9: (S)-2-(3-aminopiperidin-1-yl)-4-((3,5-bis(methylsulfonyl)phenyl)amino)pyrimidine-5-carboxamide hydrochloride $^1$H NMR (400 MHz, DMSO-d6) δ 12.19 (s, 1H), 8.80 (s, 1H), 8.60 (d, J=1.4 Hz, 2H), 8.25 (br s, 3H), 8.04 (s, 1H), 7.60 (br s, 1H), 3.61 (br s, 1H), 4.23 (d, J=11.7 Hz, 1H), 3.35 (s, 6H), 3.20 (br s, 1H), 2.09-2.01 (m, 1H), 1.87-1.78 (m, 1H), 1.75-1.64 (m, 1H), 1.62-1.51 (m, 1H). m/z (ES+) (M+H)$^+$ 469.3; t$_R$=1.96 min. HPLC Method 1.

Example 10: (S)-2-(3-aminopiperidin-1-yl)-4-((2'-methyl-[1,1'-biphenyl]-3-yl)amino)pyrimidine-5-carboxamide $^1$H NMR (300 MHz, MeOD) δ 8.51 (s, 1H), 7.90 (s, 1H), 7.44-7.31 (m, 2H), 7.28-7.16 (m, 4H), 6.97 (dt, J=7.0, 1.6 Hz, 1H), 4.69-4.38 (m, 2H), 3.07-2.86 (m, 1H), 2.84-2.50 (m, 2H), 2.24 (s, 3H), 2.06-1.84 (m, 1H), 1.80-1.55 (m, 1H), 1.54-1.22 (m, 2H). HRMS m/z [M+H]+ calc C$_{23}$H$_{27}$N$_6$O 403.2246 found 403.2252.

Example 11: 4-((3,5-di-tert-butylphenyl)amino)-2-((3S,5R)-3,5-diaminopiperidin-1-yl)pyrimidine-5-carboxamide dihydrochloride Prepared by an analogous method to example 3 using Boc-cis-3,5 diaminopiperidine (synthesised according to D. Wall et al. *Bioorg. & Med. Chem. Lett.* 17 (2007) 1206-1210). m/z (ES+) (M+H)$^+$ 440.5; t$_R$=2.12 min. HPLC Method 1. $^1$H NMR (300 MHz, MeOD) δ 8.58 (s, 1H), 7.39-7.37 (m, 3H), 3.58-3.42 (m, 2H), 3.30-3.13 (m, 2H), 2.67-2.57 (m, 2H), 1.97-1.77 (m, 2H), 1.36 (s, 18H).

Example 12: (S)-2-(3-aminopiperidin-1-yl)-4-((3-(2-oxopiperidin-1-yl)phenyl)amino)pyrimidine-5-carboxamide 1-(3-Amino-phenyl)-piperidin-2-one (0.099 g, 0.52 mmol), 2,4-dichloropyrimidine-5-carboxamide (0.100 g, 0.52 mmol) and triethylamine (0.16 mL, 1.15 mmol) were dissolved in anhydrous dioxane (10 mL) and DMF (1 mL). The mixture was heated at 50° C. for 3 h and then left to cool to RT. Triethylamine (0.16 mL, 1.15 mmol) and tert-butyl (S)-piperidin-3-ylcarbamate (0.104 g, 0.52 mmol) were added and the mixture was heated to 50° C. for a further 2 h. EtOAc (40 mL) was added and the solution washed sequentially with water (5×20 mL) and brine (20 mL). The organic phase was dried over MgSO$_4$, filtered and concentrated under reduced pressure to give the crude product from two displacements which was used without further purification. The crude product (0.054 g, 0.126 mmol) was dissolved in dioxane (5.4 mL) followed by the drop-wise addition of 4M HCl in dioxane (1 mL). The reaction mixture was stirred at RT for 8 h. Hexane (20 mL) was added and the resulting solid was filtered and washed with additional portions of hexane (3×10 mL) to give the hydrochloride salt of the title compound as a white solid (0.025 g, 11%). $^1$H NMR (400 MHz, DMSO-d6) δ 12.00 (br s, 1H), 8.74 (s, 1H), 8.63-8.28 (m, 4H), 7.90-7.55 (m, 2H), 7.52-7.38 (m, 1H), 7.33 (d, J=12.0 Hz, 1H), 7.17-7.00 (m, 1H), 3.68-3.58 (m, 2H), 3.46-3.17 (m, 3H), 2.48-2.37 (m, 2H), 2.11-1.99 (m, 1H), 1.93-1.79 (m, 5H), 1.79-1.65 (m, 1H), 1.63-1.49 (m, 1H), 1.31-1.2 (m, 1H), 0.89-0.79 (m, 1H). LCMS: m/z (ES+) (M+H)$^+$ 410.0; t$_R$=1.67 min. HPLC Method 3 (Acid).

Example 13: (S)-2-(3-aminopiperidin-1-yl)-4-((3-(2-oxopyrrolidin-1-yl)phenyl)amino)pyrimidine-5-carboxamide 1-(3-Aminophenyl)pyrrolidin-2-one (0.100 g, 0.52 mmol), 2,4-dichloropyrimidine-5-carboxamide (0.100 g, 0.52 mmol) and triethylamine (0.16 mL, 1.15 mmol) were dissolved in anhydrous dioxane (10 mL) and DMF (1 mL). The mixture was heated at 50° C. for 2 h and then left to cool to RT. EtOAc (40 mL) was added and the solution washed sequentially with water (5×20 mL) and brine (20 mL). The organic phase was dried over MgSO$_4$, filtered and concentrated under reduced pressure to give the crude product from one displacement (0.100 g, 58%), which was used in the next step without further purification. The crude product, 2-chloro-4-((3-(2-oxopyrrolidin-1-yl)phenyl)amino)pyrimidine-5-carboxamide (80 mg, 0.24 mmol), tert-butyl (S)-piperidin-3-ylcarbamate (0.049 g, 0.24 mmol) and triethylamine (0.04 mL, 0.29 mmol) were dissolved in anhydrous DMF (5 mL) and heated to 50° C. for 2 h. The reaction mixture was allowed to cool to RT whereupon a white solid precipitated. Hexane (20 mL) was added and the suspension stirred for 10 min. The solid was filtered and dissolved in Et$_2$O (5 mL), 4M HCl in dioxane (1 mL) was added and the mixture stirred at RT for 64 h. The resulting suspension was filtered and the solid washed with hexane (10 mL) and dried to give the hydrochloride salt of the title compound as a white solid (0.040 g, 18%). $^1$H NMR (400 MHz, DMSO-d6) δ 12.01 (br s, 1H), 8.72 (s, 1H), 8.57-8.08 (m, 4H), 7.80-7.50 (m, 1H), 7.47-7.35 (m, 1H), 7.35-7.21 (m, 2H), 4.50 (app d, J=16 Hz, 1H), 4.34-3.95 (m, 2H), 3.86 (t, J=8.0 Hz, 2H), 3.55-3.46 (m, 1H), 3.41 (app t, J=10.4 Hz, 1H), 3.36-3.19 (m, 1H), 2.53 (t, J=8.0 Hz, 2H), 2.13-2.00 (m, 3H), 1.90-1.79 (m, 1H), 1.79-1.66 (m, 1H), 1.64-1.50 (m, 1H). LCMS: m/z (ES+) (M+H)$^+$ 396.0; t$_R$=1.64 min. HPLC Method 3 (Acid).

Example 14: (S)-2-(3-aminopiperidin-1-yl)-4-((3-(3-methyl-2-oxoimidazolidin-1-yl)phenyl)amino)pyrimidine-5-carboxamide 1-(3-Aminophenyl)-3-methylimidazolidin-2-one (0.100 g, 0.52 mmol), 2,4-dichloropyrimidine-5-carboxamide (0.100 g, 0.52 mmol), triethylamine (0.16 mL, 1.15 mmol) were dissolved in anhydrous dioxane (9 mL) and DMF (2 mL). The mixture was heated at 50° C. for 2 h and then left to cool to RT. tert-Butyl (S)-piperidin-3-ylcarbamate (0.104 g, 0.52 mmol) and triethylamine (0.16 mL, 1.15 mmol) were added and the reaction mixture was heated at 50° C. for a further 1.5 h. The reaction mixture was left to cool to RT whereupon a white solid precipitated. The solid was filtered, washed with MeOH (5 mL) and dried to give the crude product which was used without further purification (0.134 g, 50%). The crude product (0.113 g, 0.22 mmol) was dissolved in Et$_2$O (10 mL) followed by the drop-wise addition of 4M HCl in dioxane (2.0 mL). The resulting mixture was stirred at RT overnight and the suspension filtered to give the hydrochloride salt of the title compound as a white solid (0.098 g, 99%). $^1$H NMR (400 MHz, DMSO-d6) δ 12.19 (br s, 1H), 8.74 (s, 1H), 8.67-8.37 (m, 3H), 8.36-8.13 (m, 1H), 7.41-7.29 (m, 1H), 7.23-7.06 (m, 2H), 4.40 (app d, J=11.6 Hz, 1H), 4.15-4.05 (m, 1H), 3.81 (t, J=8.0 Hz, 2H), 3.74-3.62 (m, 1H), 3.61-3.51 (m, 1H), 3.47 (t, J=8.4 Hz, 2H), 3.39-3.26 (m, 1H), 2.78 (s, 3H), 2.11-2.00 (m, 1H), 1.93-1.72 (m, 2H), 1.67-1.53 (m, 1H). LCMS: m/z (ES+) (M+H)$^+$ 411.0; t$_R$=1.66 min. HPLC Method 3 (Acid)

Example 15: (S)-2-(3-aminopiperidin-1-yl)-4-((3-(2-oxooxazolidin-3-yl)phenyl)amino)pyrimidine-5-carboxamide 3-(3-Aminophenyl)oxazolidin-2-one (0.093 g, 0.52 mmol), 2,4-dichloropyrimidine-5-carboxamide (0.100 g, 0.52 mmol), triethylamine (0.16 mL, 1.15 mmol) were dissolved in anhydrous dioxane (9 mL) and DMF (2 mL). The mixture was heated at 50° C. for 2 h and then left to cool to RT. tert-Butyl (S)-piperidin-3-ylcarbamate (0.104 g, 0.52 mmol) and triethylamine (0.16 mL, 1.15 mmol) were added and the reaction mixture was heated at 50° C. overnight. EtOAc (40 mL) was added and the solution washed sequentially with water (5×20 mL) and brine (20 mL). The organic phase was dried over MgSO$_4$, filtered and concentrated under reduced pressure to give the crude product from two displacements which was used without further purification. The crude product was dissolved in Et$_2$O (10 mL) followed by the drop-wise addition of 4M HCl in dioxane (5.0 mL). The suspension was stirred at RT for 4 h, filtered and dried to give the hydrochloride salt of the title compound as a white solid (0.195 g, 83%). $^1$H NMR (400 MHz, DMSO-d6) δ 12.13 (br s, 1H), 8.75 (s, 1H), 8.54-8.29 (m, 3H), 8.08 (s, 1H), 7.50-7.37 (m, 1H), 7.29 (app t, J=9.2 Hz, 1H), 4.46 (t, J=11.2 Hz, 2H), 4.48-4.38 (m, 1H), 4.24-4.13 (m, 1H), 4.09 (t, J=10.8 Hz, 2H), 3.63-3.52 (m, 1H), 3.45 (app t, J=13.2 Hz, 1H), 3.36-3.20 (m, 1H), 2.12-1.96 (m, 1H), 1.92-1.67 (m, 2H), 1.66-1.47 (m, 1H). LCMS: m/z (ES+) (M+H)$^+$ 398.0; t$_R$=1.56 min. HPLC Method 3 (Acid).

Example 16: (S)-2-(3-aminopiperidin-1-yl)-4-((6-methoxy-[1,1'-biphenyl]-3-yl)amino)pyrimidine-5-carboxamide A mixture of 2,4-dichloropyrimidine-5-carboxamide (81 mg, 0.42 mmol), 6-methoxy-[1,1'-biphenyl]-3-amine hydrochloride (100 mg, 0.42 mmol) and triethylamine (0.17 mL, 0.92 mmol) in 1,4-dioxane (8 mL) was stirred at 50° C. for 5 h. (S)-Tert-butyl piperidin-3-ylcarbamate (84 mg, 0.42 mmol) and triethylamine (0.07 mL, 0.46 mmol) were added and the mixture was stirred at 50° C. overnight. The resulting mixture was allowed to reach RT, concentrated under reduced pressure, dry-loaded into a column and purified by flash chromatography [Hexane:EtOAc (3:7)] affording tert-butyl (S)-(1-(5-carbamoyl-4-((6-methoxy-[1,1'-biphenyl]-3-yl)amino)pyrimidin-2-yl)piperidin-3-yl)carbamate as a white solid (100 mg, 46%). This was suspended into a mixture of dioxane:Et$_2$O (1:1, 4 mL) and 4N HCl in dioxane (2 mL) was added. The suspension was stirred at RT overnight. Et$_2$O was added (ca. 4 mL) and the precipitate was filtered under reduced pressure, washed with Et$_2$O (ca. 10 mL) and dried under air. The hydrochloride salt of the title compound was isolated as a white solid (80 mg, 99%). $^1$H NMR (400 MHz, MeOD) δ 8.52 (s, 1H), 7.63-7.48 (m, 4H), 7.41 (app. t, J=7.6 Hz, 2H), 7.37-7.29 (m, 1H), 7.19 (d, J=8.8 Hz, 1H), 4.40-4.27 (m, 1H), 4.11-4.00 (m, 1H), 3.85 (s, 3H), 3.78-3.67 (m, 1H), 3.65-3.46 (m, 2H), 2.25-2.15 (m, 1H), 2.02-1.66 (m, 3H); m/z (ES$^+$) (M+H)$^+$ 419.0; $t_R$=2.31 min. HPLC Method 3 (Base).

Example 17: (S)-2-(3-aminopiperidin-1-yl)-4-((3-methyl-5-(morpholine-4-carbonyl)phenyl)amino)pyrimidine-5-carboxamide Step 17-1: (3-methyl-5-nitrophenyl)(morpholino)methanone. 3-Methyl-5-nitrobenzoic acid (0.368 g, 2.03 mmol) was dissolved in thionyl chloride (5.0 mL, excess) and the mixture heated to reflux for 2 h under an argon atmosphere. Excess thionyl chloride was removed under reduced pressure and the acid chloride was dissolved in anhydrous DCM (5.0 mL). The solution of acid chloride was added drop-wise to a flask containing morpholine (0.20 mL, 2.29 mmol), triethylamine (0.31 mL, 2.22 mmol) and anhydrous DCM (5.0 mL) at 0° C. The cooling bath was removed and the reaction mixture was stirred at RT for 3 h. DCM (20 mL) was added and the organic solution was washed sequentially with water (2×20 mL), saturated solution of NH$_4$Cl (20 mL) and saturated solution of NaHCO$_3$ (20 mL). The organic phase was dried over MgSO$_4$, filtered and concentrated under reduced pressure to give the crude product, which was purified by flash column chromatography (EtOAc) to give the title compound as a white solid (0.415 g, 82%). $^1$H NMR (400 MHz, CDCl$_3$) δ 8.09 (s, 1H), 8.04 (s, 1H), 7.56 (s, 1H), 3.94-3.29 (m, 8H), 2.50 (s, 3H). $^{13}$C NMR (101 MHz, CDCl$_3$) δ 168.1, 148.2, 141.0, 136.9, 134.0, 125.3, 119.5, 66.9, 48.4 (broadened), 42.8 (broadened), 21.5.

Step 17-2: (3-amino-5-methylphenyl)(morpholino)methanone. Iron powder (0.124 g, 2.22 mmol) was added portion-wise to EtOH (2.0 mL) followed by concentrated HCl (aq) (0.04 mL). The mixture was heated at 65° C. for 2 h and then allowed to cool to 50° C. 25% NH$_4$Cl (aq) solution (0.64 mL) was added drop-wise followed by a solution of (3-Methyl-5-nitrophenyl)(morpholino)methanone (0.200 g, 0.80 mmol) in EtOH (4.0 mL). The mixture was reheated to 65° C. for 4 h and allowed to cool to RT. The reaction mixture was filtered through a pad of Celite® under reduced pressure using MeOH (30 mL). The filtrate was concentrated under reduced pressure and the crude product purified by flash column chromatography (1:4 hexane:EtOAc) to give the title compound as a colourless semi-solid (0.086, 49%). $^1$H NMR (400 MHz, CDCl$_3$) δ 6.55 (s, 1H), 6.52 (s, 1H), 6.48 (s, 1H), 95-3.3 (m, 8H), 2.25 (s, 3H). LCMS: m/z (ES+) (M+H)$^+$ 221.0; $t_R$=1.51 min. HPLC Method 3 (Acid).

Step 17-3: (S)-2-(3-aminopiperidin-1-yl)-4-((3-methyl-5-(morpholine-4-carbonyl)phenyl)amino)pyrimidine-5-carboxamide. (3-Amino-5-methylphenyl)(morpholino)methanone (0.127 g, 0.58 mmol), 2,4-dichloropyrimidine-5-carboxamide (0.111 g, 0.58 mmol), triethylamine (0.16 mL, 1.15 mmol) were dissolved in anhydrous dioxane (9 mL) and DMF (2 mL). The mixture was heated at 50° C. for 1 h and then left to cool to RT. tert-Butyl (S)-piperidin-3-ylcarbamate (0.116 g, 0.58 mmol) and triethylamine (0.16 mL, 1.15 mmol) were added and the reaction mixture was heated at 50° C. for 2 h. EtOAc (3 mL) was added and the crude product from two displacements was precipitated using hexane (30 mL). The resulting product was filtered and dried and used in the next step without further purification (0.144 g, 46%). The crude product (0.098 g, 0.18 mmol) was dissolved in dioxane (10 mL) and 4M HCl in dioxane (2.0 mL) was added drop-wise. The reaction mixture was stirred at RT overnight and hexane (20 mL) was added. The resulting solid was filtered, washed with additional portions of hexane (3×5 mL) and dried to give the hydrochloride salt of the title compound as a white solid (0.087 g, quantitative). $^1$H NMR (400 MHz, DMSO-d6) δ 11.96 (br s, 1H), 8.77 (s, 1H), 8.65-8.32 (m, 3H), 8.00-7.65 (m, 1H), 7.58 (s, 1H), 7.47 (s, 1H), 7.01 (s, 1H), 4.46-4.29 (m, 1H), 4.21-3.97 (m, 1H), 3.73-3.17 (m, 11H), 2.35 (s, 3H), 2.12-1.97 (m, 1H), 1.92-1.67 (m, 2H), 1.66-1.49 (m, 1H). LCMS: m/z (ES+) (M+H)$^+$ 440.0; $t_R$=1.66 min. HPLC Method 3 (Acid).

Example 18: (S)-2-(3-aminopiperidin-1-yl)-4-((3-bromo-5-(morpholine-4-carbonyl)phenyl) amino)pyrimidine-5-carboxamide Step 18-1: (S)-methyl 3-bromo-5-((2-(3-((tert-butoxycarbonyl)amino)piperidin-1-yl)-5-carbamoylpyrimidin-4-yl)amino)benzoate. To a stirred solution of 2,4-dichloropyrimidine-5-carboxamide (1.11 g, 5.78 mmol) and DIPEA (1.11 mL, 6.36 mmol) in 1,4-dioxane (20 mL) was added methyl 3-amino-5-bromobenzoate (1.397 g, 6.07 mmol). The reaction was heated to 80° C. and stirred for 2 h, then allowed to cool to RT. (S)-tert-butyl piperidin-3-ylcarbamate (1.216 g, 6.07 mmol) and DIPEA (1.108 mL, 6.36 mmol) were added and the solution was reheated to 80° C. for 30 min, then allowed to cool again. The reaction mixture was diluted with water (50 mL) and extracted with ethyl acetate (3×50 mL). The combined organic layers were dried over magnesium sulfate, filtered and concentrated under vacuum. The crude product was purified by chromatography on silica gel (8-10% MeOH/DCM) to afford (S)-methyl 3-bromo-5-((2-(3-((tert-butoxycarbonyl)amino)piperidin-1-yl)-5-carbamoylpyrimidin-4-yl)amino)benzoate. (1.3 g, 40.9%). m/z (M+H)$^+$ (ES$^+$) 549.1, 551.1; $t_R$=2.45 min. HPLC Method 2.

Step 18-2: (S)-3-bromo-5-((2-(3-((tert-butoxycarbonyl)amino)piperidin-1-yl)-5-carbamoylpyrimidin-4-yl)amino)benzoic acid. To a stirred solution of (S)-methyl 3-bromo-5-((2-(3-((tert-butoxycarbonyl)amino)piperidin-1-yl)-5-carbamoylpyrimidin-4-yl)amino) benzoate (0.648 g, 1.179 mmol) in THF (10 mL) and methanol (1 mL) was added lithium hydroxide (0.282 g, 11.79 mmol) in water (10 mL) and the resulting mixture was stirred at RT for 18 h. The reaction was diluted with 1M HCl (50 mL) and extracted with ethyl acetate (2×100 mL). The combined organic layers were dried over magnesium sulfate, filtered and concentrated under vacuum. The material was used directly in the next step, assuming 100%. m/z (M+H)$^+$ (ES$^+$) 535.0, 536.9; $t_R$=2.08 min. HPLC Method 2.

Step 18-3: (S)-tert-butyl (1-(4-((3-bromo-5-(morpholine-4-carbonyl)phenyl)amino)-5-carbamoylpyrimidin-2-yl)piperidin-3-yl)carbamate. To a stirred solution of (S)-3-bromo-5-((2-(3-((tert-butoxycarbonyl)amino)piperidin-1-yl)-5-carbamoylpyrimidin-4-yl)amino)benzoic acid (0.631 g, 1.179 mmol) and HATU (0.493 g, 1.296 mmol) in DMF (10 mL) was added DIPEA (0.412 mL, 2.357 mmol) followed by morpholine (0.112 mL, 1.296 mmol). The reaction was stirred at RT for 4 h, then diluted with water (50 mL). The mixture was extracted with ethyl acetate (3×50 mL) and the combined organic layers were dried over magnesium sulfate, filtered and concentrated under vacuum. The crude product was purified by chromatography on silica gel (0-10% MeOH/DCM) to afford (S)-tert-butyl (1-(4-((3-bromo-5-(morpholine-4-carbonyl)phenyl)amino)-5-carbamoylpyrimidin-2-yl)piperidin-3-yl)carbamate. (0.501 g, 69%). m/z (M+H)$^+$ (ES$^+$) 604.0, 606.0; $t_R$=1.94 min. HPLC Method 2.

Step 18-4: (S)-2-(3-aminopiperidin-1-yl)-4-((3-bromo-5-(morpholine-4-carbonyl)phenyl) amino)pyrimidine-5-carboxamide. To a stirred solution of (S)-tert-butyl (1-(4-((3-bromo-5-(morpholine-4-carbonyl)phenyl)amino)-5-carbamoylpyrimidin-2-yl)piperidin-3-yl)carbamate (0.03 g, 0.050 mmol) in 1,4-dioxane (1 mL) was added hydrogen chloride (4M in 1,4-dioxane, 0.248 mL, 0.993 mmol) and the solution was stirred at RT for 20 h. The reaction mixture was concentrated under vacuum and purified by chromatography on silica gel (0-10% (0.7 M Ammonia/MeOH)/DCM) to afford (S)-2-(3-aminopiperidin-1-yl)-4-((3-bromo-5-(morpholine-4-carbonyl)phenyl)amino)pyrimidine-5-carboxamide. (7 mg, 25%). 1H NMR (400 MHz, MeOD) δ 8.59 (s, 1H), 8.08 (br s, 1H), 7.82 (br s, 1H), 7.27 (t, 1H, J=1.6 Hz), 4.69-4.62 (m, 1H), 4.57-4.46 (m, 1H), 3.90-3.40 (br m, 8H), 3.18-3.06 (m, 1H), 2.99-2.80 (m, 2H), 2.11-2.02 (m, 1H), 1.90-1.80 (m, 1H), 1.66-1.53 (m, 1H), 1.52-1.41 (m, 1H). m/z (M+H)+ (ES+) 504.1, 506.2; $t_R$=1.59 min. HPLC Method 2.

Example 19: (S)-2-(3-aminopiperidin-1-yl)-4-((2'-chloro-5-(morpholine-4-carbonyl)-[1,1'-biphenyl]-3-yl)amino)pyrimidine-5-carboxamide Step 19-1: (S)-tert-butyl (1-(5-carbamoyl-4-((2'-chloro-5-(morpholine-4-carbonyl)-[1,1'-biphenyl]-3-yl)amino)pyrimidin-2-yl)piperidin-3-yl)carbamate. A stirred solution of (S)-tert-butyl (1-(4-((3-bromo-5-(morpholine-4-carbonyl)phenyl)amino)-5-carbamoylpyrimidin-2-yl)piperidin-3-yl)carbamate (0.054 g, 0.089 mmol), sodium bicarbonate (0.023 g, 0.268 mmol) and (2-chlorophenyl)boronic acid (0.015 g, 0.098 mmol) in 1,4-dioxane (1.5 mL) and water (0.5 mL) was purged with nitrogen for 10 min. PdCl$_2$dppf (3.27 mg, 4.47 μmol) was added and purging was continued for a further 10 min. The reaction was then heated to 90° C. and stirred under nitrogen for 4 h, then allowed to cool. The mixture was diluted with water (20 mL) and extracted with ethyl acetate (3×20 mL). The combined organic layers were dried over magnesium sulfate, filtered and concentrated under vacuum. The crude product was purified by chromatography on silica gel (0-10% (0.7 M Ammonia/MeOH)/DCM) to afford (S)-tert-butyl (1-(5-carbamoyl-4-((2'-chloro-5-(morpholine-4-carbonyl)-[1,1'-biphenyl]-3-yl)amino)pyrimidin-2-yl)piperidin-3-yl)carbamate. (0.028 g, 48.8%). m/z (M+H)+ (ES+) 636.0, 638.1; $t_R$=2.12 min. HPLC Method 2.

Step 19-2: (S)-2-(3-aminopiperidin-1-yl)-4-((2'-chloro-5-(morpholine-4-carbonyl)-[1,1'-biphenyl]-3-yl)amino)pyrimidine-5-carboxamide. Prepared by an analogous method to example 18 (0.012 mg, 47.5%). 1H NMR (400 MHz, MeOD) δ 8.58 (s, 1H), 8.01 (br s, 1H), 7.78 (br s, 1H), 7.56-7.52 (m, 1H), 7.48-7.36 (m, 3H), 7.16 (t, 1H, J=1.5 Hz), 6.69-4.60 (m, 1H), 4.58-4.41 (m, 1H), 3.92-3.48 (br m, 8H), 3.11-3.00 (m, 1H), 2.94-2.77 (m, 2H), 2.08-1.98 (m, 1H), 1.82-1.70 (m, 1H), 1.60-1.36 (m, 2H). m/z (M+H)+ (ES+) 536.2; $t_R$=1.42 min. HPLC Method 2.

Example 20: (S)-2-(3-aminopiperidin-1-yl)-4-((2',6'-dimethyl-5-(morpholine-4-carbonyl)-[1,1'-biphenyl]-3-yl)amino)pyrimidine-5-carboxamide Step 20-1: (S)-methyl 5-((2-(3-((tert-butoxycarbonyl)amino)piperidin-1-yl)-5-carbamoyl pyrimidin-4-yl)amino)-2',6'-dimethyl-[1,1'-biphenyl]-3-carboxylate. Prepared by an analogous method to step 19-1, using (2,6-dimethylphenyl) boronic acid (1.1 eq). 90° C., 1 h. (0.139 g, 41.4%). m/z (M+H)+ (ES−) 575.1; $t_R$=2.69 min. HPLC Method 2.

Step 20-2: (S)-5-((2-(3-((tert-butoxycarbonyl)amino)piperidin-1-yl)-5-carbamoyl pyrimidin-4-yl)amino)-2',6'-dimethyl-[1,1'-biphenyl]-3-carboxylic acid. To a stirred solution of (S)-methyl 5-((2-(3-((tert-butoxycarbonyl)amino)piperidin-1-yl)-5-carbamoylpyrimidin-4-yl)amino)-2',6'-dimethyl-[1,1'-biphenyl]-3-carboxylate (0.139 g, 0.24 mmol) in THE (5 mL) was added sodium hydroxide (0.097 g, 2.42 mmol) in water (5 mL). Methanol (1 mL) was added and the solution was stirred for 16 h at RT. The reaction mixture was quenched by addition of 1M phosphoric acid to pH 4-5, and then diluted with water (20 mL). The mixture was extracted with ethyl acetate (3×20 mL) and the combined organic layers were dried over magnesium sulfate, filtered and concentrated under vacuum to afford (S)-5-((2-(3-((tert-butoxycarbonyl)amino)piperidin-1-yl)-5-carbamoylpyrimidin-4-yl)amino)-2',6'-dimethyl-[1,1'-biphenyl]-3-carboxylic acid. (0.125 g, 89%). m/z (M+H)+ (ES+) 561.3; $t_R$=2.31 min. HPLC Method 2.

Step 20-3: (S)-tert-butyl (1-(5-carbamoyl-4-((2',6'-dimethyl-5-(morpholine-4-carbonyl)-[1,1'-biphenyl]-3-yl)amino)pyrimidin-2-yl)piperidin-3-yl)carbamate. Prepared by an analogous method to step 18-3. (3 h, RT). (0.11 g, 79%). m/z (M+H)+ (ES+) 630.3; $t_R$=2.24 min. HPLC Method 2.

Step 20-4: (S)-2-(3-aminopiperidin-1-yl)-4-((2',6'-dimethyl-5-(morpholine-4-carbonyl)-[1,1'-biphenyl]-3-yl)amino)pyrimidine-5-carboxamide. Prepared by an analogous method to step 18-4. (18 h, RT). (0.03 g, 31.4%). 1H NMR (400 MHz, MeOD) δ 8.58 (s, 1H), 7.91 (br s, 1H), 7.65 (s, 1H), 7.21-7.11 (m, 3H), 6.88 (t, 1H, J=1.5 Hz), 4.64-4.56 (m, 1H), 4.56-4.40 (m, 1H), 4.90-3.45 (m, 8H), 3.04-2.94 (m, 1H), 2.90-2.68 (m, 2H), 2.09 (d, 6H, J=2.3 Hz), 2.05-1.96 (m, 1H), 1.78-1.65 (m, 1H), 1.56-1.29 (m, 2H). m/z (M+H)+ (ES+) 530.3; $t_R$=1.45 min. HPLC Method 2.

Example 21: (S)-2-(3-aminopiperidin-1-yl)-4-((5-(morpholine-4-carbonyl)-[1,1'-biphenyl]-3-yl)amino) pyrimidine-5-carboxamide Step 21-1: 5-nitro-[1,1'-biphenyl]-3-carboxylic acid. A stirred solution of bromobenzene (1.669 mL, 15.89 mmol), (3-(methoxycarbonyl)-5-nitrophenyl)boronic acid (3.25 g, 14.45 mmol) and sodium bicarbonate (3.64 g, 43.3 mmol) in 1,4-dioxane (100 mL) and water (30 mL) was purged with nitrogen for 10 min. PdCl$_2$dppf (0.521 g, 0.722 mmol) was then added and purging was continued for a further 10 min. The reaction was heated to 100° C. and stirred under nitrogen for 6 h. The reaction was then allowed to cool, diluted with 1M HCl (100 mL) and extracted with ethyl acetate (2×100 mL) and DCM (100 mL). The combined organic layers were dried over magnesium sulfate, filtered and concentrated under vacuum. The crude product was purified by chromatography on silica gel (0-50% EtOAc/isohexane) to afford 5-nitro-[1,1'-biphenyl]-3-carboxylic acid. (1.755 g, 49%). m/z (M+H)+ (ES+) 244.0; $t_R$=2.38 min. HPLC Method 2.

Step 21-2: Morpholino(5-nitro-[1,1'-biphenyl]-3-yl) methanone.

To a stirred solution of 5-nitro-[1,1'-biphenyl]-3-carboxylic acid (0.825 g, 3.39 mmol) and HATU (1.419 g, 3.73 mmol) in DMF (20 mL) was added DIPEA (1.185 mL, 6.78 mmol) followed by morpholine (0.322 mL, 3.73 mmol). The reaction was stirred at RT for 1 h. The mixture was diluted with water (50 mL) and extracted with ethyl acetate (2×100 mL). The combined organic layers were washed with 1M HCl (200 mL), sat. sodium bicarbonate (200 mL) and brine (2×200 mL). The organic phase was then dried over magnesium sulfate, filtered and concentrated under vacuum. The crude product was purified by chromatography on silica gel (0-50% EtOAc/isohexane) to afford morpholino(5-nitro-[1,1'-biphenyl]-3-yl)methanone. (0.863 g, 81%). m/z (M+H)+ (ES+) 313.1; $t_R$=2.08 min. HPLC Method 2.

Step 21-3: (5-amino-[1,1'-biphenyl]-3-yl)(morpholino)methanone. A stirred solution/suspension of ammonium chloride (0.059 g, 1.105 mmol), iron (1.543 g, 27.6 mmol) and morpholino(5-nitro-[1,1'-biphenyl]-3-yl)methanone (0.863 g, 2.76 mmol) in EtOH (40 mL), water (5 mL) and THF (5 mL) was heated to reflux and stirred for 1 h. The reaction was allowed to cool and filtered over a pad of Celite®, rinsing with ethanol (2×50 mL). The filtrate was concentrated under vacuum to afford (5-amino-[1,1'-biphenyl]-3-yl)(morpholino)methanone. (0.607 g, 78%). m/z (M+H)+ (ES+) 283.1; $t_R$=1.58 min. HPLC Method 2.

Step 21-4: (S)-tert-butyl (1-(5-carbamoyl-4-((5-(morpholine-4-carbonyl)-[1,1'-biphenyl]-3-yl)amino)pyrimidin-2-yl)piperidin-3-yl)carbamate. To a stirred solution of DIPEA (0.143 mL, 0.816 mmol) and (5-amino-[1,1'-biphenyl]-3-yl)(morpholino)methanone (0.22 g, 0.779 mmol) in 1,4-dioxane (3 mL) was added 2,4-dichloropyrimidine-5-carboxamide (0.142 g, 0.74 mmol) and the reaction was heated to 50° C. and stirred for 3 h. The reaction mixture was then allowed to cool and (S)-tert-butyl piperidin-3-ylcarbamate (0.074 g, 0.37 mmol) and DIPEA (0.143 mL, 0.82 mmol) were added. The reaction was reheated to 50° C. for 30 min, allowed to cool and concentrated under vacuum. The crude product was purified by chromatography on silica gel (0-10% (0.7 M Ammonia/MeOH)/DCM) to afford (S)-tert-butyl (1-(5-carbamoyl-4-((5-(morpholine-4-carbonyl)-[1,1'-biphenyl]-3-yl)amino)pyrimidin-2-yl)piperidin-3-yl)carbamate. (0.099 g, 21.3%). m/z (M+H)+ (ES+) 602.3; $t_R$=2.13 min. HPLC Method 2.

Step 21-5: (S)-2-(3-aminopiperidin-1-yl)-4-((5-(morpholine-4-carbonyl)-[1,1'-biphenyl]-3-yl)amino)pyrimidine-5-carboxamide. To a stirred solution of (S)-tert-butyl (1-(5-carbamoyl-4-((5-(morpholine-4-carbonyl)-[1,1'-biphenyl]-3-yl)amino)pyrimidin-2-yl)piperidin-3-yl)carbamate (0.099 g, 0.17 mmol) in 1,4-dioxane (1 mL) was added HCl (4M in 1,4-dioxane, 0.823 mL, 3.29 mmol) and the reaction was stirred at RT for 20 h. The reaction mixture was concentrated under vacuum, dissolved in methanol (1 mL) and loaded onto SCX (ca. 1 g). This was eluted with methanol (3×20 mL), followed by 0.7M ammonia in methanol (3×20 mL). The combined ammoniacal fractions were concentrated under vacuum to afford (S)-2-(3-aminopiperidin-1-yl)-4-((5-(morpholine-4-carbonyl)-[1,1'-biphenyl]-3-yl)amino) pyrimidine-5-carboxamide. (0.04 g, 43.6%). 1H NMR (500 MHz, DMSO-d6, 90° C.) δ 11.62 (s, 1H), 8.04-8.02 (m, 1H), 7.72-7.66 (m, 3H), 7.51-7.46 (m, 2H), 7.42-7.38 (m, 1H), 7.34 (br s, 1H), 7.30-7.28 (m, 1H), 4.50-4.44 (m, 1H), 4.43-4.36 (m, 1H), 3.66-3.60 (m, 4H), 3.59-3.52 (m, 4H), 3.11-3.04 (m, 1H), 2.83 (dd, 1H, J=12.6, 9.3 Hz), 2.74-2.67 (m, 1H), 1.93-1.87 (m, 1H), 1.76-1.69 (m, 1H), 1.56-1.40 (m, 2H), 1.36-1.20 (m, 2H). m/z (M+H)+ (ES+) 502.3; $t_R$=1.78 min. HPLC Method 2.

Example 22: (S)-2-(3-aminopiperidin-1-yl)-4-((3-(pyrrolidine-1-carbonyl)phenyl)amino) pyrimidine-5-carboxamide Step 22-1: Methyl (S)-3-((2-(3-((tert-butoxycarbonyl)amino)piperidin-1-yl)-5-carbamoylpyrimidin-4-yl)amino)benzoate. The title intermediate was synthesized by a method analogous to step to 3-1, using methyl 3-aminobenzoate. White solid (2.1 g, 88.9%). 1H NMR (300 MHz, DMSO-d6) δ 11.78 (s, 1H), 8.76 (s, 1H), 8.65 (s, 1H), 7.99 (s, 1H), 7.61 (d, J=7.1 Hz, 1H), 7.48-7.31 (m, 2H), 6.95 (d, J=7.8 Hz, 1H), 4.51 (dd, J=39.0, 12.5 Hz, 2H), 3.86 (s, 3H), 3.21-2.71 (m, 1H), 1.81-1.79 (m, 2H), 1.39 (s, 9H), 1.29-1.15 (m, 2H). m/z (ES+) (M+H)+ 471.

Step 22-2: (S)-3-((2-(3-((tert-butoxycarbonyl)amino)piperidin-1-yl)-5-carbamoylpyrimidin-4-yl)amino)benzoic acid. To a solution of methyl (S)-3-((2-(3-((tert-butoxycarbonyl)amino)piperidin-1-yl)-5-carbamoylpyrimidin-4-yl)amino)benzoate (0.5 g, 1.06 mmol) in THF (6.2 mL), EtOH (6.2 mL) and H2O (1 mL), 1 N NaOH aq (2 eq) was added. The reaction mixture was heated at 75° C. for 6 h. 1 N HCl was then added and the reaction mixture was concentrated under reduced pressure. The residue was triturated in water and the resulting precipitate was recovered by filtration to give the pure product as white solid (0.28 g, 58%). 1H NMR (300 MHz, DMSO-d6) δ 11.93 (s, 1H), 8.66 (s, 1H), 8.21 (s, 1H), 7.65 (d, J=7.6 Hz, 1H), 7.47 (t, J=7.9 Hz, 1H), 6.98 (s, 1H), 4.63-4.02 (m, 2H), 3.52-3.26 (m, 1H), 3.26-2.81 (m, 2H), 1.94-1.67 (m, 2H), 1.59 (s, J=49.1 Hz, 2H), 1.46-1.21 (m, 9H). m/z (ES+) (M+H)+ 457.

Step 22-3: (S)-2-(3-aminopiperidin-1-yl)-4-((3-(pyrrolidine-1-carbonyl)phenyl)amino) pyrimidine-5-carboxamide. To a solution of (S)-3-((2-(3-((tert-butoxycarbonyl) amino) piperidin-1-yl)-5-carbamoylpyrimidin-4-yl)amino)benzoic acid (0.15 g, 0.328 mmol) in DMF (3 mL), HBTU (0.136 g), DIPEA (0.17 mL) and pyrrolidine (0.03 mL) were added. The reaction mixture was stirred at RT overnight. The residue was diluted with DCM (5 mL) and treated with TFA (1.8 mL). The reaction mixture was stirred at RT for 2.5 h. The solvent was removed under reduced pressure and the residue was purified by gradient RP-HPLC (CH3CN/H2O) to afford the title compound as a white solid (30 mg, 22%). 1H NMR (300 MHz, MeOD) δ 8.56 (s, 1H), 8.34 (s, 1H), 7.48-7.32 (m, 2H), 7.25 (d, J=7.0 Hz, 2H), 4.74-4.68 (m, 1H), 4.38-4.32 (m, 1H), 3.61-3.51 (m, 4H), 3.40-3.33 (m, 2H) 2.17-2.12 (m, 1H), 2.01-1.79 (m, 5H), 1.72-1.59 (m, 2H). HRMS m/z [M+H]+ calc $C_{21}H_{28}N_7O_2$ 410.2304 found 410.2303.

Example 23: (S)-2-(3-aminopiperidin-1-yl)-4-((3-(dimethylcarbamoyl)phenyl)amino)pyrimidine-5-carboxamide Prepared by an analogous method to example 22. (0.030 g, 32%). 1H NMR (300 MHz, MeOD) δ 8.55 (s, 1H), 8.15 (s, 1H), 7.43-7.31 (m, 2H), 7.17 (d, J=7.1 Hz, 1H), 4.68-4.64 (m, 1H), 4.24-4.19 (m, 1H), 3.40-4.32 (m, 3H), 3.07 (d, J=15.5 Hz, 6H), 2.16-2.10 (m, 1H), 1.89-1.84 (m, 1H), 1.70-1.62 (m, 2H). HRMS m/z [M+H]+ calc $C_{19}H_{28}N_7O_2$ 384.2148 found 384.2147.

Example 24: (S)-2-(3-aminopiperidin-1-yl)-4-((3-(morpholine-4-carbonyl)phenyl)amino)pyrimidine-5-carboxamide Prepared by an analogous method to example 22 and isolated by gradient flash chromatography (MeOH/DCM; 1:9, 2:8). White solid (80 mg, 35%). 1H NMR (300 MHz, MeOD) δ 8.60 (s, 1H), 8.18 (s, 1H), 7.44-7.42 (m, 2H), 7.15-7.12 (m, 1H), 4.69-4.65 (m, 1H), 4.36-4.31 (m, 1H), 3.84-3.82 (m, 3H), 3.77 (bs, 2H), 3.68-3.62 (m, 2H), 3.54-3.52 (m, 1H), 3.14-3.11 (m, 3H), 2.20-2.10 (m, 1H), 1.89-1.81 (m, 1H), 1.74-1.62 (m, 2H). HRMS m/z [M+H]+ calc $C_{21}H_{28}N_7O_3$ 426.2254 found 426.2253.

Example 25: (S)-2-(3-aminopiperidin-1-yl)-4-((3-((2-(dimethylamino)ethyl)(methyl)carbamoyl) phenyl) amino) pyrimidine-5-carboxamide Prepared by an analogous method to example 22 and isolated by gradient RP-HPLC (CH$_3$CN/H$_2$O). White solid (25 mg, 17%) $^1$H NMR (300 MHz, MeOD) δ 8.57 (s, 1H), 8.09 (s, 1H), 7.43-7.38 (m, 2H), 7.22-7.16 (m, 1H), 4.75-4.71 (m, 1H), 4.39-4.36 (m, 1H), 3.88 (br s, 2H), 3.27-3.17 (m, 3H), 3.11 (s, 3H), 2.79 (s, 5H), 2.68 (s, 1H), 2.37 (s, 2H), 2.28 (s, 1H), 2.21-2.18 (m, 1H), 1.89-1.82 (m, 1H), 1.78-1.71 (m, 1H), 1.67-1.60 (m, 1H). HRMS m/z [M+H]+ calc C$_{22}$H$_{33}$N$_8$O$_2$ 441.2726 found 441.2727.

Example 26: (S)-2-(3-aminopiperidin-1-yl)-4-((3-(piperidine-1-carbonyl)phenyl)amino)pyrimidine-5-carboxamide Prepared by an analogous method to example 22 and isolated by filtration with SCX cartridge, washing with MeOH (3 column volumes) and eluting with 2M NH$_3$ in MeOH (3 column volumes). White solid (60 mg, 32%). $^1$H NMR (300 MHz, MeOD) δ 8.46 (s, 1H), 8.01 (s, 1H), 7.35-7.28 (m, 2H), 6.98-6.95 (m, 1H), 4.60-4.57 (m, 1H), 4.40-4.36 (m, 1H), 3.62 (br s, 2H), 3.34 (br s, 1H), 3.00-2.96 (m, 2H), 2.89-2.82 (m, 2H), 1.99-1.96 (m, 1H), 1.70-1.59 (m, 6H), 1.49-1.42 (m, 3H). HRMS m/z [M+H]+ calc C$_{22}$H$_{30}$N$_7$O$_2$ 424.2461 found 424.2462.

Example 27: (S)-2-(3-aminopiperidin-1-yl)-4-((3-(tert-butyl)-5-(dimethylcarbamoyl)phenyl)amino) pyrimidine-5-carboxamide Step 27-1: 3-(tert-butyl)-5-(methoxycarbonyl)benzoic acid. A solution of 5-(tert-butyl)isophthalic acid (6 g, 27 mmol) in THF/MeOH (4:1, 180 mL) was stirred at reflux for 4 h. The solvents were removed and the crude solid purified by flash column chromatography (gradient: hexane/diethyl ether=(4:1) to (2:1)) to furnish the desired product (2.5 g, 40%). $^1$H NMR (400 MHz, CDCl$_3$) δ 8.61 (t, J=1.6 Hz, 1H), 8.35 (d, J=1.5 Hz, 2H), 3.99 (s, 3H), 1.42 (s, 9H); m/z (ES) C$_{13}$H$_{15}$O$_4$ [MH]+ 237.1.

Step 27-2: methyl 3-((tert-butoxycarbonyl)amino)-5-(tert-butyl)benzoate. A solution of 3-(tert-butyl)-5-(methoxycarbonyl)benzoic acid (472 mg, 2 mmol), DPPA (520 μL, 2.5 mmol) and DIPEA (440 μL, 2.5 mmol) in $^t$BuOH/dioxane (3:2, 10 mL) was stirred at 80° C. for 4 h. Upon complete consumption of the starting material the mixture was allowed to reach RT the mixture, diluted with EtOAc and sequentially washed with NaHCO$_3$ (1×15 mL) and brine (1×15 mL), dried with MgSO$_4$, and condensed. The crude was purified by flash column chromatography (gradient: hexane/ethyl acetate=(3:1) to (1:1)) to give the desired product as a clear oil (530 mg) in 86%. $^1$H NMR (300 MHz, CDCl$_3$) δ 7.82 (s, 1H), 7.66 (t, J=1.6 Hz, 1H), 7.61 (s, 1H), 3.80 (s, 3H), 1.23 (s, 9H); m/z (ES) C$_{17}$H$_{25}$NO$_4$ [MNa]+ 308.1.

Step 27-3: methyl 3-amino-5-(tert-butyl)benzoate. To a solution of methyl 3-((tert-butoxycarbonyl)amino)-5-(tert-butyl)benzoate (530 mg, 1.72 mmol) in DCM (10 mL), TFA (2 mL) was added in one pot and the mixture was stirred at RT for 2 h. The reaction mixture was then washed with NaHCO$_3$ (2×15 mL) and brine (1×15 mL), dried with MgSO$_4$, and condensed. The crude was purified by flash column chromatography (gradient: hexane/ethyl acetate=(3:1) to (1:1)) to give the desired product as a clear oil (268 mg, 75%). $^1$H NMR (300 MHz, CDCl$_3$) δ 7.50 (t, J=1.6 Hz, 1H), 7.21 (dd, J=2.3, 1.4 Hz, 1H), 6.94-6.90 (m, 1H), 3.91 (s, 3H), 3.71 (s, 2H), 1.33 (s, 9H); m/z (ES) C$_{12}$H$_{17}$NO$_2$ [MH]+ 208.1.

Step 27-4: Methyl (S)-3-((2-(3-((tert-butoxycarbonyl)amino)piperidin-1-yl)-5-carbamoylpyrimidin-4-yl)amino)-5-(tert-butyl)benzoate. Prepared by an analogous method to example 3. (Step 3: THF, DIPEA, 12 h, RT), using methyl 3-amino-5-(tert-butyl)benzoate, prepared as described in example 27. White solid (686 mg, 72%). $^1$H NMR (300 MHz, MeOD) δ 8.55 (s, 1H), 8.41 (s, 1H), 7.77 (d, J=1.5 Hz, 2H), 4.57 (d, J=10.5 Hz, 1H), 4.46 (d, J=11.4 Hz, 1H), 3.93 (s, 3H), 3.55 (d, J=8.8 Hz, 1H), 3.30-3.09 (m, 2H), 2.05-1.96 (m, 1H), 1.91-1.77 (m, 1H), 1.65-1.50 (m, 2H), 1.42 (s, 9H), 1.38 (s, 9H); m/z (ES) C$_{27}$H$_{38}$N$_6$O$_5$[MH]+ 527.3.

Step 27-5: (S)-2-(3-aminopiperidin-1-yl)-4-((3-(tert-butyl)-5-(dimethylcarbamoyl)phenyl)amino) pyrimidine-5-carboxamide. Prepared from methyl (S)-3-((2-(3-((tert-butoxycarbonyl)amino)piperidin-1-yl)-5-carbamoylpyrimidin-4-yl)amino)-5-(tert-butyl)benzoate by an analogous method to example 22 and isolated by reverse phase HPLC (H$_2$O: MeOH gradient). White solid (20.7 mg, 24%). $^1$H NMR (400 MHz, MeOD) δ 8.48 (s, 1H), 7.83 (s, 1H), 7.39 (s, 1H), 7.09 (t, J=1.5 Hz, 1H), 4.59 (d, J=10.7 Hz, 1H), 4.31 (d, J=12.7 Hz, 1H), 3.22-3.08 (m, 2H), 3.04 (s, 3H), 2.97 (s, 2H), 2.03 (d, J=9.3 Hz, 1H), 1.74 (dd, J=9.0, 4.1 Hz, 1H), 1.61-1.42 (m, 2H), 1.27 (s, 9H); m/z (ES HRMS) C$_{23}$H$_{34}$N$_7$O$_2$ calc 440.2774, found [MH]+ 440.2772.

Example 28: (S)-2-(3-aminopiperidin-1-yl)-4-((3-(tert-butyl)-5-(pyrrolidine-1-carbonyl)phenyl)amino) pyrimidine-5-carboxamide Prepared from methyl (S)-3-((2-(3-((tert-butoxycarbonyl)amino)piperidin-1-yl)-5-carbamoylpyrimidin-4-yl)amino)-5-(tert-butyl)benzoate by an analogous method to example 22 and isolated by reverse phase HPLC (H$_2$O:MeOH gradient). White solid (18.2 mg, 20%). $^1$H NMR (400 MHz, MeOD) δ 8.48 (s, 1H), 7.98 (s, 1H), 7.37 (s, 1H), 7.21 (s, 1H), 4.62 (s, 1H), 4.31 (d, J=13.0 Hz, 1H), 3.53 (t, J=6.9 Hz, 2H), 3.47-3.40 (m, 2H), 3.22-3.13 (m, 2H), 3.12-3.04 (m, 1H), 2.04 (d, J=9.6 Hz, 1H), 1.97-1.88 (m, 2H), 1.83 (dt, J=15.3, 4.6 Hz, 2H), 1.75 (dd, J=9.3, 4.1 Hz, 1H), 1.63-1.47 (m, 2H), 1.28 (s, 9H); m/z (ES HRMS) C$_{25}$H$_{36}$N$_7$O$_2$ calc 466.2930, found [MH]+ 466.2926

Example 29: (S)-2-(3-aminopiperidin-1-yl)-4-((3-(tert-butyl)-5-(morpholine-4-carbonyl)phenyl) amino)pyrimidine-5-carboxamide Prepared from methyl (S)-3-((2-(3-((tert-butoxycarbonyl)amino)piperidin-1-yl)-5-carbamoylpyrimidin-4-yl)amino)-5-(tert-butyl)benzoate by an analogous method to example 22 and isolated by reverse phase HPLC (H$_2$O:MeOH gradient). White solid (15.4 mg, 17%). $^1$H NMR (400 MHz, MeOD) δ 8.49 (s, 1H), 7.81 (s, 1H), 7.44 (s, 1H), 7.07 (t, J=1.6 Hz, 1H), 4.58 (d, J=10.8 Hz, 1H), 4.30 (d, J=12.7 Hz, 1H), 3.69 (s, 4H), 3.55 (s, 2H), 3.43 (s, 2H), 3.21-3.11 (m, 2H), 3.11-3.00 (m, 1H), 2.04 (d, J=9.0 Hz, 1H), 1.80-1.69 (m, 1H), 1.62-1.49 (m, 2H), 1.27 (s, 9H); m/z (ES HRMS) C$_{25}$H$_{36}$N$_7$O$_3$ calc 482.2880, found [MH]+ 482.2876

Example 30: (S)-2-(3-aminopiperidin-1-yl)-4-((3-(3,3-dimethylmorpholine-4-carbonyl)phenyl)amino) pyrimidine-5-carboxamide Prepared by an analogous method to example 22 and isolated by flash chromatography (MeOH/DCM 1:99).

White solid (65 g, 28%). $^1$H NMR (400 MHz, MeOD) δ 8.53 (s, 1H), 8.17 (s, 1H), 7.45-7.36 (m, 2H), 7.08 (d, J=7.2 Hz, 1H), 4.70-4.67 (m, 1H), 4.54-4.50 (m, 1H), 3.74-372 (m, 2H), 3.49 (s, 2H), 3.43-3.42 (m, 2H), 3.07-3.01 (m, 1H), 2.87-2.79 (m, 2H), 2.04-2.01 (m, 1H), 1.83-1.79 (m, 1H), 1.51 (s, 7H), 1.45-1.35 (m, 1H). HRMS m/z [M+H]+ calc $C_{23}H_{32}N_7O_3$ 454.2567 found 458.2568.

Example 31: (S)-2-(3-aminopiperidin-1-yl)-4-((3-(piperidine-1-carbonyl)-5-(trifluoromethyl)phenyl) amino) pyrimidine-5-carboxamide Step 31-1: Methyl 3-((2-(3-((tert-butoxycarbonyl)amino) piperidin-1-yl)-5-carbamoylpyrimidin-4-yl)amino)-5-(trifluoromethyl)benzoate. The title intermediate was synthesized by an analogous method to example 3 (Step 1: THF, DIPEA, 12 h, RT), using methyl 3-amino-5-(trifluoromethyl)benzoate. White solid (0.79 g, quant). $^1$H NMR (300 MHz, MeOD) δ 8.58 (s, 2H), 8.30 (s, 1H), 7.86 (s, 1H), 6.71 (d, J=7.8 Hz, 1H), 4.54 (d, J=12.2 Hz, 1H), 4.40 (d, J=12.9 Hz, 1H), 3.96 (s, 3H), 3.62-3.45 (m, 1H), 3.24-3.10 (m, 2H), 2.07-1.90 (m, 1H), 1.90-1.74 (m, 1H), 1.62-1.50 (m, 2H), 1.41 (s, 9H). m/z (ES) [M+H]$_+$ 539.4.

Step 32-2: (S)-2-(3-aminopiperidin-1-yl)-4-((3-(piperidine-1-carbonyl)-5-(trifluoromethyl)phenyl) amino) pyrimidine-5-carboxamide. Prepared from methyl 3-((2-(3-((tert-butoxycarbonyl)amino)piperidin-1-yl)-5-carbamoylpyrimidin-4-yl)amino)-5-(trifluoromethyl) benzoate by an analogous method to example 22 and isolated by flash chromatography (MeOH/DCM 2:8). Colourless oil (50 mg, 32%). $^1$H NMR (300 MHz, MeOD) δ 8.58 (s, 1H), 8.19 (s, 1H), 7.94 (s, 1H), 7.32 (s, 1H), 4.64-4.61 (m, 1H), 4.51-4.47 (m, 1H), 3.72 (bs, 2H), 3.40 (bs, 2H), 3.11-3.04 (m, 1H), 2.88-2.80 (m, 2H), 2.04 (bs, 1H), 1.83-1.39 (m, 9H). HRMS m/z [M+H]+ calc $C_{23}H_{29}F_3N_7O_2$ 492.2335 found 492.2332.

Example 32: (S)-2-(3-aminopiperidin-1-yl)-4-((3-(3, 3-dimethylmorpholine-4-carbonyl)-5-(trifluoromethyl)phenyl)amino)pyrimidine-5-carboxamide Step 32-1: Methyl 3-((5-carbamoyl-2-chloropyrimidin-4-yl)amino)-5-(trifluoromethyl)benzoate. To a solution of 2,4-dichloropyrimidine-5-carboxamide (0.662 g) and ethyl 3-amino-5-(trifluoromethyl)benzoate (0.76 g), DIPEA (0.7 mL, 1.25 eq) was added. The reaction mixture was stirred at RT for 16 h. The solvent was evaporated under reduced pressure and the residue was solubilized in acetonitrile and precipitate with Et$_2$O. The pure product was recovered by filtration. White solid (0.557 g, 43%). $^1$H NMR (300 MHz, MeOD) δ 8.76 (s, 1H), 8.47 (s, 2H), 8.02 (s, 1H), 3.98 (s, 3H).

Step 32-2: Methyl 3-((2-(3-((tert-butoxycarbonyl)amino) piperidin-1-yl)-5-carbamoylpyrimidin-4-yl)amino)-5-(trifluoromethyl)benzoate. To a solution of Methyl 3-((5-carbamoyl-2-chloropyrimidin-4-yl)amino)-5-(trifluoromethyl) benzoate (0.557 g, 1.47 mmol) in DCM (6 mL), DIPEA (0.26 mL) and tert-butyl (S)-piperidin-3-ylcarbamate (0.3 g) were added. The reaction mixture was stirred at RT for 72 h. The solvent was evaporated under pressure, the residue was triturated in Et$_2$O and the resulting precipitated was recovered by filtration to give the pure product as white solid (0.79 g, quant). $^1$H NMR (300 MHz, MeOD) δ 8.58 (s, 2H), 8.30 (s, 1H), 7.86 (s, 1H), 6.71 (d, J=7.8 Hz, 1H), 4.54 (d, J=12.2 Hz, 1H), 4.40 (d, J=12.9 Hz, 1H), 3.96 (s, 3H), 3.62-3.45 (m, 1H), 3.24-3.10 (m, 2H), 2.07-1.90 (m, 1H), 1.90-1.74 (m, 1H), 1.62-1.50 (m, 2H), 1.41 (s, 9H).

Step 32-3: 3-((2-(3-((tert-butoxycarbonyl)amino)piperidin-1-yl)-5-carbamoylpyrimidin-4-yl)amino)-5-(trifluoromethyl)benzoic acid. To a solution of Methyl 3-((2-(3-((tert-butoxycarbonyl)amino)piperidin-1-yl)-5-carbamoylpyrimidin-4-yl)amino)-5-(trifluoromethyl) benzoate (0.79 g, 1.47 mmol) in THF (8.5 mL), EtOH (8.5 mL) and H$_2$O (1.38 mL), 1 N NaOH aq (2.9 mL) was added. The reaction mixture was heated at 75° C. for 6 h. 1 N HCl was then added and the reaction mixture was concentrated under reduced pressure. The residue was triturated in water and the resulting precipitate was recovered by filtration to give the pure product as white solid (0.587 g, 75.4%). $^1$H NMR (300 MHz, DMSO-d6) δ 13.51 (s, 1H), 12.00 (s, 1H), 8.69 (s, 1H), 8.44 (s, 1H), 8.04 (s, 1H), 7.79 (s, 1H), 7.46 (s, 1H), 6.93 (s, 1H), 4.66-4.25 (m, 2H), 3.18-2.83 (m, 2H), 1.79 (d, J=31.3 Hz, 2H), 1.48-1.11 (m, 12H).

Step 32-4: (S)-2-(3-aminopiperidin-1-yl)-4-((3-(3,3-dimethylmorpholine-4-carbonyl)-5-(trifluoromethyl)phenyl) amino)pyrimidine-5-carboxamide. To a solution of 3-((2-(3-((tert-butoxycarbonyl)amino)piperidin-1-yl)-5-carbamoylpyrimidin-4-yl)amino)-5-(trifluoromethyl) benzoic acid. (115 mg, 0.355 mmol) in DCM (2 mL), HBTU (0.390 mmol), DIPEA (0.390 mmol) and 3,3-dimethylmorpholine (0.390 mmol were added. The reaction mixture was stirred at RT for 72 h, then TFA (2.5 mL) was added. The reaction mixture was stirred at RT for 2.5 h. The solvent was removed under reduced pressure. The residue was filtrated with SCX cartridge, washing with MeOH (3 column volumes) and eluting with 2M NH$_3$ in MeOH (3 column volumes) and concentrated. The residue was washed with Et$_2$O to remove residue of DIPEA. White solid (20 mg, 10%). $^1$H NMR (300 MHz, MeOD) δ 8.58 (s, 1H), 8.15-7.09 (m, 2H), 7.33 (s, 1H), 4.70-4.50 (m, 1H), 4.43-4.17 (m, 1H), 3.84-3.61 (m, 2H), 3.49 (s, 2H), 3.37 (t, J=5.0 Hz, 2H), 3.14-2.92 (m, 3H), 2.03-1.97 (m, 1H), 1.86-1.77 (m, 1H), 1.57-1.55 (m, 1H), 1.50 (s, 6H), 1.15 (t, J=7.0 Hz, 1H). HRMS m/z [M+H]$^+$ calc $C_{24}H_{31}F_3N_7O_3$ 522.2440 found 522.2437.

Example 33: 2-((S)-3-aminopiperidin-1-yl)-4-((3-((3S,5R)-3,5-dimethylmorpholine-4-carbonyl)phenyl)amino)pyrimidine-5-carboxamide hydrochloride Step 33-1: tert-butyl ((S)-1-(5-carbamoyl-4-((3-((3S,5R)-3,5-dimethylmorpholine-4-carbonyl)phenyl)amino)pyrimidin-2-yl)piperidin-3-yl)carbamate. To a stirred solution of (S)-3-((2-(3-((tert-butoxycarbonyl)amino)piperidin-1-yl)-5-carbamoylpyrimidin-4-yl)amino)benzoic acid (0.09 g, 0.197 mmol) and DIPEA (0.069 mL, 0.394 mmol) was added 2-(3H-[1,2,3]triazolo[4,5-b]pyridin-3-yl)-1,1,3,3-tetramethylisouronium hexafluorophosphate(V) (0.079 g, 0.207 mmol) followed by (3R,5S)-3,5-dimethylmorpholine (0.024 g, 0.207 mmol). The reaction was stirred at RT for 18 h, then diluted with water (20 mL) and extracted with ethyl acetate (2×20 mL) and DCM (1×20 mL). The combined organic layers were dried over magnesium sulfate, filtered and concentrated under vacuum. The crude product was purified by silica gel chromatography (0-5% (0.7 M Ammonia/MeOH)/DCM) to afford tert-butyl ((S)-1-(5-carbamoyl-4-((3-((3S,5R)-3,5-dimethylmorpholine-4-carbonyl)phenyl) amino)pyrimidin-2-yl)piperidin-3-yl)carbamate. (0.038 g, 33.8%). m/z (M+H)+(ES$^+$) 554.3; $t_R$=1.84 min. HPLC Method 2.

Step 33-2: 2-((S)-3-aminopiperidin-1-yl)-4-((3-((3S,5R)-3,5-dimethylmorpholine-4-carbonyl)phenyl)amino)pyrimidine-5-carboxamide hydrochloride. To a stirred solution of tert-butyl ((S)-1-(5-carbamoyl-4-((3-((3S,5R)-3,5-dimethylmorpholine-4-carbonyl)phenyl) amino)pyrimidin-2-yl)piperidin-3-yl)carbamate (0.038 g, 0.069 mmol) in 1,4-dioxane (1 mL) was added hydrogen chloride (0.343 mL, 1.373 mmol) (4M in 1,4-dioxane) and the reaction was stirred at RT for 16 h. The reaction mixture was concentrated under vacuum to afford the hydrochloride salt of the title compound. (0.028 g, 79%). $^1$H NMR (400 MHz, MeOD) δ 8.53 (s, 1H), 7.94, (s, 1H), 7.50 (t, 1H, J=7.8 Hz), 7.46-7.39 (m, 1H), 7.28 (d, 1H, J=7.4 Hz), 4.68-4.52 (br m, 1H), 4.32-3.94 (m, 3H), 3.77-3.52 (m, 6H), 3.50-3.35 (br m, 3H), 2.24-2.12 (br m, 1H), 2.02-1.90 (br m, 1H), 1.84-1.68 (br m, 2H), 1.41-1.30 (m, 8H); m/z (M+H)$^+$ (ES$^+$) 454.1; $t_R$=1.44 min. HPLC Method 4

Example 34: 2-((S)-3-aminopiperidin-1-yl)-4-((3-((R)-octahydropyrrolo[1,2-a]pyrazine-2-carbonyl) phenyl)amino)pyrimidine-5-carboxamide Prepared by an analogous method to example 33. Step 2 purification: The product was dissolved in methanol (1 mL) and loaded onto a SCX cartridge, washing with MeOH (3 column volumes) and eluting with 1% NH$_3$ in MeOH (3 column volumes). The ammoniacal fractions were concentrated under reduced pressure. The product was further purified by silica gel chromatography (0-10% (0.7 M Ammonia/MeOH)/DCM). (0.054 g, 48%). $^1$H NMR (500 MHz, MeOD) δ 8.56 (s, 1H), 8.16 (br s, 1H), 7.55-7.46 (m, 1H), 7.46-7.41 (m, 1H), 7.12-7.07 (m, 1H), 4.82-4.62 (m, 2H), 4.53 (br d, 1H, J=12.3 Hz), 3.94-3.74 (m, 1H), 3.32-2.94 (m, 5H), 2.92-2.77 (m, 2H), 2.33-2.14 (m, 2H), 2.12-1.95 (m, 2H), 1.92-1.72 (m, 4H), 1.62-1.25 (m, 3H); m/z (M+H)$^+$ (ES$^+$) 454.1; $t_R$=1.44 min. HPLC Method 4.

Example 35: (S)-2-(3-aminopiperidin-1-yl)-4-((3-(5-methoxyisoindoline-2-carbonyl)phenyl)amino)pyrimidine-5-carboxamide Prepared by an analogous method to example 33. Step 2 purification: The product was purified by silica gel chromatography (0-10% (0.7 M Ammonia/MeOH)/DCM). (0.041 g, 39.8%). $^1$H NMR (400 MHz, DMSO-d6, 100° C.) δ 11.47 (s, 1H), 8.62 (s, 1H), 8.10-8.07 (m, 1H), 7.59-7.54 (m, 1H), 7.43 (t, 1H, J=7.7 Hz), 7.29-7.18 (m, 4H), 6.94-6.89 (br m, 1H), 6.86 (dd, 1H, J=8.4, 2.4 Hz), 4.80 (s, 2H), 4.75 (s, 2H), 4.47-4.41 (m, 1H), 4.39-4.31 (m, 1H), 3.77 (s, 3H), 3.09-3.00 (m, 1H), 2.81 (dd, 1H, J=12.4, 9.2 Hz), 2.74-2.65 (m, 1H), 1.90-1.81 (m, 1H), 1.80-1.62 (m, 3H), 1.46-1.34 (m, 1H), 1.32-1.20 (m, 1H). m/z (M+H)$^+$ (ES$^+$) 488.1; $t_R$=1.63 min. HPLC Method 4.

Example 36: 2-((S)-3-aminopiperidin-1-yl)-4-((3-((R)-2-(methoxymethyl)pyrrolidine-1-carbonyl)phenyl)amino)pyrimidine-5-carboxamide hydrochloride Prepared by an analogous method to example 33 to give the hydrochloride salt. (0.029 g, 59.0%). $^1$H NMR (500 MHz, DMSO-d6, 90° C.) δ 11.60 (s, 1H), 8.70 (s, 1H), 8.25 (br s, 3H), 7.89-7.85 (m, 1H), 7.64-7.59 (m, 1H), 7.47-7.41 (m, 1H), 7.20-7.16 (m, 1H), 4.60-4.50 (m, 1H), 4.29-4.21 (br m, 1H), 4.20-4.15 (m, 1H), 3.56-3.31 (m, 6H), 3.30-3.18 (br m, 4H), 2.13-2.05 (m, 1H), 2.04-1.97 (m, 1H), 1.96-1.70 (m, 5H), 1.61-1.50 (m, 1H). m/z (M+H)$^+$ (ES$^+$) 454.1; $t_R$=1.48 min. HPLC Method 4.

Example 37: (S)-2-(3-aminopiperidin-1-yl)-4-((3-(3-(2-hydroxypropan-2-yl)azetidine-1-carbonyl)phenyl) amino)pyrimidine-5-carboxamide hydrochloride Prepared by an analogous method to example 33 to give the hydrochloride salt. (0.012 g, 30%). $^1$H NMR (400 MHz, MeOD) δ 8.63 (br s, 1H), 8.57 (s, 1H), 7.55-7.48 (m, 2H), 7.46-7.38 (br m, 1H), 4.85-4.70 (br m, 2H), 4.51-4.29 (m, 2H), 4.20-4.05 (m, 3H), 3.59-3.45 (m, 3H), 2.81-2.72 (m, 1H), 2.31-2.20 (br m, 1H), 2.08-1.97 (br m, 1H), 1.90-1.76 (br m, 2H), 1.20-1.13 (m, 6H). m/z (M+H)$^+$ (ES+) 454.1; $t_R$=1.30 min. HPLC Method 4.

Example 38: (S)-2-(3-aminopiperidin-1-yl)-4-((3-(4-methyl-3-oxopiperazine-1-carbonyl)phenyl)amino) pyrimidine-5-carboxamide hydrochloride Prepared by an analogous method to example 33 to give the hydrochloride salt. (0.058 g, 88%). $^1$H NMR (500 MHz, DMSO-d6, 90° C.) δ 11.60 (s, 1H), 8.70 (s, 1H), 8.21 (br s, 3H), 7.82-7.80 (m, 1H), 7.69-7.65 (m, 1H), 7.47 (t, 1H, J=7.8 Hz), 7.16-7.12 (m, 1H), 4.58-4.52 (m, 1H), 4.23-4.17 (m, 1H), 4.09 (s, 2H), 3.77-3.69 (m, 2H), 3.56-3.49 (m 1H), 3.46-3.41 (m, 1H), 3.39 (t, 2H, J=5.5 Hz), 3.35-3.27 (m, 1H), 3.23 (br s, 1H), 2.89 (s, 3H), 2.12-2.04 (m, 1H), 1.86-1.79 (m, 1H), 1.78-1.69 (m, 1H), 1.60-1.49 (m, 1H). m/z (M+H)$^+$ (ES$^+$) 453.1; $t_R$=1.19 min. HPLC Method 4.

Example 39: 2-((S)-3-aminopiperidin-1-yl)-4-((3-((2R,6S)-2,6-dimethylmorpholine-4-carbonyl)phenyl)amino)pyrimidine-5-carboxamide Prepared by an analogous method to example 33. Step 2 purification: The product was purified by silica gel chromatography (0-10% (0.7 M Ammonia/MeOH)/DCM). (0.036 g, 54%). $^1$H NMR (400 MHz, DMSO-d6, 100° C.) δ 11.46 (s, 1H), 8.62 (s, 1H), 7.89 (t, 1H, J=1.9 Hz), 7.55-7.51 (m, 1H), 7.39 (t, 1H, J=7.8 Hz), 7.25 (br s, 2H), 7.05-7.01 (m, 1H), 4.48-4.41 (m, 1H), 4.39-4.32 (m, 1H), 4.00-3.86 (m, 2H), 3.60-3.50 (m, 2H), 3.12-3.04 (m, 1H), 2.84 (dd, 1H, J=12.6, 9.2 Hz), 2.77-2.69 (m, 1H), 2.69-2.60 (m, 2H), 1.96-1.86 (m, 1H), 1.78-1.62 (m, 3H), 1.50-1.38 (m, 1H), 1.37-1.26 (m, 1H), 1.09 (d, 6H, J=6.2 Hz). m/z (M+H)$^+$ (ES+) 454.1; $t_R$=1.42 min. HPLC Method 4.

Example 40: (S)-2-(3-aminopiperidin-1-yl)-4-((3-(4-(thiazol-2-yl)piperazine-1-carbonyl)phenyl)amino) pyrimidine-5-carboxamide hydrochloride Prepared by an analogous method to example 33 to give the hydrochloride salt. (0.026 g, 92%). $^1$H NMR (500 MHz, DMSO-d6, 90° C.) δ 11.65 (s, 1H), 8.71 (s, 1H), 8.28 (br s, 3H), 7.82-7.78 (m, 1H), 7.71-7.65 (m, 1H), 7.68 (d, 1H, J=7.5 Hz), 7.52-7.46 (m, 1H), 7.23 (d, 1H, J=3.8 Hz), 7.16 (d, 1H, J=7.5 Hz), 6.90 (d, 1H, J=3.8 Hz), 4.58-4.50 (m, 1H), 4.24-4.16 (m, 1H), 3.74-3.63 (m, 4H), 3.60-3.53 (m, 4H), 3.50-3.44 (m, 1H), 3.38-3.31 (m, 1H), 3.29-3.19 (m, 1H), 2.12-2.04 (m, 1H), 1.87-1.70 (m, 2H), 1.61-1.51 (m, 1H). m/z (M+H)$^+$ (ES$^+$) 508.2; $t_R$=1.09 min. HPLC Method 2.

Example 41: 2-((S)-3-aminopiperidin-1-yl)-4-((3-((R)-3-phenylpiperidine-1-carbonyl)phenyl)amino) pyrimidine-5-carboxamide Prepared by an analogous method to example 33. The product was purified by silica gel chromatography (0-10% (0.7 M Ammonia/MeOH)/DCM). (0.011 g, 16.73%). $^1$H NMR (400 MHz, MeOD) δ 8.57 (s, 1H), 8.17 (br s, 1H), 7.52-7.10 (m, 8H), 4.75-4.63 (m, 2H), 4.60-4.46 (m, 1H), 3.92-3.76 (m, 1H), 3.25-3.03 (m, 2H), 3.00-2.73 (m, 4H), 2.12-1.38 (m, 8H). m/z (M+H)$^+$ (ES$^+$) 500.1; $t_R$=1.45 min. HPLC Method 2.

Example 42: (S)-2-(3-aminopiperidin-1-yl)-4-((3-(dimethylcarbamoyl)-5-(trifluoromethyl)phenyl) amino) pyrimidine-5-carboxamide Step 42-1: 3-amino-N,N-dimethyl-5-(trifluoromethyl) benzamide. Dimethylamine hydrochloride (0.239 g, 2.92 mmol) was added to a solution of HATU (0.667 g, 1.75 mmol), Triethylamine (0.612 mL, 4.39 mmol) and 3-amino-5-(trifluoromethyl)benzoic acid (0.300 g, 1.46 mmol) in DMF (5 mL). The reaction was stirred at RT for 4 h. The reaction was quenched with water (10 mL) and the aqueous layer was extracted with EtOAc (2×20 mL). The combined organic layers were dried ($Na_2SO_4$) and concentrated under reduced pressure. The residue was purified by silica gel chromatography (EtOAc/Hexane). (0.298 g, 74%). m/z ($ES^+$) $(M+H)^+$ 233; $t_R$=1.48 min. HPLC Method 2.

Step 42-2: (S)-2-(3-aminopiperidin-1-yl)-4-((3-(dimethylcarbamoyl)-5-(trifluoromethyl)phenyl) amino) pyrimidine-5-carboxamide. Prepared by an analogous method to example 3, using 3-amino-N,N-dimethyl-5-(trifluoromethyl)benzamide. (0.0256 g, 58%). $^1$H NMR (400 MHz, MeOD) δ 8.62-8.60 (m, 1H), 7.41-7.39 (m, 1H), 4.66-4.45 (m, 2H), 3.24-2.92 (m, 9H), 2.09 (br s, 1H), 1.89-1.85 (m, 1H), 1.66-1.46 (m, 2H). m/z ($ES^+$) $(M+H)^+$ 452; $t_R$=1.20 min. HPLC Method 2.

Example 43: (S)-2-(3-aminopiperidin-1-yl)-4-((3-(morpholine-4-carbonyl)-5-(trifluoromethyl)phenyl) amino)pyrimidine-5-carboxamide Prepared by an analogous method to example 42, using (3-amino-5-(trifluoromethyl)phenyl)(morpholino)methanone. (0.052 g, 73%). $^1$H NMR (400 MHz, MeOD) δ 8.61 (s, 1H), 8.28 (br s, 2H), 7.47-7.33 (m, 1H), 4.66 (d, 1H), 4.53 (s, 1H), 3.83-3.63 (m, 6H), 3.54-3.44 (m, 2H), 3.17-2.78 (m, 3H), 2.09-2.01 (m, 1H), 1.88-1.81 (m, 1H), 1.64-1.40 (m, 2H). m/z ($ES^+$) $(M+H)^+$ 494; $t_R$=1.19 min. HPLC Method 2.

Example 44: (S)-2-(3-aminopiperidin-1-yl)-4-((2'-methyl-5-(morpholine-4-carbonyl)-[1,1'-biphenyl]-3-yl)amino)pyrimidine-5-carboxamide Step 44-1: (2'-methyl-5-nitro-[1,1'-biphenyl]-3-yl)(morpholino)methanone. To a solution of 6-methyl-3'-nitro-[1,1'-biphenyl]-2-carboxylic acid (0.3 g, 1eq) in DCM (5 mL), HBTU (0.486 g), DIPEA (0.223 mL) and morpholine (0.112 mL) were added. The reaction mixture was stirred at RT overnight and then concentrated under vacuum. The residue was purified by gradient flash chromatography (EtOAc/PE 4:6). White solid (0.3 g, 79%). $^1$H NMR (300 MHz, $CDCl_3$) δ 8.31-8.20 (m, 2H), 7.70 (t, J=1.5 Hz, 1H), 7.39-7.29 (m, 3H), 7.22 (d, J=7.1 Hz, 1H), 4.04-3.30 (m, 8H), 2.29 (s, 3H).

Step 44-2: (5-amino-2'-methyl-[1,1'-biphenyl]-3-yl) (morpholino)methanone. To a solution of (2'-methyl-5-nitro-[1,1'-biphenyl]-3-yl)(morpholino)methanone. (40 mg) in MeOH/EtOAc (1:1, 10 mL), Pd/C cat. was added. The reaction was stirred at RT for 12 h under H2 atmosphere (80 psi). Pd/C was filtered off and the solvents were evaporated to give the pure product as a white solid (35 mg). $^1$H NMR (300 MHz, MeOD) δ 7.24-7.20 (m, 2H), 7.19-7.13 (m, 2H), 6.71 (dd, 2.2, 1.5 Hz, 1H), 6.68 (dd, J=2.2, 1.5 Hz, 1H), 6.56 (t, J=1.5 Hz, 1H), 3.79-3.35 (m, 5H), 3.25-3.06 (m, 3H), 2.24 (s, 3H).

Step 44-3: (S)-2-(3-aminopiperidin-1-yl)-4-((2'-methyl-5-(morpholine-4-carbonyl)-[1,1'-biphenyl]-3-yl)amino)pyrimidine-5-carboxamide. A solution of (5-amino-2'-methyl-[1,1'-biphenyl]-3-yl)(morpholino)methanone, 2,4-dichloropyrimidine-5-carboxamide and DIPEA in $CH_3CN$ was heated at 80° C. for 48 h. The reaction was cooled down, DIPEA and (S)-piperidin-3-amine hydrochloride were added. The reaction mixture was allowed to stir under heating at 80° C. for 12 h. The solvent was removed under vacuum and the residue was triturated in $Et_2O$. The resulting precipitate was collected by filtration. Grey solid (20 mg, 34%). $^1$H NMR (300 MHz, MeOD) δ 8.59 (s, 1H), 8.12 (s, 1H), 7.42 (s, 1H), 7.32-7.25 (m, 2H), 7.24-7.20 (m, 1H), 7.05 (s, 1H), 4.74-4.56 (m, 1H), 4.32-4.15 (m, 1H), 3.78-3.71 (m, 3H), 3.65-3.58 (m, 2H), 2.91-2.82 (m, 1H), 2.27 (s, 3H), 2.13-1.96 (m, 2H), 1.86-1.52 (m, 6H). HRMS m/z [M+H]+ calc $C_{28}H_{34}N_7O_3$ 516.2723 found 516.2722.

Example 45: Methyl (S)-3-((2-(3-aminopiperidin-1-yl)-5-carbamoylpyrimidin-4-yl)amino)-5-(2-cyanopropan-2-yl)benzoate Prepared by an analogous route to example 3 using methyl 3-amino-5-(2-cyanopropan-2-yl)benzoate (prepared following WO2006040568). $^1$H NMR (400 MHz, MeOD) δ 8.7 (br s, 1H), 8.54 (s, 1H), 7.84-7.78 (m, 2H), 4.72-4.50 (m, 2H), 3.29 (s, 3H) 3.14-3.03 (m, 1H) 2.96-2.72 (m, 2H), 2.07-1.98 (m, 1H), 1.89-1.72 (m, 7H), 1.63-1.30 (m, 2H). m/z ($ES^+$) $(M+H)^+$ 438.3.

Example 46: (S)-2-(3-aminopiperidin-1-yl)-4-((3-(2-cyanopropan-2-yl)-5-(dimethylcarbamoyl)phenyl) amino)pyrimidine-5-carboxamide Prepared by an analogous route to example 22 using methyl 3-amino-5-(2-cyanopropan-2-yl)benzoate (prepared following WO2006040568) in step 1 and dimethylamine in step 3. $^1$H NMR (400 MHz, MeOD) δ 8.56-8.52 (m, 1H), 7.86 (br s, 2H), 7.24-7.21 (m, 1H), 4.70-4.48 (m, 2H), 3.16-2.99 (m, 7H), 2.90-2.71 (m, 2H), 2.07-1.98 (m, 1H), 1.86-1.72 (m, 7H), 1.63-1.30 (m, 2H). m/z ($ES^+$) $(M+H)^+$ 451.3.

Example 47: (S)-2-(3-aminopiperidin-1-yl)-4-((3-(2-cyanopropan-2-yl)-5-(pyrrolidine-1-carbonyl)phenyl)amino)pyrimidine-5-carboxamide Prepared by an analogous route to example 46 using pyrrolidine in step 3. $^1$H NMR (400 MHz, MeOD) δ 8.56 (s, 1H), 8.03-7.81 (m, 2H), 7.31-7.29 (m, 1H), 4.70-4.48 (m, 2H), 3.60 (t, 2H), 3.49 (t, 3H), 3.12-3.00 (m, 1H), 2.92-2.66 (m, 2H), 2.08-72 (m, 11H), 1.63-1.30 (m, 2H). m/z ($ES^+$) $(M+H)^+$ 477.3.

Example 48: (S)-2-(3-aminopiperidin-1-yl)-4-((3-(2-cyanopropane-2-yl)-5-(morpholine-4-carbonyl)phenyl)amino)pyrimidine-5-carboxamide Prepared by an analogous route to example 46 using morpholine in step 3. $^1$H NMR (400 MHz, MeOD) δ 8.58-8.52 (m, 1H), 7.88 (br s, 2H), 7.22-7.19 (m, 1H), 4.70-4.48 (m, 2H), 3.65 (t, 4H), 3.14-3.00 (m, 1H), 2.92-2.70 (m, 6H), 2.07-1.98 (m, 1H), 1.86-1.72 (m, 7H), 1.63-1.30 (m, 2H). m/z ($ES^+$) $(M+H)^+$ 493.3.

Example 49: (S)-2-(3-aminopiperidin-1-yl)-4-((3-chloro-5-(morpholine-4-carbonyl)phenyl)amino) pyrimidine-5-carboxamide Step 49-1: (3-chloro-5-nitrophenyl)(morpholino)methanone. Prepared by an analogous method to example 17 step 1, using 3-chlorol-5-nitrobenzoic acid (0.500 g, 2.48 mmol), thionyl chloride (5.0 mL), triethylamine (0.35 mL, 2.5 mmol), morpholine (0.22 mL, 2.52 mmol) and DCM (10 mL) to give the title compound without need for further purification as a light-yellow viscous oil (0.477 g, 71%). $^1$H NMR (400 MHz, CDCl$_3$) δ 8.27 (s, 1H), 8.15 (s, 1H), 7.73 (s, 1H), 4.09-3.80 (m, 8H). $^{13}$C NMR (101 MHz, CDCl$_3$) δ 166.4, 148.7, 138.2, 136.2, 133.3, 125.0, 120.5, 66.7, 48.3 (broadened), 42.8 (broadened).

Step 49-2: (3-amino-5-chlorophenyl)(morpholino)methanone. Prepared by an analogous method to example 17 step 2, using iron powder (0.407 g, 7.29 mmol), EtOH (2.35 mL), conc. HCl (aq) (0.06 mL), 25% NH$_4$Cl (aq) solution (1.18 mL) and (3-chloro-5-nitrophenyl)(morpholino)methanone (0.168 g, 0.621 mmol), purified by flash column chromatography (EtOAc) to give the title compound as a colourless oil (0.139 g, 93%). $^1$H NMR (400 MHz, CDCl$_3$) δ 6.68 (app s, 2H), 6.53 (s, 1H), 4.17-3.29 (m, 10H). LCMS: m/z (ES+) (M+H)$^+$ 241.0; t$_R$=1.78 min. HPLC Method 3 (Acid).

Step 49-3: (S)-2-(3-aminopiperidin-1-yl)-4-((3-chloro-5-(morpholine-4-carbonyl)phenyl)amino)pyrimidine-5-carboxamide. (3-Amino-5-chlorophenyl)(morpholino)methanone (0.112 g, 0.46 mmol), 2,4-dichloropyrimidine-5-carboxamide (0.090 g, 0.47 mmol), triethylamine (0.14 mL, 1.01 mmol) were dissolved in anhydrous dioxane (10 mL) and DMF (2 mL). The mixture was heated at 50° C. for 7 h and then left to cool to RT. Further triethylamine (0.14 mL, 1.01 mmol) and 2,4-dichloropyrimidine-5-carboxamide (0.090 g, 0.47 mmol) were added and the mixture was stirred at 50° C. overnight. tert-Butyl (S)-piperidin-3-ylcarbamate (0.093 g, 0.46 mmol) and triethylamine (0.14 mL, 1.01 mmol) were added and the reaction mixture was heated at 50° C. for 24 h. EtOAc (40 mL) was added and the solution washed sequentially with water (5×20 mL) and brine (20 mL). The organic phase was dried over MgSO$_4$, filtered and concentrated under reduced pressure to give the crude product from two displacements which was purified by flash column chromatography (EtOAc) to give the product from two displacements (0.082 g, 32%). A portion of this product (0.030 g, 0.12 mmol) was dissolved in Et$_2$O (5.0 mL) and 4M HCl in dioxane (5.0 mL) was added drop-wise. The mixture was left to stir at RT for 2 h and hexane (20 mL) was added, the solid filtered and dried to give the hydrochloride salt of the title compound as a white solid (0.027 g, quantitative). $^1$H NMR (400 MHz, MeOD) δ 8.60 (s, 1H), 7.98 (br s, 1H), 7.60 (br s, 1H), 7.36 (s, 1H), 4.71-4.56 (m, 1H), 4.09 (app d, J=13.6 Hz, 1H), 3.87-3.93 (m, 11H), 2.29-2.17 (m, 1H), 2.07-1.95 (m, 1H), 1.88-1.74 (m, 2H). LCMS: m/z (ES+) (M+H)$^+$ 460.2; t$_R$=1.95 min. HPLC Method 3 (Acid).

Example 50: (S)-2-(3-aminopiperidin-1-yl)-4-((3,5-bis(2-cyanopropane-2-yl)phenyl)amino)pyrimidine-5-carboxamide Step 50-1: N,N-dibenzyl-3,5-dibromoaniline. To 3,5-dibromoaniline (2.50 g, 9.96 mmol), potassium carbonate (4.13 g, 29.88 mmol) and benzyl bromide (3.55 mL, 29.89 mmol) was added MeCN (40 mL). The mixture was heated to reflux and left to stir overnight. After allowing the mixture to cool to RT, MeCN was removed under reduced pressure and EtOAc (60 mL) was added. The organic solution washed with water (3×50 mL), dried over MgSO$_4$, filtered and concentrated under reduced pressure to give the crude product, which was purified first by flash column chromatography (95:5 hexane: EtOAc) and then by recrystallisation from boiling hot hexane with a small amount of EtOAc (filtered while hot and left to cool) to give the title compound as a white solid (3.13 g, 73%). $^1$H NMR (400 MHz, CDCl$_3$) δ 7.35 (app t, J=7.2 Hz, 4H), 7.31-7.25 (m, 2H), 7.19 (d, J=7.6 Hz, 4H), 6.97 (s, 1H), 6.79 (s, 2H), 4.59 (s, 4H). LCMS: m/z (ES+) (M+H)$^+$ 431.8; t$_R$=3.24 min. HPLC Method 2 (Acid).

Step 50-2: 2,2'-(5-(dibenzylamino)-1,3-phenylene)bis(2-methylpropanenitrile) and 2-(3-bromo-5-(dibenzylamino)phenyl)-2-methylpropanenitrile. N,N-dibenzyl-3,5-dibromoaniline (1.00 g, 2.32 mmol), Xantphos (0.160 g, 0.28 mmol), Pd$_2$allyl$_2$Cl$_2$ (0.037 g, 4 mol %) and potassium 2-cyano-2-methylpropanoate (0.840 g, 5.55 mmol) were added to a pressure vessel which was flushed with N2 through a septum for 15 min. Mesitylene (5.5 mL) was introduced, the septum quickly replaced with a screwcap and the mixture stirred vigorously for 5 min at RT. The flask was lowered into an oil bath pre-heated to 140° C. and left to stir vigorously overnight. Following cooling, the crude reaction mixture was transferred to a round bottomed flask with the aid of EtOAc (20 mL) and concentrated under reduced pressure. The resulting residue was purified by flash column chromatography on silica (hexane then 7:1 hexane: EtOAc followed by 6:1 and finally 5:1) to give 2,2'-(5-(dibenzylamino)-1,3-phenylene)bis(2-methylpropanenitrile) as a light-yellow oil which solidified on standing (0.500 g, 53%). $^1$H NMR (400 MHz, CDCl$_3$) δ 7.34 (app t, J=7.6 Hz, 4H), 7.31-7.22 (m, 6H), 6.83 (s, 1H), 6.75 (d, J=2.0 Hz, 2H), 4.70 (s, 4H), 1.60 (s, 12H). LCMS: m/z (ES+) (M+H)$^+$ 408.3; t$_R$=2.88 min. HPLC Method 3 (Acid).

2-(3-bromo-5-(dibenzylamino)phenyl)-2-methylpropanenitrile was also isolated as a light-yellow oil which solidified on standing (0.20 g, 20%). m/z (M+H)$^+$ (ES$^+$) 419.3, 421.2; t$_R$=3.14 min. HPLC Method 2 (Base); $^1$H NMR (400 MHz, CDCl$_3$) δ 7.40-7.33 (m, 4H), 7.32-7.23 (m, 6H), 6.90 (app. t, J=1.6 Hz, 1H), 6.85 (dd, J=2.4, 1.6 Hz, 1H), 6.73 (app. t, J=2.0 Hz, 1H), 4.67 (s, 4H), 1.58 (s, 6H).

Step 50-3: 2,2'-(5-amino-1,3-phenylene)bis(2-methylpropanenitrile). 2,2'-(5-(dibenzylamino)-1,3-phenylene)bis(2-methylpropanenitrile) (3.05 g, 7.48 mmol) was introduced to a flask which was flushed with N2 for 10 min. Pd(OH)$_2$ (1.05 g, 10-20% Pd basis), DCM (8.0 mL) and finally MeOH (30.0 mL) were added and the flask purged with H2. The mixture was left to stir vigorously at RT for 3 h after which the flask was opened to the air and the mixture filtered through a pad of Celite® under reduced pressure. The cake was washed with additional MeOH (30 mL) and DCM (30 mL), the filtrate concentrated under reduced pressure and the crude product purified by flash column chromatography on silica (1:1 hexane: EtOAc) to give the title compound as a light-yellow oil which slowly solidified on standing (1.68 g, 98%). $^1$H NMR (400 MHz, CDCl$_3$) δ 6.85 (t, J=2.0 Hz, 1H), 6.73 (d, J=2.4 Hz, 1H), 3.36-2.78 (br s, 2H), 1.70 (s, 12H). LCMS: m/z (ES+) (M+H)$^+$ 228.2; t$_R$=2.15 min. HPLC Method 3 (Acid).

Step 50-4: (S)-2-(3-aminopiperidin-1-yl)-4-((3,5-bis(2-cyanopropan-2-yl)phenyl)amino)pyrimidine-5-carboxamide. 2,2'-(5-amino-1,3-phenylene)bis(2-methylpropanenitrile) (0.764 g, 3.36 mmol), 2,4-dichloropyrimidine-5-carboxamide (0.822 g, 4.28 mmol), triethylamine (1.01 mL, 7.25 mmol) were dissolved in anhydrous dioxane (35 mL). The mixture was heated at 50° C. for 3 h and then left to cool to RT. Additional 2,4-dichloropyrimidine-5-carboxamide (0.061 g, 0.32 mmol) and triethylamine (0.09 mL, 0.65 mmol) were added and the mixture heated to 50° C. for a further 1.5 h. The reaction mixture was allowed to cool to RT, and tert-Butyl (S)-piperidin-3-ylcarbamate (0.726 g, 3.62 mmol) and triethylamine (1.01 mL, 7.25 mmol) were added and the reaction mixture heated at 50° C. for 75 min.

EtOAc (60 mL) was added and the solution washed sequentially with water (5×30 mL) and brine (30 mL). The organic phase was dried over MgSO$_4$, filtered and concentrated under reduced pressure to give the crude product from two displacements which was purified by flash column chromatography (1:2 hexane: EtOAc followed by 1:3) to give the product from two displacements (1.30 g, 71%). Dioxane (30 mL) was added followed by the drop-wise addition of 4M HCl in dioxane (15 mL) and the reaction mixture was stirred at RT for 24 h. Hexane (30 mL) was added and the solid filtered and triturated with Et$_2$O to remove residual dioxane. The resulting solid was filtered and dried to give the hydrochloride salt of the title compound as a light-yellow powder (1.12 g, 98%). $^1$H NMR (400 MHz, CD$_3$OD) δ 8.60 (s, 1H), 7.83 (d, J=1.6 Hz, 2H), 7.50 (t, J=1.6 Hz, 1H), 4.39 (dd, J=13.6, 3.2 Hz, 1H), 4.14-3.95 (m, 1H), 3.89-3.77 (m, 1H), 3.68-3.62 (m, 1H), 3.57-3.49 (m, 1H), 2.23-2.13 (m, 1H), 2.07-1.95 (m, 1H), 1.89-1.80 (m, 1H), 1.79 (s, 12H). LCMS: m/z (ES+) (M+H)$^+$ 447.0; t$_R$=1.91 min. HPLC Method 3 (Acid).

Example 51: (S)-2-(3-aminopiperidin-1-yl)-4-((3,5-bis(1-cyanocyclopropyl)phenyl)amino)pyrimidine-5-carboxamide Step 51-1: 1,1'-(5-(dibenzylamino)-1,3-phenylene)bis(cyclopropane-1-carbonitrile). Racemic BINAP (0.116 g, 0.19 mmol) and Pd$_2$dba$_3$ (0.088 g, 5 mol %) were added to a septum-equipped 100 mL round bottomed flask which was flushed with N2 for 15 min. Previously degassed THF (8.0 mL) was added and the suspension stirred at RT for 20 min. Cyclopropanecarbonitrile (0.28 mL, 3.80 mmol), N,N-dibenzyl-3,5-dibromoaniline (0.400 g, 0.93 mmol) and cyclopentylmethyl ether (20 mL) were added to a separate flask under a N2 atmosphere and the solution was degassed with N2 for 15 min. Following this, the suspension of catalyst in THF was transferred by syringe to the reaction flask. LiHMDS (1 M in THF, 3.72 mL, 3.72 mmol) was added drop-wise with stirring and following completion of addition the reaction mixture was heated to 80° C. for 1.5 h. The reaction mixture was diluted with EtOAc (30 mL) and washed sequentially with water (3×20 mL) and brine (20 mL). The organic phase was dried over MgSO$_4$, filtered and concentrated under reduced pressure to give the crude product which was purified by flash column chromatography (9:1 hexane: EtOAc followed by 4.5:1) and then a second time (50:1 toluene: EtOAc) to give the title compound as a white solid (0.299 g, 80%). $^1$H NMR (400 MHz, CDCl$_3$) δ 7.35 (app t, J=7.2 Hz, 4H), 7.28 (t, J=7.2 Hz, 2H), 7.24 (d, J=7.2 Hz, 4H), 4.68 (s, 4H), 1.62-1.55 (m, 4H), 1.25-1.20 (m, 1H). LCMS: m/z (ES+) (M+H)+404.0; t$_R$=2.86 min. HPLC Method 3 (Acid).

Step 51-2: 1,1'-(5-amino-1,3-phenylene)bis(cyclopropane-1-carbonitrile). 1,1'-(5-(Dibenzylamino)-1,3-phenylene)bis(cyclopropane-1-carbonitrile) (0.100 g, 0.25 mmol) was introduced to a flask which was flushed with N2 for 10 min. 10% Pd/C (0.027 g, 10 mol %) and MeOH (2.0 mL) were added and the flask purged with H2. The mixture was left to stir vigorously at RT overnight. The reaction mixture was purged with N2 and additional 10% Pd/C (0.027 g, 10 mol %) and DCM (2.0 mL) were added. The reaction mixture was purged with H2 once more and left to stir at RT for 2 h after which the flask was opened to the air and the mixture filtered through a pad of Celite® under reduced pressure. The cake was washed with additional MeOH (15 mL) and EtOAc (15 mL) and the filtrate concentrated under reduced pressure to give the crude product which was purified by column chromatography on silica (toluene) to give the title compound (0.020 g, 36%). $^1$H NMR (400 MHz, CDCl$_3$) δ 6.54 (d, J=1.2 Hz, 2H), 6.48-6.43 (m, 1H), 3.94-3.68 (br s, 2H), 1.71-1.63 (m, 4H), 1.40-1.33 (m, 4H). LCMS: m/z (ES+) (M+H)+224.1; t$_R$=2.05 min. HPLC Method 3 (Acid).

Step 51-3: (S)-2-(3-aminopiperidin-1-yl)-4-((3,5-bis(1-cyanocyclopropyl)phenyl)amino)pyrimidine-5-carboxamide. 1,1'-(5-Amino-1,3-phenylene)bis(cyclopropane-1-carbonitrile) (0.020 g, 0.09 mmol), 2,4-dichloropyrimidine-5-carboxamide (0.017 g, 0.09 mmol), triethylamine (0.02 mL, 0.15 mmol) were dissolved in anhydrous dioxane (2.0 mL) and DMF (0.5 mL). The mixture was heated at 50° C. for 1 h and then left to cool to RT. Additional 2,4-dichloropyrimidine-5-carboxamide (3 mg, 0.02 mmol) and triethylamine (0.01 mL, 0.07 mmol) were added and the mixture heated to 50° C. overnight. tert-Butyl (S)-piperidin-3-ylcarbamate (0.018 g, 0.09 mmol) and triethylamine (0.02 mL, 0.15 mmol) were added and the reaction mixture was heated at 50° C. for 1.5 h. The reaction mixture was diluted with EtOAc (15 mL), washed sequentially with water (3×10 mL) and brine (10 mL). The organic phase was dried over MgSO$_4$, filtered and concentrated under reduced pressure. Et$_2$O (2.0 mL) was added followed by the drop-wise addition of 4M HCl in dioxane (2.0 mL) and the mixture was stirred at RT for 3 h. Hexane (10 mL) was added and the solid obtained filtered and dried to give the hydrochloride salt of the title compound as a white powder (0.033 g, 77%). $^1$H NMR (400 MHz, MeOD) δ 8.59 (s, 1H), 7.71 (s, 2H), 6.96 (s, 1H), 4.45 (app d, J=12.4 Hz, 1H), 4.14-3.92 (m, 1H), 3.83-3.73 (m, 1H), 3.68-3.58 (m, 1H), 3.58-3.45 (m, 1H), 2.45-2.11 (m, 1H), 2.10-1.95 (m, 1H), 1.91-1.72 (m, 7H), 1.61-1.53 (m, 4H). LCMS: m/z (ES+) (M+H)$^+$ 443.0; t$_R$=1.87 min. HPLC Method 3 (Acid).

Example 52: (S)-2-(3-aminopiperidin-1-yl)-4-((3,5-bis(1-cyanocyclobutyl)phenyl)amino)pyrimidine-5-carboxamide Step 52-1: 1,1'-(5-(dibenzylamino)-1,3-phenylene)bis(cyclobutane-1-carbonitrile). As in example 51 step 1, using racemic BINAP (0.087 g, 0.14 mmol), Pd$_2$dba$_3$ (0.066 g, 5 mol %), THF (6.0 mL), cyclobutanecarbonitrile (0.26 mL, 2.78 mmol), N,N-dibenzyl-3,5-dibromoaniline (0.300 g, 0.70 mmol), cyclopentylmethyl ether (15 mL) and LiHMDS (1 M in THF, 2.79 mL, 2.79 mmol). Crude product was purified by flash column chromatography on silica (50:1 toluene: EtOAc) to give the title compound as a white solid (0.226 g, 75%). $^1$H NMR (400 MHz, CDCl$_3$) δ 7.35 (app t, J=7.2 Hz, 4H), 7.30-7.23 (m, 6H), 6.68 (t, J=1.6 Hz, 1H), 6.63 (d, J=1.6 Hz, 2H), 4.69 (s, 4H), 2.75-2.65 (m, 4H), 2.49-2.39 (m, 4H), 2.39-2.26 (m, 2H), 1.98-1.87 (m, 2H). LCMS: m/z (ES+) (M+H)$^+$ 432.0; t$_R$=2.99 min. HPLC Method 3 (Acid).

Step 52-2: 1,1'-(5-amino-1,3-phenylene)bis(cyclobutane-1-carbonitrile). As in example 51 step 2, using 1,1'-(5-(dibenzylamino)-1,3-phenylene)bis(cyclobutane-1-carbonitrile) (0.100 g, 0.23 mmol), 10% Pd/C (0.035 g, 14 mol %), MeOH (2.0 mL) and DCM (2.0 mL) to give the crude product, which was purified by flash column chromatography on silica (toluene) to give the title compound as a yellow oil (0.030 g, 52%). $^1$H NMR (400 MHz, CDCl$_3$) δ 6.76 (t, J=1.6 Hz, 1H), 6.63 (d, J=1.6 Hz, 2H), 3.95-3.78 (br s, 2H), 2.83-2.73 (m, 4H), 2.60 (app dq, J=9.6, 2.4 Hz, 4H), 2.49-2.35 (m, 2H), 2.11-1.99 (m, 2H). LCMS: m/z (ES+) (M+H)$^+$ 252.1; t$_R$=2.24 min. HPLC Method 3 (Acid).

Step 52-3: (S)-2-(3-aminopiperidin-1-yl)-4-((3,5-bis(1-cyanocyclobutyl)phenyl)amino)pyrimidine-5-carboxamide. 1,1'-(5-amino-1,3-phenylene)bis(cyclobutane-1-carbonitrile) (0.030 g, 0.12 mmol), 2,4-dichloropyrimidine-5-carboxamide (0.023 g, 0.12 mmol), triethylamine (0.02 mL, 0.15 mmol) were dissolved in anhydrous dioxane (2.0 mL) and DMF (0.5 mL). The mixture was heated at 50° C. for 3 h and then left to cool to RT. Additional 2,4-dichloropyrimidine-5-carboxamide (8 mg, 0.04 mmol) and triethylamine (0.01 mL, 0.07 mmol) were added and the mixture heated to 50° C. overnight. tert-Butyl (S)-piperidin-3-ylcarbamate (0.024 g, 0.12 mmol) and triethylamine (0.02 mL, 0.15 mmol) were added and the reaction mixture was heated at 50° C. for 1.5 h. The reaction mixture was diluted with EtOAc (15 mL), washed sequentially with water (3×10 mL) and brine (10 mL). The organic phase was dried over $MgSO_4$, filtered and concentrated under reduced pressure. $Et_2O$ (2.0 mL) was added followed by the drop-wise addition of 4M HCl in dioxane (2.0 mL) and the mixture was stirred at RT for 3 h. Hexane (10 mL) was added and the solid obtained filtered and dried to give the hydrochloride salt of the title compound as a white powder (0.045 g, 75%). $^1$H NMR (400 MHz, MeOD) δ 8.59 (s, 1H), 7.70 (s, 2H), 7.40 (s, 1H), 4.42 (app d, J=12.4 Hz, 1H), 4.11-3.97 (m, 1H), 3.80-3.69 (m, 1H), 3.66-3.56 (m, 1H), 3.56-3.44 (m, 1H), 2.89-2.69 (m, 9H), 2.52-2.37 (m, 2H), 2.23-2.06 (m, 3H), 2.06-1.94 (m, 1H), 1.89-1.74 (m, 1H). LCMS: m/z (ES+) $(M+H)^+$ 470.9; $t_R$=1.98 min. HPLC Method 3 (Acid).

Example 53: (S)-2-(3-aminopiperidin-1-yl)-4-((3,5-dicyclopropylphenyl)amino)pyrimidine-5-carboxamide Step 53-1: 3,5-dicyclopropylaniline. A solution of tricyclohexylphosphine (0.112 g, 0.399 mmol), diacetoxypalladium (0.045 g, 0.199 mmol), 3,5-dibromoaniline (0.500 g, 1.993 mmol), cyclopropylboronic acid (0.856 g, 9.96 mmol, 5 eq) and potassium phosphate (3.38 g, 15.94 mmol, 8 eq) in toluene (18 mL) and water (2 mL) was degassed with N2, The reaction was heated at 100° C. for 6 h and stood at rt for 12 h. The reaction was diluted with water (10 mL) and extracted with EtOAc (3×20 mL). The combined organic layers were dried ($Na_2SO_4$) and concentrated under reduced pressure. The residue was loaded onto a SCX cartridge, washing with MeOH (3 column volumes) and eluting with 1% $NH_3$ in MeOH (3 column volumes). The ammoniacal MeOH was concentrated under reduced pressure, no further purification was required. (0.300 g, 85%). m/z (ES$^+$) $(M+H)^+$ 174; $t_R$=1.74 min. HPLC Method 2.

Step 53-2: (S)-2-(3-aminopiperidin-1-yl)-4-((3,5-dicyclopropylphenyl)amino)pyrimidine-5-carboxamide. Prepared by an analogous method to example 3, using 3,5-dicyclopropylaniline prepared as described. (0.063 g, quant). $^1$H NMR (400 MHz, MeOD) δ 8.52 (s, 1H), 7.14 (s, 2H), 6.63 (s, 1H), 4.62-4.56 (m, 1H), 4.50 (d, J=13.2 Hz, 1H), 3.17 (s, 1H), 3.01-2.92 (m, 1H), 2.90-2.78 (m, 1H), 2.05 (d, J=12.5 Hz, 1H), 1.92-1.78 (m, 3H), 1.68-1.53 (m, 1H), 1.52-1.42 (m, 1H), 1.01-0.90 (m, 4H), 0.75-0.62 (m, 4H). m/z (ES$^+$) $(M+H)^+$ 393; $t_R$=1.51 min. HPLC Method 2.

Example 54: (S)-2-(3-aminopiperidin-1-yl)-4-((2,6-diisopropylpyridin-4-yl)amino)pyrimidine-5-carboxamide hydrochloride Step 54-1: 2,6-di(prop-1-en-2-yl)pyridin-4-amine. A stirred solution of sodium bicarbonate (0.367 g, 4.37 mmol), 4,4,5,5-tetramethyl-2-(prop-1-en-2-yl)-1,3,2-dioxaborolane (0.933 mL, 4.96 mmol) and 2,6-dibromopyridin-4-amine (0.500 g, 1.985 mmol) in 1,4-dioxane (7 mL) and water (3 mL) was purged with nitrogen for 10 min. $PdCl_2dppf$ (0.145 g, 0.198 mmol) was added and purging was continued for a further 10 min. The reaction was then heated 90° C. and stirred under nitrogen for 4 h. Upon cooling, the solution was diluted with water (20 mL) and extracted with ethyl acetate (3×20 mL). The combined organic layers were dried over magnesium sulfate, filtered and concentrated under vacuum. The crude product was purified by chromatography on silica gel (0-50% EtOAc/isohexane) to afford 2,6-di(prop-1-en-2-yl)pyridin-4-amine. (0.200 g, 54%). m/z $(M+H)^+$ (ES$^+$) 175.2; $t_R$=0.62 min. HPLC Method 2

Step 54-2: 2,6-diisopropylpyridin-4-amine A solution of 2,6-di(prop-1-en-2-yl)pyridin-4-amine (0.2 g, 1.148 mmol) in methanol (4 mL) was hydrogenated in an H-Cube (10% Pd/C, 30×4 mm, Full hydrogen, 40° C., 1 mL/min) and concentrated under vacuum to afford 2,6-diisopropylpyridin-4-amine. (0.155 g, 75%). m/z $(M+H)^+$ (ES$^+$) 179.2; $t_R$=1.13 min. HPLC Method 4.

Step 54-3: 2-chloro-4-((2,6-diisopropylpyridin-4-yl)amino)pyrimidine-5-carboxamide. To a stirred solution of 2,4-dichloropyrimidine-5-carboxamide (0.965 g, 5.02 mmol) in 1,4-dioxane (20 mL) was added 2,6-diisopropylpyridin-4-amine (0.689 g, 3.86 mmol) and DIPEA (1.346 mL, 7.73 mmol). The reaction was heated to 110° C. and stirred for 7 h. The mixture was allowed to cool and concentrated under vacuum. The crude product was purified by chromatography on silica gel (0-2% (0.7 M Ammonia/MeOH)/DCM) to afford 2-chloro-4-((2,6-diisopropylpyridin-4-yl)amino)pyrimidine-5-carboxamide. (0.91 g, 67%). $^1$H NMR (500 MHz, DMSO-d6) δ 11.66 (s, 1H), 8.86 (s, 1H), 8.50 (s, 1H), 8.04 (s, 1H), 7.40 (s, 2H), 2.95 (sept, 2H, J=6.9 Hz), 1.24 (d, 12H, J=6.9 Hz). m/z $(M+H)^+$ (ES$^+$) 334.2; $t_R$=2.26 min. HPLC Method 4.

Step 54-4: (S)-tert-butyl (1-(5-carbamoyl-4-((2,6-diisopropylpyridin-4-yl)amino)pyrimidin-2-yl)piperidin-3-yl)carbamate. To a stirred solution of 2-chloro-4-((2,6-diisopropylpyridin-4-yl)amino)pyrimidine-5-carboxamide (0.9 g, 2.70 mmol) in 1,4-dioxane (20 mL) was added (S)-tert-butyl piperidin-3-ylcarbamate (0.567 g, 2.83 mmol) and DIPEA (0.494 mL, 2.83 mmol). The reaction was heated to 90° C. and stirred for 30 min, then allowed to cool and concentrated under vacuum. The crude product was purified by chromatography on silica gel (0.7 M Ammonia/MeOH)/DCM) to afford (S)-tert-butyl (1-(5-carbamoyl-4-((2,6-diisopropylpyridin-4-yl)amino)pyrimidin-2-yl)piperidin-3-yl)carbamate. (1.19 g, 88%). m/z $(M+H)^+$ (ES$^+$) 498.5; $t_R$=2.49 min. HPLC Method 4.

Step 54-5: (S)-2-(3-aminopiperidin-1-yl)-4-((2,6-diisopropylpyridin-4-yl)amino)pyrimidine-5-carboxamide hydrochloride. To a stirred solution of (S)-tert-butyl (1-(5-carbamoyl-4-((2,6-diisopropylpyridin-4-yl)amino)pyrimidin-2-yl)piperidin-3-yl)carbamate (1.19 g, 2.391 mmol) in 1,4-dioxane (10 mL) was added hydrochloric acid (4M in 1,4-dioxane, 11.96 mL, 47.8 mmol) and the reaction was stirred at RT for 4 h. The reaction mixture was then concentrated under vacuum. The resulting residue was slurried in ethyl acetate (10 mL) and collected by filtration to afford (S)-2-(3-aminopiperidin-1-yl)-4-((2,6-diisopropylpyridin-4-yl)amino)pyrimidine-5-carboxamide hydrochloride. (0.851 g, 78%). $^1$H NMR (500 MHz, MeOD) δ 8.67 (s, 1H), 7.50 (s, 1H), 4.51 (br d, 1H, J=13.0 Hz), 4.27-4.18 (m, 1H), 3.77-3.66 (m, 2H), 3.41-3.31 (m, 1H), 3.06 (sept, 2H, J=7.0 Hz), 2.23-2.11 (br m, 1H), 1.95-1.86 (m, 1H), 1.85-1.68 (m, 2H), 1.32 (d, 12H, J=7.0 Hz). m/z $(M+H)^+$ (ES$^+$) 398.3; $t_R$=1.79 min. HPLC Method 4.

Example 55: (R)-2-(3-aminoazepan-1-yl)-4-((2,6-diisopropylpyridin-4-yl)amino)pyrimidine-5-carboxamide Prepared by analogous method to example 3 (Step 3: dioxane, DIPEA, 105° C., 20 h) with 2,6-diisopropylpyridin-4-amine to give the 2-chloro-4-(2,6-diisopropylpyridin-4-yl-amino)pyriimidine-5-carboxamide which was purified by chromatography on silica (40 g) with a gradient DCM/MECN (0, 10, 20, 25%). The off-white solid from recovered from chromatography was further recrystallized from DCM and petroleum ether to afford the title compound (1.31 g, 47%) $^1$H NMR (300 MHz, $d_6$ DMSO) δ 11.67 (s, 1H), 8.85 (s, 1H), 8.50 (s, 1H), 8.03 (s, 1H), 7.39 (s, 1H), 2.94 (sept, J=6.8 Hz, 1H), 1.23 (d, J=7.1 Hz, 12H), m/z (ES$^+$) (M+H)$^+$ 334.2/336.2; $t_R$=2.10 min. HPLC Method 1.

The 2-chloro-4-(2,6-diisopropylpyridin-4-yl-amino)pyrimidine-5-carboxamide intermediate was further reacted with (R)-tert-butyl azepan-3-ylcarbamate (step $C_2$: $CH_3CN$ DIPEA, 70° C., 1 h) to give the corresponding tert-butyl (R)-(1-(5-carbamoyl-4-((2,6-diisopropylpyridin-4-yl)amino)pyrimidin-2-yl)azepan-3-yl)carbamate. (m/z (ES$^+$) (M+H)$^+$ 512.1; $t_R$=2.34 min. HPLC Method 1). Boc deprotection afforded the hydrochloride salt of the title compound. $^1$H NMR (300 MHz, DMSO-d6+D$_2$O) δ 8.84 (s, 1H), 7.90 (s, 1H), 4.25 (dd, J=14.3, 5.0 Hz, 1H), 3.92-3.85 (m, 1H), 3.80-3.71 (m, 2H), 3.46-3.40 (m, 1H), 1.94-1.66 (m, 5H), 1.65-1.35 (m, 2H), 1.31 (d, J=7.0 Hz, 6H), m/z (ES+) (M+H)$^+$ 412.4; $t_R$=1.93 min. HPLC Method 1.

Example 56: (S)-2-(3-aminoazepan-1-yl)-4-((2,6-diisopropylpyridin-4-yl)amino)pyrimidine-5-carboxamide Prepared using an analogous procedure to example 55, using (S) tert-Butyl azepan-3-ylcarbamate to give the hydrochloride salt. $^1$H NMR (300 MHz, DMSO-d6+D$_2$O) δ 8.84 (s, 1H), 7.90 (s, 1H), 4.25 (dd, J=14.3, 5.0 Hz, 1H), 3.92-3.85 (m, 1H), 3.80-3.71 (m, 2H), 3.46-3.40 (m, 1H), 1.94-1.66 (m, 5H), 1.65-1.35 (m, 2H), 1.31 (d, J=7.0 Hz, 6H), m/z (ES$^+$) (M+H)+412.4; $t_R$=1.93 min. HPLC Method 1.

Example 57: (S)-2-(3-aminopiperidin-1-yl)-4-((2-(prop-1-en-2-yl)-6-(trifluoromethyl)pyridin-4-yl)amino)pyrimidine-5-carboxamide Step 57-1: 2-(prop-1-en-2-yl)-6-(trifluoromethyl)pyridin-4-amine 2-trifluoromethyl-6-chloropyridine-4-amine (1 mmol, 200 mg) was dissolved in dioxane (10 mL) followed by addition of 4,4,5,5-tetramethyl-2-(prop-1-en-2-yl)-1,3,2-dioxaborolane (376 uL, 2 mmol), KOAc (3.0 mmol, 300 mg). The solution was flushed with nitrogen before adding PdCl$_2$(dppf) (5% mol, 0.05 mmol, 40 mg). The solution was stirred at 90° C. Boronate ester (100 uL) was added and the solution was degassed again before addition of PdCl$_2$(dppf) (20 mg). The reaction was heated at 90° C. for another 8 h. The crude was filtered through a pad of silica (2-3 g) and washed with DCM. The crude solution was evaporated to dryness and purified by chromatography on silica (25 g) using 100% DCM to give a clear oil (60 mg, 30%). $^1$H NMR (300 MHz, CDCl$_3$) δ 6.75 (s, 1H), 5.89 (s, 1H), 5.28 (s, 1H), 4.41 (br s, 2H), 2.15, m/z (ES+) (M+H)$^+$ 203.1; $t_R$=3.29 min. HPLC Method 1.

Step 57-2: (S)-2-(3-aminopiperidin-1-yl)-4-((2-(prop-1-en-2-yl)-6-(trifluoromethyl)pyridin-4-yl)amino)pyrimidine-5-carboxamide was prepared by an analogous method to example 3 with 2-(prop-1-en-2-yl)-6-(trifluoromethyl)pyridin-4-amine and (S)-3-NBoc-aminopiperidine (Step 1: $CH_3CN$, Diethylaniline, 105° C., 16 h; Step 2: $CH_3CN$ DIPEA, 60° C., 3 h) to give intermediate (S)-tert-butyl 1-(5-carbamoyl-4-(2-(prop-1-en-2-yl)-6-(trifluoromethyl)pyridin-4-ylamino)pyrimidin-2-yl)piperidin-3-ylcarbamate which was purified by chromatography on silica cartridge (10 g) using gradient eluent PET(100%) to DCM(100%)/Acetontrile (25, 50% Acetonitrile). Rf (50% Acetonitrile/DCM)=0.75 (fluorescent blue UV) to give a solid (pale brown/orangey) (110 mg, 84%), m/z (ES$^+$) (M+H)$^+$ 522.3/466.2; $t_R$=3.17 min. (HPLC Method 1), before Boc deprotection to give the hydrochloride salt of the title compound as an off white solid. $^1$H NMR (300 MHz, DMSO-d6+D$_2$O) δ 8.78 (s, 1H), 8.16 (s, 1H), 7.91 (s, 1H), 5.98 (s, 1H), 5.40 (s, 1H), 4.51 (br s, 1H), 4.07 (d, J=11.2 Hz, 1H), 3.62-3.34 (m, 2H), 3.23 (br s, 1H), 2.13 (s, 3H), 2.09-2.01 (m, 1H), 1.86-1.67 (m, 2H), 1.63-1.52 (m, 1H), m/z (ES$^+$) (M+H)+ 422.4; $t_R$=2.40 min. (HPLC Method 1).

Example 58: (S)-2-(3-aminopiperidin-1-yl)-4-((2-isopropyl-6-phenylpyridin-4-yl)amino)pyrimidine-5-carboxamide Step 58-1: 4-nitro-2-phenyl-6-(prop-1-en-2-yl)pyridine
To a solution of 2,6-dibromo-4-nitropyridine (281 mg, 1.0 mmol), phenyl boronic acid (121 mg, 1.0 mmol) and 4,4,5,5-tetramethyl-2-(prop-1-en-2-yl)-1,3,2-dioxaborolane (168 mg, 1 mmol) in 1,4-dioxane (10 mL) and water (3 mL), Pd(PPh$_3$)$_4$ (231 mg, 0.2 mmol) and K$_2$CO$_3$ (414 mg, 3.0 mmol) were added and the reaction was stirred at 100° C. under N$_2$ for 5 h. The resulting mixture was quenched with water, and extracted with ethyl acetate. The combined organic layers were dried over sodium sulphate, filtered and concentrated under vacuum. The crude product was purified by silica gel chromatography (0-40% DCM/Pet. Ether). = 63%; HPLC (Method 1): $t_R$=3.19 min, m/z (ES+) (M+H)$^+$ 241.2.

Step 58-2: 2-isopropyl-6-phenylpyridin-4-amine. To a solution of 4-nitro-2-phenyl-6-(prop-1-en-2-yl)pyridine (150 mg, 0.625 mmol), 10% in MeOH, Pd/C (10%) was added and the reaction was stirred under H2 gas at RT for 2 h. Pd/C was removed by filtration, the solution concentrated to dryness and the crude mixture was used in the next step, without any further purification. =70%, HPLC (Method 1): $t_R$=1.97 min, m/z (ES+) (M+H)$^+$ 213.3.

Step 58-3: (S)-2-(3-aminopiperidin-1-yl)-4-((2-isopropyl-6-phenylpyridin-4-yl)amino)pyrimidine-5-carboxamide
Prepared by an analogous method to example 3 using 2-isopropyl-6-phenylpyridin-4-amine prepared as described to give the hydrochloride salt of the title compound. HPLC (Method 1): $t_R$-1.94 min, m/z (ES+) (M+H)+432.2; $^1$H NMR (400 MHz, DMSO-d6) δ 8.81 (s, 1H), 8.25 (s, 1H), 8.03 (s, 1H), 7.83-87.81 (m, 2H), 7.70-7.61 (m, 3H), 4.45-4.42 (br s, 1H), 3.60-3.45 (br m, 2H), 3.42-3.34 (m, 2H), 3.27-3.19 (br m, 1H), 2.09-2.00 (br m, 1H), 1.75-1.62 (br m, 2H), 1.60-1.49 (br m, 2H), 1.36-1.32 (m, 6H) 1.27-1.24 (d, 1H).

Example 59: (S)-2-(3-aminopiperidin-1-yl)-4-((2-isopropyl-6-(trifluoromethyl)pyridin-4-yl)amino) pyri-midine-5-carboxamide Step 59-1: (S)-tert-butyl 1-(5-carbamoyl-4-(2-isopropyl-6-(trifluoromethyl)pyridin-4-ylamino)pyrimidin-2-yl)piperidin-3-ylcarbamate:
To a solution of (S)-tert-butyl 1-(5-carbamoyl-4-(2-(prop-1-en-2-yl)-6-(trifluoromethyl)pyridin-4-ylamino)pyrimidin- 2-yl)piperidin-3-ylcarbamate (70 mg) in MeOH (and THF to fully dissolve) Pd/C was added. The suspension was degassed using a cycle of vacuum and N2 filling (3×), before being place under a hydrogen atmosphere. After 6 h the crude reaction mixture was filtered through a celite pad, concentrated under vacuum, and purified by chromatography on silica (5 g) eluting with a gradient DCM and acetonitrile 100% DCM, then acetonitrile (10, 25%) to give a white solid (52 mg, 74%), m/z (ES+) (M+H)+524.3/468.2; $t_R$=3.09 min. HPLC Method 1.

Step 59-2: (S)-2-(3-aminopiperidin-1-yl)-4-((2-isopropyl-6-(trifluoromethyl)pyridin-4-yl)amino) pyri-midine-5-carboxamide. Prepared using an analogous method to step 3-3 to provide the hydrochloride salt of the title compound as an off white solid. $^1$H NMR (300 MHz, D6 DMSO+D$_2$O) δ 8.77 (s, 1H), 8.16 (s, 1H), 7.64 (s, 1H), 4.50 (br s, 1H), 4.09 (d, J=12.2 Hz, 1H), 3.59-3.37 (m, 2H), 3.23 (br s, 1H), 3.04 (hept., J=6.8 Hz, 1H), 2.08-2.00 (m, 1H), 1.86-1.65 (m, 2H), 1.64-1.52 (m, 1H), 1.23 (d, J=6.8 Hz, 6H). m/z (ES$^+$) (M+H)+424.4; $t_R$=2.26 min. HPLC Method 1.

Example 60: (S)-2-(3-aminopiperidin-1-yl)-4-((4-phenyl-1H-indazol-6-yl)amino)pyrimidine-5-carboxamide Step 60-1: 4-phenyl-1H-indazol-6-amine. A stirred solution of sodium carbonate (0.126 g, 1.19 mmol), 4,4,5,5-tetramethyl-2-phenyl-1,3,2-dioxaborolane (0.134 g, 0.66 mmol) and 4-chloro-1H-indazol-6-amine (0.1 g, 0.60 mmol) in 1,4-dioxane (3 mL) and water (1 mL) was purged with nitrogen for 10 min. PdCl$_2$dppf (0.044 g, 0.06 mmol) was added and purging was continued for a further 10 min. The reaction was then heated to 90° C. and stirred under nitrogen for 16 h. The reaction mixture was allowed to cool to RT, diluted with water (20 mL) and extracted with ethyl acetate (3×20 mL). The combined organic layers were dried over magnesium sulfate, filtered and concentrated under vacuum to afford 4-phenyl-1H-indazol-6-amine (0.018 g, 10%). m/z (M+H)$^+$ (ES+) 210.1; $t_R$=1.72 min. HPLC Method 4.

Step 60-2: (S)-tert-butyl (1-(5-carbamoyl-4-((4-phenyl-1H-indazol-6-yl)amino)pyrimidin-2-yl)piperidin-3-yl)carbamate. To a stirred solution of 4-phenyl-1H-indazol-6-amine (0.018 g, 0.086 mmol) in 1,4-dioxane (2 mL) was added 2,4-dichloropyrimidine-5-carboxamide (0.017 g, 0.086 mmol) and DIPEA (0.03 mL, 0.172 mmol). The reaction was heated to 100° C. and stirred for 1 h, then allowed to cool to RT. (S)-tert-butyl piperidin-3-ylcarbamate (0.017 g, 0.086 mmol) and DIPEA (0.03 mL, 0.172 mmol) were added and the reaction was reheated to 100° C. for 30 min. Upon cooling, the mixture was concentrated under vacuum and purified by chromatography on silica gel (10-5% (0.7 M Ammonia/MeOH)/DCM) to afford (S)-tert-butyl (1-(5-carbamoyl-4-((4-phenyl-1H-indazol-6-yl)amino)pyrimidin-2-yl)piperidin-3-yl)carbamate (0.019 g, 38%). m/z (M+H)+(ES+) 529.4; $t_R$=2.19 min. HPLC Method 4.

Step 60-3: 2: (S)-2-(3-aminopiperidin-1-yl)-4-((4-phenyl-1H-indazol-6-yl)amino)pyrimidine-5-carboxamide. To a stirred solution of (S)-tert-butyl (1-(5-carbamoyl-4-((4-phenyl-1H-indazol-6-yl)amino)pyrimidin-2-yl)piperidin-3-yl) carbamate (0.018 g, 0.034 mmol) in 1,4-dioxane (1 mL) was added hydrochloric acid (4M in 1,4-dioxane, 0.170 mL, 0.681 mmol) and the reaction was stirred at RT for 24 h. The reaction mixture was concentrated under vacuum and purified by chromatography on silica gel (0-10% (0.7 M Ammonia/MeOH)/DCM) to afford (S)-2-(3-aminopiperidin-1-yl))-4-((4-phenyl-1H-indazol-6-yl)amino)pyrimidine-5-carboxamide. (8 mg, 49%). $^1$H NMR (500 Mhz, DMSO d-6) δ 13.27 (s, 1H), 12.50 (s, 1H), 8.71 (s, 1H), 8.49-8.41 (m, 1H), 8.15-9.76 (m, 2H), 7.80-7.65 (m, 2H), 7.53-7.44 (m, 3H), 7.42-7.37 (m, 2H), 4.65-4.50 (m, 1H), 4.49-4.40 (m, 1H), 3.15-3.02 (m, 1H), 2.91-2.84 (m, 1H), 2.78-2.71 (m, 1H), 1.95-1.86 (m, 1H), 1.77-1.69 (m, 1H), 1.56-1.41 (m, 1H), 1.40-1.26 (m, 1H). m/z (M+H)$^+$ (ES$^+$) 429.3; $t_R$=1.25 min. HPLC Method 2.

Example 61: (S)-2-(3-aminopiperidin-1-yl)-4-((1-isopropyl-4-phenyl-1H-indazol-6-yl)amino) pyrimidine-5-carboxamide Step 61-1: 4-chloro-1-isopropyl-1H-indazol-6-amine. To a stirred solution of 4-chloro-1H-indazol-6-amine (0.150 g, 0.895 mmol) in methanol (2 mL) was added benzaldehyde (0.096 mL, 0.940 mmol). The reaction was stirred at RT for 2 h, and then concentrated under vacuum. The residue was re-dissolved in DMF (2 mL), cooled to 0° C. and sodium hydride (60%, 0.107 g, 2.69 mmol) was added. After 20 min, 2-bromopropane (0.101 mL, 1.074 mmol) was added and the reaction was allowed to warm to RT and stirred for 20 h. The reaction mixture was cooled to 0° C. and quenched by dropwise addition of 1M HCl (5 mL) and stirred at RT for 4 h. The mixture was brought to pH 7 by addition of sat. sodium bicarbonate solution and extracted with ethyl acetate (3×10 mL). The combined organic layers were dried over magnesium sulfate, filtered and concentrated under vacuum. The crude product was purified by chromatography on silica gel (0-50% EtOAc/isohexane) to afford 4-chloro-1-isopropyl-1H-indazol-6-amine (0.075 g, 26%). m/z (M+H)$^+$ (ES$^+$) 429.3; $t_R$=1.25 min. HPLC Method 2.

Step 61-2: 1-isopropyl-4-phenyl-1H-indazol-6-amine. A stirred solution of 4,4,5,5-tetramethyl-2-phenyl-1,3,2-dioxaborolane (0.082 g, 0.40 mmol), 4-chloro-1-isopropyl-1H-indazol-6-amine (0.07 g, 0.33 mmol) and sodium bicarbonate (0.084 g, 1.00 mmol) in 1,4-dioxane (1.5 mL) and water (0.5 mL) was purged with nitrogen for 10 min. PdCl$_2$dppf (0.024 g, 0.03 mmol) was added and purging was continued for a further 10 min. The reaction was then heated to reflux and stirred under nitrogen for 2 h. Upon cooling, the reaction mixture was diluted with water (10 mL) and extracted with ethyl acetate (3×10 mL). The combined organic layers were dried over magnesium sulfate, filtered and concentrated under vacuum. The crude product was purified by chromatography on silica gel (0-3% (0.7 M Ammonia/MeOH)/DCM) to afford 1-isopropyl-4-phenyl-1H-indazol-6-amine (0.01 g, 9%). m/z (M+H)$^+$ (ES$^+$) 252.2; $t_R$=2.17 min. HPLC Method 4.

Step 61-3: (S)-2-(3-aminopiperidin-1-yl)-4-((1-isopropyl-4-phenyl-1H-indazol-6-yl)amino) pyrimidine-5-carboxamide. Prepared by an analogous method to example 3 using 1-isopropyl-4-phenyl-1H-indazol-6-amine. (3 mg, 36%). $^1$H NMR (500 MHz, DMSO d6) δ 12.51 (s, 1H), 8.72 (s, 1H), 8.47 (br s, 1H), 8.08 (br s, 1H), 8.02 (s, 1H), 7.82-7.73 (br m, 2H), 7.62 (s, 1H), 7.54-7.46 (m, 2H), 7.42-7.37 (m, 1H), 5.11 (sept, 1H, J=6.5 Hz), 4.65-4.40 (m, 2H), 3.18-3.08 (br m, 1H), 2.96-2.88 (m, 1H), 2.84-2.74 (br m, 1H), 1.97-1.86 (br m, 1H), 1.78-1.71 (br m, 1H), 1.51 (d, 6H, J=6.5 Hz), 1.44-1.31 (br m, 2H). m/z (M+H)$^+$ (ES$^+$) 471.3; $t_R$=2.07 min. HPLC Method 4.

Example 62

Step 62-1: (S)-tert-butyl (1-(4-((3-bromophenyl)amino)-5-carbamoylpyrimidin-2-yl) piperidin-3-yl)carbamate. To a stirred solution of 2,4-dichloropyrimidine-5-carboxamide (6.2 g, 32.3 mmol) in 1,4-dioxane (100 mL) was added 3-bromoaniline (3.52 mL, 32.3 mmol) and DIPEA (11.28 mL, 64.6 mmol). The reaction was heated to 90° C. and stirred for 2 h, then allowed to cool to RT. (S)-tert-butyl piperidin-3-ylcarbamate (6.79 g, 33.9 mmol) and DIPEA (11.28 mL, 64.6 mmol) were added and the mixture was again heated to 90° C. for 2 h, then allowed to cool to RT. The reaction mixture was diluted with water (200 mL) and extracted with ethyl acetate (2×200 mL). The combined organic layers were dried over magnesium sulfate, filtered and concentrated under vacuum. The crude residue was slurried in MTBE/hexanes (1:1, 150 mL) and collected by filtration to afford (S)-tert-butyl (1-(4-((3-bromophenyl)amino)-5-carbamoylpyrimidin-2-yl)piperidin-3-yl) carbamate (11.43 g, 72%). m/z (ES$^+$) (M+H)$^+$ 491.3, 493.2; $t_R$=2.45 min. HPLC Method 4.

Step 62-2: (S)-tert-butyl (1-(5-carbamoyl-4-((2',3'-difluoro-[1,1'-biphenyl]-3-yl)amino) pyrimidin-2-yl)piperidin-3-yl)carbamate. A stirred solution of (S)-tert-butyl (1-(4-((3-bromophenyl)amino)-5-carbamoylpyrimidin-2-yl)piperidin-3-yl)carbamate (0.1 g, 0.204 mmol), sodium hydrogencarbonate (0.068 g, 0.81 mmol) and (2,3-difluorophenyl)boronic acid (0.035 g, 0.22 mmol) was purged with nitrogen for 10 min. PdCl$_2$dppf (0.015 g, 0.02 mmol) was then added and purging was continued for a further 10 min. The reaction was then heated to 90° C. and stirred under nitrogen for 1 h, then allowed to cool to RT. The mixture was diluted with brine (20 mL) and extracted with ethyl acetate (3×20 mL). The combined organic layers were dried over magnesium sulfate, filtered and concentrated under vacuum. The crude product was purified by chromatography on silica gel (0-5% (0.7 M Ammonia/MeOH)/DCM) to afford (S)-tert-butyl (1-(5-carbamoyl-4-((2',3'-difluoro-[1,1'-biphenyl]-3-yl)amino)pyrimidin-2-yl)piperidin-3-yl)carbamate. (0.075 g, 70%). m/z (ES$^+$) (M+H)$^+$ 525.3; $t_R$=2.60 min. HPLC Method 4.

Step 62-3: (S)-2-(3-aminopiperidin-1-yl)-4-((2',3'-difluoro-[1,1'-biphenyl]-3-yl)amino) pyrimidine-5-carboxamide. To a stirred solution of (S)-tert-butyl (1-(5-carbamoyl-4-((2',3'-difluoro-[1,1'-biphenyl]-3-yl)amino)pyrimidin-2-yl)piperidin-3-yl)carbamate (0.072 g, 0.14 mmol) in 1,4-dioxane (1 mL) was added hydrogen chloride (4M in 1,4-dioxane, 0.686 mL, 2.75 mmol) and the reaction was stirred at RT for 16 h. The mixture was concentrated under vacuum, re-dissolved in methanol (1 mL) and loaded onto SCX (ca. 1 g). This was washed with methanol (20 mL) and then eluted with ammonia solution (0.7M in methanol). The ammoniacal fraction was concentrated under vacuum to afford (S)-2-(3-aminopiperidin-1-yl)-4-((2',3'-difluoro-[1,1'-biphenyl]-3-yl)amino)pyrimidine-5-carboxamide. (0.055 g, 90%). $^1$H NMR (500 MHz, DMSO-d6, 90° C.) δ 11.55 (s, 1H), 8.63 (s, 1H), 8.08-8.07 (m, 1H), 7.55-7.51 (m, 1H), 7.46 (t, 1H J=7.8 Hz), 7.43-7.26 (m, 5H), 7.24-7.21 (m, 1H), 4.45-4.39 (m, 1H), 4.37-4.31 (m, 1H), 3.09-3.02 (m, 1H), 2.82 (dd, 1H, J=12.6, 9.2 Hz), 2.72-2.64 (m, 1H), 1.91-1.83 (m, 1H), 1.78-1.23 (m, 5H). m/z (ES$^+$) (M+H)$^+$ 425.3; $t_R$=1.99 min. HPLC Method 4.

Example 63: (S)-2-(3-aminopiperidin-1-yl)-4-((2'-chloro-5'-methoxy-[1,1'-biphenyl]-3-yl)amino)pyrimidine-5-carboxamide Prepared by an analogous method to example 62. Step 2: (2-chloro-5-methoxyphenyl) boronic acid was used. (S)-tert-butyl (1-(5-carbamoyl-4-((2'-chloro-5'-methoxy-[1,1'-biphenyl]-3-yl)amino)pyrimidin-2-yl)piperidin-3-yl)carbamate. (0.075 g, 65%). m/z (ES$^+$) (M+H)$^+$ 553.4, 555.3; $t_R$=2.64 min. HPLC Method 4. Step 3: (S)-2-(3-aminopiperidin-1-yl)-4-((2'-chloro-5'-methoxy-[1,1'-biphenyl]-3-yl)amino) pyrimidine-5-carboxamide. (0.058 g, 87%). $^1$H NMR (500 MHz, DMSO-d6) δ 11.50 (s, 1H), 8.61 (s, 1H), 7.89 (t, 1H, J=2.0 Hz), 7.55-7.51 (m, 1H), 7.45-7.36 (m, 2H), 7.29 (br s, 2H), 7.10-7.06 (m, 1H), 7.00-6.93 (m, 2H), 4.43-4.36 (m, 1H), 4.35-4.29 (m, 1H), 3.81 (s, 3H), 3.06-2.99 (m, 1H), 2.79 (dd, 1H, J=12.6, 9.2 Hz), 2.69-2.62 (m, 1H), 1.89-1.82 (m, 1H), 1.69-1.61 (m, 1H), 1.56-1.20 (m, 4H). m/z (ES$^+$) (M+H)$^+$ 453.3, 455.2; $t_R$=2.03 min. HPLC Method 4.

Example 64: (S)-2-(3-aminopiperidin-1-yl)-4-((2,6-bis(2-cyanopropan-2-yl)pyridin-4-yl)amino)pyrimidine-5-carboxamide Step 64-1: 2,6-dibromo-N,N-bis(4-methoxybenzyl)pyridin-4-amine. 2,6-Dibromopyridin-4-amine (3.0 g, 11.91 mmol) was added to a flask which was then flushed with N$_2$ for 15 min. Anhydrous DMF (25 mL) was added and the mixture cooled to 0° C. Sodium hydride (60% dispersion in mineral oil, 1.06 g, 26.5 mmol) was added and the reaction mixture left to stir for 30 min. 4-Methoxybenzyl chloride (3.41 mL, 25.15 mmol) was added drop-wise, the cooling bath removed and the mixture stirred at RT for 1 h. The reaction mixture was diluted with EtOAc (40 mL), washed sequentially with water (6×30 mL) and brine (20 mL). The organic phase was dried over MgSO$_4$, filtered and concentrated under reduced pressure to give the crude product, which was purified by recrystallisation (boiling hot hexane with a small amount of EtOAc followed by cooling to RT and finally being left in a fridge overnight) to give the title compound as light-blue needles (4.70 g, 80%). $^1$H NMR (400 MHz, CDCl$_3$) δ 7.06 (d, J=8.4 Hz, 4H), 6.89 (d, J=8.4 Hz, 4H), 6.73 (s, 2H), 4.50 (s, 4H), 3.81 (s, 6H). LCMS: m/z (ES+) (M+H)$^+$ 493.0; $t_R$=3.01 min. HPLC Method 3 (Acid).

Step 64-2: 2,2'-(4-(bis(4-methoxybenzyl)amino)pyridine-2,6-diyl)bis(2-methylpropanenitrile). As in example 7 step 2, using 2,6-dibromo-N,N-bis(4-methoxybenzyl)pyridin-4-amine (0.671 g, 1.36 mmol), Xantphos (0.094 g, 0.16 mmol), Pd$_2$allyl$_2$Cl$_2$ (0.022 g, 4 mol %), potassium 2-cyano-2-methylpropanoate (0.494 g, 3.27 mmol) and mesitylene (3.2 mL), which was purified by flash column chromatography on silica (hexane, followed by 5:1 hexane: EtOAc) to give the title compound as a colourless viscous oil which solidified on standing (0.463 g, 73%). $^1$H NMR (400 MHz, CDCl$_3$) δ 7.14 (d, J=8.8 Hz, 4H), 6.88 (d, J=8.8 Hz, 4H), 6.81 (s, 2H), 4.62 (s, 4H), 3.80 (s, 6H), 1.64 (s, 12H). LCMS: m/z (ES+) (M+H)$^+$ 469.4; $t_R$=3.06 min. HPLC Method 3 (Acid).

Step 64-3: 2,2'-(4-aminopyridine-2,6-diyl)bis(2-methylpropanenitrile). Trifluoroacetic acid (22.0 mL, excess) was added drop-wise to a solution of 2,2'-(4-(bis(4-methoxybenzyl)amino)pyridine-2,6-diyl)bis(2-methylpropanenitrile) (0.463 g, 0.988 mmol) in DCM (20.0 mL). The reaction mixture was heated to 50° C. for 48 h; LCMS analysis indicated the major product was from mono 4-methoxybenzyl deprotection. The reaction mixture was neutralised by the drop-wise addition of a saturated solution of NaHCO$_3$ (final pH=8-9) and diluted with DCM (30 mL). The organic layer was washed with water (2×20 mL) and the initial aqueous phase extracted with DCM (15 mL). The combined organic extracts were dried over MgSO$_4$, filtered and concentrated under reduced pressure to give the crude mixture. To the crude mixture was added was added Pd(OH)$_2$ (0.600 g, 10-20% Pd basis), DCM (3.5 mL) and finally MeOH (10.0 mL) and the flask purged with H$_2$. The flask was left to stir vigorously at RT for 3 h after which the flask was opened to the air and the mixture filtered through a pad of Celite® under reduced pressure. The cake was washed with additional MeOH (20 mL) and DCM (20 mL), the filtrate concentrated under reduced pressure and the crude product purified by flash column chromatography on silica (6:1 hexane: EtOAc followed by 5:1) to give the title compound as a colourless oil (0.070 g, 31%). $^1$H NMR (400 MHz, CDCl$_3$) δ 6.75 (s, 2H), 4.43-4.28 (br s, 2H), 1.69 (s, 12H). LCMS: m/z (ES+) (M+H)$^+$ 229.2; $t_R$=2.42 min. HPLC Method 3 (Acid).

Step 64-4: (S)-2-(3-aminopiperidin-1-yl)-4-((2,6-bis(2-cyanopropan-2-yl)pyridin-4-yl)amino)pyrimidine-5-carboxamide. 2,2'-(4-Aminopyridine-2,6-diyl)bis(2-methylpropanenitrile) (0.051 g, 0.22 mmol), 2,4-dichloropyrimidine-5-carboxamide (0.043 g, 0.22 mmol), triethylamine (0.06 mL, 0.43 mmol) were dissolved in anhydrous dioxane (5.0 mL) and DMF (0.5 mL). The mixture was heated at 50° C. overnight and then left to cool to RT. tert-Butyl (S)-piperidin-3-ylcarbamate (0.042 g, 0.21 mmol) and triethylamine (0.06 mL, 0.43 mmol) were added and the reaction mixture was heated at 50° C. for 2 h. The reaction mixture was diluted with EtOAc (15 mL), washed sequentially with water (3×10 mL) and brine (10 mL). The organic phase was dried over MgSO$_4$, filtered and concentrated under reduced pressure to give the crude product, which was purified by flash column chromatography on silica (2:1 hexane: EtOAc, followed by 1:1, 1:2 and EtOAc) to give the product from two displacements (0.026 g, 21%). The intermediate was dissolved in dioxane (2.0 mL) and 4M HCl in dioxane (2.0 mL) was added drop-wise and the mixture was stirred at RT overnight. Hexane was added (15 mL) and the precipitate filtered and dried to give the hydrochloride salt of the title compound as a white powder (0.018 g, 78%). $^1$H NMR (400 MHz, CD$_3$OD) δ 8.69 (s, 1H), 7.93 (s, 2H), 4.47 (app d, J=12.4 Hz, 1H), 4.20-4.03 (m, 1H), 3.99-3.82 (m, 1H), 3.77-3.62 (m, 2H), 2.28-2.14 (m, 1H), 2.12-1.97 (m, 1H), 1.91-1.82 (m, 2H), 1.79 (s, 12H). LCMS: m/z (ES+) (M+H)$^+$ 448.3; $t_R$=2.26 min. HPLC Method 3 (Acid).

Example 65: (S)-2-(3-aminopiperidin-1-yl)-4-((3,3-dimethyl-2-oxoindolin-5-yl)amino)pyrimidine-5-carboxamide Step 65-1: 3,3-dimethylindolin-2-one. "BuLi (1.6 M in hexane, 9.3 mL, 14.95 mmol) was added into a solution of 3-methylindolin-2-one (1.0 g, 6.79 mmol) in dry THF (23 mL) at −78° C. under an inert atmosphere. The mixture was stirred at −78° C. for 30 min. Methyl iodide (0.47 mL, 7.47 mmol) was added drop-wise and the mixture was stirred at −78° C. for an additional 30 min, then allowed to warm up to RT and stirred for 1.5 h. The reaction mixture was quenched with a saturated solution of NH$_4$Cl (ca. 40 mL) and extracted with EtOAc (3×30 mL). The organic phases were combined and washed with brine, dried over MgSO$_4$, filtered and concentrated under reduced pressure. The residue was purified by flash chromatography [Hexane:EtOAc (4:1)] affording the title product as a white solid (477 mg, 44%). $^1$H NMR (300 MHz, CDCl$_3$) δ 8.75 (s, 1H), 7.25-7.15 (m, 2H), 7.04 (app. t, J=7.3 Hz, 1H), 6.94 (d, J=8.1 Hz, 1H), 1.41 (s, 6H); m/z (ES$^-$) (M−H)$^+$ 160.0; $t_R$=1.96 min. HPLC Method 3 (Acid).

Step 65-2: 3,3-dimethyl-5-nitroindolin-2-one. A mixture of 3,3-dimethylindolin-2-one (477 mg, 2.96 mmol) and H$_2$SO$_4$ (95-98%, 3.75 mL) was cooled down to −40° C. while vigorously stirring. A solution of concentrated HNO$_3$ (90%, 0.14 mL, 2.96 mmol) in H$_2$SO$_4$ (0.7 mL) was added drop-wise at −40° C. The reaction mixture was allowed to reach RT and stirred for 5 h. The mixture was poured into an ice-cooled solution of water (ca. 150 mL) precipitating a pale-green solid that was isolated by filtration, washed with water (ca. 10 mL) and dried under air. The precipitate was dissolved in EtOAc (ca. 30 mL) and the organic phase was dried over MgSO$_4$, filtered and concentrated under reduced pressure, dry-loaded into a column and purified by flash chromatography [Hexane:EtOAc (3:2)] affording the title product as a white solid (253 mg, 41%). $^1$H NMR (400 MHz, CDCl$_3$) δ 8.20 (dd, J=8.6, 2.3 Hz, 1H), 8.16 (br. s, 1H), 8.10 (d, J=2.3 Hz, 1H), 7.00 (d, J=8.6 Hz, 1H), 1.46 (s, 6H); m/z (ES$^-$) (M−H)$^+$ 205.0; $t_R$=1.98 min. HPLC Method 3 (Acid).

Step 65-3: 5-amino-3,3-dimethylindolin-2-one. Iron powder (341 mg, 6.11 mmol) was added into a solution of HCl (36%, 0.05 mL, 0.61 mmol) in EtOH (2.00 mL). The suspension was stirred at 65° C. for 2 h. The suspension was allowed to cool down to 55° C. and a NH$_4$Cl solution (25%, 1.50 mL) was added. A solution of 3,3-dimethyl-5-nitroindolin-2-one (214 mg, 1.22 mmol) in EtOH (1 mL) was added drop-wise into the reaction mixture and stirred at 55° C. for 30 min. The mixture was allowed to reach RT and was diluted with EtOH (4 mL), filtered through Celite® and washed with more EtOH (ca. 40 mL). The filtrate was taken to neutral pH using a saturated aq. solution of NaHCO$_3$ and the solvent was removed under reduced pressure. The residue was dissolved in EtOAc (ca. 20 mL) and washed with a saturated aq. solution of NaHCO$_3$ (ca. 10 mL) and brine (ca. 10 mL). The organic phase was dried over MgSO$_4$, filtered and concentrated under reduced affording a yellow solid that was used in the next step without further purification. $^1$H NMR (400 MHz, CDCl$_3$) δ 9.01 (br. s, 1H), 6.72 (d, J=8.1 Hz, 1H), 6.59 (d, J=2.2 Hz, 1H), 6.52 (dd, J=8.1, 2.2 Hz, 1H), 3.54 (br. s, 2H), 1.36 (s, 6H); $^{13}$C NMR (101 MHz, CDCl$_3$) δ 184.1, 141.9, 137.7, 131.9, 113.9, 110.9, 110.5, 45.0, 24.4.

Step 65-4: tert-butyl (S)-(1-(5-carbamoyl-4-((3,3-dimethyl-2-oxoindolin-5-yl)amino)pyrimidin-2-yl)piperidin-3-yl)carbamate. A mixture of 2,4-dichloropyrimidine-5-carboxamide (55 mg, 0.28 mmol), 5-amino-3,3-dimethylindolin-2-one (50 mg, 0.28 mmol) and triethylamine (0.04 mL, 0.31 mmol) in 1,4-dioxane (5.6 mL) and DMF (1 mL) was stirred at 50° C. for 5 h. (S)-Tert-butyl piperidin-3-ylcarbamate (56 mg, 0.28 mmol) and triethylamine (0.04 mL, 0.31 mmol) were added and the mixture was stirred at 50° C. for 3 h. The resulting mixture was allowed to reach RT and concentrated under reduced pressure. The residue was dissolved in EtOAc (20 mL) and washed with brine (3×20 mL). The organic phase was dried over MgSO$_4$, filtered, dry-loaded into a column and purified by flash chromatography [gradient Hexane:EtOAc (3:7→1:9)] affording the title product as a white solid (62 mg, 45%). The compound was directly taken into the next step.

Step 65-5: (S)-2-(3-aminopiperidin-1-yl)-4-((3,3-dimethyl-2-oxoindolin-5-yl)amino)pyrimidine-5-carboxamide. tert-Butyl (S)-(1-(5-carbamoyl-4-((3,3-dimethyl-2-oxoindolin-5-yl)amino)pyrimidin-2-yl)piperidin-3-yl)carbamate (49 mg, 0.10 mmol) was suspended into dioxane (5 mL) and 4N HCl in dioxane (3 mL) was added. The suspension was stirred at RT overnight. Et$_2$O was added (ca. 4 mL) and the precipitate was filtered under reduced pressure, washed with Et$_2$O (ca. 10 mL) and dried under air. The title product was isolated as a white solid (35 mg, 89%). $^1$H NMR (400 MHz, Chloroform-d) δ 8.51 (br, s, 1H), 7.52 (br. s, 1H), 7.45-7.35 (m, 1H), 6.99 (d, J=8.3 Hz, 1H), 4.35-4.24 (m, 1H), 4.12-3.91 (m, 1H), 3.76-3.62 (m, 1H), 3.62-3.52 (m, 1H), 3.50-3.40 (m, 1H), 2.22-2.10 (m, 1H), 1.99-1.86 (m, 1H), 1.85-1.69 (m, 2H), 1.36 (s, 6H); m/z (ES$^+$) (M+H)$^+$ 396.3; $t_R$=1.90 min. HPLC Method 3 (Base).

Example 66: (S)-2-(3-aminopiperidin-1-yl)-4-((7-bromo-3,3-dimethyl-2-oxoindolin-5-yl)amino)pyrimidine-5-carboxamide Step 66-1: 7-bromo-3,3-dimethyl-5-nitroindolin-2-one. NBS (267 mg, 1.50 mmol) was added portion-wise to a solution of 3,3-dimethyl-5-nitroindolin-2-one (206 mg, 1.00 mmol) in $H_2SO_4$ (2 mL) at RT and stirred for 1.5 h. The reaction mixture was poured into an ice-cooled solution of water (ca. 150 mL) precipitating a beige solid that was isolated by filtration, washed with water (ca. 10 mL) and dried under air. The precipitate was dissolved in EtOAc (ca. 30 mL) and the organic phase was dried over $MgSO_4$, filtered and concentrated under reduced pressure, dry-loaded into a column and purified by flash chromatography [Hexane:EtOAc (7:3)] affording the title product as a white solid (103 mg, 36%). $^1$H NMR (300 MHz, $CDCl_3$) δ 8.73 (br. s, 1H), 8.35 (d, J=2.1 Hz, 1H), 8.04 (d, J=2.1 Hz, 1H), 1.48 (s, 6H); m/z (ES$^-$) (M−H)$^-$ 282.2 for $^{79}$Br; $t_R$=2.23 min. HPLC Method 3 (Base).

Step 66-2: 5-amino-7-bromo-3,3-dimethylindolin-2-one. Zn dust (157 mg, 2.40 mmol) was added portion-wise into an ice-cooled solution of 7-bromo-3,3-dimethyl-5-nitroindolin-2-one (84 mg, 0.30 mmol) and $NH_4Cl$ (253 mg, 4.73 mmol) in $THF:H_2O$ (5:1, 5 mL). The mixture was allowed to reach RT and stirred for 30 min. The reaction mixture was filtered through Celite® and washed with EtOAc (ca. 20 mL). The filtrate was dried over $MgSO_4$, filtered and concentrated under reduced pressure affording a yellow solid that was used in the next step without further purification (75 mg, 98%). $^1$H NMR (300 MHz, Methanol-$d_4$) δ 7.89 (s, 1H), 6.73 (s, 1H), 6.66 (s, 1H), 1.30 (s, 6H); m/z (ES$^+$) (M+H)$^+$ 255.0; $t_R$=0.81 min. HPLC Method 3 (Acid).

Step 66-3: tert-butyl (S)-(1-(4-((7-bromo-3,3-dimethyl-2-oxoindolin-5-yl)amino)-5-carbamoylpyrimidin-2-yl)piperidin-3-yl)carbamate. A mixture of 2,4-dichloropyrimidine-5-carboxamide (50 mg, 0.26 mmol), 5-amino-7-bromo-3,3-dimethyloxoindolin-2-one (66 mg, 0.26 mmol) and triethylamine (0.04 mL, 0.29 mmol) in 1,4-dioxane (5.2 mL) and DMF (1 mL) was stirred at 50° C. for 2.5 h. (S)-Tert-butyl piperidin-3-ylcarbamate (52 mg, 0.26 mmol) and triethylamine (0.04 mL, 0.29 mmol) were added and the mixture was stirred at 50° C. overnight. The resulting mixture was allowed to reach RT and concentrated under reduced pressure. The residue was dissolved in EtOAc (20 mL) and washed with brine (3×20 mL). The organic phase was dried over $MgSO_4$, filtered, dry-loaded into a column and purified by flash chromatography [gradient Hexane:EtOAc (1:1->1:4)] affording the title product as a white solid (75 mg, 50%). The compound was directly taken into the next step.

Step 66-4: (S)-2-(3-aminopiperidin-1-yl)-4-((7-bromo-3,3-dimethyl-2-oxoindolin-5-yl)amino)pyrimidine-5-carboxamide. tert-Butyl (S)-(1-(4-((7-bromo-3,3-dimethyl-2-oxoindolin-5-yl)amino)-5-carbamoylpyrimidin-2-yl)piperidin-3-yl)carbamate (75 mg, 0.13 mmol) was suspended into dioxane (5 mL) and 4N HCl in dioxane (3 mL) was added. The suspension was stirred at RT overnight. $Et_2O$ was added (ca. 4 mL) and the precipitate was filtered under reduced pressure, washed with $Et_2O$ (ca. 10 mL) and dried under air. The hydrochloride salt of the title product was isolated as a white solid (60 mg, 91%). $^1$H NMR (300 MHz, DMSO-$d_6$) δ 11.64 (s, 1H), 10.68 (s, 1H), 8.71 (s, 1H), 8.31 (br. s, 2H), 7.70 (s, 1H), 7.58 (s, 1H), 4.78-4.14 (m, 3H), 4.09-3.95 (m, 1H), 3.67-3.34 (m, 2H), 3.24 (app. br. s, 1H), 2.02 (app. br. s, 1H), 1.91-1.66 (m, 2H), 1.58 (app. br. s, 1H), 1.28 (s, 6H); m/z (ES$^+$) (M+H)$^+$ 473.9 for $^{79}$Br; $t_R$=1.75 min. HPLC Method 3 (Acid).

Example 67: (S)-2-(3-aminopiperidin-1-yl)-4-((7-isopropyl-3,3-dimethyl-2-oxoindolin-5-yl)amino)pyrimidine-5-carboxamide Step 67-1: 3,3-dimethyl-5-nitro-7-(prop-1-en-2-yl)indolin-2-one. A mixture of 7-bromo-3,3-dimethyl-5-nitroindolin-2-one (100 mg, 0.35 mmol), 4,4,5,5-tetramethyl-2-(prop-1-en-2-yl)-1,3,2-dioxaborolane (0.13 mL, 0.70 mmol) and $K_2CO_3$ (145 mg, 1.05 mmol) in dioxane:$H_2O$ (4:1, 6 mL) was degassed with a $N_2$ flow for 20 min. Bis(triphenylphosphine)palladium(II) dichloride (25 mg, 0.04 mmol) was added and the reaction mixture was stirred at 100° C. for 1 h. The resulting mixture was concentrated under reduced pressure and the residue dissolved in EtOAc (ca. 30 mL) and washed with brine (3×20 mL). The organic phase was dried over $MgSO_4$, filtered, concentrated under reduced pressure and purified by flash chromatography [Hexane:EtOAc (4:1)] affording the title product as a colourless oil (68 mg, 79%). $^1$H NMR (300 MHz, $CDCl_3$) δ 8.48 (br. s, 1H), 8.09 (d, J=2.3 Hz, 1H), 7.98 (d, J=2.3 Hz, 1H), 5.46 (app. s, 1H), 5.26-5.18 (m, 1H), 2.18 (s, 3H), 1.46 (s, 6H); m/z (ES$^-$) (M−H)$^+$ 245.0; $t_R$=2.31 min. HPLC Method 3 (Acid).

Step 67-2: 5-amino-7-isopropyl-3,3-dimethylindolin-2-one. A mixture of 3,3-dimethyl-5-nitro-7-(prop-1-en-2-yl)indolin-2-one (68 mg, 0.28 mmol) and palladium on carbon (10 wt. %, 100 mg, 0.09 mmol) in EtOH (6 mL) was stirred at RT under H2 atmosphere (1 atm) for 2 h. The reaction mixture was flushed with Ar, filtered through Celite® and washed with MeOH (ca. 20 mL). The filtrate was concentrated under reduced pressure and the residue was directly taken into the next step without further purification (60 mg, 99%). $^1$H NMR (300 MHz, $CDCl_3$) δ 8.90 (br. s, 1H), 6.66-6.14 (m, 2H), 3.26 (br. s, 2H), 2.97-2.82 (m, 1H), 1.36 (s, 6H), 1.23 (d, J=6.9 Hz, 6H); m/z (ES$^+$) (M+H)$^+$ 219.0; $t_R$=0.77 min. HPLC Method 3 (Acid).

Step 67-3: tert-butyl (S)-(1-(5-carbamoyl-4-((7-isopropyl-3,3-dimethyl-2-oxoindolin-5-yl)amino)pyrimidin-2-yl)piperidin-3-yl)carbamate. A mixture of 2,4-dichloropyrimidine-5-carboxamide (54 mg, 0.28 mmol), 5-amino-7-isopropyl-3,3-dimethylindolin-2-one (61 mg, 0.28 mmol) and triethylamine (0.04 mL, 0.31 mmol) in 1,4-dioxane (5.0 mL) and DMF (1 mL) was stirred at 50° C. overnight. (S)-Tert-butyl piperidin-3-ylcarbamate (56 mg, 0.28 mmol) and triethylamine (0.04 mL, 0.31 mmol) were added and the mixture was stirred at 50° C. overnight. The resulting mixture was allowed to reach RT and concentrated under reduced pressure. The residue was dissolved in EtOAc (20 mL) and washed with brine (3×20 mL). The organic phase was dried over $MgSO_4$, filtered, dry-loaded into a column and purified by flash chromatography [gradient Hexane:EtOAc (3:7→1:9)] affording the title product as a white solid (84 mg, 56%). The compound was directly taken into the next step.

Step 67-4: (S)-2-(3-aminopiperidin-1-yl)-4-((7-isopropyl-3,3-dimethyl-2-oxoindolin-5-yl)amino)pyrimidine-5-carboxamide. tert-Butyl (S)-(1-(5-carbamoyl-4-((7-isopropyl-3,3-dimethyl-2-oxoindolin-5-yl)amino)pyrimidin-2-yl)piperidin-3-yl)carbamate (84 mg, 0.16 mmol) was suspended into dioxane (5 mL) and 4N HCl in dioxane (3 mL) was added. The suspension was stirred at RT overnight. $Et_2O$ was added (ca. 4 mL) and the precipitate was filtered under reduced pressure, washed with $Et_2O$ (ca. 10 mL) and dried under air. The hydrochloride salt of the title product was isolated as a white solid (55 mg, 81%). $^1$H NMR (300 MHz, DMSO-$d_6$) δ 11.73 (br. s, 1H), 10.46 (s, 1H), 8.70 (s, 1H), 8.48-8.32 (m, 3H), 7.69 (br. s, 1H), 7.41 (s, 1H), 7.29 (s, 1H), 4.06-3.91 (m, 1H), 3.82-3.51 (m, 2H), 3.29 (app. br. s, 1H), 3.11 (sept, J=6.5 Hz, 1H), 2.08-1.94 (m, 1H), 1.92-1.69 (m, 2H), 1.70-1.50 (m, 1H), 1.26 (s, 6H), 1.18 (d, J=6.5 Hz, 6H); m/z (ES$^+$) (M+H)$^+$ 438.0; $t_R$=1.77 min. HPLC Method 3 (Acid).

Example 68: (S)-2-(3-aminopiperidin-1-yl)-4-((7-cyclohexyl-3,3-dimethyl-2-oxoindolin-5-yl)amino)pyrimidine-5-carboxamide Step 68-1: 7-(cyclohex-1-en-1-yl)-3,3-dimethyl-5-nitroindolin-2-one. A mixture of 7-bromo-3,3-dimethyl-5-nitroindolin-2-one (150 mg, 0.53 mmol), cyclohex-1-en-1-ylboronic acid (133 mg, 1.06 mmol) and $K_2CO_3$ (221 mg, 1.59 mmol) in dioxane:$H_2O$ (4:1, 10 mL) was degassed with a N2 flow for 20 min. Bis(triphenylphosphine)palladium(II) dichloride (37 mg, 0.05 mmol) was added and the reaction mixture was stirred at 100° C. for 2 h. The resulting mixture was concentrated under reduced pressure and the residue dissolved in EtOAc (ca. 30 mL) and washed with brine (3×20 mL). The organic phase was dried over $MgSO_4$, filtered, concentrated under reduced pressure and purified by flash chromatography [Hexane:EtOAc (4:1)] affording the title product as a colourless oil (101 mg, 67%). $^1$H NMR (400 MHz, CDCl$_3$) δ 9.50 (br. s, 1H), 8.03 (d, J=2.2 Hz, 1H), 7.95 (d, J=2.2 Hz, 1H), 6.00-5.94 (m, 1H), 2.40-2.31 (m, 2H), 2.32-2.22 (m, 2H), 1.90-1.79 (m, 2H), 1.80-1.69 (m, 2H), 1.44 (s, 6H); m/z (ES$^-$) (M−H)$^+$ 284.9; $t_R$ 2.59 min. HPLC Method 3 (Base).

Step 68-2: 5-amino-7-cyclohexyl-3,3-dimethylindolin-2-one. A mixture of 7-(cyclohex-1-en-1-yl)-3,3-dimethyl-5-nitroindolin-2-one (60 mg, 0.21 mmol) and palladium on carbon (10 wt. %, 23 mg, 0.02 mmol) in DCM:MeOH (1:1, 4 mL) was stirred at RT under H2 atmosphere (1 atm) for 2 h. The reaction mixture was flushed with Ar, filtered through Celite® and washed with MeOH (ca. 10 mL) and DCM (ca. 10 mL). The filtrate was concentrated under reduced pressure and the residue, rapidly turning darker, was directly taken into the next step without further purification (54 mg, 99%).

Step 68-3: tert-butyl (S)-(1-(5-carbamoyl-4-((7-cyclohexyl-3,3-dimethyl-2-oxoindolin-5-yl)amino)pyrimidin-2-yl)piperidin-3-yl)carbamate. A mixture of 2,4-dichloropyrimidine-5-carboxamide (40 mg, 0.21 mmol), 5-amino-7-cyclohexyl-3,3-dimethylindolin-2-one (54 mg, 0.21 mmol) and triethylamine (0.03 mL, 0.23 mmol) in 1,4-dioxane (4.0 mL) was stirred at 50° C. overnight. (S)-Tert-butyl piperidin-3-ylcarbamate (42 mg, 0.21 mmol) and triethylamine (0.03 mL, 0.23 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3-+1:4)] affording the title product as a white solid (46 mg, 38%). The compound was directly taken into the next step.

Step 68-4: (S)-2-(3-aminopiperidin-1-yl)-4-((7-cyclohexyl-3,3-dimethyl-2-oxoindolin-5-yl)amino)pyrimidine-5-carboxamide. tert-Butyl (S)-(1-(5-carbamoyl-4-((7-cyclohexyl-3,3-dimethyl-2-oxoindolin-5-yl)amino)pyrimidin-2-yl)piperidin-3-yl)carbamate (46 mg, 0.08 mmol) was suspended into dioxane:Et$_2$O (1:1, 4 mL) and 4N HCl in dioxane (2 mL) was added. The suspension was stirred at RT overnight. Et$_2$O was added (ca. 4 mL) and the precipitate was filtered under reduced pressure, washed with Et$_2$O (ca. 10 mL) and dried under air. The resulting solid was dissolved in MeOH (ca. 5 mL) and concentrated under reduced pressure giving the hydrochloride salt of the title product as a white solid (36 mg, 95%). $^1$H NMR (300 MHz, DMSO-$d_6$) δ 11.72 (br. s, 1H), 10.50 (br. s, 1H), 8.70 (br. s, 1H), 8.54-8.20 (m, 3H), 7.75-7.55 (m, 1H), 7.42-7.25 (m, 2H), 4.50-4.10 (m, 3H), 4.06-3.89 (m, 2H), 3.78-3.47 (m, 2H), 3.29 (app. br. s, 1H), 2.73 (app. br. s, 1H), 2.11-1.94 (m, 2H), 1.87-1.64 (m, 6H), 1.59 (app. br. s, 1H), 1.51-1.28 (m, 3H), 1.25 (s, 6H); m/z (ES$^+$) (M+H)$^+$ 478.0; $t_R$=2.17 min. HPLC Method 3 (Base).

Example 69: (S)-2-(3-aminopiperidin-1-yl)-4-((7-(cyclohex-1-en-1-yl)-3,3-dimethyl-2-oxoindolin-5-yl)amino)pyrimidine-5-carboxamide Step 69-1: 5-amino-7-(cyclohex-1-en-1-yl)-3,3-dimethylindolin-2-one. Zn dust (99 mg, 1.52 mmol) was added portion-wise into an ice-cooled solution of 7-(cyclohex-1-en-1-yl)-3,3-dimethyl-5-nitroindolin-2-one (55 mg, 0.19 mmol) and NH$_4$Cl (165 mg, 3.08 mmol) in THF:$H_2O$ (5:1, 3 mL). The mixture was allowed to reach RT and stirred for 5 h. The reaction mixture was filtered through Celite® and washed with EtOAc (ca. 20 mL). The filtrate was dried over MgSO$_4$, filtered and concentrated under reduced pressure affording a yellow solid that was used in the next step without further purification (51 mg, 99%). $^1$H NMR (300 MHz, Chloroform-d) δ 8.25 (br. s, 1H), 6.51 (d, J=2.2 Hz, 1H), 6.44 (d, J=2.2 Hz, 1H), 5.88-5.76 (m, 1H), 3.58 (br. s, 2H), 2.31-2.10 (m, 4H), 1.82-1.59 (m, 4H), 1.33 (s, 6H); m/z (ES$^+$) (M+H)$^+$ 257.1; $t_R$=2.14 min. HPLC Method 3 (Base).

Step 69-2: tert-butyl (S)-(1-(5-carbamoyl-4-((7-(cyclohex-1-en-1-yl)-3,3-dimethyl-2-oxoindolin-5-yl)amino)pyrimidin-2-yl)piperidin-3-yl)carbamate. A mixture of 2,4-dichloropyrimidine-5-carboxamide (38 mg, 0.20 mmol), 5-amino-7-(cyclohex-1-en-1-yl)-3,3-dimethylindolin-2-one (51 mg, 0.20 mmol) and triethylamine (0.03 mL, 0.22 mmol) in 1,4-dioxane (4.0 mL) was stirred at 50° C. overnight. (S)-tert-butyl piperidin-3-ylcarbamate (40 mg, 0.20 mmol) and triethylamine (0.03 mL, 0.22 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3-+3:7)] affording the title product as a white solid (57 mg, 50%). The compound was directly taken into the next step.

Step 69-3: (S)-2-(3-aminopiperidin-1-yl)-4-((7-(cyclohex-1-en-1-yl)-3,3-dimethyl-2-oxoindolin-5-yl)amino)pyrimidine-5-carboxamide. tert-Butyl (S)-(1-(5-carbamoyl-4-((7-(cyclohex-1-en-1-yl)-3,3-dimethyl-2-oxoindolin-5-yl)amino)pyrimidin-2-yl)piperidin-3-yl)carbamate (57 mg, 0.10 mmol) was suspended into dioxane:Et$_2$O (1:1, 4 mL) and 4N HCl in dioxane (2 mL) was added. The suspension was stirred at RT overnight. Et$_2$O was added (ca. 4 mL) and the precipitate was filtered under reduced pressure, washed with Et$_2$O (ca. 10 mL) and dried under air. The hydrochloride salt of the title product was isolated as a white solid (45 mg, 94%). $^1$H NMR (400 MHz, Methanol-$d_4$) δ 8.53 (br. s, 1H), 7.44 (br. s, 1H), 7.23 (br. s, 1H), 5.93-5.73 (m, 1H), 4.33-4.22 (m, 1H), 4.07 (app. br. s, 1H), 3.77 (app. br. s, 1H), 3.66-3.58 (m, 1H), 3.57-3.44 (m, 1H), 2.37-2.28 (m, 2H), 2.29-2.15 (m, 3H), 2.02-1.90 (m, 1H), 1.90-1.69 (m, 6H), 1.39 (s, 6H); m/z (ES$^+$) (M+H)$^+$ 476.0; $t_R$=2.17 min. HPLC Method 3 (Base).

Example 70: (S)-2-(3-aminopiperidin-1-yl)-4-((3,3-dimethyl-2-oxo-7-phenylindolin-5-yl)amino)pyrimidine-5-carboxamide Step 70-1: 3,3-dimethyl-5-nitro-7-phenylindolin-2-one. A mixture of 7-bromo-3,3-dimethyl-5-nitroindolin-2-one (206 mg, 0.72 mmol), 4,4,5,5-tetramethyl-2-phenyl-1,3,2-dioxaborolane (166 mg, 0.81 mmol) and $K_2CO_3$ (170 mg, 1.23 mmol) in dioxane:$H_2O$ (4:1, 7 mL) was degassed with a N2 flow for 20 min. Bis(triphenylphosphine)palladium(II) dichloride (29 mg, 0.04 mmol) was added and the reaction mixture was stirred at 100° C. for 2 h. The resulting mixture was concentrated under reduced pressure and the residue dissolved in EtOAc (ca. 30 mL) and washed with brine (3×20 mL). The organic phase was dried over $MgSO_4$, filtered, concentrated under reduced pressure and purified by flash chromatography [Hexane:EtOAc (4:1)] affording the title product as a yellow solid (171 mg, 84%). $^1$H NMR (400 MHz, $CDCl_3$) δ 8.23 (d, J=2.2 Hz, 1H), 8.08 (d, J=2.2 Hz, 1H), 8.00 (br. s, 1H), 7.57-7.51 (m, 2H), 7.50-7.43 (m, 3H), 1.49 (s, 6H); m/z (ES$^-$) (M–H)$^+$ 280.9; $t_R$=2.43 min. HPLC Method 3 (Base).

Step 70-2: 5-amino-3,3-dimethyl-7-phenylindolin-2-one. Zn dust (185 mg, 2.84 mmol) was added portion-wise into an ice-cooled solution of 3,3-dimethyl-5-nitro-7-phenylindolin-2-one (100 mg, 0.35 mmol) and $NH_4Cl$ (300 mg, 5.60 mmol) in THF:$H_2O$ (5:1, 6 mL). The mixture was allowed to reach RT and stirred for 5 h. The reaction mixture was filtered through Celite® and washed with EtOAc (ca. 20 mL). The filtrate was dried over $MgSO_4$, filtered and concentrated under reduced pressure affording a yellow solid that was used in the next step without further purification (85 mg, 99%). $^1$H NMR (400 MHz, $CDCl_3$) δ 7.63 (br. s, 1H), 7.47-7.39 (m, 4H), 7.38-7.32 (m, 1H), 6.62-6.54 (m, 2H), 3.50 (br. s, 2H), 1.39 (s, 6H); m/z (ES$^+$) (M+H)$^+$ 253.0; $t_R$=2.00 min. HPLC Method 3 (Base).

Step 70-3: tert-butyl (S)-(1-(5-carbamoyl-4-((3,3-dimethyl-2-oxo-7-phenylindolin-5-yl)amino)pyrimidin-2-yl)piperidin-3-yl)carbamate. A mixture of 2,4-dichloropyrimidine-5-carboxamide (67 mg, 0.35 mmol), 5-amino-3,3-dimethyl-7-phenylindolin-2-one (98 mg, 0.35 mmol) and triethylamine (0.05 mL, 0.38 mmol) in 1,4-dioxane (7.0 mL) was stirred at 50° C. for 2 h. (S)-Tert-butyl piperidin-3-ylcarbamate (70 mg, 0.35 mmol) and triethylamine (0.05 mL, 0.38 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3-1:4)] affording the title product as a white solid (129 mg, 65%). The compound was directly taken into the next step.

Step 70-4: (S)-2-(3-aminopiperidin-1-yl)-4-((3,3-dimethyl-2-oxo-7-phenylindolin-5-yl)amino)pyrimidine-5-carboxamide. tert-Butyl (S)-(1-(5-carbamoyl-4-((3,3-dimethyl-2-oxo-7-phenylindolin-5-yl)amino)pyrimidin-2-yl) piperidin-3-yl)carbamate (129 mg, 0.23 mmol) was suspended into dioxane:$Et_2O$ (1:1, 4 mL) and 4N HCl in dioxane (2 mL) was added. The suspension was stirred at RT overnight. $Et_2O$ was added (ca. 4 mL) and the precipitate was filtered under reduced pressure, washed with $Et_2O$ (ca. 10 mL) and dried under air. The hydrochloride salt of the title product was isolated as a white solid (79 mg, 74%). $^1$H NMR (400 MHz, DMSO-d$_6$) δ 11.86 (s, 1H), 10.29 (s, 1H), 8.73 (s, 1H), 8.54-8.27 (m, 3H), 7.79-7.58 (m, 2H), 7.55-7.43 (m, 5H), 7.43-7.32 (m, 1H), 4.30 (app. br. s, 2H), 4.05-3.87 (m, 1H), 3.72 (app. br. s, 1H), 3.31 (app. br. s, 1H), 2.13-1.94 (m, 1H), 1.89-1.70 (m, 2H), 1.64-1.51 (m, 1H), 1.32 (s, 6H); m/z (ES$^+$) (M+H)$^+$ 471.9; $t_R$=2.07 min. HPLC Method 3 (Base).

Example 71: (S)-2-(3-aminopiperidin-1-yl)-4-((2'-oxospiro[cyclohexane-1,3'-indolin]-5'-yl)amino) pyrimidine-5-carboxamide Step 71-1: spiro[cyclohexane-1,3'-indolin]-2'-one. Lithium bis(trimethylsilyl)amide (1M in hexane, 50 mL, 50 mmol) was added drop-wise into a solution of 2-oxindole (3.0 g, 23 mmol) in dry THF (70 mL) at −78° C. The mixture was brought up to −50° C. and was stirred at that temperature for 30 min. The mixture was cooled down to −78° C. and 1,5-dibromopentane (3.0 mL, 23 mmol) was added. The reaction mixture was stirred at RT for 3 h, then at reflux for 4 h. After cooling, the mixture was partitioned between $Et_2O$ and saturated $NH_4Cl$. The organic layer was concentrated and purified by flash chromatography [Hexane:EtOAc (95:5)] affording the title compound as a white solid (2.7 g, 58%). $^1$H NMR (300 MHz, $CDCl_3$) δ 8.06 (br. s, 1H), 7.45 (d, J=7.5 Hz, 1H), 7.21 (app. td, J=7.7, 1.3 Hz, 1H), 7.02 (app. td, J=7.6, 1.2 Hz, 1H), 6.91 (d, J=7.7 Hz, 1H), 2.01-1.55 (m, 10H); m/z (ES$^+$) (M+H)$^+$ 200.1; $t_R$=2.34 min. HPLC Method 3 (Acid).

Step 71-2: 5'-nitrospiro[cyclohexane-1,3'-indolin]-2'-one. A mixture of spiro[cyclohexane-1,3'-indolin]-2'-one (750 mg, 3.73 mmol) and $H_2SO_4$ (95-98%, 5.0 mL) was cooled down to −20° C. while vigorously stirring. A solution of concentrated $HNO_3$ (90%, 0.17 mL, 3.73 mmol) in $H_2SO_4$ (0.7 mL) was added drop-wise at −20° C. The reaction mixture was allowed to reach RT and stirred for 2 h. The mixture was poured into an ice-cooled solution of water (ca. 150 mL) precipitating a pale-green solid that was isolated by filtration, washed with water (ca. 10 mL) and dried under air. The precipitate was dissolved in EtOAc (ca. 30 mL) and the organic phase was dried over $MgSO_4$, filtered and concentrated under reduced pressure, dry-loaded into a column and purified by flash chromatography [Hexane:EtOAc (4:1)] affording the title product as an off-white solid (340 mg, 37%). $^1$H NMR (400 MHz, $CDCl_3$) δ 9.56 (br. s, 1H), 8.34 (s, 1H), 8.24 (d, J=8.6 Hz, 1H), 7.08 (d, J=8.6 Hz, 1H), 2.15-1.50 (m, 10H); m/z (ES$^-$) (M–H)$^+$ 245.0; $t_R$=2.34 min. HPLC Method 3 (Acid).

Step 71-3: 5'-aminospiro[cyclohexane-1,3'-indolin]-2'-one. Zn dust (212 mg, 3.25 mmol) was added portion-wise into an ice-cooled solution of 5'-nitrospiro[cyclohexane-1,3'-indolin]-2'-one (100 mg, 0.41 mmol) and $NH_4Cl$ (348 mg, 6.50 mmol) in THF:$H_2O$ (5:1, 7 mL). The mixture was allowed to reach RT and stirred for 2 h. The reaction mixture was filtered through Celite® and washed with EtOAc (ca. 20 mL). The filtrate was dried over $MgSO_4$, filtered and concentrated under reduced pressure affording a yellow solid that was used in the next step without further purification (89 mg, 99%). $^1$H NMR (400 MHz, Chloroform-d) δ 8.75 (br. s, 1H), 6.87 (d, J=2.2 Hz, 1H), 6.72 (d, J=8.1 Hz, 1H), 6.55 (dd, J=8.1, 2.2 Hz, 1H), 3.48 (br. s, 2H), 2.01-1.80 (m, 4H), 1.77-1.52 (m, 6H); m/z (ES$^+$) (M+H)$^+$ 217.0; $t_R$=1.84 min. HPLC Method 3 (Acid).

Step 71-4: tert-butyl (S)-(1-(5-carbamoyl-4-((2'-oxospiro[cyclohexane-1,3'-indolin]-5'-yl)amino)pyrimidin-2-yl)piperidin-3-yl)carbamate. A mixture of 2,4-dichloropyrimidine-5-carboxamide (79 mg, 0.41 mmol), 5'-aminospiro [cyclohexane-1,3'-indolin]-2'-one (88 mg, 0.41 mmol) and triethylamine (0.06 mL, 0.45 mmol) in 1,4-dioxane (7 mL) was stirred at 50° C. for 2 h. (S)-tert-Butyl piperidin-3-ylcarbamate (82 mg, 0.41 mmol) and triethylamine (0.06 mL, 0.41 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3->3:7)] affording the title product as a white solid (89 mg, 40%). The compound was directly taken into the next step.

Step 71-5: (S)-2-(3-aminopiperidin-1-yl)-4-((2'-oxospiro[cyclohexane-1,3'-indolin]-5'-yl)amino)pyrimidine-5-carboxamide. tert-Butyl (S)-(1-(5-carbamoyl-4-((2'-oxospiro[cyclohexane-1,3'-indolin]-5'-yl)amino)pyrimidin-2-yl)piperidin-3-yl)carbamate (89 mg, 0.17 mmol) was suspended into dioxane:Et$_2$O (1:1, 4 mL) and 4N HCl in dioxane (2 mL) was added. The suspension was stirred at RT overnight. Et$_2$O was added (ca. 4 mL) and the precipitate was filtered under reduced pressure, washed with Et$_2$O (ca. 10 mL) and dried under air. The hydrochloride salt of the title product was isolated as a white solid (60 mg, 83%). $^1$H NMR (400 MHz, DMSO-d$_6$) δ 11.84 (br. s, 1H), 10.44 (s, 1H), 8.71 (s, 1H), 8.64-8.37 (m, 4H), 7.90-7.18 (m, 2H), 7.05-6.85 (m, 1H), 4.36-4.15 (s, 1H), 4.10-3.92 (m, 1H), 3.79-3.45 (m, 2H), 3.38-3.23 (m, 1H), 3.10-2.99 (m, 1H), 2.12-1.95 (m, 1H), 1.95-1.73 (m, 3H), 1.74-1.46 (m, 9H); m/z (ES$^+$) (M+H)$^+$ 436.0; t$_R$=1.99 min. HPLC Method 3 (Acid).

Example 72: (S)-2-(3-aminopiperidin-1-yl)-4-((7'-isopropyl-2'-oxospiro[cyclohexane-1,3'-indolin]-5'-yl)amino)pyrimidine-5-carboxamide Step 72-1: 7'-bromo-5'-nitrospiro[cyclohexane-1,3'-indolin]-2'-one. NBS (320 mg, 1.86 mmol) was added portionwise to a solution of 5'-nitrospiro[cyclohexane-1,3'-indolin]-2'-one (200 mg, 0.82 mmol) in H$_2$SO$_4$ (95-98%, 5 mL) at RT and stirred for 48 h. The reaction mixture was poured into an ice-cooled solution of water (ca. 150 mL) precipitating a beige solid that was isolated by filtration, washed with water (ca. 10 mL) and dried under air. The precipitate was dissolved in EtOAc (ca. 30 mL) and the organic phase was dried over MgSO$_4$, filtered and concentrated under reduced pressure, dry-loaded into a column and purified by flash chromatography [Hexane:EtOAc (4:1)] affording the title product as a pale orange solid (250 mg, 93%). $^1$H NMR (400 MHz, CDCl$_3$) δ 8.63 (br. s, 1H), 8.36 (d, J=2.0 Hz, 1H), 8.22 (d, J=2.0 Hz, 1H), 2.06-1.96 (m, 2H), 1.96-1.87 (m, 2H), 1.74-1.66 (m, 6H); m/z (ES$^-$) (M–H)$^+$ 322.8 for $^{79}$Br; t$_R$=2.45 min. HPLC Method 3 (Base).

Step 72-2: 5'-nitro-7'-(prop-1-en-2-yl)spiro[cyclohexane-1,3'-indolin]-2'-one. A mixture of 7-bromo-5'-nitrospiro[cyclohexane-1,3'-indolin]-2'-one (93 mg, 0.29 mmol), 4,4,5,5-tetramethyl-2-(prop-1-en-2-yl)-1,3,2-dioxaborolane (0.08 mL, 0.43 mmol) and K$_2$CO$_3$ (120 mg, 0.87 mmol) in dioxane:H$_2$O (4:1, 5 mL) was degassed with a N2 flow for 20 min. Bis(triphenylphosphine)palladium(II) dichloride (21 mg, 0.03 mmol) was added and the reaction mixture was stirred at 100° C. for 2 h. The resulting mixture was concentrated under reduced pressure and the residue dissolved in EtOAc (ca. 30 mL) and washed with brine (3×20 mL). The organic phase was dried over MgSO$_4$, filtered, concentrated under reduced pressure and purified by flash chromatography [Hexane:EtOAc (9:1)] affording the title product as a brown solid (72 mg, 87%). $^1$H NMR (400 MHz, CDCl$_3$) δ 8.30 (br. s, 1H), 8.17 (d, J=2.2 Hz, 1H), 8.10 (d, J=2.2 Hz, 1H), 5.48-5.41 (m, 1H), 5.20-5.16 (m, 1H), 2.17 (s, 3H), 2.10-1.96 (m, 2H), 1.96-1.84 (m, 2H), 1.83-1.63 (m, 6H); m/z (ES$^-$) (M–H)$^+$ 245.0; t$_R$=2.57 min. HPLC Method 3 (Base).

Step 72-3: 5'-amino-7'-(prop-1-en-2-yl)spiro[cyclohexane-1,3'-indolin]-2'-one. A mixture of 5'-nitro-7'-(prop-1-en-2-yl)spiro[cyclohexane-1,3'-indolin]-2'-one (72 mg, 0.25 mmol) and palladium on carbon (10 wt. %, 26 mg, 0.02 mmol) in DCM:MeOH (1:1, 4 mL) was stirred at RT under H$_2$ atmosphere (1 atm) overnight. After this time, LCMS analysis indicated that only the nitro group was reduced leaving the isoprene untouched. The reaction mixture was flushed with Ar, filtered through Celite® and washed with MeOH (ca. 10 mL) and DCM (ca. 10 mL). The filtrate was concentrated under reduced pressure and the residue was directly taken into the next step without further purification.

Step 72-4: tert-butyl (S)-(1-(5-carbamoyl-4-((2'-oxo-7'-(prop-1-en-2-yl)spiro[cyclohexane-1,3'-indolin]-5'-yl)amino)pyrimidin-2-yl)piperidin-3-yl)carbamate. A mixture of 2,4-dichloropyrimidine-5-carboxamide (48 mg, 0.25 mmol), 5'-amino-7'-(prop-1-en-2-yl)spiro[cyclohexane-1,3'-indolin]-2'-one (64 mg, 0.25 mmol) and triethylamine (0.04 mL, 0.27 mmol) in 1,4-dioxane (3 mL) was stirred at 50° C. for 1 h. (S)-Tert-butyl piperidin-3-ylcarbamate (50 mg, 0.25 mmol) and triethylamine (0.04 mL, 0.27 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3-3:7)] affording the title product as a white solid (59 mg, 40%). $^1$H NMR (400 MHz, CDCl$_3$) δ 10.88 (br. s, 1H), 8.41 (br. s, 1H), 8.25 (s, 1H), 7.55 (s, 1H), 7.34 (s, 1H), 6.22 (br. s, 2H), 5.30-5.26 (m, 1H), 5.12-5.08 (m, 1H), 4.79-4.57 (m, 1H), 4.38-3.86 (m, 2H), 3.76-3.29 (m, 3H), 2.50-2.22 (m, 1H), 2.01-1.80 (m, 4H), 1.79-1.48 (m, 10H), 1.40 (s, 9H); m/z (ES$^+$) (M+H)$^+$ 576.3; t$_R$=2.56 min. HPLC Method 3 (Base).

Step 72-5: (S)-2-(3-aminopiperidin-1-yl)-4-((7'-isopropyl-2'-oxospiro[cyclohexane-1,3'-indolin]-5'-yl)amino)pyrimidine-5-carboxamide. tert-Butyl (S)-(1-(5-carbamoyl-4-((2'-oxo-7'-(prop-1-en-2-yl)spiro[cyclohexane-1,3'-indolin]-5'-yl)amino)pyrimidin-2-yl)piperidin-3-yl)carbamate (59 mg, 0.10 mmol) and palladium on carbon (10 wt. %, 15 mg, 0.01 mmol) in DCM:MeOH (1:1, 4 mL) was stirred at RT under H2 atmosphere (1 atm) for 2 h. The reaction mixture was flushed with Ar, filtered through Celite® and washed with MeOH (ca. 10 mL) and DCM (ca. 10 mL). The filtrate was concentrated under reduced pressure and the residue was suspended into dioxane:Et$_2$O (1:1, 4 mL) and 4N HCl in dioxane (2 mL) was added. The suspension was stirred at RT overnight. Et$_2$O was added (ca. 4 mL) and the precipitate was filtered under reduced pressure, washed with Et$_2$O (ca. 10 mL) and dried under air. The hydrochloride salt of the title product was isolated as a white solid (31 mg, 67%). $^1$H NMR (400 MHz, Methanol-d$_4$) δ 8.50 (br. s, 1H), 7.46 (s, 1H), 7.32 (s, 1H), 4.29-4.19 (m, 1H), 4.14-3.98 (m, 1H), 3.81-3.68 (m, 1H), 3.64-3.55 (s, 1H), 3.52-3.43 (m, 1H), 3.06 (sept, J=6.8 Hz, 1H), 2.22-2.12 (s, 1H), 2.02-1.89 (s, 3H), 1.91-1.54 (m, 10H), 1.25 (d, J=6.8 Hz, 6H); m/z (ES$^-$) (M–H)$^+$ 478.4; t$_R$=2.16 min. HPLC Method 3 (Acid).

Example 73: 2-((S)-3-aminopiperidin-1-yl)-4-((3-methylsulfonimidoyl)phenyl)amino)pyrimidine-5-carboxamide Step 73-1: 3-(methylsulfinyl)aniline. A mixture of 3-(methylthio)aniline (714 mg, 5.48 mmol) in H$_2$O$_2$ (30 v/v % in water, 0.58 mL, 5.64 mmol) was stirred at 70° C. for 1 h. The resulting mixture was saturated with NaCl and extracted with EtOAc (3×25 mL). The combined organic extracts were washed with a saturated aqueous solution of Na$_2$S2O$_3$ (15 mL). The organic phase was dried over MgSO$_4$, filtered and concentrated under reduced pressure. The residue was purified by flash chromatography [DCM:MeOH (20:1)] affording the title product as a colourless oil (268 mg, 34%). The compound was directly taken into the next step.

Step 73-2: (rac)-(3-aminophenyl)(imino)(methyl)-λ$^6$-sulfanone. Sodium azide (250 mg, 3.84 mmol) was added into a mixture of 3-(methylsulfinyl)aniline (307 mg, 1.98 mmol) in Eaton's reagent (Phosphorus pentoxide, 7.7 wt. % in methanesulfonic acid, 4.5 mL) at RT. The mixture was stirred at 50° C., releasing N2. After 2 h. the mixture was cooled down to 0° C. and a saturated aqueous solution NaHCO$_3$ was added drop-wise until neutral pH. The mixture was extracted with DCM:MeOH (10:1, 5×20 mL), washed with brine (ca. 20 mL), dried over MgSO$_4$, filtered and concentrated under reduced pressure. The residue was purified by flash chromatography [DCM:MeOH (20:1)] affording the title product as an off-white solid (125 mg, 37%). $^1$H NMR (400 MHz, CDCl$_3$) δ 7.32-7.21 (m, 3H), 6.88-6.80 (m, 1H), 3.47 (br. s, 1H), 3.05 (s, 3H); $^{13}$C NMR (101 MHz, CDCl$_3$) δ 147.5, 144.2, 130.2, 119.1, 116.9, 113.3, 46.0.

Step 73-3: tert-butyl ((3S)-1-(5-carbamoyl-4-((3-(S-methylsulfonimidoyl)phenyl)amino)pyrimidin-2-yl)piperidin-3-yl)carbamate. A mixture of 2,4-dichloropyrimidine-5-carboxamide (100 mg, 0.52 mmol), (3-aminophenyl)(imino)(methyl)-λ$^6$-sulfanone (89 mg, 0.52 mmol) and triethylamine (0.08 mL, 0.57 mmol) in 1,4-dioxane (10 mL) and DMF (1 mL) was stirred at 50° C. for 2 h. (S)-Tert-butyl piperidin-3-ylcarbamate (104 mg, 0.52 mmol) and triethylamine (0.08 mL, 0.57 mmol) were added and the mixture was stirred at 50° C. for 2 h. The resulting mixture was allowed to reach RT, concentrated under reduced pressure. The residue was dissolved in EtOAc (20 mL) and washed with brine (3×20 mL). The organic phase was dried over MgSO$_4$, filtered, dry-loaded into a column and purified by flash chromatography [DCM:MeOH (95:5)] affording the title product as a mixture of diasteromers. The compound was directly taken into the next step.

Step 73-4: 2-((S)-3-aminopiperidin-1-yl)-4-(((3-methylsulfonimidoyl)phenyl)amino)pyrimidine-5-carboxamide. tert-Butyl ((3S)-1-(5-carbamoyl-4-((3-(S-methylsulfonimidoyl)phenyl)amino)pyrimidin-2-yl)piperidin-3-yl)carbamate (69 mg, 0.14 mmol) was suspended into dioxane (5 mL) and 4N HCl in dioxane (3 mL) was added. The suspension was stirred at RT overnight. Et$_2$O was added (ca. 4 mL) and the precipitate was filtered under reduced pressure, washed with Et$_2$O (ca. 10 mL) and dried under air. The hydrochloride salt of the title product was isolated as an inseparable mixture of diasteromers (49 mg, 88%). $^1$H NMR (400 MHz, DMSO-d$_6$) δ 12.27 (br. s, 1H), 9.00-8.22 (m, 7H), 8.10-7.73 (s, 3H), 4.70-4.09 (m, 2H), 4.00 (s, 3H), 3.77-3.04 (m, 3H), 2.13-1.99 (m, 1H), 1.96-1.65 (m, 2H), 1.65-1.45 (m, 1H); m/z (ES$^+$) (M+H)$^+$ 390.0; t$_R$=1.43 min. HPLC Method 3 (Acid).

Example 74: (S)-2-(3-aminopiperidin-1-yl)-4-((4-hydroxy-3,5-diisopropylphenyl)amino)pyrimidine-5-carboxamide Step 74-1: 2,6-diisopropyl-4-nitrophenol. 2,6-Diisopropylphenol (2.0 mL, 10.79 mmol) was dissolved in hexane (10 mL) and cooled to 0° C. 70% Nitric acid (0.7 mL) was added slowly drop-wise with stirring, after which the cooling bath was removed and the reaction mixture stirred at RT for 1 h. The resulting precipitate was filtered and dried to give the title compound as a light-yellow solid (2.02 g, 84%). $^1$H NMR (400 MHz, DMSO-d6) δ 7.88 (s, 2H), 4.09-3.87 (br s, 1H), 3.34 (sept, J=6.8 Hz, 2H), 1.19 (d, J=6.8 Hz, 12H). LCMS: m/z (ES$^-$) (M–H)$^+$ 222.0; t$_R$=1.65 min. HPLC Method 3 (Acid).

Step 74-2: 2,6-diisopropyl-4-aminophenol. Prepared as in example 5 step 2, using iron powder (1.12 g, 20.05 mmol), EtOH (6.50 mL), conc. HCl (aq) (0.17 mL), 25% NH$_4$Cl (aq) solution (3.26 mL) and 2,6-diisopropyl-4-nitrophenol (0.400 g, 1.79 mmol), purified by flash column chromatography (4:1 hexane: EtOAc) to give the title compound (0.090 g, 35%) as a yellow viscous oil which quickly darkened in colour (sample stored in fridge freezer and used within 24 h). $^1$H NMR (400 MHz, CDC$_3$) δ 6.44 (s, 2H), 3.12 (sept, J=6.8 Hz, 2H), 1.23 (d, J=6.8 Hz, 12H). LCMS: m/z (ES+) (M+H)$^+$ 194.1; t$_R$=2.12 min. HPLC Method 3 (Acid).

Step 74-3: (S)-2-(3-aminopiperidin-1-yl)-4-((4-hydroxy-3,5-diisopropylphenyl)amino)pyrimidine-5-carboxamide. 2,6-Diisopropyl-4-aminophenol (0.085 g, 0.44 mmol), 2,4-dichloropyrimidine-5-carboxamide (0.084 g, 0.44 mmol), triethylamine (0.13 mL, 0.93 mmol) were dissolved in anhydrous dioxane (5.0 mL) and DMF (1.0 mL). The mixture was heated at 50° C. for 2 h and left to cool to RT. tert-Butyl (S)-piperidin-3-ylcarbamate (0.088 g, 0.44 mmol) and triethylamine (0.13 mL, 0.93 mmol) were added and the reaction mixture was heated at 50° C. for 1 h. The reaction mixture was diluted with EtOAc (15 mL), washed sequentially with water (3×10 mL) and brine (10 mL). The organic phase was dried over MgSO$_4$, filtered and concentrated under reduced pressure to give the crude product, which was purified by flash column chromatography on silica (1:4 hexane: EtOAc) to give the product from two displacements. The intermediate was dissolved in Et$_2$O (10.0 mL) and 4M HCl in dioxane (5.0 mL) was added drop-wise and the mixture was stirred at RT overnight. Hexane was added (15 mL) and the precipitate filtered and dried to give the hydrochloride salt of the title compound as a light-yellow powder (0.154 g, 80%). $^1$H NMR (400 MHz, CD$_3$OD) δ 8.48 (s, 1H), 7.22 (s, 2H), 4.26 (dd, J=13.6, 3.2 Hz, 1H), 4.18-3.97 (m, 1H), 3.84-3.71 (m, 1H), 3.65-3.77 (m, 1H), 3.54-3.44 (m, 1H), 3.36 (sept, J=6.8 Hz, 2H), 2.23-2.13 (m, 1H), 1.98-1.89 (m, 1H), 1.88-1.71 (m, 2H), 1.23 (d, J=6.8 Hz, 12H). LCMS: m/z (ES+) (M+H)$^+$ 440.0; t$_R$=1.93 min. HPLC Method 3 (Acid).

Example 75: (S)-2-(3-aminopiperidin-1-yl)-4-((3,5-diisopropyl-4-methoxyphenyl)amino)pyrimidine-5-carboxamide Step 75-1: 1,3-diisopropyl-2-methoxy-5-nitrobenzene. 2,6-Diisopropyl-4-aminophenol (0.287 g, 1.29 mmol) was added to a flask which was then flushed with N$_2$ for 15 min. Anhydrous DMF (5.0 mL) was added and the mixture cooled to 0° C. Sodium hydride (60% dispersion in mineral oil, 0.154 g, 3.85 mmol) was added and the reaction mixture left to stir for 30 min. Methyl iodide (0.24 mL, 3.86 mmol) was added drop-wise, the cooling bath removed and the mixture stirred at RT overnight. The reaction mixture was diluted with EtOAc (40 mL), washed sequentially with water (7×30 mL) and brine (20 mL). The organic phase was dried over MgSO$_4$, filtered and concentrated under reduced pressure to give the crude product which did not require further purification (0.315 g, quantitative). $^1$H NMR (400 MHz, CDCl$_3$) δ 7.99 (s, 2H), 3.80 (s, 3H), 3.36 (sept, J=6.8 Hz, 2H), 1.27 (d, J=6.8 Hz, 12H). $^{13}$C NMR (101 MHz, CDCl$_3$) δ 160.3, 143.8, 120.3, 62.6, 27.1, 23.9.

Step 75-2: 3,5-diisopropyl-4-methoxyaniline. 1,3-Diisopropyl-2-methoxy-5-nitrobenzene (0.315 g, 1.01 mmol), was dissolved in THF (16.4 mL) and water (3.6 mL). The solution was cooled to 0° C. before ammonium chloride (0.859 g, 16.1 mmol) and zinc (0.534 g, 8.17 mmol) were added. The cooling bath was removed and the reaction mixture stirred at RT for 2.5 h. The reaction mixture was filtered through a pad of Celite® under reduced pressure using EtOAc (30 mL). The filtrate was washed with water (2×30 mL), dried over MgSO$_4$, filtered and concentrated under reduced pressure to give the crude product which did not require further purification (0.208 g, 76%). $^1$H NMR (400 MHz, CDCl$_3$) δ 6.43 (s, 2H), 3.67 (s, 3H), 3.27 (sept, J=6.8 Hz, 2H), 1.20 (d, J=6.8 Hz, 12H). LCMS: m/z (ES+) (M+H)$^+$ 208.1; $t_R$=2.49 min. HPLC Method 3 (Acid).

Step 75-3: (S)-2-(3-aminopiperidin-1-yl)-4-((3,5-diisopropyl-4-methoxyphenyl)amino)pyrimidine-5-carboxamide. 3,5-Diisopropyl-4-methoxyaniline (0.056 g, 0.27 mmol), 2,4-dichloropyrimidine-5-carboxamide (0.053 g, 0.28 mmol), triethylamine (0.08 mL, 0.57 mmol) were dissolved in anhydrous dioxane (5.0 mL) and DMF (1.0 mL). The mixture was heated at 50° C. for 2 h and left to cool to RT. tert-Butyl (S)-piperidin-3-ylcarbamate (0.054 g, 0.27 mmol) and triethylamine (0.08 mL, 0.57 mmol) were added and the reaction mixture was heated at 50° C. overnight. The reaction mixture was diluted with EtOAc (15 mL), washed sequentially with water (3×10 mL) and brine (10 mL). The organic phase was dried over MgSO$_4$, filtered and concentrated under reduced pressure to give the crude product from two displacements, which was dissolved in Et$_2$O (10.0 mL) and 4M HCl in dioxane (5.0 mL) was added drop-wise and the mixture was stirred at RT for 6 h. Hexane was added (15 mL) and the suspension filtered to give a viscous material that was collected and dissolved in MeOH (1.0 mL). Et$_2$O (10 mL) and hexane (10 mL) were added and the mixture was triturated overnight. The resulting powder was filtered and dried to give the hydrochloride salt of the title compound as a light yellow powder (0.022 g, 18%). $^1$H NMR (400 MHz, CD$_3$OD) δ 8.52 (s, 1H), 7.32 (s, 2H), 4.28 (app d, J=13.6 Hz), 4.18-4.10 (m, 1H), 3.82-3.71 (m, 1H), 3.75 (s, 3H), 3.70-3.58 (m, 1H), 3.56-3.44 (m, 1H), 3.38 (sept, J=6.8 Hz, 2H), 2.24-2.13 (m, 1H), 2.01-1.89 (m, 1H), 1.88-1.70 (m, 3H), 1.25 (d, J=6.8 Hz, 12H). LCMS: m/z (ES+) (M+H)$^+$ 427.1; $t_R$=2.52 min. HPLC Method 3 (Acid).

Example 76: (S)-2-(3-aminopiperidin-1-yl)-4-((1,5-diisopropyl-6-oxo-1,6-dihydropyridin-3-yl)amino) pyrimidine-5-carboxamide Step 76-1: 3-bromo-1-isopropyl-5-nitropyridin-2(1H)-one. A mixture of 3-bromo-2-hydroxy-5-nitropyridine (1.0 g, 4.57 mmol), 2-bromopropane (1.29 mL, 13.71 mmol) and cesium fluoride (2.0 g, 13.71 mmol) in DMF (40 mL) was stirred at 50° C. for 3 days. The resulting mixture was allowed to reach RT, partitioned between EtOAc (ca. 40 mL) and water (30 mL) and washed with brine (3×30 mL). The organic phase was dried over MgSO$_4$, filtered, concentrated under reduced pressure and purified by flash chromatography [Hexane:EtOAc (4:1)] affording the title product as a pale green solid (720 mg, 61%). $^1$H NMR (400 MHz, CDCl$_3$) δ 8.62 (d, J=2.9 Hz, 1H), 8.49 (d, J=2.9 Hz, 1H), 5.24 (sept, J=6.8 Hz, 1H), 1.46 (d, J=6.8 Hz, 6H); $^{13}$C NMR (101 MHz, CDCl$_3$) δ 157.7, 136.6, 134.7, 130.6, 114.0, 51.5, 21.6.

Step 76-2: 1-isopropyl-5-nitro-3-(prop-1-en-2-yl)pyridin-2(1H)-one. A mixture of 3-bromo-1-isopropyl-5-nitropyridin-2(1H)-one (150 mg, 0.57 mmol), 4,4,5,5-tetramethyl-2-(prop-1-en-2-yl)-1,3,2-dioxaborolane (0.22 mL, 1.15 mmol) and K$_2$CO$_3$ (236 mg, 1.71 mmol) in dioxane:H$_2$O (4:1, 10 mL) was degassed with a N$_2$ flow for 20 min. Bis(triphenylphosphine)palladium(II) dichloride (40 mg, 0.06 mmol) was added and the reaction mixture was stirred at 100° C. for 1 h. The resulting mixture was concentrated under reduced pressure and the residue dissolved in EtOAc (ca. 30 mL) and washed with brine (3×20 mL). The organic phase was dried over MgSO$_4$, filtered, concentrated under reduced pressure and purified by flash chromatography [Hexane:EtOAc (4:1)] affording the title product as a colourless oil (126 mg, 99%). $^1$H NMR (400 MHz, CDCl$_3$) δ 8.57 (d, J=3.0 Hz, 1H), 8.05 (d, J=3.0 Hz, 1H), 5.86-5.81 (m, 1H), 5.36-5.33 (m, 1H), 5.26 (sept, J=6.8 Hz, 1H), 2.12 (s, 3H), 1.44 (d, J=6.8 Hz, 6H); $^{13}$C NMR (101 MHz, Chloroform-d) δ 160.1, 139.3, 133.5, 131.2, 130.5, 128.3, 119.2, 48.7, 22.1, 22.0.

Step 76-3: 5-amino-1,3-diisopropylpyridin-2(1H)-one. A mixture of 1-isopropyl-5-nitro-3-(prop-1-en-2-yl)pyridin-2(1H)-one (126 mg, 0.57 mmol) and palladium on carbon (10 wt. %, 60 mg, 0.06 mmol) in EtOH (5 mL) was stirred at RT under H$_2$ atmosphere (1 atm) for 3 h. The reaction mixture was flushed with Ar, filtered through Celite@ and washed with MeOH (ca. 20 mL). The filtrate was concentrated under reduced pressure and the residue was directly taken into the next step without further purification (108 mg, 97%). $^1$H NMR (400 MHz, Chloroform-d) δ 6.85 (d, J=2.9 Hz, 1H), 6.70 (d, J=2.9 Hz, 1H), 5.31 (sept, J=6.9 Hz, 1H), 3.20 (sept, J=6.9 Hz, 1H), 1.28 (d, J=6.9 Hz, 6H), 1.14 (d, J=6.9 Hz, 6H); m/z (ES$^-$) (M–H)$^+$ 196.0; $t_R$=1.67 min. HPLC Method 3 (Acid).

Step 76-4: tert-butyl (S)-(1-(5-carbamoyl-4-((1,5-diisopropyl-6-oxo-1,6-dihydropyridin-3-yl)amino)pyrimidin-2-yl)piperidin-3-yl)carbamate. A mixture of 2,4-dichloropyrimidine-5-carboxamide (106 mg, 0.55 mmol), 5-amino-1,3-diisopropylpyridin-2(1H)-one (108 mg, 0.55 mmol) and triethylamine (0.08 mL, 0.58 mmol) in 1,4-dioxane (8.0 mL) was stirred at 50° C. for 5 h. (S)-Tert-butyl piperidin-3-ylcarbamate (110 mg, 0.55 mmol) and triethylamine (0.08 mL, 0.58 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3→3:7)] affording the title product as a white solid (103 mg, 37%). The compound was directly taken into the next step.

Step 76-5: (S)-2-(3-aminopiperidin-1-yl)-4-((1,5-diisopropyl-6-oxo-1,6-dihydropyridin-3-yl)amino)pyrimidine-5-carboxamide. tert-Butyl (S)-(1-(5-carbamoyl-4-((1,5-diisopropyl-6-oxo-1,6-dihydropyridin-3-yl)amino)pyrimidin-2-yl)piperidin-3-yl)carbamate (95 mg, 0.18 mmol) was suspended into dioxane:Et$_2$O (1:1, 4 mL) and 4N HCl in dioxane (2 mL) was added. The suspension was stirred at RT overnight. Et$_2$O was added (ca. 4 mL) and the precipitate was filtered under reduced pressure, washed with Et$_2$O (ca. 10 mL) and dried under air. The resulting sticky solid was dissolved in MeOH (ca. 5 mL) and precipitated by addition of Et$_2$O (ca. 3 mL). The mother liquor was removed and the resulting solid was dried under reduced pressure giving the hydrochloride salt of the pure title product as a beige solid (78 mg, 98%). $^1$H NMR (400 MHz, DMSO-d6) δ 11.24 (br. s, 1H), 8.69 (s, 1H), 8.54-8.10 (m, 3H), 7.83 (d, J=2.6 Hz, 1H), 7.63 (br. s, 1H), 7.40 (d, J=2.6 Hz, 1H), 5.15 (sept, J=6.8 Hz, 1H), 4.35-4.18 (m, 1H), 3.99-3.89 (m, 1H), 3.71-3.56 (m, 1H), 3.55-3.40 (m, 1H), 3.29-3.19 (m, 1H), 3.08 (sept, J=6.9 Hz, 1H), 2.08-1.95 (m, 1H), 1.91-1.69 (m, 2H), 1.60-1.51 (m, 1H), 1.29 (app. dd, J=6.8, 3.0 Hz, 6H), 1.11 (app. dd, J=6.9, 2.3 Hz, 6H); m/z (ES$^-$) (M–H)$^+$ 414.2; $t_R$=1.95 min. HPLC Method 3 (Base).

Example 77: (S)-2-(3-aminopiperidin-1-yl)-4-((1-isopropyl-6-oxo-5-phenyl-1,6-dihydropyridin-3-yl)amino)pyrimidine-5-carboxamide Step 77-1: 1-isopropyl-5-nitro-3-phenylpyridin-2(1H)-one. A mixture of 3-bromo-1-isopropyl-5-nitropyridin-2(1H)-one (70 mg, 0.27 mmol), 4,4,5,5-tetramethyl-2-phenyl-1,3,2-dioxaborolane (110 mg, 0.54 mmol) and $K_2CO_3$ (113 mg, 0.81 mmol) in dioxane:$H_2O$ (4:1, 5 mL) was degassed with a $N_2$ flow for 20 min. Bis(triphenylphosphine)palladium(II) dichloride (19 mg, 0.03 mmol) was added and the reaction mixture was stirred at 100° C. for 1 h. The resulting mixture was concentrated under reduced pressure and the residue dissolved in EtOAc (ca. 30 mL) and washed with brine (3×20 mL). The organic phase was dried over $MgSO_4$, filtered, concentrated under reduced pressure and purified by flash chromatography [Hexane:EtOAc (4:1)] affording the title product as a colourless oil (52 mg, 78%). $^1$H NMR (400 MHz, $CDCl_3$) δ 8.65 (d, J=3.0 Hz, 1H), 8.22 (d, J=3.0 Hz, 1H), 7.72-7.64 (m, 2H), 7.53-7.34 (m, 3H), 5.31 (sept, J=6.8 Hz, 1H), 1.49 (d, J=6.8 Hz, 6H); m/z ($ES^+$) $(M+H)^+$ 259.0; $t_R$=2.46 min. HPLC Method 3 (Base).

Step 77-2: 5-amino-1-isopropyl-3-phenylpyridin-2(1H)-one. Zn dust (101 mg, 1.55 mmol) was added portion-wise into an ice-cooled solution of 1-isopropyl-5-nitro-3-phenylpyridin-2(1H)-one (50 mg, 0.19 mmol) and $NH_4Cl$ (166 mg, 3.10 mmol) in THF:$H_2O$ (5:1, 4.5 mL). The mixture was allowed to reach RT and stirred for 30 min. The reaction mixture was filtered through Celite® and washed with EtOAc (ca. 20 mL). The filtrate was dried over $MgSO_4$, filtered and concentrated under reduced pressure affording a colourless oil which rapidly turned darker. The residue was directly taken into the next step without further purification.

Step 77-3: tert-butyl (S)-(1-(5-carbamoyl-4-((1-isopropyl-6-oxo-5-phenyl-1,6-dihydropyridin-3-yl)amino)pyrimidin-2-yl)piperidin-3-yl)carbamate. A mixture of 2,4-dichloropyrimidine-5-carboxamide (37 mg, 0.19 mmol), 5-amino-1-isopropyl-3-phenylpyridin-2(1H)-one (44 mg, 0.19 mmol) and triethylamine (0.03 mL, 0.21 mmol) in 1,4-dioxane (3.0 mL) was stirred at 50° C. for 2 h. (S)-tert-Butyl piperidin-3-ylcarbamate (38 mg, 0.19 mmol) and triethylamine (0.03 mL, 0.21 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3→1:4)] affording the title product as a white solid (77 mg, 73%). The compound was directly taken into the next step.

Step 77-4: (S)-2-(3-aminopiperidin-1-yl)-4-((1-isopropyl-6-oxo-5-phenyl-1,6-dihydropyridin-3-yl)amino)pyrimidine-5-carboxamide. tert-Butyl (S)-(1-(5-carbamoyl-4-((1-isopropyl-6-oxo-5-phenyl-1,6-dihydropyridin-3-yl)amino)pyrimidin-2-yl)piperidin-3-yl)carbamate (77 mg, 0.14 mmol) was suspended into dioxane:$Et_2O$ (1:1, 4 mL) and 4N HCl in dioxane (2 mL) was added. The suspension was stirred at RT overnight. $Et_2O$ was added (ca. 4 mL) and the precipitate was filtered under reduced pressure, washed with $Et_2O$ (ca. 10 mL) and dried under air. The resulting sticky solid was dissolved in MeOH (ca. 5 mL) and precipitated by addition of $Et_2O$ (ca. 3 mL). The mother liquor was removed and the resulting solid was dried under reduced pressure giving the hydrochloride salt of the title product as a pale yellow solid (45 mg, 72%). $^1$H NMR (400 MHz, DMSO-$d_6$) δ 11.35 (br. s, 1H), 8.71 (s, 1H), 8.51-8.31 (m, 4H), 8.04 (d, J=2.8 Hz, 1H), 7.75 (d, J=2.8 Hz, 1H), 7.71 (d, J=7.2 Hz, 2H), 7.40 (app. t, J=7.5 Hz, 2H), 7.37-7.30 (m, 1H), 5.22 (sept, J=6.8 Hz, 1H), 4.35-4.23 (m, 1H), 3.99-3.90 (m, 1H), 3.72-3.60 (m, 1H), 3.61-3.48 (m, 1H), 3.34-3.24 (m, 1H), 2.07-1.93 (m, 1H), 1.79-1.70 (m, 2H), 1.56-1.48 (m, 1H), 1.35 (app. dd, J=6.8, 3.7 Hz, 6H); m/z ($ES^-$) $(M-H)^-$ 446.0; $t_R$=2.02 min. HPLC Method 3 (Base).

Example 78: (S)-2-(3-aminopiperidin-1-yl-4-((5-(4-chlorophenyl)-1-isopropyl-6-oxo-1,6-dihydropyridin-3-yl)amino)pyrimidine-5-carboxamide Step 78-1: 3-(4-chlorophenyl)-1-isopropyl-5-nitropyridin-2(1H)-one. A mixture of 3-bromo-1-isopropyl-5-nitropyridin-2(1H)-one (80 mg, 0.31 mmol), (4-chlorophenyl)boronic acid (62 mg, 0.40 mmol) and $K_2CO_3$ (129 mg, 0.93 mmol) in dioxane:$H_2O$ (4:1, 5 mL) was degassed with a $N_2$ flow for 20 min. Bis(triphenylphosphine)palladium(II) dichloride (22 mg, 0.03 mmol) was added and the reaction mixture was stirred at 100° C. for 1 h. The resulting mixture was concentrated under reduced pressure and the residue dissolved in EtOAc (ca. 30 mL) and washed with brine (3×20 mL). The organic phase was dried over $MgSO_4$, filtered, concentrated under reduced pressure and purified by flash chromatography [Hexane:EtOAc (9:1)] affording the title product as a colourless oil (71 mg, 78%). $^1$H NMR (400 MHz, $CDCl_3$) δ 8.58 (d, J=3.0 Hz, 1H), 8.13 (d, J=3.0 Hz, 1H), 7.57 (d, J=8.6 Hz, 2H), 7.33 (d, J=8.6 Hz, 2H), 5.22 (sept, J=6.8 Hz, 1H), 1.41 (d, J=6.8 Hz, 6H); $^{13}$C NMR (101 MHz, $CDCl_3$) δ 160.3, 134.9, 134.2, 133.4, 130.9, 130.0, 129.8, 129.4, 128.6, 49.3, 22.0.

Step 78-2: 5-amino-3-(4-chlorophenyl)-1-isopropylpyridin-2(1H)-one. Zn dust (127 mg, 1.93 mmol) was added portion-wise into an ice-cooled solution of 3-(4-chlorophenyl)-1-isopropyl-5-nitropyridin-2(1H)-one (71 mg, 0.24 mmol) and $NH_4Cl$ (205 mg, 3.84 mmol) in THF:$H_2O$ (5:1, 5.0 mL). The mixture was allowed to reach RT and stirred for 1.5 h. The reaction mixture was filtered through Celite® and washed with EtOAc (ca. 20 mL). The filtrate was dried over $MgSO_4$, filtered and concentrated under reduced pressure affording a colourless oil which rapidly turned darker. The residue was directly taken into the next step without further purification.

Step 78-3: tert-butyl (S)-(1-(5-carbamoyl-4-((5-(4-chlorophenyl)-1-isopropyl-6-oxo-1,6-dihydropyridin-3-yl)amino)pyrimidin-2-yl)piperidin-3-yl)carbamate. A mixture of 2,4-dichloropyrimidine-5-carboxamide (44 mg, 0.23 mmol), 5-amino-3-(4-chlorophenyl)-1-isopropylpyridin-2(1H)-one (62 mg, 0.23 mmol) and triethylamine (0.03 mL, 0.25 mmol) in 1,4-dioxane (4.0 mL) was stirred at 50° C. for 5 h. (S)-Tert-butyl piperidin-3-ylcarbamate (46 mg, 0.23 mmol) and triethylamine (0.03 mL, 0.25 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3→3:7)] affording the title product as a white solid (51 mg, 38%). The compound was directly taken into the next step.

Step 78-4: (S)-2-(3-aminopiperidin-1-yl)-4-((5-(4-chlorophenyl)-1-isopropyl-6-oxo-1,6-dihydropyridin-3-yl)amino)pyrimidine-5-carboxamide. tert-Butyl (S)-(1-(5-carbamoyl-4-((5-(4-chlorophenyl)-1-isopropyl-6-oxo-1,6-dihydropyridin-3-yl)amino)pyrimidin-2-yl)piperidin-3-yl)carbamate (51 mg, 0.09 mmol) was suspended into dioxane:$Et_2O$ (1:1, 4 mL) and 4N HCl in dioxane (2 mL) was added. The suspension was stirred at RT overnight. $Et_2O$ was added (ca. 4 mL) and the precipitate was filtered under reduced pressure, washed with $Et_2O$ (ca. 10 mL) and dried under air. The resulting sticky solid was dissolved in MeOH (ca. 5 mL) and precipitated by addition of $Et_2O$ (ca. 3 mL). The mother liquor was removed and the resulting solid was dried under reduced pressure giving the hydrochloride salt of the title product as a pale yellow solid (43 mg, 99%). $^1$H NMR (400 MHz, Methanol-d4) δ 8.55 (s, 1H), 8.03 (d, J=2.4 Hz, 1H), 7.83 (d, J=2.4 Hz, 1H), 7.67 (d, J=8.2 Hz, 2H), 7.42 (d, J=8.2 Hz, 2H), 5.32 (sept, J=6.8 Hz, 1H), 4.36-4.25 (m, 1H), 4.07-3.98 (m, 1H), 3.76-3.63 (m, 1H), 3.63-3.51 (m, 2H), 2.21-2.16 (m, 1H), 2.02-1.63 (m, 3H), 1.45 (app. dd, J=6.8, 2.3 Hz, 6H); m/z (ES$^+$) (M+H)$^+$ 482.3; $t_R$=2.26 min. HPLC Method 3 (Base).

Example 79: (S)-2-(3-aminopiperidin-1-yl)-4-((1-isopropyl-6-oxo-5-(4-(trifluoromethyl)phenyl)-1,6-dihydropyridin-3-yl)amino)pyrimidine-5-carboxamide Step 79-1: 1-isopropyl-5-nitro-3-(4-(trifluoromethyl)phenyl)pyridin-2(H)-one. A mixture of 3-bromo-1-isopropyl-5-nitropyridin-2(1H)-one (100 mg, 0.39 mmol), (4-(trifluoromethyl)phenyl)boronic acid (109 mg, 0.57 mmol) and K$_2$CO$_3$ (163 mg, 1.17 mmol) in dioxane:H$_2$O (4:1, 6 mL) was degassed with a N2 flow for 20 min. Bis(triphenylphosphine)palladium(II) dichloride (27 mg, 0.04 mmol) was added and the reaction mixture was stirred at 100° C. for 1 h. The resulting mixture was concentrated under reduced pressure and the residue dissolved in EtOAc (ca. 30 mL) and washed with brine (3×20 mL). The organic phase was dried over MgSO$_4$, filtered, concentrated under reduced pressure and purified by flash chromatography [Hexane:EtOAc (85:15)] affording the title product as a colourless oil (130 mg, 99%). $^1$H NMR (400 MHz, CDCl$_3$) δ 8.69 (d, J=3.0 Hz, 1H), 8.26 (d, J=3.0 Hz, 1H), 7.81 (d, J=8.1 Hz, 2H), 7.69 (d, J=8.1 Hz, 2H), 5.30 (sept, J=6.8 Hz, 1H), 1.49 (d, J=6.8 Hz, 6H); m/z (ES$^+$) (M+H)$^+$ 327.1; $t_R$=2.77 min. HPLC Method 3 (Acid).

Step 79-2: 5-amino-1-isopropyl-3-(4-(trifluoromethyl)phenyl)pyridin-2(1H)-one. Zn dust (209 mg, 3.20 mmol) was added portion-wise into an ice-cooled solution of 1-isopropyl-5-nitro-3-(4-(trifluoromethyl)phenyl)pyridin-2(1H)-one (130 mg, 0.40 mmol) and NH$_4$Cl (342 mg, 6.40 mmol) in THF:H$_2$O (5:1, 8.0 mL). The mixture was allowed to reach RT and stirred for 2.5 h. The reaction mixture was filtered through Celite® and washed with EtOAc (ca. 20 mL). The filtrate was dried over MgSO$_4$, filtered and concentrated under reduced pressure affording a colourless oil which rapidly turned darker. The residue was directly taken into the next step without further purification.

Step 79-3: tert-butyl (S)-(1-(5-carbamoyl-4-((1-isopropyl-6-oxo-5-(4-(trifluoromethyl)phenyl)-1,6-dihydropyridin-3-yl)amino)pyrimidin-2-yl)piperidin-3-yl)carbamate. A mixture of 2,4-dichloropyrimidine-5-carboxamide (75 mg, 0.39 mmol), 5-amino-1-isopropyl-3-(4-(trifluoromethyl)phenyl)pyridin-2(1H)-one (115 mg, 0.39 mmol) and triethylamine (0.06 mL, 0.43 mmol) in 1,4-dioxane (5.0 mL) was stirred at 50° C. for 2 h. (S)-Tert-butyl piperidin-3-ylcarbamate (78 mg, 0.39 mmol) and triethylamine (0.06 mL, 0.43 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3->3:7)] affording the title product as a pale green solid (150 mg, 63%). The compound was directly taken into the next step.

Step 79-4: (S)-2-(3-aminopiperidin-1-yl)-4-((1-isopropyl-6-oxo-5-(4-(trifluoromethyl)phenyl)-1,6-dihydropyridin-3-yl)amino)pyrimidine-5-carboxamide. tert-Butyl (S)-(1-(5-carbamoyl-4-((1-isopropyl-6-oxo-5-(4-(trifluoromethyl) phenyl)-1,6-dihydropyridin-3-yl)amino)pyrimidin-2-yl) piperidin-3-yl)carbamate (150 mg, 0.24 mmol) was suspended into dioxane:Et$_2$O (1:1, 4 mL) and 4N HCl in dioxane (2 mL) was added. The suspension was stirred at RT overnight. Et$_2$O was added (ca. 4 mL) and the precipitate was filtered under reduced pressure, washed with Et$_2$O (ca. 10 mL) and dried under air. The resulting sticky solid was dissolved in MeOH (ca. 5 mL) and precipitated by addition of Et$_2$O (ca. 3 mL). The mother liquor was removed and the resulting solid was dried under reduced pressure giving the hydrochloride salt of the title product as a pale yellow solid (120 mg, 98%). $^1$H NMR (400 MHz, Methanol-d4) δ 8.55 (s, 1H), 8.05 (d, J=2.6 Hz, 1H), 7.93-7.84 (m, 3H), 7.73 (d, J=8.2 Hz, 2H), 5.34 (sept, J=6.8 Hz, 1H), 4.36-4.29 (m, 1H), 4.06-3.98 (m, 1H), 3.74-3.62 (m, 1H), 3.60-3.47 (m, 2H), 2.22-2.14 (m, 1H), 1.95-1.86 (m, 1H), 1.86-1.65 (m, 2H), 1.46 (app. dd, J=6.8, 1.7 Hz, 6H); m/z (ES$^+$) (M+H)$^+$ 516.3; $t_R$=2.35 min. HPLC Method 3 (Base).

Example 80: (S)-2-(3-aminopiperidin-1-yl)-4-((5-(4,4-difluorocyclohex-1-en-1-yl)-1-isopropyl-6-oxo-1,6-dihydropyridin-3-yl)amino)pyrimidine-5-carboxamide Step 80-1: 3-(4,4-difluorocyclohex-1-en-1-yl)-1-isopropyl-5-nitropyridin-2(1H)-one. 3-Bromo-1-isopropyl-5-nitropyridin-2(1H)-one (0.299 g, 1.15 mmol), 2-(4,4-difluorocyclohex-1-en-1-yl)-4,4,5,5-tetramethyl-1,3,2-dioxaborolane (0.281 g, 1.15 mmol) and potassium carbonate (0.318 g, 2.30 mmol) were dissolved in dioxane (9.0 mL) and water (2.0 mL). The reaction mixture was degassed with N$_2$ for 20 min and Pd(PPh$_3$)$_2$Cl$_2$ was added quickly, followed by purging of the flask with N$_2$ for a further 10 min. The reaction mixture was heated to 100° C. for 2 h and allowed to cool to RT. The reaction mixture was diluted with EtOAc (40 mL), washed with water (3×20 mL), dried over MgSO$_4$, filtered and concentrated under reduced pressure to give the crude product, which was purified by flash column chromatography on silica (4:1 hexane: EtOAc followed by 3:1) to give the title compound as a light yellow oil (0.298 g, 87%). $^1$H NMR (400 MHz, CDCl$_3$) δ 8.57 (d, J=3.2 Hz, 1H), 8.00 (d, J=2.8 Hz, 1H), 6.34-6.28 (m, 1H), 5.23 (sept, J=6.8 Hz, 1H), 2.77-2.60 (m, 4H), 2.21-2.08 (m, 2H), 1.44 (d, J=6.8 Hz, 6H). LCMS: m/z (ES+) (M+H)$^+$ 299.1; $t_R$=2.62 min. HPLC Method 3 (Acid).

Step 80-2: 5-amino-3-(4,4-difluorocyclohex-1-en-1-yl)-1-isopropylpyridin-2(1H)-one. Prepared as in step 75-2, but left to stir at RT overnight, using 3-(4,4-difluorocyclohex-1-en-1-yl)-1-isopropyl-5-nitropyridin-2(1H)-one (0.151 g, 0.51 mmol), THF (7.0 mL), water (1.5 mL), zinc (0.271 g, 4.14 mmol) and NH$_4$Cl (0.43 g, 8.04 mmol) to give the title compound as a green viscous oil (0.100 g, 74%). $^1$H NMR (400 MHz, MeOD) δ 7.16-7.13 (m, 2H), 5.93-5.86 (m, 1H), 5.24 (sept, J=6.8 Hz, 1H), 4.92-4.76 (br s, 2H), 2.72-2.58 (m, 4H), 2.19-2.06 (m, 2H), 1.34 (d, J=6.8 Hz, 6H). LCMS: m/z (ES+) (M+H)$^+$ 269.2; $t_R$=2.03 min. HPLC Method 3 (Acid).

Step 80-3: (S)-2-(3-aminopiperidin-1-yl)-4-((5-(4,4-difluorocyclohex-1-en-1-yl)-1-isopropyl-6-oxo-1,6-dihydropyridin-3-yl)amino)pyrimidine-5-carboxamide. 5-Amino-3-(4,4-difluorocyclohex-1-en-1-yl)-1-isopropylpyridin-2 (1H)-one (0.069 g, 0.26 mmol), 2,4-dichloropyrimidine-5-carboxamide (0.050 g, 0.26 mmol), triethylamine (0.07 mL, 0.50 mmol) were dissolved in anhydrous dioxane (5.0 mL) and DMF (0.5 mL). The mixture was heated at 50° C. for 1.5 h and left to cool to RT. tert-Butyl (S)-piperidin-3-ylcarbamate (0.052 g, 0.26 mmol) and triethylamine (0.07 mL, 0.50 mmol) were added and the reaction mixture was heated at 50° C. overnight. The reaction mixture was diluted with EtOAc (15 mL), washed sequentially with water (3×10 mL) and brine (10 mL). The organic phase was dried over $MgSO_4$, filtered and concentrated under reduced pressure to give the crude product from two displacements, which was purified by flash column chromatography on silica (1:3 hexane: EtOAc followed by EtOAc). The intermediate was dissolved in $Et_2O$ (2.5 mL) and 4M HCl in dioxane (2.5 mL) was added drop-wise and the mixture was stirred at RT for 2 h. Hexane was added (15 mL) and the solid filtered and dried to give the hydrochloride salt of the title compound as a light brown powder (0.039 g, 48%). $^1$H NMR (400 MHz, $CD_3OD$) δ 8.60-8.44 (br s, 1H), 7.95-7.76 (m, 1H), 7.64-7.47 (m, 1H), 5.37-5.17 (m, 1H), 4.36-4.18 (m, 1H), 4.17-3.99 (m, 1H), 3.80-3.66 (m, 1H), 3.63-3.46 (m, 1H), 3.04-2.91 (m, 1H), 2.28-2.08 (m, 2H), 2.07-1.72 (m, 7H), 1.70-1.50 (m, 2H), 1.50-1.35 (m, 6H). LCMS: m/z (ES+) (M+H)$^+$ 488.3; $t_R$=2.15 min. HPLC Method 3 (Acid).

Example 81: (S)-2-(3-aminopiperidin-1-yl)-4-((1-isopropyl-5-morpholino-6-oxo-1,6-dihydropyridin-3-yl)amino)pyrimidine-5-carboxamide Step 81-1: 1-isopropyl-3-morpholino-5-nitropyridin-2(1H)-one. A mixture of 3-bromo-1-isopropyl-5-nitropyridin-2(1H)-one (100 mg, 0.38 mmol), morpholine (0.03 mL, 0.38 mmol), palladium(II) acetate (4 mg, 0.02 mmol), Xantphos (11 mg, 0.02 mmol) and cesium carbonate (146 mg, 0.76 mmol) in dry and degassed dioxane (3.0 mL) was stirred at 105° C. under inert atmosphere overnight. The resulting mixture was concentrated under reduced pressure and the residue dissolved in EtOAc (ca. 30 mL) and washed with brine (3×20 mL). The organic phase was dried over $MgSO_4$, filtered, concentrated under reduced pressure and purified by flash chromatography [Hexane:EtOAc (3:1)] affording the title product as a yellow solid (70 mg, 69%). $^1$H NMR (400 MHz, $CDCl_3$) δ 8.34 (d, J=2.8 Hz, 1H), 7.31 (d, J=2.8 Hz, 1H), 5.25 (sept, J=6.8 Hz, 1H), 3.92-3.82 (m, 4H), 3.28-3.13 (m, 4H), 1.42 (d, J=6.8 Hz, 6H); m/z (ES$^+$) (M+H)$^+$ 268.0; $t_R$=2.05 min. HPLC Method 3 (Base).

Step 81-2: 5-amino-1-isopropyl-3-morpholinopyridin-2(1H)-one. Zn dust (117 mg, 1.80 mmol) was added portion-wise into an ice-cooled solution of 1-isopropyl-3-morpholino-5-nitropyridin-2(1H)-one (60 mg, 0.22 mmol) and $NH_4Cl$ (188 mg, 3.52 mmol) in THF:$H_2O$ (5:1, 4.0 mL). The mixture was allowed to reach RT and stirred for 10 min. The reaction mixture was filtered through Celite® and washed with EtOAc (ca. 20 mL). The filtrate was dried over $MgSO_4$, filtered and concentrated under reduced pressure affording a colourless oil which rapidly turned darker. The residue was directly taken into the next step without further purification.

Step 81-3: tert-butyl (S)-(1-(5-carbamoyl-4-((1-isopropyl-5-morpholino-6-oxo-1,6-dihydropyridin-3-yl)amino)pyrimidin-2-yl)piperidin-3-yl)carbamate. A mixture of 2,4-dichloropyrimidine-5-carboxamide (42 mg, 0.22 mmol), 5-amino-1-isopropyl-3-morpholinopyridin-2(1H)-one (52 mg, 0.22 mmol) and triethylamine (0.03 mL, 0.24 mmol) in 1,4-dioxane (4.0 mL) was stirred at 50° C. for 1.5 h. (S)-Tert-butyl piperidin-3-ylcarbamate (44 mg, 0.22 mmol) and triethylamine (0.03 mL, 0.24 mmol) were added and the mixture was stirred at 50° C. overnight. The resulting mixture was allowed to reach RT, concentrated under reduced pressure, dry-loaded into a column and purified by flash chromatography [EtOAc (100%)] affording the title product as a dark brown solid (74 mg, 60%). The compound was directly taken into the next step.

Step 81-4: (S)-2-(3-aminopiperidin-1-yl)-4-((1-isopropyl-5-morpholino-6-oxo-1,6-dihydropyridin-3-yl)amino)pyrimidine-5-carboxamide. tert-Butyl (S)-(1-(5-carbamoyl-4-((1-isopropyl-5-morpholino-6-oxo-1,6-dihydropyridin-3-yl)amino)pyrimidin-2-yl)piperidin-3-yl)carbamate (74 mg, 0.13 mmol) was suspended into dioxane:$Et_2O$ (1:1, 4 mL) and 4N HCl in dioxane (2 mL) was added. The suspension was stirred at RT overnight. $Et_2O$ was added (ca. 4 mL) and the precipitate was filtered under reduced pressure, washed with $Et_2O$ (ca. 10 mL) and dried under air. The resulting sticky solid was dissolved in MeOH (ca. 5 mL) and precipitated by addition of $Et_2O$ (ca. 3 mL). The mother liquor was removed and the resulting solid was dried under reduced pressure giving the hydrochloride salt of the title product as a red solid (60 mg, 98%). $^1$H NMR (400 MHz, Methanol-d4) δ 8.58 (s, 1H), 8.33 (s, 1H), 8.11 (s, 1H), 5.26 (sept, J=6.8 Hz, 1H), 4.39-4.31 (m, 1H), 4.17-4.12 (m, 4H), 4.00-3.88 (m, 1H), 3.86-3.71 (m, 5H), 3.67-3.60 (m, 1H), 3.58-3.46 (m, 1H), 2.23-2.16 (m, 1H), 2.02-1.93 (m, 1H), 1.92-1.70 (m, 2H), 1.46 (d, J=6.8 Hz, 6H); m/z (ES$^-$) (M–H)$^+$ 456.2; $t_R$=1.58 min. HPLC Method 3 (Base).

Example 82: (S)-2-(3-aminopiperidin-1-yl)-4-((5-cyclohexyl-1-isopropyl-6-oxo-1,6-dihydropyridin-3-yl)amino)pyrimidine-5-carboxamide Step 82-1: 3-(cyclohex-1-en-1-yl)-1-isopropyl-5-nitropyridin-2(1H)-one. A mixture of 3-bromo-1-isopropyl-5-nitropyridin-2(1H)-one (180 mg, 0.69 mmol), cyclohex-1-en-1-ylboronic acid (174 mg, 1.38 mmol) and $K_2CO_3$ (286 mg, 2.07 mmol) in dioxane:$H_2O$ (4:1, 11 mL) was degassed with a $N_2$ flow for 20 min. Bis(triphenylphosphine)palladium(II) dichloride (48 mg, 0.07 mmol) was added and the reaction mixture was stirred at 100° C. for 2.5 h. The resulting mixture was concentrated under reduced pressure and the residue dissolved in EtOAc (ca. 30 mL) and washed with brine (3×20 mL). The organic phase was dried over $MgSO_4$, filtered, concentrated under reduced pressure and purified by flash chromatography [Hexane:EtOAc (85:15)] affording the title product as a colourless oil (179 mg, 99%). $^1$H NMR (400 MHz, $CDCl_3$) δ 8.52 (d, J=3.0 Hz, 1H), 7.95 (d, J=3.0 Hz, 1H), 6.46 (t, J=2.0 Hz, 1H), 5.25 (sept, J=6.8 Hz, 1H), 2.39-2.30 (m, 2H), 2.27-2.19 (m, 2H), 1.80-1.72 (m, 2H), 1.71-1.57 (m, 2H), 1.43 (d, J=6.8 Hz, 6H); m/z (ES$^+$) (M+H)$^+$ 261.1; $t_R$=2.66 min. HPLC Method 3 (Base).

Step 82-2: 5-amino-3-cyclohexyl-1-isopropylpyridin-2(1H)-one. A mixture of 3-(cyclohex-1-en-1-yl)-1-isopropyl-5-nitropyridin-2(1H)-one (80 mg, 0.31 mmol) and palladium on carbon (10 wt. %, 32 mg, 0.03 mmol) in DCM:MeOH (1:1, 5 mL) was stirred at RT under $H_2$ atmosphere (1 atm) for 1 h. The reaction mixture was flushed with Ar, filtered through Celite® and washed with MeOH (ca. 20 mL). The filtrate was concentrated under reduced pressure affording a colourless oil which rapidly turned darker. The residue was directly taken into the next step without further purification.

Step 82-3: tert-butyl (S)-(1-(5-carbamoyl-4-((5-cyclohexyl-1-isopropyl-6-oxo-1,6-dihydropyridin-3-yl)amino)pyrimidin-2-yl)piperidin-3-yl)carbamate. A mixture of 2,4-dichloropyrimidine-5-carboxamide (58 mg, 0.30 mmol), 5-amino-3-cyclohexyl-1-isopropylpyridin-2(1H)-one (70 mg, 0.30 mmol) and triethylamine (0.05 mL, 0.33 mmol) in 1,4-dioxane (4.0 mL) was stirred at 50° C. for 1 h. (S)-Tert-butyl piperidin-3-ylcarbamate (60 mg, 0.30 mmol) and triethylamine (0.05 mL, 0.33 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3→3:7)] affording the title product as a white solid (81 mg, 49%). The compound was directly taken into the next step.

Step 82-4: (S)-2-(3-aminopiperidin-1-yl)-4-((5-cyclohexyl-1-isopropyl-6-oxo-1,6-dihydropyridin-3-yl)amino) pyrimidine-5-carboxamide. tert-Butyl (S)-(1-(5-carbamoyl-4-((5-cyclohexyl-1-isopropyl-6-oxo-1,6-dihydropyridin-3-yl)amino)pyrimidin-2-yl)piperidin-3-yl)carbamate (81 mg, 0.15 mmol) was suspended into dioxane:Et$_2$O (1:1, 4 mL) and 4N HCl in dioxane (2 mL) was added. The suspension was stirred at RT overnight. Et$_2$O was added (ca. 4 mL) and the precipitate was filtered under reduced pressure, washed with Et$_2$O (ca. 10 mL) and dried under air. The resulting sticky solid was dissolved in MeOH (ca. 5 mL) and precipitated by addition of Et$_2$O (ca. 3 mL). The mother liquor was removed and the resulting solid was dried under reduced pressure giving the hydrochloride salt of the title product as a white solid (66 mg, 99%). $^1$H NMR (400 MHz, Methanol-d4) δ 8.53 (s, 1H), 7.82 (d, J=2.2 Hz, 1H), 7.50 (d, J=2.2 Hz, 1H), 5.28 (sept, J=6.7 Hz, 1H), 4.33-4.24 (m, 1H), 4.11-4.01 (m, 1H), 3.76-3.64 (m, 1H), 3.63-3.43 (m, 2H), 2.91-2.84 (m, 1H), 2.27-2.11 (m, 1H), 1.95-1.75 (m, 7H), 1.52-1.43 (m, 2H), 1.40 (app. dd, J=6.8, 1.6 Hz, 6H), 1.35-1.21 (m, 4H); m/z (ES$^−$) (M−H)$^−$ 452.0; t$_R$=2.14 min. HPLC Method 3 (Base).

Example 83: (S)-2-(3-aminopiperidin-1-yl)-4-((5-(4,4-difluorocyclohexyl)-1-isopropyl-6-oxo-1,6-dihydropyridin-3-yl)amino)pyrimidine-5-carboxamide Step 83-1: 5-amino-3-(4,4-difluorocyclohexyl)-1-isopropylpyridin-2(1H)-one. Prepared by an analogous method to step 82-2, using 3-(4,4-difluorocyclohex-1-en-1-yl)-1-isopropyl-5-nitropyridin-2(1H)-one (0.119 g, 0.40 mmol), 10% Pd/C (0.050 g, 12 mol %), MeOH (10.0 mL) and DCM (3.0 mL) to give the title compound as a white solid, without the need for purification (0.041 g, 38%). $^1$H NMR (400 MHz, CDCl$_3$) δ 6.84 (d, J=2.4 Hz, 1H), 6.71 (d, J=3.2 Hz, 1H), 5.29 (sept, J=6.8 Hz, 1H), 3.00 (app t, J=12 Hz, 1H), 2.22-2.01 (m, 2H), 1.99-1.90 (m, 3H), 1.83 (tt, J=13.2, 4 Hz, 1H), 1.59-1.45 (m, 2H), 1.30 (d, J=6.8 Hz, 6H). LCMS: m/z (ES+) (M+H)$^+$ 271.2; t$_R$=2.02 min. HPLC Method 3 (Acid).

Step 83-2: (S)-2-(3-aminopiperidin-1-yl)-4-((5-(4,4-difluorocyclohexyl)-1-isopropyl-6-oxo-1,6-dihydropyridin-3-yl)amino)pyrimidine-5-carboxamide. Prepared by an analogous method to example 3, using 5-amino-3-(4,4-difluorocyclohexyl)-1-isopropylpyridin-2(1H)-one (0.041 g, 0.15 mmol), 2,4-dichloropyrimidine-5-carboxamide (0.031 g, 0.16 mmol), triethylamine (0.05 mL, 0.38 mmol), dioxane (5.0 mL), DMF (0.5 mL), tert-butyl (S)-piperidin-3-ylcarbamate (0.031 g, 0.15 mmol) and triethylamine (0.05 mL, 0.38 mmol) to give the hydrochloride salt of the title compound as a brown powder (intermediate was purified under identical conditions) (0.041 g, 51%). $^1$H NMR (400 MHz, MeOD) δ 8.53 (br s, 1H), 7.91-7.78 (m, 1H), 7.65-7.47 (m, 1H), 5.35-5.19 (m, 1H), 4.35-4.19 (m, 1H), 4.18-3.99 (m, 1H), 3.81-3.62 (m, 1H), 3.62-3.44 (m, 1H), 3.05-2.90 (m, 1H), 2.28-2.06 (m, 3H), 2.07-1.71 (m, 7H), 1.72-1.50 (m, 2H), 1.49-1.34 (m, 6H). LCMS: m/z (ES+) (M+H)$^+$ 490.3; t$_R$=2.14 min. HPLC Method 3 (Acid).

Example 84: (S)-2-(3-aminopiperidin-1-yl)-4-((1-isopropyl-6-oxo-5-(piperidine-1-carbonyl)-1,6-dihydropyridin-3-yl)amino)pyrimidine-5-carboxamide Step 84-1: 1-isopropyl-5-nitro-3-(piperidine-1-carbonyl) pyridin-2(1H)-one. 3-Bromo-1-isopropyl-5-nitropyridin-2 (1H)-one (100 mg, 0.38 mmol), piperidine-1-carbaldehyde (1.9 mL, 17.10 mmol), palladium(II) acetate (4 mg, 0.02 mmol), Xantphos (22 mg, 0.04 mmol) and phosphorus oxychloride (0.07 mL, 0.76 mmol) were combined in a pressure vessel under an inert atmosphere and stirred at 165° C. for 24 h. The resulting mixture was dissolved in EtOAc (ca. 30 mL) and washed with brine (3×20 mL). The organic phase was dried over MgSO$_4$, filtered, concentrated under reduced pressure and purified by flash chromatography [Hexane:EtOAc (4:1)] affording the title product as a colourless oil (40 mg, 36%). $^1$H NMR (400 MHz, CDCl$_3$) δ 8.63 (d, J=3.0 Hz, 1H), 8.16 (d, J=3.0 Hz, 1H), 5.18 (sept, J=6.8 Hz, 1H), 3.75-3.62 (m, 2H), 3.27-3.20 (m, 2H), 1.72-1.59 (m, 6H), 1.43 (d, J=6.8 Hz, 6H); m/z (ES$^+$) (M+H)$^+$ 294.2; t$_R$=2.16 min. HPLC Method 3 (Acid).

Step 84-2: 5-amino-1-isopropyl-3-(piperidine-1-carbonyl)pyridin-2(1H)-one. Zn dust (71 mg, 1.09 mmol) was added portion-wise into an ice-cooled solution of 1-isopropyl-5-nitro-3-(piperidine-1-carbonyl)pyridin-2(1H)-one (40 mg, 0.14 mmol) and NH$_4$Cl (120 mg, 2.24 mmol) in THF:H$_2$O (5:1, 3.0 mL). The mixture was allowed to reach RT and stirred for 30 min. The reaction mixture was filtered through Celite® and washed with EtOAc (ca. 20 mL). The filtrate was dried over MgSO$_4$, filtered and concentrated under reduced pressure affording a colourless oil which rapidly turned darker. The residue was directly taken into the next step without further purification.

Step 84-3: tert-butyl (S)-(1-(5-carbamoyl-4-((1-isopropyl-6-oxo-5-(piperidine-1-carbonyl)-1,6-dihydropyridin-3-yl)amino)pyrimidin-2-yl)piperidin-3-yl)carbamate. A mixture of 2,4-dichloropyrimidine-5-carboxamide (27 mg, 0.14 mmol), 5-amino-1-isopropyl-3-(piperidine-1-carbonyl)pyridin-2(1H)-one (37 mg, 0.14 mmol) and triethylamine (0.02 mL, 0.15 mmol) in 1,4-dioxane (4.0 mL) was stirred at 50° C. for 3 h. (S)-Tert-butyl piperidin-3-ylcarbamate (28 mg, 0.14 mmol) and triethylamine (0.02 mL, 0.15 mmol) were added and the mixture was stirred at 50° C. overnight. The resulting mixture was allowed to reach RT, concentrated under reduced pressure, dry-loaded into a column and purified by flash chromatography [gradient DCM:MeOH (99:1->9:1)] affording the title product as a colourless oil (33 mg, 40%). The compound was directly taken into the next step.

Step 84-4: (S)-2-(3-aminopiperidin-1-yl)-4-((1-isopropyl-6-oxo-5-(piperidine-1-carbonyl)-1,6-dihydropyridin-3-yl) amino)pyrimidine-5-carboxamide. tert-Butyl (S)-(1-(5-carbamoyl-4-((1-isopropyl-6-oxo-5-(piperidine-1-carbonyl)-1, 6-dihydropyridin-3-yl)amino)pyrimidin-2-yl)piperidin-3-yl)carbamate (33 mg, 0.06 mmol) was suspended into dioxane:Et$_2$O (1:1, 4 mL) and 4N HCl in dioxane (2 mL) was added. The suspension was stirred at RT overnight. Et$_2$O was added (ca. 4 mL) and the mother liquor was removed. The resulting solid was dried under reduced pressure giving the hydrochloride salt of the title product as a white solid (26 mg, 90%). $^1$H NMR (400 MHz, MeOD) δ 8.55 (br. s, 1H), 8.19-7.99 (m, 1H), 7.94 (br. s, 1H), 5.23-5.16 (m, 1H), 4.72-4.50 (m, 1H), 4.14-4.05 (m, 1H), 3.78-3.65 (m, 2H), 3.60-3.41 (m, 3H), 2.36-2.15 (m, 1H), 2.08-1.98 (m, 1H), 1.93-1.75 (m, 2H), 1.76-1.54 (m, 8H), 1.42 (d, J=6.8, 6H); m/z (ES$^+$) (M+H)$^+$ 483.3; t$_R$=1.99 min. HPLC Method 3 (Acid).

Example 85: (S)-2-(3-aminopiperidin-1-yl)-4-((5-isopropyl-6-oxo-1-phenyl-1,6-dihydropyridin-3-yl) amino)pyrimidine-5-carboxamide Step 85-1: 5-nitro-3-(prop-1-en-2-yl)pyridin-2(1H)-one. Prepared by an analogous method to step 80-1, heated at 100° C. over the weekend using 3-bromo-1-isopropyl-5-nitropyridin-2(1H)-one (0.500 g, 2.78 mmol), 4,4,5,5-tetramethyl-2-(prop-1-en-2-yl)-1,3,2-dioxaborolane (0.86 mL, 4.57 mmol), dioxane (18.0 mL), water (4.0 mL), potassium carbonate (0.946 g, 6.85 mmol) and Pd(PPh$_3$)$_2$Cl$_2$ (0.160 g, 0.23 mmol). The crude product was purified by flash column chromatography on silica (2:1 hexane: EtOAc) to give the title compound as a yellow solid (0.170 g, 41%). $^1$H NMR (400 MHz, CD$_3$OD) δ 8.54 (d, J=3.2 Hz, 1H), 8.16 (d, J=2.8 Hz, 1H), 5.89-5.87 (m, 1H), 5.33 (app pent, J=2.8 Hz, 1H), 2.12 (dd, J=0.8, 0.4 Hz, 3H). LCMS: m/z (ES$^-$) (M−H)$^+$ 178.9; t$_R$=0.95 min. HPLC Method 3 (Acid).

Step 85-2: 5-nitro-1-phenyl-3-(prop-1-en-2-yl)pyridin-2(1H)-one. 5-Nitro-3-(prop-1-en-2-yl)pyridin-2(1H)-one (0.090 g, 0.50 mmol), CuCl (5 mg, 10 mol %), triethylamine (0.14 mL, 1.00 mmol), diphenyliodonium triflate (0.280 g, 0.651 mmol) and toluene (5.0 mL) were added to a flask under Ar. The reaction mixture was stirred at RT for 2 h and then concentrated under reduced pressure to give the crude product, which was purified by flash column chromatography on silica (3:1 hexane: EtOAc) to give the title compound as a yellow solid (0.106 g, 83%). $^1$H NMR (400 MHz, CDCl$_3$) δ 8.60 (d, J=3.2 Hz, 1H), 8.17 (d, J=3.2 Hz, 1H), 7.58-7.57 (m, 3H), 7.42-7.36 (m, 2H), 5.99-5.95 (m, 1H), 5.38 (app pent, J=1.2 Hz, 1H), 2.17-2.14 (m, 3H). $^{13}$C NMR (101 MHz, CDCl$_3$) δ 160.3, 139.8, 138.8, 137.8, 131.9, 130.6, 129.8, 129.8, 129.2, 126.5, 120.0, 22.3.

Step 85-3: 5-amino-3-isopropyl-1-phenylpyridin-2(1H)-one. As in example 8 step 2, using 5-nitro-1-phenyl-3-(prop-1-en-2-yl)pyridin-2(1H)-one (0.075 g, 0.29 mmol), 10% Pd/C (0.035 g, 11 mol %), MeOH (10.0 mL) and DCM (3.0 mL) to give the title compound as a green residue which immediately began to take a darker colour (0.065 g, 98%). The product was quickly used in the next reaction without characterisation. LCMS: m/z (ES+) (M+H)$^+$ 229.2; t$_R$=1.79 min. HPLC Method 3 (Acid).

Step 85-4: (S)-2-(3-aminopiperidin-1-yl)-4-((5-isopropyl-6-oxo-1-phenyl-1,6-dihydropyridin-3-yl)amino)pyrimidine-5-carboxamide. 5-amino-3-isopropyl-1-phenylpyridin-2(1H)-one (0.065 g, 0.28 mmol), 2,4-dichloropyrimidine-5-carboxamide (0.055 g, 0.29 mmol), triethylamine (0.08 mL, 0.57 mmol) were dissolved in anhydrous dioxane (5.0 mL) and DMF (0.5 mL). The mixture was heated at 50° C. for 1 h and left to cool to RT. tert-Butyl (S)-piperidin-3-ylcarbamate (0.057 g, 0.28 mmol) and triethylamine (0.07 mL, 0.57 mmol) were added and the reaction mixture was heated at 50° C. overnight. The reaction mixture was diluted with EtOAc (15 mL), washed sequentially with water (3×10 mL) and brine (10 mL). The organic phase was dried over MgSO$_4$, filtered and concentrated under reduced pressure to give the crude product from two displacements, which was purified by flash column chromatography on silica (1:2 hexane: EtOAc followed by 1:4). The intermediate was dissolved in Et$_2$O (5.0 mL) and 4M HCl in dioxane (5.0 mL) was added drop-wise and the mixture was stirred at RT overnight. Hexane was added (15 mL) and the solid filtered and dried to give the hydrochloride salt of the title compound as a white powder (0.065 g, 47%). $^1$H NMR (400 MHz, CD$_3$OD) δ 8.53 (s, 1H), 7.91 (s, 1H), 7.63 (s, 1H), 7.57 (app t, J=7.2 Hz, 2H), 7.50 (t, J=7.2 Hz, 1H), 7.45 (d, J=7.2 Hz, 2H), 4.25 (app d, J=12.4 Hz, 1H), 4.10-3.91 (m, 1H), 3.77-3.64 (m, 1H), 3.62-3.45 (m, 1H), 3.21 (sept, J=6.8 Hz, 1H), 2.23-2.11 (m, 1H), 1.95-1.64 (m, 3H), 1.25 (d, J=6.8 Hz, 6H). LCMS: m/z (ES+) (M+H)$^+$ 448.3; t$_R$=2.05 min. HPLC Method 3 (Acid).

Example 86: (S)-2-(3-aminopiperidin-1-yl)-4-((6-oxo-1,5-diphenyl-1,6-dihydropyridin-3-yl)amino)pyrimidine-5-carboxamide Step 86-1: 3-bromo-5-nitro-1-phenylpyridin-2(1H)-one. 3-Bromo-1-isopropyl-5-nitropyridin-2(1H)-one (90 mg, 0.50 mmol), CuCl (5 mg, 0.05 mmol), triethylamine (0.14 mL, 1.00 mmol), diphenyliodonium triflate (280 mg, 0.65 mmol) and toluene (5.0 mL) were added to a flask under Ar. The reaction mixture was stirred at RT for 2 h and then concentrated under reduced pressure to give the crude product, which was purified by flash column chromatography on silica (3:1 hexane: EtOAc) to give the title compound as a yellow solid (0.106 g, 83%). $^1$H NMR (400 MHz, CDCl$_3$) δ 8.60 (d, J=3.2 Hz, 1H), 8.17 (d, J=3.2 Hz, 1H), 7.58-7.57 (m, 3H), 7.42-7.36 (m, 2H); m/z (ES$^+$) (M+H)$^+$ 296.2 for $^{79}$Br; t$_R$=2.54 min. HPLC Method 3 (Base).

Step 86-2: 5-nitro-1,3-diphenylpyridin-2(1H)-one. A mixture of 3-bromo-5-nitro-1-phenylpyridin-2(1H)-one (88 mg, 0.30 mmol), 4,4,5,5-tetramethyl-2-phenyl-1,3,2-dioxaborolane (91 mg, 0.45 mmol) and K$_2$CO$_3$ (125 mg, 0.90 mmol) in dioxane:H$_2$O (4:1, 6 mL) was degassed with a N$_2$ flow for 20 min. Bis(triphenylphosphine)palladium(II) dichloride (21 mg, 0.03 mmol) was added and the reaction mixture was stirred at 100° C. for 1.5 h. The resulting mixture was concentrated under reduced pressure and the residue dissolved in EtOAc (ca. 30 mL) and washed with brine (3×20 mL). The organic phase was dried over MgSO$_4$, filtered, concentrated under reduced pressure and purified by flash chromatography [Hexane:EtOAc (4:1)] affording the title product as an off-white solid (60 mg, 69%). $^1$H NMR (400 MHz, CDCl$_3$) δ 8.68 (d, J=3.0 Hz, 1H), 8.33 (d, J=3.0 Hz, 1H), 7.74 (d, J=7.3 Hz, 2H), 7.61-7.50 (m, 3H), 7.49-7.35 (m, 5H); m/z (ES$^+$) (M+H)$^+$ 293.1; t$_R$=2.51 min. HPLC Method 3 (Base).

Step 86-3: 5-amino-1,3-diphenylpyridin-2(1H)-one. Zn dust (107 mg, 1.64 mmol) was added portion-wise into an ice-cooled solution of 5-nitro-1,3-diphenylpyridin-2(1H)-one (60 mg, 0.21 mmol) and NH$_4$Cl (178 mg, 3.36 mmol) in THF:H$_2$O (5:1, 4.0 mL). The mixture was allowed to reach RT and stirred for 30 min. The reaction mixture was filtered through Celite® and washed with EtOAc (ca. 20 mL). The filtrate was dried over MgSO$_4$, filtered and concentrated under reduced pressure affording a colourless oil which rapidly turned darker. The residue was directly taken into the next step without further purification.

Step 86-4: tert-butyl (S)-(1-(5-carbamoyl-4-((6-oxo-1,5-diphenyl-1,6-dihydropyridin-3-yl)amino)pyrimidin-2-yl)piperidin-3-yl)carbamate. A mixture of 2,4-dichloropyrimidine-5-carboxamide (38 mg, 0.20 mmol), 5-amino-1,3-diphenylpyridin-2(1H)-one (52 mg, 0.20 mmol) and triethylamine (0.03 mL, 0.22 mmol) in 1,4-dioxane (4.0 mL) was stirred at 50° C. for 3 h. (S)-Tert-butyl piperidin-3-ylcarbamate (40 mg, 0.20 mmol) and triethylamine (0.03 mL, 0.22 mmol) were added and the mixture was stirred at 50° C. overnight. The resulting mixture was allowed to reach RT, concentrated under reduced pressure, dry-loaded into a column and purified by flash chromatography [gradient Hexane:EtOAc (2:3-+3:7)] affording the title product as a white solid (27 mg, 23%). The compound was directly taken into the next step.

Step 86-5: (S)-2-(3-aminopiperidin-1-yl)-4-((6-oxo-1,5-diphenyl-1,6-dihydropyridin-3-yl)amino)pyrimidine-5-carboxamide. tert-Butyl (S)-(1-(5-carbamoyl-4-((6-oxo-1,5-diphenyl-1,6-dihydropyridin-3-yl)amino)pyrimidin-2-yl)piperidin-3-yl)carbamate (27 mg, 0.04 mmol) was suspended into dioxane:Et$_2$O (1:1, 4 mL) and 4N HCl in dioxane (2 mL) was added. The suspension was stirred at RT overnight. Et$_2$O was added (ca. 4 mL) and the precipitate was filtered under reduced pressure, washed with Et$_2$O (ca. 10 mL) and dried under air. The resulting sticky solid was dissolved in MeOH (ca. 5 mL) and precipitated by addition of Et$_2$O (ca. 3 mL). The mother liquor was removed and the resulting solid was dried under reduced pressure giving the hydrochloride salt of the title product as a pale green (20 mg, 89%). $^1$H NMR (400 MHz, MeOD) δ 8.54 (s, 1H), 8.11-8.00 (m, 1H), 7.91 (d, J=2.9 Hz, 1H), 7.73-7.68 (m, 2H), 7.62-7.55 (m, 2H), 7.56-7.47 (m, 3H), 7.46-7.40 (m, 2H), 7.39-7.33 (m, 1H), 4.29 (app. dd, J=13.6, 3.8 Hz, 1H), 4.12-3.81 (m, 1H), 3.73-3.58 (m, 1H), 3.57-3.38 (m, 2H), 2.30-2.02 (m, 1H), 1.93-1.58 (m, 3H); m/z (ES$^-$) (M−H)$^-$ 482.3; $t_R$=2.09 min. HPLC Method 3 (Base).

Example 87: (S)-2-(3-aminopiperidin-1-yl)-4-((3-isopropyl-5-(2-methoxypropan-2-yl)phenyl)amino) pyrimidine-5-carboxamide Step 87-1: methyl 3-bromo-5-(dibenzylamino)benzoate. A stirred solution of methyl 3-amino-5-bromobenzoate (10.00 g, 43.5 mmol) and DIPEA (15.94 mL, 91 mmol) in acetonitrile (200 mL) was heated to 80° C. and benzyl bromide (10.86 mL, 91 mmol) was added dropwise over 1 h. The reaction was then stirred for 24 h, then allowed to cool to RT, diluted with sat. sodium bicarbonate solution (400 mL) and extracted with ethyl acetate (2×400 mL). The combined organic layers were dried over magnesium sulfate, filtered and concentrated under vacuum. The crude product was purified by silica gel chromatography (0-30% EtOAc/isohexane). (14.68 g, 78%). m/z (M+H)$^+$ (ES$^+$) 410.1, 412.1; $t_R$=3.07 min. HPLC Method 2.

Step 87-2: 2-(3-bromo-5-(dibenzylamino)phenyl)propan-2-ol. To a stirred solution of methyl 3-bromo-5-(dibenzylamino)benzoate (7.38 g, 17.99 mmol) in THF (100 mL) at 0° C. was added methylmagnesium bromide (3M in THF, 14.99 mL, 45.0 mmol) dropwise. The reaction was then stirred for 2 h at 0° C. then quenched with sat. ammonium chloride solution (100 mL) and extracted with ethyl acetate (3×100 mL). The combined organic layers were washed with water (300 mL), dried over magnesium sulfate, filtered and concentrated under vacuum. (7.20 g, 93%). m/z (M+H)$^+$ (ES$^+$) 410.2, 412.2; $t_R$=2.86 min. HPLC Method 2.

Step 87-3: N,N-dibenzyl-3-bromo-5-(2-methoxypropan-2-yl)aniline. To a stirred solution of 2-(3-bromo-5-(dibenzylamino)phenyl)propan-2-ol (2 g, 4.87 mmol) in THF (40 mL) was added sodium hydride (0.390 g, 9.75 mmol) portion-wise. After 20 minutes, methyl iodide (0.366 mL, 5.85 mmol) was added and the solution was stirred at RT for 24 h. The reaction was quenched with sat. ammonium chloride solution (50 mL) and extracted with ethyl acetate (3×100 mL). The combined organic layers were dried over magnesium sulfate, filtered and concentrated under vacuum. The crude product was purified by silica gel chromatography (0-20% EtOAc/isohexane). (1.75 g, 80%). m/z (M+H)+ (ES$^+$) 424.2, 426.1; $t_R$=3.16 min. HPLC Method 2.

Step 87-4: N,N-dibenzyl-3-(2-methoxypropan-2-yl)-5-(prop-1-en-2-yl)aniline. A stirred solution of 4,4,5,5-tetramethyl-2-(prop-1-en-2-yl)-1,3,2-dioxaborolane (0.125 mL, 0.665 mmol), sodium hydrogen carbonate (0.140 g, 1.661 mmol) and N,N-dibenzyl-3-bromo-5-(2-methoxypropan-2-yl)aniline (0.235 g, 0.554 mmol) in 1,4-dioxane (3 mL) and water (1 mL) was purged with nitrogen for 10 minutes. PdCl$_2$dppf (0.041 g, 0.055 mmol) was added and purging was continued for a further 10 minutes. The solution was then heated to 90° C. and stirred under nitrogen for 2 h. The reaction was then allowed to cool to RT, diluted with water (10 mL) and extracted with ethyl acetate (3×10 mL). The combined organic layers were dried over magnesium sulfate, filtered and concentrated under vacuum. The crude product was purified by silica gel chromatography (0-10% EtOAc/isohexane). (0.123 g, 55.9%). m/z (M+H)+(ES$^+$) 386.7; $t_R$=3.17 min. HPLC Method 2.

Step 87-5: 3-isopropyl-5-(2-methoxypropan-2-yl)aniline. A solution of N,N-dibenzyl-3-(2-methoxypropan-2-yl)-5-(prop-1-en-2-yl)aniline (0.123 g, 0.319 mmol) in methanol (10 mL) was hydrogenated in an H-Cube (10% Pd/C, 30×4 mm, Full hydrogen, 40° C., 1 mL/min) and concentrated under vacuum. (0.055 g, 58.2%). m/z (M+H)+(ES$^+$) 208.2; $t_R$=1.49 min. HPLC Method 2 @ 215 nm.

Step 87-6: (S)-2-(3-aminopiperidin-1-yl)-4-((3-isopropyl-5-(2-methoxypropan-2-yl)phenyl)amino)pyrimidine-5-carboxamide. To a stirred solution of 3-isopropyl-5-(2-methoxypropan-2-yl)aniline (0.055 g, 0.265 mmol) and 2,4-dichloropyrimidine-5-carboxamide (0.051 g, 0.265 mmol) in 1,4-dioxane (2 mL) was added DIPEA (0.093 mL, 0.531 mmol). The solution was heated to 90° C., stirred for 2 h and then allowed to cool to RT. (S)-piperidin-3-amine (0.027 g, 0.265 mmol) and DIPEA (0.093 mL, 0.531 mmol) were added and the solution was reheated to 90° C. for a further 30 minutes. The reaction was left to cool to RT and concentrated under vacuum. The crude product was purified by silica gel chromatography (0-10% (0.7 M Ammonia/MeOH)/DCM). (0.035 g, 28%). $^1$H NMR (400 MHz, DMSO-d6) δ 11.52 (s, 1H), 8.59 (s, 1H), 8.10-7.15 (br m, 5H), 6.92-6.90 (m, 1H), 4.64-4.46 (m, 2H), 3.03-2.82 (m, 5H), 2.78-2.57 (m, 2H), 2.10-1.80 (m, 3H), 1.74-1.65 (m, 1H), 1.50-1.35 (m, 6H), 1.32-1.13 (m, 7H). m/z (M+H)+(ES$^+$) 427.3; $t_R$=1.51 min. HPLC Method 2.

Example 88: (S)-2-(3-aminopiperidin-1-yl)-4-((3-(2-hydroxypropan-2-yl)-5-isopropylphenyl) amino) pyrimidine-5-carboxamide Step 88-1: 2-(3-amino-5-isopropylphenyl)propan-2-ol. Prepared from 2-(3-bromo-5-(dibenzylamino)phenyl)propan-2-ol by an analogous method to steps 87-4 and 87-5. m/z (M+H)+(ES$^+$) 194.3; $t_R$=1.03 min. HPLC Method 2.

Step 88-2: (S)-tert-butyl (1-(5-carbamoyl-4-((3-(2-hydroxypropan-2-yl)-5-isopropylphenyl) amino)pyrimidin-2-yl)piperidin-3-yl)carbamate. To a stirred solution of 2-(3-amino-5-isopropylphenyl)propan-2-ol (0.03 g, 0.15 mmol) and DIPEA (0.054 mL, 0.31 mmol) in 1,4-dioxane (2 mL) was added 2,4-dichloropyrimidine-5-carboxamide (0.030 g, 0.155 mmol). The reaction was heated to 80° C. and stirred for 2 h. The reaction was allowed to cool to RT, then (S)-tert-butyl piperidin-3-ylcarbamate (0.031 g, 0.15 mmol) and DIPEA (0.054 mL, 0.31 mmol) were added. The reaction was heated to 50° C. for 10 min, allowed to cool and concentrated under vacuum. The crude product was purified by chromatography on silica gel (0.7 M Ammonia/MeOH)/DCM) to afford (S)-tert-butyl (1-(5-carbamoyl-4-((3-(2-hydroxypropan-2-yl)-5-isopropylphenyl)amino)pyrimidin-2-yl)piperidin-3-yl)carbamate. (0.053 g, 65%). m/z (M+H)$^+$ (ES$^+$) 513.4; $t_R$=2.04 min. HPLC Method 2.

Step 88-3: (S)-2-(3-aminopiperidin-1-yl)-4-((3-(2-hydroxypropan-2-yl)-5-isopropylphenyl) amino)pyrimidine-5-carboxamide. To a stirred solution of (S)-tert-butyl (1-(5-carbamoyl-4-((3-(2-hydroxypropan-2-yl)-5-isopropylphenyl)amino)pyrimidin-2-yl)piperidin-3-yl)carbamate (0.053 g, 0.103 mmol) in 1,4-dioxane (1 mL) was added hydrogen chloride (4M in 1,4-dioxane, 0.517 mL, 2.068 mmol) and the reaction was stirred at RT for 16 h. The reaction was concentrated under vacuum and purified by chromatography on silica gel (0-10% (0.7 M Ammonia/MeOH)/DCM) to afford (S)-2-(3-aminopiperidin-1-yl)-4-((3-(2-hydroxypropan-2-yl)-5-isopropylphenyl)amino)pyrimidine-5-carboxamide. (0.02 g, 42%). $^1$H NMR (400 MHz, MeOD) δ 8.53, (s, 1H), 7.85 (br s, 1H), 7.28 (br s, 1H), 7.10-7.05 (m, 1H), 4.73-4.64 (m, 1H), 4.59-4.50 (m, 1H), 3.19-3.10 (m, 1H), 3.00-2.89 (m, 2H), 2.88-2.79 (m, 1H), 2.09-2.00 (m, 1H), 1.86-1.78 (m, 1H), 1.65-1.52 (m, 7H), 1.51-1.39 (m, 1H), 1.29 (dd, 6H, J=6.9, 0.7 Hz), m/z (M+H)$^+$ (ES$^+$) 413.3; $t_R$=1.33 min. HPLC Method 2.

Example 89: (S)-2-(3-aminopiperidin-1-yl)-4-((3-(2-hydroxypropan-2-yl)-5-(trifluoromethyl)phenyl)amino)pyrimidine-5-carboxamide Step 89-1: 2-(3-amino-5-(trifluoromethyl)phenyl)propan-2-ol). N,N-dibenzyl-3-(2-methoxypropan-2-yl)-5-(prop-1-en-2-yl)aniline (J. Org. Chem., Vol. 56, No. 13, 1991) was dissolved in ethanol and degassed before Pd/C was added. The mixture was stirred at RT under a hydrogen atmosphere overnight (16 h). The suspension was filtered through Celite. The filtrate was concentrated to dryness to give a pale brown solid. m/z (ES$^+$) (M+H)$^+$ 219.8; $t_R$=2.48 min. HPLC Method 1.

Step 89-2: (S)-2-(3-aminopiperidin-1-yl)-4-((3-(2-hydroxypropan-2-yl)-5-(trifluoromethyl)phenyl) amino)pyrimidine-5-carboxamide. Prepared by an analogous method to example 3 with 2-(3-amino-5-(trifluoromethyl)phenyl)propan-2-ol) (Step 1: CH$_3$CN, DIPEA, 60° C., 3 h) to give the 2-chloro-4-((3-(2-hydroxypropan-2-yl)-5-(trifluoromethyl)phenyl)amino)pyrimidi-ne-5-carboxa-mide which was purified by chromatography on silica using a gradient PET/EtOAc (80%) to give white solid (88 mg (52%), m/z (ES$^+$) (M+H)$^+$ 375.0; $t_R$=2.74 min. HPLC Method 1). The unprotected (S)-3-aminopiperidine was used (Step 2: CH$_3$CN DIPEA, RT, 16 h) to give the title compound as a white solid (63 mg, 81%), $^1$H NMR (300 MHz, MeOD) δ 8.55 (s, 1H), 8.02 (br s, 2H), 7.42 (s, 1H), 4.64 (br d, J=13.2 Hz, 1H), 4.48 (br d, J=13.9 Hz, 1H), 3.11 (t, J=11.1 Hz, 1H), 2.94 (dd, J=9.6, 12.6 Hz, 1H), 2.86-2.79 (m, 1H), 2.06-1.99 (m, 1H), 1.84-1.76 (m, 1H), 1.61-1.49 (m, 1H) 1.56 (s, 6H), 1.49-1.38 (m, 1H), m/z (ES$^+$) (M+H)$^+$ 439.2; $t_R$=2.17 min. HPLC Method 1.

Example 90: (S)-2-(3-aminopiperidin-1-yl)-4-((3,5-bis(2-hydroxypropan-2-yl)phenyl)amino) pyrimidine-5-carboxamide Step 90-1: 2,2'-(5-(dibenzylamino)-1,3-phenylene)bis(propan-2-oi). In an analogous method to step 87-2 dimethyl 5-(dibenzylamino)isophthalate was reacted with methyl lithium to give the title compound after purification (325 mg, 81%), $^1$H NMR (300 MHz, MeOD) δ 7.30-7.26 (m, 8H), 7.23-7.17 (m, 2H), 6.93 (t, J=1.5 Hz, 1H), 6.79 (d, J=1.5 Hz, 2H), 4.65 (s, 4H), 1.40 (s, 12H). m/z (ES$^+$) (M+H)$^+$ 390.0; $t_R$=2.94 min. HPLC Method 1.

Step 90-2: 2,2'-(5-amino-1,3-phenylene)bis(propan-2-ol). Prepared by an analogous method to step 87-5. ($^1$H NMR (300 MHz, MeOD) δ 6.99 (t, J=1.5 Hz, 1H), 6.76 (d, J=1.5 Hz, 2H), 1.50 (s, 12H). m/z (ES$^+$) (M+H)$^+$ 210.4; $t_R$=0.46 min. HPLC Method 1).

Step 90-3: (S)-2-(3-aminopiperidin-1-yl)-4-((3,5-bis(2-hydroxypropan-2-yl)phenyl)amino) pyrimidi-ne-5-carboxamide. Prepared by an analogous method to example 3 with 2,2'-(5-amino-1,3-phenylene)bis(propan-2-ol) (Step 1: CH$_3$CN, DIPEA, 70° C., 3 h) to give the 4-((3,5-bis(2-hydroxypropan-2-yl)phenyl)amino)-2-chloropyrimidine-5-carboxamide. The unprotected (S)-3-aminopiperidine was used (step C$_2$: CH$_3$CN DIPEA, RT, 16 h) to give the title compound as a pale yellow solid (55 mg, 49%). $^1$H NMR (300 MHz, MeOD) δ 8.50 (s, 1H), 7.75 (s, 2H), 7.29 (s, 1H), 4.71 (br d, J=11.9 Hz, 1H), 4.53 (br d, J=13.2 Hz, 1H), 3.12-3.05 (m, 1H), 2.93-2.87 (m, 1H), 2.85-2.78 (m, 1H), 2.04-1.98 (m, 1H), 1.82-1.75 (m, 1H), 1.61-1.48 (m, 1H), 1.55 (s, 6H), 1.45-1.36 (m, 1H). m/z (ES$^+$) (M+H)$^+$ 429.3; $t_R$=1.95 min. HPLC Method 1.

Example 91: (S)-2-(3-aminopiperidin-1-yl)-4-((3-(tert-butyl)-5-(2-hydroxypropan-2-yl)phenyl)amino) pyrimidine-5-carboxamide Step 91-1: 2-(3-amino-5-(tert-butyl)phenyl)propan-2-ol. Prepared by an analogous method to step 88-1, using methyl 3-amino-5-(tert-butyl)benzoate. $^1$H NMR (300 MHz, CDCl$_3$) δ 6.93 (s, 1H), 6.69 (s, 1H), 6.64 (s, 1H), 1.55 (s, 6H), 1.29 (s, 9H). m/z (ES$^+$) (M+H)$^+$ 208.1; $t_R$=2.84 min. HPLC Method 1). (S)-2-(3-aminopiperidin-1-yl)-4-((3-(tert-butyl)-5-(2-hydroxypropan-2-yl)phenyl)amino) pyrimidine-5-carboxamide. Prepared by an analogous method to example 3 (Step 1: CH$_3$CN, DIPEA, 70° C., 3 h). The unprotected (S)-3-aminopiperidine was used in step 2 (CH$_3$CN DIPEA, RT, 16 h) to give the hydrochloride salt of the compound as a pale yellow solid (144 mg, 64%). $^1$H NMR (300 MHz, MeOD) δ 8.50 (s, 1H), 7.82 (br s, 1H), 7.39 (br s, 1H), 7.25 (s, 1H), 4.65 (d, J=12.2 Hz, 1H), 4.51 (d, J=14.1 Hz, 1H), 3.14-3.07 (m, 1H), 2.93 (dd, J=9.4, 12.7 Hz, 1H), 2.85-2.78 (m, 1H), 2.03-1.97 (m, 1H), 1.81-1.74 (m, 1H), 1.60-1.50 (m, 1H), 1.55 (d, J=1.0 Hz, 6H), 1.43-1.39 (m, 1H), 1.33 (s, 9H). m/z (ES$^+$) (M+H)$^+$ 427.4; $t_R$=2.18 min. HPLC Method 1.

Example 92: (S)-2-(3-aminopiperidin-1-yl)-4-((3,5-bis(2-fluoropropan-2-yl)phenyl)amino)pyrimidine-5-carboxamide Step 92-1: N,N-dibenzyl-3,5-bis(2-fluoropropan-2-yl)aniline. 2,2'-(5-(Dibenzylamino)-1,3-phenylene)bis(propan-2-ol) (0.500 g, 1.28 mmol) was added to a pre-dried flask equipped with a magnetic stirrer bar and septum after which the flask was flushed with N$_2$ for 20 min. Anhydrous DCM (20 mL) was added and the solution cooled to 0° C. DAST (0.92 mL, 6.96 mmol) was added drop-wise and the reaction mixture was stirred for 1 h before the cooling bath was removed and the mixture was allowed to stir at RT overnight. A saturated solution of NaHCO$_3$ (aq, 10 mL) was added drop-wise, the organic layer was separated and the aqueous layer twice extracted with further DCM (2×20 mL). The combined organic layers were dried over MgSO$_4$, filtered and concentrated under reduced pressure to give the crude product (0.516 g), which consisted of a 7:3 mixture of the title compound and N,N-dibenzyl-3-(2-fluoropropan-2-yl)-5-(prop-1-en-2-yl)aniline by LCMS analysis. The mixture was used in the next step without further purification to the instability of the title compound on silica.

Step 92-2: 3,5-bis(2-fluoropropan-2-yl)aniline. Prepared using an analogous method to step 50-3, using the mixture from step 92-1 (0.516 g), Pd(OH)$_2$, (0.500 g, 10-20% Pd basis), DCM (2.0 mL) MeOH (10.0 mL) and H$_2$ (1 atmosphere). The crude product was purified by flash column chromatography on silica (7:1 hexane: EtOAc, followed by 6:1 and 5:1) to give the title compound as a colourless viscous oil (0.105 g, 27%). $^1$H NMR (400 MHz, CDCl$_3$) δ 6.74 (t, J=1.6 Hz, 1H), 6.64 (d, J=1.6 Hz, 2H), 3.89-3.58 (br s, 2H), 1.66 (d, J=22.0 Hz, 12H). $^{13}$C NMR (101 MHz, CDCl$_3$) δ 147.5, 147.3, 146.4, 109.8-109.6 (m), 96.0 (d, J=68.7 Hz), 29.4 (d, J=26.3 Hz).

Step 92-3: (S)-2-(3-aminopiperidin-1-yl)-4-((3,5-bis(2-fluoropropan-2-yl)phenyl)amino)pyrimidine-5-carboxamide. 3,5-bis(2-fluoropropan-2-yl)aniline (0.056 g, 0.26 mmol), 2,4-dichloropyrimidine-5-carboxamide (0.051 g, 0.26 mmol), triethylamine (0.07 mL, 0.50 mmol) were dissolved in anhydrous dioxane (5.0 mL) and DMF (1.0 mL). The mixture was heated at 50° C. for 1.5 h and left to cool to RT. (S)-Piperidin-3-amine (0.046 g, 0.26 mmol) and triethylamine (0.06 mL, 0.50 mmol) were added and the reaction mixture was heated at 50° C. overnight. The reaction mixture was diluted with EtOAc (10 mL) and washed with water (2×10 mL). The organic phase was dried over MgSO$_4$, filtered and concentrated under reduced pressure to give the crude product, which was triturated with hexane (20 mL) whereupon a white powder precipitated. The solid was filtered and dried to give the title compound as a white solid (0.060 g, 53%). $^1$H NMR (300 MHz, CD$_3$OD) δ 8.53 (s, 1H), 7.71 (s, 2H), 7.07 (s, 1H), 4.65 (app d, J=13.2 Hz, 1H), 4.52 (app d, J=13.2 Hz, 1H), 3.13 (app t, J=12.9 Hz, 1H), 2.96 (app t, J=12.0 Hz, 1H), 2.89-2.76 (m, 1H), 2.10-1.95 (m, 1H), 1.89-1.75 (m, 1H), 1.68 (d, J=21.9 Hz, 12H), 1.60-1.36 (m, 2H). LCMS: m/z (ES+) (M+H)$^+$ 433.4; t$_R$=2.36 min. HPLC Method 3 (Acid).

Example 93: (S)-2-(3-aminopiperidin-1-yl)-4-((3,5-bis(2-methoxypropan-2-yl)phenyl)amino)pyrimidine-5-carboxamide Step 93-1: Dimethyl 5-(dibenzylamino)isophthalate. Prepared by an analogous method to step 50-1, using dimethyl 5-aminoisophthalate (5.00 g, 23.90 mmol), potassium carbonate (9.89 g, 71.67 mmol), benzyl bromide (8.53 mL, 71.72 mmol) and MeCN (80 mL). The crude product was purified by flash column chromatography on silica (5:1 hexane: EtOAc) to give the title compound as a light-yellow solid (7.54 g, 81%). $^1$H NMR (400 MHz, CDCl$_3$) δ 8.01 (t, J=1.2 Hz, 1H), 7.64 (d, J=1.2 Hz, 2H), 7.34 (app t, J=7.6 Hz, 4H), 7.31-7.21 (m, 6H), 4.71 (s, 4H), 3.87 (s, 6H). LCMS: m/z (ES+) (M+H)$^+$ 390.0; t$_R$=2.88 min. HPLC Method 3 (Acid).

Step 93-2: 2,2'-(5-(dibenzylamino)-1,3-phenylene)bis(propan-2-ol). Dimethyl 5-(dibenzylamino)isophthalate (1.0 g, 2.57 mmol) was added to a pre-dried flask equipped with a magnetic stirrer bar and a septum. The flask was flushed with N$_2$ for 20 min, anhydrous THF (20 mL) added and the solution cooled to 0° C. A solution of MeMgCl (3M in THF, 2.60 mL, 7.80 mmol) was added drop-wise with stirring. Upon completion of addition, the cooling bath was removed and the reaction mixture was allowed to at RT overnight. TLC-analysis indicated incomplete reaction and so a further portion of MeMgCl (3M in THF, 2.00 mL, 6.00 mmol) was added drop-wise at 0° C. The cooling bath was removed and the reaction mixture stirred at RT for a further 2 h. The reaction mixture was diluted with EtOAc (40 mL), washed sequentially with water (5×15 mL) and brine (15 mL). The organic phase was dried over MgSO$_4$, filtered and concentrated under reduced pressure to give the crude product, which was purified by flash column chromatography on silica (5:3 hexane: EtOAc followed by EtOAc) to give the title compound as a light-yellow solid (0.738 g, 74%). $^1$H NMR (400 MHz, CDCl$_3$) δ 7.39-7.22 (m, 10H), 6.99 (t, J=1.2 Hz, 1H), 6.83 (d, J=1.2 Hz, 2H), 4.70 (s, 4H), 1.52 (s, 12H). LCMS: m/z (ES+) (M+H)$^+$ 390.0; t$_R$=2.77 min. HPLC Method 3 (Acid).

Step 93-3: N,N-dibenzyl-3,5-bis(2-methoxypropan-2-yl)aniline. Prepared by an analogous method to step 75-2, using 2,2'-(5-(dibenzylamino)-1,3-phenylene)bis(propan-2-ol) (0.500 g, 1.28 mmol), sodium hydride (60% dispersion in mineral oil, 0.154 g, 3.85 mmol), anhydrous DMF (5.0 mL) and methyl iodide (0.24 mL, 3.86 mmol). The crude product was purified by flash column chromatography on silica (5:1 hexane: EtOAc) to give the title compound as a colourless oil (0.189 g, 35%), $^1$H NMR (400 MHz, CDCl$_3$) δ 7.38-7.30 (m, 8H), 7.30-7.24 (m, 2H), 6.80-7.78 (m, 1H), 6.78-6.76 (m, 2H), 4.70 (s, 4H), 2.99 (s, 6H), 1.48 (s, 12H). LCMS: m/z (ES+) (M+H)$^+$ 418.1; t$_R$=3.06 min. HPLC Method 3 (Acid). Also isolated was 2-(3-(dibenzylamino)-5-(2-methoxypropan-2-yl)phenyl)propan-2-ol as a colourless oil (0.186 g, 36%). $^1$H NMR (400 MHz, CDCl$_3$) δ 7.38-7.30 (m, 8H), 7.30-7.24 (m, 2H), 6.86 (app d, J=1.6 Hz, 2H), 6.75 (app t, J=1.6 Hz, 1H), 4.70 (s, 4H), 2.97 (s, 3H), 1.85-1.74 (br s, 1H), 1.53 (s, 6H), 1.47 (s, 6H). LCMS: m/z (ES+) (M+H)$^+$ 404.1; t$_R$=2.81 min. HPLC Method 3 (Acid).

Step 93-4: 3,5-bis(2-methoxypropan-2-yl)aniline. Prepared by an analogous method to step 50-2, using N,N-dibenzyl-3,5-bis(2-methoxypropan-2-yl)aniline (0.209 g, 0.50 mmol), Pd(OH)$_2$, (0.25 g, 10-20% Pd basis), DCM (2.0 mL) MeOH (5.0 mL) and H2 (1 atmosphere) to give the title compound without the need for further purification (0.118 g, quantitative). $^1$H NMR (400 MHz, CDCl$_3$) δ 6.84 (t, J=1.2 Hz, 1H), 6.64 (d, J=1.2 Hz, 2H), 3.72-3.58 (br s, 2H), 3.07 (s, 6H), 1.50 (s, 12H). LCMS: m/z (ES+) (M+H)$^+$ 238.1; t$_R$=2.09 min. HPLC Method 3 (Acid).

Step 93-5: (S)-2-(3-aminopiperidin-1-yl)-4-((3,5-bis(2-methoxypropan-2-yl)phenyl)amino)pyrimidine-5-carboxamide. 3,5-Bis(2-methoxypropan-2-yl)aniline (0.051 g, 0.21 mmol), 2,4-dichloropyrimidine-5-carboxamide (0.041 g, 0.21 mmol), triethylamine (0.06 mL, 0.43 mmol) were dissolved in anhydrous dioxane (5.0 mL) and DMF (1.0 mL). The mixture was heated at 50° C. for 2.5 h and left to cool to RT. (S)-Piperidin-3-amine (0.037 g, 0.21 mmol) and triethylamine (0.06 mL, 0.43 mmol) were added and the reaction mixture was heated at 50° C. overnight. The reaction mixture was diluted with EtOAc (5 mL) and hexane (25 mL), filtered and the filtrate washed with a saturated solution of NaHCO$_3$ (20 mL). The organic phase was dried over MgSO$_4$, filtered and concentrated under reduced pressure to give the crude product, which was dissolved in EtOAc (2.5 mL). The solution was triturated with hexane (20 mL) whereupon a white powder precipitated. The solid was filtered and dried to give the title compound as a white solid (0.020 g, 20%). $^1$H NMR (400 MHz, CD$_3$OD) δ 8.58 (s, 1H), 7.71 (s, 2H), 7.16 (s, 1H), 4.63 (app d, J=12.0 Hz, 1H), 4.37 (app d, J=13.2 Hz, 1H), 3.54-3.38 (m, 2H), 3.31-3.24 (m, 1H), 3.11 (s, 6H), 2.21-2.12 (m, 1H), 1.91-1.82 (m, 1H), 1.79-1.61 (m, 2H), 1.55 (app d, J=2.0 Hz, 12H). LCMS: m/z (ES+) (M+H)$^+$ 457.0; t$_R$=2.24 min. HPLC Method 3 (Acid).

Example 94: (S)-2-(3-aminopiperidin-1-yl)-4-((3-(2-hydroxypropan-2-yl)-5-(2-methoxypropan-2-yl)phenyl)amino)pyrimidine-5-carboxamide Step 94-1: 2-(3-amino-5-(2-methoxypropan-2-yl)phenyl)propan-2-ol. A solution of 2-(3-(dibenzylamino)-5-(2-methoxypropan-2-yl)phenyl)propan-2-ol (isolated in step 93-3, 0.14 g, 0.347 mmol) in methanol (10 mL) was hydrogenated in the H-Cube (10% Pd/C, 30×4 mm, Full hydrogen, 40° C., 1 mL/min) then concentrated under vacuum to afford 2-(3-amino-5-(2-methoxypropan-2-yl)phenyl)propan-2-ol. (0.05 g, 50%). m/z (M+H)$^+$ (ES$^+$) 224.3; t$_R$=0.98 min. HPLC Method 2.

Step 93-2: (S)-2-(3-aminopiperidin-1-yl)-4-((3-(2-hydroxypropan-2-yl)-5-(2-methoxypropan-2-yl)phenyl)amino)pyrimidine-5-carboxamide. Prepared by an analogous method to example 3, using 2-(3-amino-5-(2-methoxypropan-2-yl)phenyl)propan-2-ol. (0.038 g, 33%); $^1$H NMR (500 MHz, DMSO-d6, 90° C.) δ 11.38 (s, 1H), 8.59 (s, 1H), 7.63-7.61 (m, 1H), 7.59 (t, 1H, J=1.8 Hz), 7.26 (br s, 1H), 7.19 (t, 1H, J=1.5 Hz), 4.56-4.50 (m, 1H), 4.44 (dt, 1H, J=13.1, 4.2 Hz), 3.12-3.05 (m, 1H), 3.04 (s, 3H), 2.85 (dd, 1H, J=12.6, 9.2 Hz), 2.77-2.70 (m, 1H), 1.94-1.87 (m, 1H), 1.77-1.69 (m, 1H), 1.50-1.40 (m, 13H), 1.36-1.24 (m, 1H). m/z (M+H)$^+$ (ES$^+$) 443.3; $t_R$=1.15 min. HPLC Method 2.

Example 95: (S)-2-(3-aminopiperidin-1-yl)-4-((3-(2-methoxypropan-2-yl)-5-(trifluoromethyl)phenyl)amino)pyrimidine-5-carboxamide Step 95-1: 3-(2-methoxypropan-2-yl)-5-(trifluoromethyl)aniline. N,N-dibenzyl-3-(2-methoxypropan-2-yl)-5-(trifluoromethyl)aniline (J. Org. Chem., Vol. 56, No. 13, 1991) was dissolved in ethanol and degassed before Pd/C was added. The mixture was stirred at RT under a hydrogen atmosphere overnight (16 h). The suspension was filtered through Celite. The filtrate was concentrated to dryness to give a pale brown solid (53 mg, 83%), m/z (ES$^+$) (M+H)$^+$ 233.9; $t_R$=2.79 min. HPLC Method 1.

Step 95-2: (S)-2-(3-aminopiperidin-1-yl)-4-((3-(2-methoxypropan-2-yl)-5-(trifluoromethyl)phenyl) amino)pyrimidine-5-carboxamide. Prepared using an analogous method to example 3 with 3-(2-methoxypropan-2-yl)-5-(trifluoromethyl)aniline (Step 1: CH$_3$CN, DIPEA, 70° C., 3 h) to give the 2-chloro-4-(3-(2-methoxypropan-2-yl)-5-(trifluoromethyl)phenylamino)pyrimidine-5-carbo-xamide as a pale yellow solid, m/z (ES$^+$) (M+H)$^+$ 389.1/391.1; $t_R$=2.96 min. HPLC Method 1. The unprotected (S)-3-aminopiperidine dihydrochloride was used to avoid Boc deprotection stage (Step 2: CH$_3$CN DIPEA, RT, 16 h) to give the title compound as a yellow solid which was purified by chromatography on silica (5 g) using a gradient DCM/THF (0, 50, 100%) then DCM/1N NH$_3$ in MeOH (5 mg, 10%). $^1$H NMR (300 MHz, MeOD) δ 8.57 (s, 1H), 8.00 (br s, 2H), 7.32 (s, 1H), 4.68 (br d, J=11.6 Hz, 1H), 4.53 (br d, J=12.3 Hz, 1H), 3.12 (d, J=1 Hz, 3H), 2.98-2.90 (m, 1H), 2.88-2.80 (m, 1H), 2.07-2.00 (m, 1H), 1.85-1.77 (m, 1H), 1.62-1.51 (m, 1H), 1.56 (d, J=1.7 Hz, 6H). 1.50-1.33 (m, 1H), 1.31-1.27 (m, 1H). m/z (ES$^+$) (M+H)$^+$ 453.1; $t_R$=2.28 min. HPLC Method 1.

Example 96: (S)-2-(3-aminopiperidin-1-yl)-4-((3-(2-fluoropropan-2-yl)-5-(trifluoromethyl)phenyl)amino)-yrimidine-5-carboxamide Step 96-1: N,N-dibenzyl-3-(2-fluoropropan-2-yl)-5-(trifluoromethyl)aniline. To a stirred solution of 2-(3-(dibenzylamino)-5-(trifluoromethyl)phenyl)propan-2-ol (201 mg, 0.5 mmol) dissolved in DCM (24 mL), cooled to 0° C. was added dropwise DAST (0.65 mmol, 86 uL) in DCM (10 mL). The reaction was allowed to warm to RT and stirred for 1 h. The reaction was diluted with saturated aqueous NaHCO$_3$ (20 mL) and extracted with DCM (2×25 mL). The combined organic layers were dried over sodium sulfate, filtered and concentrated under vacuum. The crude was purified on silica (5 g), with a slow gradient (PET/DCM (2%, 4%, 10%) to isolate N,N-dibenzyl-3-(2-fluoropropan-2-yl)-5-(trifluoromethyl)aniline as a colourless oil (30 mg); and the by-product N,N-dibenzyl-3-(prop-1-en-2-yl)-5-(trifluoromethyl)aniline also a colourless oil (43 mg).

N,N-dibenzyl-3-(prop-1-en-2-yl)-5-(trifluoromethyl)aniline: $^1$H NMR (300 MHz, CDCl$_3$) δ 7.40-7.34 (m, 4H), 7.33-7.26 (m, 6H), 7.06 (s, 1H), 6.97 (s, 1H), 6.93 (s, 1H), 5.25 (s, 1H), 5.07 (s, 1H), 4.72 (s, 4H), 2.06 (s, 3H). m/z (ES$^+$) (M+H)$^+$ 382.2; $t_R$=3.47 min. HPLC Method 1.

N,N-dibenzyl-3-(2-fluoropropan-2-yl)-5-(trifluoromethyl)aniline $^1$H NMR (300 MHz, CDCl$_3$) δ 7.42-7.37 (m, 4H), 7.35-7.29 (m, 6H), 7.00 (s, 1H), 6.98 (s, 2H), 4.74 (s, 4H), 1.66 (s, 3H), 1.61 (s, 3H). m/z (ES$^+$) (M+H)$^+$ 401.9; $t_R$=3.38 min. HPLC Method 1.

Step 96-2: 3-(2-fluoropropan-2-yl)-5-(trifluoromethyl)aniline

To a solution of N,N-dibenzyl-3-(2-fluoropropan-2-yl)-5-(trifluoromethyl)aniline (130 mg, 0.325 mmol) in MeOH (25 mL), Pd/C was added and the suspension was degassed using a cycle of vacuum/N$_2$ flush (2×) and finally placed under an H$_2$ atmosphere. The suspension was stirred at RT for 16 h. The crude was filtered through a celite pad and evaporated to dryness to give the product as a yellow oil (43 mg) containing 40% of de-fluorinated compound not present before hydrogenation. This material was used without further purification.

Step 96-3: (S)-2-(3-aminopiperidin-1-yl)-4-((3-(2-fluoropropan-2-yl)-5-(trifluoromethyl)phenyl)ami-no)-yrimidine-5-carboxamide. Prepared using an analogous method to example 3 with 3-(2-fluoropropan-2-yl)-5-(trifluoromethyl) aniline (Step 1: CH$_3$CN, DIPEA, 65° C., 16 h) to give the 2-chloro-4-(3-(2-fluoropropan-2-yl)-5-(trifluoromethyl) phenylamino)pyrimidine-5-carboxamide, which was further reacted with the (S)-3-aminopiperidine dihydrochloride (Step 2: CH$_3$CN DIPEA, RT, 64 h) to give a crude compound which was purified by preparative HPLC (phenomenex 20 mm×100 mm C18 5 m column and using a slow gradient Water/MECN (5 to 40% over 10 min) to give the title compound. $^1$H NMR (300 MHz, MeOD) δ 8.63 (s, 1H), 8.14 (s, 1H), 7.86 (s, 1H), 7.36 (s, 1H), 4.48 (d, J=12.9 Hz, 1H), 4.20-4.13 (m, 1H), 3.71-3.59 (m, 2H), 2.20-2.11 (m, 1H), 1.91-1.82 (m, 1H), 1.82-1.6 (m, 3H), 1.74 (s, 3H), 1.68 (s, 3H). m/z (ES$^+$) (M+H)$^+$ 441.4; $t_R$=3.89 min. HPLC Method 1.

Example 97: (S)-2-(3-aminopiperidin-1-yl)-4-((3-(tert-butyl)-5-isopropylphenyl)amino)pyrimidine-5-carboxamide Step 97-1: N,N-dibenzyl-3-(tert-butyl)-5-(prop-1-en-2-yl)aniline. To a stirred solution of 2-(3-(tert-butyl)-5-(dibenzylamino)phenyl)propan-2-ol (140 mg, 0.36 mmol) in DCM (20 mL) cooled to 0° C. was added dropwise DAST (0.47 mmol, 62 uL dissolved in DCM (10 mL). After 30 min at 0° C., the reaction was finished but there are 2 products (the target and dehydrated by-product isoprene). The reaction was diluted with saturated aqueous NaHCO$_3$ (20 mL) and extracted with EtOAc (2×25 mL). The combined organic layers were dried over sodium sulfate, filtered and concentrated under vacuum. The crude product was purified by chromatography on silica (50 g) using a multigradient system (0-100% PET/DCM/EtOAc) to afford the title compound (50 mg). $^1$H NMR (300 MHz, CDCl$_3$) δ 7.39-7.26 (m, 10H), 6.92 (s, 1H), 6.78 (s, 1H), 6.76 (s, 1H), 5.26 (s, 1H), 5.03 (s, 1H), 4.71 (s, 4H), 2.11 (s, 3H), 1.27 (s, 9H). m/z (ES$^+$) (M+H)$^+$ 370.1; $t_R$=3.69 min. HPLC Method 1.

Step 97-2: 3-(tert-butyl)-5-isopropylaniline. Prepared by an analogous method to step 54-2 (MeOH, Pd/C, RT, 2 h).

The crude was used in step 97-3 without purification. m/z (ES⁺) (M+H)⁺ 192.0; $t_R$=2.45 min. HPLC Method 1

Step 97-3: (S)-2-(3-aminopiperidin-1-yl)-4-((3-(tert-butyl)-5-isopropylphenyl)amino)pyrimidine-5-carboxamide. Prepared using an analogous method to example 3 with 3-(tert-butyl)-5-isopropylaniline and (S)-3-NBoc-aminopiperidine dihydrochloride (Step 1: CH₃CN, DIPEA, 75° C., 2 h; Step 2: CH₃CN DIPEA, RT, 64 h) to give the (R)-tert-butyl 1-(4-(3-tert-butyl-5-isopropylphenylamino)-5-carbamoylpyrimidin-2-yl)piperidin-3-ylcarbamate which was purified by chromatography on silica (5 g) using an eluent DCM/THF (5%, 10%). Rf (10% THF/DCM)=0.25 to give a pale yellow solid (125 mg, 82%). Boc deprotection (Step 3: HCl in dioxane (4M), RT) gives the hydrochloride salt of the title compound as an off-white solid (114 mg, 100%). ¹H NMR (300 MHz, MeOD) δ 8.54 (s, 1H), 7.42 (s, 1H), 7.31 (s, 1H), 7.20 (s, 1H), 4.28 (br d, J=13.5 Hz, 1H), 4.10 (br s, 1H), 3.84-3.75 (m, 1H), 3.70-3.59 (m, 1H), 3.51 (br s, 1H), 2.95 (hept., J=6.9 Hz, 1H), 2.23-2.16 (m, 1H), 1.98-1.90 (m, 1H), 1.88-1.74 (m, 2H), 1.35 (s, 9H), 1.28 (d, J=6.8 Hz, 6H). m/z (ES⁺) (M+H)⁺ 411.4; $t_R$=2.36 min. HPLC Method 1.

Example 98: (S)-2-(3-aminopiperidin-1-yl)-4-((4-fluoro-3,5-diisopropylphenyl)amino)pyrimidine-5-carboxamide Step 98-1: 2-fluoro-5-nitro-1,3-di(prop-1-en-2-yl)benzene. Prepared by an analogous method to step 80-1, heating at 100° C. for 1.5 h, using 1,3-dibromo-2-fluoro-5-nitrobenzene (0.200 g, 0.67 mmol), 4,4,5,5-tetramethyl-2-(prop-1-en-2-yl)-1,3,2-dioxaborolane (0.32 mL, 1.70 mmol), dioxane (12.0 mL), water (1.2 mL), potassium carbonate (0.556 g, 4.03 mmol) and Pd(PPh₃)₂Cl₂ (0.048 g, 0.07 mmol). The crude product was purified by flash column chromatography on silica (hexane) to give the title compound as a colourless oil (0.140 g, 95%). ¹H NMR (400 MHz, CDCl₃) δ 8.10 (d, J=8.0 Hz, 2H), 5.36 (app s, 2H), 5.30 (app s, 2H), 2.17 (s, 6H).

Step 98-2: 4-fluoro-3,5-diisopropylaniline. Prepared by an analogous method to step 51-2, using 2-fluoro-5-nitro-1,3-di(prop-1-en-2-yl)benzene (0.165 g, 0.73 mmol), 10% Pd/C (0.078 g, 10 mol %), MeOH (5.0 mL) and DCM (1.0 mL) to give the title compound as a colourless oil (0.065 g, 98%). ¹H NMR (400 MHz, CDCl₃) δ 6.40 (d, J=6.0 Hz, 2H), 3.51-3.39 (br s, 2H), 3.17 (sept, J=6.8 Hz, 2H), 1.22 (d, J=6.8 Hz, 12H). LCMS: m/z (ES+) (M+H)⁺ 196.2; $t_R$=2.29 min. HPLC Method 3 (Acid).

Step 98-3: (S)-2-(3-aminopiperidin-1-yl)-4-((4-fluoro-3,5-diisopropylphenyl)amino)pyrimidine-5-carboxamide. 4-Fluoro-3,5-diisopropylaniline (0.105 g, 0.54 mmol), 2,4-dichloropyrimidine-5-carboxamide (0.124 g, 0.65 mmol), triethylamine (0.18 mL, 1.29 mmol) were dissolved in anhydrous dioxane (4.0 mL). The mixture was heated at 50° C. for 6 h and left to cool to RT. tert-Butyl (S)-piperidin-3-ylcarbamate (0.108 g, 0.54 mmol) and triethylamine (0.18 mL, 1.29 mmol) were added and the reaction mixture was heated at 50° C. for 2 h. The reaction mixture was diluted with EtOAc (30 mL) and washed with water (5×20 mL). The organic phase was dried over MgSO₄, filtered and concentrated under reduced pressure to give the crude product, which was purified by flash column chromatography on silica (1:2 hexane: EtOAc) to give the product from two displacements (0.164 g). The intermediate was dissolved in dioxane (2.50 mL) and 4M HCl in dioxane (2.50 mL) was added drop-wise. The reaction mixture was left to stir at RT for 4 h and then hexane (20 mL) was added. The resulting suspension was filtered and the solid dried to give the hydrochloride salt of the title compound as a white powder (0.82 g, 34%). ¹H NMR (400 MHz, CD₃OD) δ 8.53 (s, 1H), 7.35 (d, J=6.4 Hz, 2H), 4.28 (dd, J=13.6, 3.6 Hz, 1H), 4.18-4.00 (m, 1H), 3.83-3.70 (m, 1H), 3.67-3.56 (m, 1H), 3.55-3.46 (m, 1H), 3.28 (sept, J=6.8 Hz, 2H), 2.24-2.13 (m, 1H), 1.99-1.90 (m, 1H), 1.90-1.72 (m, 2H), 1.27 (d, J=6.8 Hz, 12H). LCMS: m/z (ES+) (M+H)⁺ 415.4; $t_R$=2.88 min. HPLC Method 3 (Acid).

Example 99: (S)-2-(3-aminopiperidin-1-yl)-4-((2-isopropyl-6-(piperidin-1-yl)pyridin-4-yl)amino)pyrimidine-5-carboxamide Step 99-1: 2-chloro-6-(piperidin-1-yl)pyridin-4-amine. A mixture of 2,6-dichloro-4-amine (500 mg, 3.07 mmol) in piperidine (2.42 mL, 27.60 mmol) was stirred in a pressure vessel at 140° C. for 4 h. The mixture was partitioned between EtOAc and water and the organic phase was washed with brine (3×30 mL). The organic phase was dried over MgSO₄, filtered, concentrated under reduced pressure and purified by flash chromatography [Hexane:EtOAc (4:1)] affording the title product as an off-white solid (500 mg, 77%). ¹H NMR (400 MHz, CDCl₃) δ 5.94 (s, 1H), 5.69 (s, 1H), 3.99 (br. s, 2H), 3.49-3.40 (m, 4H), 1.69-1.51 (m, 6H); m/z (ES⁺) (M+H)⁺ 212.3; $t_R$=2.25 min. HPLC Method 3 (Acid).

Step 99-2: 2-(piperidin-1-yl)-6-(prop-1-en-2-yl)pyridin-4-amine. A mixture of 2-chloro-6-(piperidin-1-yl)pyridin-4-amine (250 mg, 1.18 mmol), 4,4,5,5-tetramethyl-2-(prop-1-en-2-yl)-1,3,2-dioxaborolane (0.33 mL, 1.78 mmol) and K₂CO₃ (489 mg, 3.54 mmol) in dioxane:H₂O (4:1, 20 mL) was degassed with a N₂ flow for 20 min. Bis(triphenylphosphine)palladium(II) dichloride (41 mg, 0.06 mmol) was added and the reaction mixture was stirred at 100° C. for 2 days. The resulting mixture was concentrated under reduced pressure and the residue dissolved in EtOAc (ca. 30 mL) and washed with brine (3×20 mL). The organic phase was dried over MgSO₄, filtered, concentrated under reduced pressure. The residue was directly taken into the next step without further purification.

Step 99-3: 2-isopropyl-6-(piperidin-1-yl)pyridin-4-amine. A mixture of 2-(piperidin-1-yl)-6-(prop-1-en-2-yl) pyridin-4-amine (151 mg, 0.70 mmol) and palladium on carbon (10 wt. %, 100 mg, 0.07 mmol) in DCM:MeOH (1:1, 10 mL) was stirred at RT under H2 atmosphere (1 atm) for 3 h. The reaction mixture was flushed with Ar, filtered through Celite® and washed with MeOH (ca. 20 mL). The filtrate was concentrated under reduced pressure and purified by flash chromatography [Toluene:EtOAc (1:1)] affording the title product as a colourless oil (61 mg, 44%). ¹H NMR (400 MHz, CDCl₃) δ 5.87 (d, J=1.7 Hz, 1H), 5.73 (d, J=1.7 Hz, 1H), 3.83 (br. s, 2H), 3.53-3.39 (m, 4H), 2.76 (sept, J=6.9 Hz, 1H), 1.70-1.52 (m, 6H), 1.22 (d, J=6.9 Hz, 6H); m/z (ES⁺) (M+H)⁺ 220.3; $t_R$=1.80 min. HPLC Method 3 (Acid).

Step 99-4: tert-butyl (S)-(1-(5-carbamoyl-4-((2-isopropyl-6-(piperidin-1-yl)pyridin-4-yl)amino)pyrimidin-2-yl)piperidin-3-yl)carbamate. A mixture of 2,4-dichloropyrimidine-5-carboxamide (80 mg, 0.42 mmol), 2-isopropyl-6-(piperidin-1-yl)pyridin-4-amine (61 mg, 0.28 mmol) and DIPEA (0.06 mL, 0.34 mmol) in 1,4-dioxane (4.0 mL) was stirred at 100° C. for 4 h. The resulting mixture was allowed to reach RT, concentrated under reduced pressure, dry-loaded into a column and purified by flash chromatography [Hexane:EtOAc (1:1)] affording a white solid that was re-dissolved in 1,4-dioxane (4.0 mL). (S)-Tert-butyl piperidin-3-ylcarbamate (40 mg, 0.20 mmol) and DIPEA (0.04 mL, 0.22 mmol) were added to the mixture and stirred at 50° C. overnight. The resulting mixture was allowed to reach RT, concentrated under reduced pressure, dry-loaded into a column and purified by flash chromatography [gradient Hexane:EtOAc (2:3-3:7)] affording the title product as a white solid (80 mg, 75%). The compound was directly taken into the next step.

Step 99-5: (S)-2-(3-aminopiperidin-1-yl)-4-((2-isopropyl-6-(piperidin-1-yl)pyridin-4-yl)amino)pyrimidine-5-carboxamide. tert-Butyl (S)-(1-(5-carbamoyl-4-((2-isopropyl-6-(piperidin-1-yl)pyridin-4-yl)amino)pyrimidin-2-yl)piperidin-3-yl)carbamate (80 mg, 0.15 mmol) was suspended into dioxane:Et$_2$O (1:1, 4 mL) and 4N HCl in dioxane (2 mL) was added. The suspension was stirred at RT overnight. Et$_2$O was added (ca. 4 mL) and the mother liquor was removed. The resulting solid was dried under reduced pressure giving the hydrochloride salt of the title product as a white solid (30 mg, 46%). $^1$H NMR (400 MHz, MeOD) δ 8.76 (s, 1H), 7.58 (s, 1H), 6.98 (s, 1H), 4.49-4.40 (m, 1H), 4.25-4.07 (m, 1H), 3.98-3.85 (m, 1H), 3.82-3.68 (m, 5H), 3.62-3.52 (m, 1H), 3.30-3.22 (m, 1H), 2.27-2.19 (m, 1H), 2.05-1.96 (m, 1H), 1.95-1.74 (s, 8H), 1.37 (d, J=6.8 Hz, 6H); m/z (ES$^-$) (M−H)$^-$ 437.3; t$_R$=2.00 min. HPLC Method 3 (Acid).

Example 100: (S)-2-(3-aminopiperidin-1-yl)-4-((6-fluoro-2',3',4',5'-tetrahydro-[1,1'-biphenyl]-3-yl)amino)pyrimidine-5-carboxamide Step 100-1: 6-fluoro-2',3',4',5'-tetrahydro-[1,1'-biphenyl]-3-amine. Prepared by an analogous method to step 80-1, heated at 100° C. for 1 h, using 2-bromo-1-fluoro-4-nitrobenzene (0.200 g, 1.05 mmol), cyclohexenylboronic acid (0.136 g, 1.08 mmol), dioxane (12.0 mL), water (3.0 mL), potassium carbonate (0.436 g, 3.15 mmol) and Pd(PPh$_3$)$_2$Cl$_2$ (0.048 g, 0.11 mmol). The crude product was purified by flash column chromatography on silica (3:1 hexane: EtOAc) to give the title compound as a colourless oil. $^1$H NMR (400 MHz, CDCl$_3$) δ 6.80 (dd, J=14, 11.6 Hz, 1H), 6.54 (dd, J=8.4, 4.0 Hz, 1H), 6.48 (app dt, J=11.2, 4.0 Hz, 1H), 5.93-5.80 (m, 1H), 3.65-3.35 (br s, 2H), 2.39-2.27 (m, 2H), 2.24-2.13 (m, 2H), 1.79-1.56 (m, 4H). LCMS: m/z (ES+) (M+H)$^+$ 192.1; t$_R$=2.08 min. HPLC Method 3 (Acid).

Step 100-2: (S)-2-(3-aminopiperidin-1-yl)-4-((6-fluoro-2',3',4',5'-tetrahydro-[1,1'-biphenyl]-3-yl)amino)pyrimidine-5-carboxamide. 6-Fluoro-2',3',4',5'-tetrahydro-[1,1'-biphenyl]-3-amine (0.103 g, 0.54 mmol), 2,4-dichloropyrimidine-5-carboxamide (0.103 g, 0.54 mmol), triethylamine (0.16 mL, 1.15 mmol) were dissolved in anhydrous dioxane (8.0 mL) and DMF (2.0 mL). The mixture was heated at 50° C. for 2.5 h and left to cool to RT. tert-Butyl (S)-piperidin-3-ylcarbamate (0.108 g, 0.54 mmol) and triethylamine (0.16 mL, 1.15 mmol) were added and the reaction mixture was heated at 50° C. overnight. The reaction mixture was diluted with EtOAc (30 mL) and washed with water (5×20 mL). The organic phase was dried over MgSO$_4$, filtered and concentrated under reduced pressure to give the crude product, which was dissolved in Et$_2$O (10 mL) and 4M HCl in dioxane (5.0 mL) was added drop-wise. The reaction mixture was left to stir at RT for 48 h and then hexane (20 mL) was added. The resulting suspension was filtered and the solid dried to give the hydrochloride salt of the title compound as a white powder (0.194 g, 80%). $^1$H NMR (400 MHz, DMSO-d6) δ 7.73 (s, 1H), 6.79-6.67 (m, 1H), 6.66-6.53 (m, 1H), 6.35 (dd, J=10.4, 9.2 Hz, 1H), 5.17-5.12 (m, 1H), 3.51 (dd, J=13.6, 3.2 Hz, 1H), 2.91 (dd, J=13.6, 8.4 Hz, 1H), 2.86-2.83 (m, 1H), 2.83-2.65 (m, 2H), 1.61-1.52 (m, 2H), 1.46-1.34 (m, 3H), 1.21-1.01 (m, 1H), 1.09-0.94 (4H), 0.94-0.85 (m, 2H). LCMS: m/z (ES+) (M+H)$^+$ 411.0; t$_R$=2.09 min. HPLC Method 3 (Acid).

Example 101: (S)-2-(3-aminopiperidin-1-yl)-4-((3-cyclohexyl-4-fluorophenyl)amino)pyrimidine-5-carboxamide Step 101-1: 3-cyclohexyl-4-fluoroaniline. Prepared by an analogous method to step 51-2, using 6-fluoro-2',3',4',5'-tetrahydro-[1,1'-biphenyl]-3-amine (0.100 g, 0.58 mmol), 10% Pd/C (0.090 g, 10 mol %), EtOH (3.0 mL) and H$_2$ (1 atmosphere) give the title compound as a colourless oil (0.064 g, 64%). $^1$H NMR (400 MHz, CDCl$_3$) δ 6.79 (dd, J=12.8, 11.6 Hz, 1H), 6.54 (dd, J=8.0, 3.6 Hz, 1H), 6.48-6.39 (m, 1H), 3.58-3.31 (br s, 2H), 2.87-2.67 (m, 1H), 1.93-1.68 (m, 5H), 1.52-1.13 (m, 5H). LCMS: m/z (ES+) (M+H)+ 194.1; t$_R$=2.18 min. HPLC Method 3 (Acid).

Step 101-2: (S)-2-(3-aminopiperidin-1-yl)-4-((3-cyclohexyl-4-fluorophenyl)amino)pyrimidine-5-carboxamide. 3-Cyclohexyl-4-fluoroaniline (0.072 g, 0.37 mmol), 2,4-dichloropyrimidine-5-carboxamide (0.072 g, 0.37 mmol), triethylamine (0.12 mL, 0.86 mmol) were dissolved in anhydrous dioxane (7.0 mL) and DMF (1.0 mL). The mixture was heated at 50° C. for 2 h and left to cool to RT. tert-Butyl (S)-piperidin-3-ylcarbamate (0.075 g, 0.37 mmol) and triethylamine (0.12 mL, 0.86 mmol) were added and the reaction mixture was heated at 50° C. overnight. The reaction mixture was diluted with EtOAc (30 mL) and washed with water (5×20 mL). The organic phase was dried over MgSO$_4$, filtered and concentrated under reduced pressure to give the crude product, which was dissolved in Et$_2$O (10 mL) and 4M HCl in dioxane (5.0 mL) was added drop-wise. The reaction mixture was left to stir at RT for 48 h and then hexane (20 mL) was added. The resulting suspension was filtered and the solid dried to give the hydrochloride salt of the title compound as a white powder (0.141, 84%). $^1$H NMR (400 MHz, MeOD) δ 8.54 (s, 1H), 7.56-7.37 (m, 2H), 7.14 (app t, J=9.2 Hz, 1H), 4.32 (app d, J=15.2 Hz, 1H), 4.14-3.94 (m, 1H), 3.70 (dd, J=13.6, 8.8 Hz, 1H), 3.64-3.54 (m, 1H), 3.54-3.45 (m, 1H), 2.97-2.84 (m, 1H), 2.26-2.12 (m, 1H), 2.04-1.90 (m, 1H), 1.90-1.71 (m, 7H), 1.54-1.39 (m, 4H), 1.39-1.24 (m, 1H). LCMS: m/z (ES+) (M+H)$^+$ 413.1; t$_R$=2.12 min. HPLC Method 3 (Acid).

Example 102: (S)-2-(3-aminopiperidin-1-yl)-4-((3-(1-cyanocyclopropyl)-5-isopropylphenyl)amino)pyrimidine-5-carboxamide Step 102-1: N,N-dibenzyl-3-bromo-5-chloroaniline. Prepared by an analogous method to step 50-1, using 3-bromo-5-chloroaniline (5.00 g, 24.22 mmol), potassium carbonate (11.71 g, 84.73 mmol), benzyl bromide (10.0 mL, 84.08 mmol) and MeCN (80 mL). The crude product was purified by flash column chromatography on silica (hexane) to give the title compound as a white solid (7.02 g, 75%). $^1$H NMR (400 MHz, CDCl$_3$) δ 7.38 (app t, J=7.6 Hz, 4H), 7.31 (t, J=7.6 Hz, 2H), 7.21 (d, J=7.2 Hz, 4H), 6.85 (app t, J=1.6 Hz, 1H), 6.79 (app t, J=1.6 Hz, 1H), 6.66 (app t, J=1.6 Hz, 1H), 4.62 (s, 4H). LCMS: m/z (ES+) (M+H)$^+$ 387.8; t$_R$=3.21 min. HPLC Method 3 (Acid).

Step 102-2: 1-(3-chloro-5-(dibenzylamino)phenyl)cyclopropane-1-carbonitrile. Prepared by an analogous method to step 51-1, using racemic BINAP (0.063 g, 0.10 mmol), Pd$_2$(dba)$_3$ (0.044 g, 5 mol %), THF (6.0 mL), cyclopropylcarbonitrile (0.11 mL, 1.49 mmol), N,N-dibenzyl-3-bromo-5-chloroaniline (0.359 g, 0.93 mmol), cyclopentylmethyl ether (20 mL) and LiHMDS (1M in THF, 1.39 mL, 1.39 mmol), which was purified by flash column chromatography on silica (8:1 hexane: EtOAc) to give the title compound as a white solid (0.266 g, 77%). $^1$H NMR (400 MHz, CDCl$_3$) δ 7.34 (app t, J=7.6 Hz, 4H), 7.29 (t, J=7.2 Hz, 2H), 7.22 (d, J=6.8 Hz, 4H), 6.63 (app t, J=1.6 Hz, 1H), 6.56-6.53 (m, 2H), 4.65 (s, 4H), 1.63-1.58 (m, 2H), 1.26-1.20 (m, 2H). LCMS: m/z (ES+) (M+H)$^+$ 373.0; t$_R$=3.00 min. HPLC Method 3 (Acid).

Step 102-3: 1-(3-(dibenzylamino)-5-(prop-1-en-2-yl)phenyl)cyclopropane-1-carbonitrile. 1-(3-Chloro-5-(dibenzylamino)phenyl)cyclopropane-1-carbonitrile (0.128 g, 0.34 mmol), 4,4,5,5-tetramethyl-2-(prop-1-en-2-yl)-1,3,2-dioxaborolane (0.13 mL, 0.69 mmol) and potassium carbonate (0.142 g, 1.03 mmol) were dissolved in dioxane (4.6 mL) and water (1.2 mL). The reaction mixture was degassed with N$_2$ for 20 min and (2-dicyclohexylphosphino-2',4',6'-triisopropyl-1,1'-biphenyl)[2-(2'-amino-1,1'-biphenyl)]palladium (II) methanesulfonate (0.028 g, 10 mol %) was added quickly, followed by purging of the flask with N$_2$ for a further 10 min. The reaction mixture was heated to 100° C. for 3.5 h and allowed to cool to RT. The reaction mixture was diluted with EtOAc (40 mL), washed with water (3×20 mL), dried over MgSO$_4$, filtered and concentrated under reduced pressure to give the crude product, which was purified by flash column chromatography on silica (15:1 hexane: EtOAc followed by 3:1) to give the title compound as a light yellow oil (0.053 g, 41%). $^1$H NMR (400 MHz, CDCl$_3$) δ 7.38 (app t, J=6.8 Hz, 4H), 7.34-7.27 (m, 6H), 6.80-6.77 (m, 2H), 6.60 (app t, J=2.0 Hz, 1H), 5.25-5.22 (m, 1H), 5.05 (app pent, J=1.2 Hz, 1H), 4.72 (s, 4H), 2.06 (s, 3H), 1.65-1.60 (m, 2H), 1.31-1.26 (m, 2H). LCMS: m/z (ES+) (M+H)$^+$ 379.0; t$_R$=3.05 min. HPLC Method 3 (Acid).

Step 102-4: 1-(3-amino-5-isopropylphenyl)cyclopropane-1-carbonitrile. Prepared by an analogous method to step 50-3, using 1-(3-(dibenzylamino)-5-(prop-1-en-2-yl)phenyl)cyclopropane-1-carbonitrile (0.060 g, 0.16 mmol), Pd(OH)$_2$, (0.04 g, 10-20% Pd basis), DCM (1.0 mL) MeOH (2.0 mL) and H$_2$ (1 atmosphere). The crude product was purified by flash column chromatography on silica (DCM) to give the title compound as a colourless residue (0.021 g, 66%). $^1$H NMR (400 MHz, CDCl$_3$) δ 6.52-6.50 (m, 1H), 6.48-6.46 (m, 1H), 6.44 (app t, J=2.0 Hz), 3.79-3.59 (br s, 2H), 2.79 (sept, J=6.8 Hz, 1H), 1.68-1.62 (m, 2H), 1.40-1.34 (m, 2H), 1.21 (d, J=6.8 Hz, 6H). LCMS: m/z (ES+) (M+H)$^+$ 201.1; t$_R$=2.32 min. HPLC Method 3 (Acid).

Step 102-5: (S)-2-(3-aminopiperidin-1-yl)-4-((3-(1-cyanocyclopropyl)-5-isopropylphenyl)amino)pyrimidine-5-carboxamide. 1-(3-Amino-5-isopropylphenyl)cyclopropane-1-carbonitrile (0.021 g, 0.10 mmol), 2,4-dichloropyrimidine-5-carboxamide (0.021 g, 0.11 mmol), triethylamine (0.02 mL, 0.14 mmol) were dissolved in anhydrous dioxane (2.0 mL) and DMF (0.5 mL). The mixture was heated at 50° C. for 1.5 h and left to cool to RT. tert-Butyl (S)-piperidin-3-ylcarbamate (0.021 g, 0.10 mmol) and triethylamine (0.02 mL, 0.14 mmol) were added and the reaction mixture was heated at 50° C. overnight. The reaction mixture was diluted with EtOAc (10 mL) and washed with water (5×10 mL). The organic phase was dried over MgSO$_4$, filtered and concentrated under reduced pressure to give the crude product from two displacements, which was purified by flash column chromatography on silica (1:4 hexane: EtOAc). The intermediate was dissolved in Et$_2$O (6 mL) and 4M HCl in dioxane (2.0 mL) was added drop-wise. The reaction mixture was left to stir at RT overnight and then hexane (10 mL) was added. The resulting suspension was filtered and the solid dried to give the hydrochloride salt of the title compound as a white powder (0.010, 22%). $^1$H NMR (400 MHz, CD$_3$OD) δ 8.92 (s, 1H), 8.35-8.14 (m, 1H), 7.64-7.50 (m, 1H), 7.35-7.26 (m, 1H), 4.79 (app d, J=10.0 Hz, 1H), 4.52-4.30 (m, 1H), 4.25-4.08 (m, 1H), 4.07-3.94 (m, 1H), 3.94-3.80 (1H), 2.63-2.46 (m, 1H), 2.43-2.27 (m, 1H), 2.27-2.08 (3H), 1.95-1.82 (m, 2H), 1.62 (d, J=6.8 Hz, 6H). LCMS: m/z (ES+) (M+H)$^+$ 420.0; t$_R$=2.34 min. HPLC Method 3 (Acid).

Example 103: (S)-2-(3-aminopiperidin-1-yl)-4-((3-(tert-butyl)-5-(pyrrolidin-1-ylsulfonyl)phenyl)amino)pyrimidine-5-carboxamide Step 103-1: 3-(tert-butyl)-5-nitrobenzenesulfonyl chloride. To a solution of 1-(tert-butyl)-3-nitrobenzene (179 mg, 1 mmol) in CHCl$_3$ (15 mL) chlorosulfonic acid (167 µL, 2.5 mmol) was added in one portion and the mixture was stirred at reflux for 48 h. Upon complete consumption of the starting material water (15 mL) and DCM (15 mL) were added, the crude was partitioned, the aqueous layer extracted with DCM (2×20 mL) and the combined organic layers washed with brine, dried with MgSO$_4$ and condensed. The crude was purified by flash column chromatography (gradient: hexane/ethyl acetate=(9:1) to (3:1)) to give the desired product as a brown oil (235 mg) in 85%. $^1$H NMR (300 MHz, CDCl$_3$) δ 8.73 (t, J=1.9 Hz, 1H), 8.62 (t, J=1.9 Hz, 1H), 8.35 (t, J=1.9 Hz, 1H), 1.48 (s, 9H); m/z (ES) [M+Na]$^+$ 300.0.

Step 103-2: 1-((3-(tert-butyl)-5-nitrophenyl)sulfonyl)pyrrolidine A solution of 3-(tert-butyl)-5-nitrobenzenesulfonyl chloride (415 mg, 1.5 mmol) and a secondary amine (3.4 mmol) in THF (7 mL) was stirred at RT for 2 h. Upon complete consumption of the starting material, water (7 mL) was added, the solvent was evaporated and the desired products were filtered and collected as a white solid. (0.240 g, 48%). $^1$H NMR (300 MHz, CDCl$_3$) δ 8.50-8.47 (m, 1H), 8.46 (t, J=2.0 Hz, 1H), 8.16 (t, J=1.7 Hz, 1H), 3.31 (ddd, J=6.8, 4.4, 2.6 Hz, 4H), 1.90-1.80 (m, 4H), 1.44 (s, 9H); m/z (ES) [M+Na]$^+$ 335.1.

Step 103-3: 3-(tert-butyl)-5-(pyrrolidin-1-ylsulfonyl)aniline. A solution of 1-((3-(tert-butyl)-5-nitrophenyl)sulfonyl)pyrrolidine (1 eq) and palladium on carbon (spoonful) in MeOH (4 mL) was stirred overnight under 5 atm of hydrogen. The mixture was thereafter filtered through celite, solvents were evaporated and the crude was purified by flash column chromatography (gradient: hexane/ethyl acetate=(4:1) to (2:1)) to give the desired product as a white solid (0.142 g, 60%). $^1$H NMR (300 MHz, CDCl$_3$) δ 7.10 (t, J=1.6 Hz, 1H), 6.90-6.85 (m, 1H), 6.83-6.79 (m, 1H), 3.78 (s, 1H), 3.15 (ddd, J=6.8, 4.4, 2.7 Hz, 4H), 1.70-1.62 (m, 4H), 1.22 (s, 9H); m/z (ES) [M+Na]$^+$ 305.1.

Step 103-4: (S)-2-(3-aminopiperidin-1-yl)-4-((3-(tert-butyl)-5-(pyrrolidin-1-ylsulfonyl)phenyl) amino)pyrimidine-5-carboxamide. Prepared by an analogous method to example 3 (Step 1: THF, DIPEA, 12 h, RT), using 3-(tert-butyl)-5-(pyrrolidin-1-ylsulfonyl)aniline and directly displacing with (S)-piperidin-3-amine hydrochloride in step 2 (7.9 mg, 8%). $^1$H NMR (400 MHz, MeOD) δ 8.75 (s, 1H), 8.65 (s, 1H), 7.54 (t, J=1.6 Hz, 1H), 7.51 (s, 1H), 4.70 (s, 1H), 4.37 (s, 1H), 3.50 (s, 2H), 3.43-3.35 (m, 1H), 3.27 (t, J=6.8 Hz, 4H), 2.19 (s, 1H), 1.94 (dd, J=9.2, 4.0 Hz, 1H), 1.83-1.63 (m, 6H), 1.40 (s, 9H); HRMS m/z [M+H]+ calc C$_{24}$H$_{36}$N$_7$O$_3$S 502.2600, found 502.2610.

Example 104: (S)-2-(3-aminopiperidin-1-yl)-4-((3-(tert-butyl)-5-(morpholinosulfonyl)phenyl)amino)pyrimidine-5-carboxamide Step 104-1: 3-(tert-butyl)-5-(morpholin-1-ylsulfonyl)aniline. Prepared by an analogous method to steps 103-1 to 103-3 (0.350 g, 87%). ¹H NMR (300 MHz, CDCl₃) δ 7.00 (t, J=1.6 Hz, 1H), 6.84-6.81 (m, 1H), 6.81-6.77 (m, 1H), 3.94 (s, 2H), 3.71-3.60 (m, 4H), 2.91 (dd, J=5.6, 3.9 Hz, 4H), 1.22 (s, 9H); m/z (ES) [M+Na]⁺321.1.

Step 104-2: (S)-2-(3-aminopiperidin-1-yl)-4-((3-(tert-butyl)-5-(morpholinosulfonyl)phenyl)amino) pyrimidine-5-carboxamide. Prepared by an analogous method to example 3 (Step 1: THF, DIPEA, 12 h, RT), using 3-(tert-butyl)-5-(morpholinosulfonyl)aniline and directly displacing with (S)-piperidin-3-amine hydrochloride in step 2 (0.083 g, 43%). ¹H NMR (400 MHz, MeOD) δ 8.65 (s, 1H), 8.63 (s, 1H), 7.57 (s, 1H), 7.46 (t, J=1.6 Hz, 1H), 4.65 (s, 1H), 4.35 (s, 1H), 3.77-3.66 (m, 4H), 3.51 (s, 2H), 3.41-3.36 (m, 1H), 3.02-2.95 (m, 4H), 2.18 (s, 1H), 1.92 (dd, J=9.4, 3.8 Hz, 1H), 1.84-1.64 (m, 2H), 1.41 (s, 9H); HRMS m/z [M+H]+ calc C₂₄H₃₆N₇O₄S 518.2549, found [MH]⁺ 518.2554.

Example 105: (S)-2-(3-aminopiperidin-1-yl)-4-((3-(tert-butyl)-5-(N,N-dimethylsulfamoyl)phenyl) amino) pyrimidine-5-carboxamide Step 105-1: 3-(tert-butyl)-5-(dimethylamin-1-ylsulfonyl) aniline. Prepared by an analogous method to steps 103-1 to 103-3 (0.250 g, 70%). ¹H NMR (300 MHz, CDCl₃) δ 7.03 (t, J=1.6 Hz, 1H), 6.84-6.80 (m, 1H), 3.93 (s, 2H), 2.61 (s, 6H), 1.22 (s, 9H); m/z (ES) [M+H]₊ 257.1. (S)-2-(3-aminopiperidin-1-yl)-4-((3-(tert-butyl)-5-(N,N-dimethylsulfamoyl)phenyl)amino) pyrimidine-5-carboxamide. Prepared by an analogous method to example 3 (Step 1: THF, DIPEA, 12 h, RT), using 3-(tert-butyl)-5-(dimethylamin-1-ylsulfonyl)aniline and directly displacing with (S)-piperidin-3-amine hydrochloride in step 2 (0.015 g, 5%). ¹H NMR (400 MHz, MeOD) δ 8.65 (s, 2H), 7.54 (s, 1H), 7.47 (t, J=1.6 Hz, 1H), 4.66 (s, 1H), 4.36 (s, 1H), 3.54 (s, 2H), 3.42-3.34 (m, 1H), 2.72 (s, 6H), 2.27-2.11 (m, 1H), 1.99-1.87 (m, 1H), 1.84-1.62 (m, 2H), 1.40 (s, 9H); HRMS m/z [M+H]+ calc C₂₂H₃₄N₇O₃S 476.2444, found 476.2436.

Example 106: (S)-2-(3-aminopiperidin-1-yl)-4-((3-(tert-butyl)-5-(methylsulfonyl)phenyl)amino) pyrimidine-5-carboxamide Step 106-1: 3-(tert-butyl)-5-nitrobenzenethiol. To a solution of 3-(tert-butyl)-5-nitrobenzenesulfonyl chloride (277 mg, 1 mmol) in toluene (8 mL), triphenyl phosphine (786 mg, 3 mmol) was added portion wise and the reaction was stirred at RT for 10 min. Upon complete consumption of the starting material, water (4 mL) was added and the mixture was partitioned. The organic layer was extracted with aqueous NaOH (10%, 2×15 mL) and the aqueous layer was washed EtOAc (2×15 mL), acidify with concentrated HCl and extracted with DCM (2×15 mL). The combined organic layers were dried with MgSO₄ and condensed to give the desired product as a clear oil (152 mg, 72%). ¹H NMR (400 MHz, CDCl₃) δ 7.94 (t, J=1.9 Hz, 1H), 7.87 (t, J=1.9 Hz, 1H), 7.49 (t, J=1.9 Hz, 1H), 3.62 (s, 1H), 1.27 (s, 9H); ¹³C NMR (101 MHz, CDCl₃) δ 177.5, 154.1, 133.1, 132.0, 121.0, 117.9, 35.2, 31.0; m/z (ES) C₁₀H₁₃NO₂S [M]⁺ 211.1.

Step 106-2: (3-(tert-butyl)-5-nitrophenyl)(methyl)sulfane. To a solution of 3-(tert-butyl)-5-nitrobenzenethiol (210 mg, 1 mmol) in EtOH (5 mL) NaOH (48 mg, 1.2 mmol) was added and the mixture was stirred at RT for 2 h. Methyl iodide (69 µL, 1.1 mmol) was added and the mixture was left to react overnight. The reaction was diluted with water and EtOAc, extracted with EtOAc (2×10 mL), and the combined organic layers were washed with brine (1×15 mL), dried with MgSO₄ and condensed. The crude was purified by flash column chromatography (gradient: hexane/ethyl acetate=(5:1) to (3:1)) to give the desired product as a colourless oil (220 mg, 98%). ¹H NMR (300 MHz, CDCl₃) δ 7.92 (t, J=1.8 Hz, 1H), 7.79 (t, J=1.8 Hz, 1H), 7.48 (t, J=1.8 Hz, 1H), 2.49 (s, 3H), 1.28 (s, 9H).

Step 106-3: 1-(tert-butyl)-3-(methylsulfonyl)-5-nitrobenzene. To a solution of (3-(tert-butyl)-5-nitrophenyl)(methyl) sulfane (420 mg, 1.88 mmol) in DCM (4 mL) at 0° C. mCPBA (1.1 g, 4.7 mmol) was added in one portion at RT. The mixture was left to warm up to RT and react for 2 h. Upon complete consumption of the starting material, the mixture was washed with NaHCO₃ (2×10 mL) and brine (1×10 mL), dried with MgSO₄ and condensed. The crude was purified by flash column chromatography (gradient: hexane/ethyl acetate=(4:1) to (2:1)) to give the desired product as a white solid (333 mg, 73%). ¹H NMR (300 MHz, CDCl₃) δ 8.64-8.58 (m, 1H), 8.52 (t, J=1.9 Hz, 1H), 8.28 (t, J=1.9 Hz, 1H), 3.16 (s, 3H), 1.44 (s, 9H).

Step 106-4: 3-(tert-butyl)-5-(methylsulfonyl)aniline A solution of 1-(tert-butyl)-3-(methylsulfonyl)-5-nitrobenzene (333 mg, 1.3 mmol) and palladium on carbon (spoonful) in MeOH (6 mL) was stirred overnight under 5 atm of hydrogen. The mixture was thereafter filtered through celite, solvents were evaporated and the crude was purified by flash column chromatography (gradient: hexane/ethyl acetate=(4:1) to (2:1)) to give the desired product as a white solid (230 mg, 76%). ¹H NMR (300 MHz, CDCl₃) δ 7.31 (t, J=1.6 Hz, 1H), 7.05 (dd, J=2.1, 1.7 Hz, 1H), 6.95-6.93 (m, 1H), 4.02 (s, 1H), 3.04 (s, 3H), 1.32 (s, 9H); m/z (ES) C₁₁H₁₇NO₂S [MH]⁺ 228.1.

Step 106-5: (S)-2-(3-aminopiperidin-1-yl)-4-((3-(tert-butyl)-5-(methylsulfonyl)phenyl)amino) pyrimidine-5-carboxamide. Prepared by an analogous method to example 3 (Step 1: THF, DIPEA, 12 h, RT), using 3-(tert-butyl)-5-(methylsulfonyl)aniline to give a white solid (32 mg, 10%). ¹H NMR (300 MHz, MeOD) δ 8.79 (s, 1H), 8.62 (s, 1H), 7.68 (t, J=1.6 Hz, 1H), 7.55 (s, 1H), 4.71 (s, 1H), 4.38 (d, J=11.8 Hz, 1H), 3.60-3.36 (m, 3H), 3.21 (s, 3H), 2.21 (d, J=4.3 Hz, 1H), 1.93 (dd, J=10.3, 5.0 Hz, 1H), 1.86-1.65 (m, 2H), 1.40 (s, 9H); m/z (ES HRMS) C₂₁H₃₀N₆O₃S calc 447.2178, found [MH]⁺ 447.2174.

Example 107: (S)-2-(3-aminopiperidin-1-yl)-4-((3-(pyrrolidin-1-ylsulfonyl)-5-(trifluoromethyl)phenyl) amino) pyrimidine-5-carboxamide Step 107-1: 3-(pyrrolidin-1-ylsulfonyl)-5-(trifluoromethyl)aniline. Prepared by an analogous method to steps 103-1 to 103-3 using 3-nitro-5-(trifluoromethyl)benzenesulfonyl chloride to give a white solid. ¹H NMR (300 MHz, CDCl₃) δ 7.30 (s, 1H), 7.19 (s, 1H), 6.98 (s, 1H), 4.14 (br s, 2H), 3.21-3.16 (m, 4H), 1.75-1.70 (m, 4H).

Step 107-2: (S)-2-(3-aminopiperidin-1-yl)-4-((3-(pyrrolidin-1-ylsulfonyl)-5-(trifluoromethyl)phenyl) amino) pyrimidine-5-carboxamide. Prepared by an analogous method to example 3 (Step 1: THF, DIPEA, 16 h, RT), using 3-(pyrrolidin-1-ylsulfonyl)-5-(trifluoromethyl)aniline and directly displacing with (S)-piperidin-3-amine hydrochloride in step 2. ¹H NMR (300 MHz, MeOD) δ 8.99 (br s, 1H), 8.62 (s, 1H), 7.95 (br s, 1H), 7.69 (s, 1H), 4.78-4.60 (m, 1H), 4.58-4.33 (m, 1H), 3.34-3.27 (m, 4H), 3.28-3.19 (m, 2H), 3.11-2.88 (m, 1H), 2.14-1.96 (m, 1H), 1.93-1.82 (m, 1H), 1.85-1.63 (m, 4H), 1.70-1.43 (m, 2H). HRMS m/z [M+H]+ calc C₂₁H₂₇N₇O₃F₃S 514.1848 found 514.1847.

Example 108: 2-chloro-4-((3-(N-methylsulfamoyl)-5-(trifluoromethyl)phenyl)amino)pyrimidine-5-carboxamide Step 108-1: N-methyl-3-nitro-5-(trifluoromethyl)benzenesulfonamide. Prepared by an analogous method to step 107-1. $^1$H NMR (300 MHz, CDCl$_3$) δ 7.41 (s, 1H), 7.29 (s, 1H), 7.04 (s, 1H), 4.49 (br s, 1H), 4.18 (br s, 2H), 2.69 (d, J=3.6 Hz, 3H).

Step 108-2: 2-chloro-4 ((3-(N-methylsulfamoyl)-5-(trifluoromethyl)phenyl)amino)pyrimidine-5-carboxamide. Prepared by an analogous method to example 3 (Step 1: dioxane, no base, 48 h, 100° C.), using 3-(pyrrolidin-1-ylsulfonyl)-5-(trifluoromethyl)aniline and directly displacing with (S)-piperidin-3-amine hydrochloride in step 2. $^1$H NMR (300 MHz, MeOD) δ 9.09 (s, 1H), 8.78 (s, 1H), 8.43 (s, 1H), 8.37 (s, 1H), 8.04 (s, 1H), 7.83 (s, 1H), 2.64 (s, 3H).

Example 109: (S)-2-(3-aminopiperidin-1-yl)-4-((3-(azetidin-1-yl)-5-(trifluoromethyl)phenyl)amino)pyrimidine-5-carboxamide hydrochloride Step 109-1: 3-(azetidin-1-yl)-5-(trifluoromethyl)aniline. Prepared by Ullman reaction adapted from WO2011035332. $^1$H NMR (300 MHz, CDCl$_3$) δ 6.28 (br s, 1H), 6.08 (br s, 1H), 5.84 (br s, 1H), 3.86 (tr, J=7.3 Hz, 4H), 3.70 (br s, 2H), 2.35 (pent., J=7.3 Hz, 2H). m/z (ES$^+$) (M+H)$^+$ 217.2; $t_R$=2.68 min. HPLC Method 1.

Step 109-2: (S)-2-(3-aminopiperidin-1-yl)-4-((3-(azetidin-1-yl)-5-(trifluoromethyl)phenyl)amino) pyrimidine-5-carboxamide hydrochloride. Prepared by an analogous method to example 3 using 3-(azetidin-1-yl)-5-(trifluoromethyl)aniline to give the hydrochloride salt (Step 1: nBuOH, DIPEA, 50° C., 1 h, Step 2: nBuOH, DIPEA, 50° C., 15 min; Step 3: HCl in dioxane (4M), RT). $^1$H NMR (300 MHz, MeOD) δ 8.58 (s, 1H), 7.39 (br s, 1H), 7.14 (br s, 1H), 6.90 (s, 1H), 4.33 (dd, J=13.6, 3.7 Hz, 1H), 4.07 (br s, 1H), 3.83-3.75 (m, 1H), 3.72 (tr, J=6.4 Hz, 2H), 3.67-3.60 (m, 1H), 3.57-3.51 (m, 1H), 3.36 (tr, J=6.8 Hz, 2H), 2.24-2.17 (m, 1H), 2.13 (pent, J=6.6 Hz, 2H), 2.02-1.94 (br s, 1H), 1.90-1.77 (m, 2H). m/z (ES$^+$) (M+H)$^+$ 436.2; $t_R$=2.32 min. HPLC Method 1.

Example 110: 4-((3-(3-aminoazetidin-1-yl)-5-(trifluoromethyl)phenyl)amino)-2-(3-aminopiperidin-1-yl)pyrimidine-5-carboxamide Step 110-1: tert-butyl (S)-(1-(4-((3-bromo-5-(trifluoromethyl)phenyl)amino)-5-carbamoylpyrimidin-2-yl)piperidin-3-yl)carbamate. Prepared by an analogous method to steps 3-1 and 3-2 using 3-bromo-5-(trifluoromethyl)aniline (Step 1: nBuOH, DIPEA, 70° C., 3 h). m/z (ES$^+$) (M+H)$^+$ 451.

Step 110-2: tert-butyl (S)-(1-(4-((3-(3-((tert-butoxycarbonyl)amino)azetidin-1-yl)-5-(trifluoromethyl)phenyl)amino)-5-carbamoylpyrimidin-2-yl)piperidin-3-yl)carbamate. To a solution of tert-butyl (1-(4-((3-(3-((tert-butoxycarbonyl)amino)azetidin-1-yl)-5-(trifluoromethyl)phenyl)amino)-5-carbamoylpyrimidin-2-yl)piperidin-3-yl) carbamate (50 mg, 0.1 mmol), tert-butyl azetidin-3-ylcarbamate (17.2 mg, 0.100 mmol), in 1,4-dioxane; Pd$_2$(dba)$_3$ (0.004 mmol, 4 mg), Xant-phos (0.012 mmol, 8 mg) and Cs$_2$CO$_3$ (0.3 mmol, 98 mg) were added. The reaction was stirred at 100° C. under N$_2$. After 5 hrs, another same equivalent of the reagents were added and the reaction was refluxed overnight. Water was added and the mixture extracted was with ethyl acetate and organic layer was washed with sodium bicarbonate and sodium chloride, and dried over sodium sulfate. Solvent was removed and the desired product was purified using silica gel chromatography with a gradient of Pet. Ether-DCM (0-100%) and DCM-THF (0-10%). HPLC: $t_R$=$^3$0.0$^4$ min, m/z (ES+) (M+H)+651.3. Method 1.

Step 110-3: 4-((3-(3-aminoazetidin-1-yl)-5-(trifluoromethyl)phenyl)amino)-2-(3-aminopiperidin-1-yl)pyrimidine-5-carboxamide. To a solution of tert-butyl (S)-(1-(4-((3-(3-((tert-butoxycarbonyl)amino)azetidin-1-yl)-5-(trifluoromethyl)phenyl)amino)-5-carbamoylpyrimidin-2-yl)piperidin-3-yl)carbamate (20 mg) in 1,4-dioxane (1 mL), 4N HCl in 1,4-dioxane (2 mL) was added and the reaction was stirred at RT for 1 hour. To the reaction mixture, diethyl ether was added and the solid was filter to provide the di-hydrochloride salt of the title compound (10 mg, 71%). $^1$H NMR (400 MHz, Methanol-d4) δ 8.57 (s, 1H), 7.54 (s, 1H), 7.03 (s, 1H), 6.86 (s, 1H), 4.37-4.33 (br m, 1H), 4.09 (br s, 1H), 3.99-3.80 (m, 2H), 3.84-3.71 (br m, 2H), 3.65 (s, 1H), 3.60-3.48 (m, 2H), 2.23-2.21 (br m, 1H), 2.01-1.91 (br m, 1H), 1.88-1.75 (br m, 2H).

Example 111: (S)-4-((3-(2-acetamidopropan-2-yl)-5-(trifluoromethyl)phenyl)amino)-2-(3-amino piperi-din-1-ylpyrimidine-5-carboxamide Step 111-1: N-(2-(3-amino-5-(trifluoromethyl)phenyl)propan-2-yl)acetamide. Prepared from 2-(3-amino-5-(trifluoromethyl)phenyl)propan-2-ol) according to J. Med. Chem. 2011, 54, 1836-1846 (106 mg, 89%), m/z (ES$^+$) (M+H)$^+$ 260.9; $t_R$=2.40 min. HPLC Method 1.

Step 111-2: (S)-4-((3-(2-acetamidopropan-2-yl)-5-(trifluoromethyl)phenyl)amino)-2-(3-amino piperi-din-1-yl)pyrimidine-5-carboxamide. Prepared by an analogous method to example 3 using N-(2-(3-amino-5-(trifluoromethyl)phenyl)propan-2-yl)acetamide (Step 1: CH$_3$CN, DIPEA, 60° C., 3 h), (S)-3-aminopiperidine dihydrochloride was used in step 2 (31 mg, 47%). $^1$H NMR (500 MHz, MeOD) δ 8.56 (s, 1H), 8.17 (s, 1H), 7.64 (s, 1H), 7.32 (s, 1H), 4.67-4.62 (m, 1H), 4.54-4.49 (m, 1H), 3.10 (br t, J=12.0 Hz, 1H), 2.93-2.89 (m, 1H), 2.82-2.77 (m, 1H), 2.06-2.00 (m, 1H), 1.95 (s, 3H), 1.83-1.78 (m, 1H), 1.67 (s, 3H), 1.65 (s, 3H), 1.60-1.51 (m, 1H), 1.46-1.39 (m, 1H). m/z (ES$^+$) (M+H)$^+$ 480.2; $t_R$=2.16 min. HPLC Method 1.

Example 112: (S)-2-(3-aminopiperidin-1-yl)-4-((3-(2-aminopropan-2-yl)-5-(trifluoromethyl)phenyl)amino)pyrimidine-5-carboxamide Step 112-1: tert-butyl (2-(3-amino-5-(trifluoromethyl)phenyl)propan-2-yl)carbamate. Prepared from 3-(2-aminopropan-2-yl)-5-(trifluoromethyl)aniline according to J. Med. Chem. 2011, 54, 1836-1846. m/z (ES$^+$) (M+H)$^+$319.1; $t_R$=2.89 min. HPLC Method 1.

Step 112-2: (S)-2-(3-aminopiperidin-1-yl)-4-((3-(2-aminopropan-2-yl)-5-(trifluoromethyl)phenyl) amino)pyrimidine-5-carboxamide. Prepared by an analogous method to example 3 using tert-butyl (2-(3-amino-5-(trifluoromethyl)phenyl)propan-2-yl)carbamate to give the hydrochloride salt (Step 1: CH$_3$CN, DIPEA, 60° C., 3 h), (54 mg, 96%). $^1$H NMR (300 MHz, MeOD) δ 8.65 (s, 1H), 8.32 (br s, 1H), 7.86 (s, 1H), 7.72 (s, 1H), 4.36 (dd, =13.6, 3.5 Hz, 1H), 4.09 (br s, 1H), 3.82-3.71 (m, 1H), 3.68-3.56 (m, 1H), 3.55-3.48 (m, 1H), 2.25-2.16 (m, 1H), 2.03-1.92 (m, 1H), 1.90-1.74 (m, 1H), 1.82 (s, 6H). m/z (ES$^+$) (M+H)$^+$438.1; $t_R$=1.91 min. HPLC Method 1.

Example 113: (S)-4-((3-(2-acetamidopropan-2-yl)-5-(tert-butyl)phenyl)amino)-2-(3-aminopiperidin-1-yl)pyrimidine-5-carboxamide Step 113-1: tert-butyl (2-(3-amino-5-(tert-butyl)phenyl)propan-2-yl)carbamate. Prepared from 2-(3-amino-5-(tert-butyl)phenyl)propan-2-ol) by an analogous method to step 111-1.

Step 113-2: (S)-4-((3-(2-acetamidopropan-2-yl)-5-(tert-butyl)phenyl)amino)-2-(3-aminopiperidin-1-yl)pyrimidine-5-carboxamide. Prepared by an analogous method to example 3 using N-(2-(3-amino-5-(tert-butyl)phenyl)propan-2-yl)acetamide (Step 1: $CH_3CN$, DIPEA, 70° C., 3 h) (95 mg, 67%). $^1H$ NMR (300 MHz, MeOD) δ 8.50 (s, 1H), 7.47 (br s, 1H), 7.16 (s, 1H), 4.65 (br d, J=11.6 Hz, 1H), 4.52 (br d, J=13.8 Hz, 1H), 3.76-3.56 (m, 2H), 3.15-3.07 (m, 1H), 2.97-2.92 (m, 1H), 2.87-2.79 (m, 1H), 2.05-1.98 (m, 1H), 1.94 (s, 3H), 1.82-1.74 (m, 1H), 1.66 (s, 3H), 1.63 (s, 3H), 1.33 (s, 9H). m/z (ES$^+$) (M+H)$^+$ 468.3; $t_R$=2.17 min. HPLC Method 1).

Example 114: (S)-2-(3-aminopiperidin-1-yl)-4-((3-(azetidin-3-yl)-5-(trifluoromethyl)phenyl)amino)pyri-midine-5-carboxamide Step 114-1: tert-butyl 3-(3-chloro-5-(trifluoromethyl)phenyl)azetidine-1-carboxylate. tert-butyl 3-(2-((4-methoxyphenyl)sulfonyl)hydrazono)azetidine-1-carboxylate (2.2 mmol, 750 mg), (3-chloro-5-(trifluoromethyl)phenyl)boronic acid (4.5 mmol, 1 g) and cesium carbonate (3.3 mmol, 1.08 g) were placed in an oven-dried microwave vessel. Dry 1,4-dioxane (20 mL) was added. The solution was degassed by bubbling $N_2$ through. The tube was sealed and heated to 120° C. for 7 h by microwave. The crude was diluted with ethyl acetate and washed with saturated aqueous $NH_4Cl$, sat aqueous $NaHCO_3$, brine and finally dried on $Na_2SO_4$. Sodium sulfate was filtered off and the solvent was evaporated in vacuo to give a crude residue, which was purified by chromatography on silica using a gradient PET/DCM to give the title compounds as a very pale yellow oil (225 mg, 30%). $^1H$ NMR (300 MHz, CDCl$_3$) δ 7.51 (br s, 2H), 7.43 (br s, 1H), 4.36 (tr, J=8.8 Hz, 2H), 3.94 (dd, J=8.8, 5.9 Hz, 1H), 3.79-3.72 (m, 1H), 1.47 (s, 9H). m/z (ES+) (M+H)$^+$ 336.1; $t_R$=3.22 min. HPLC Method 1.

Step 114-2: tert-butyl 3-(3-(benzylamino)-5-(trifluoromethyl)phenyl)azetidine-1-carboxylate. To a solution of tert-butyl 3-(3-chloro-5-(trifluoromethyl)phenyl)azetidine-1-carboxylate (140 mg, 0.42 mmol) in 1,4-dioxane (6 mL) in a microwave vessel was added benzylamine (0.5 mmol, 55 uL), Xant-phos ligand (0.12 mmol, 70 mg) and $Cs_2CO_3$ (0.5 mmol, 160 mg). The suspension was degassed with $N_2$ for 5 min and Pd(dba)$_2$ (0.04 mmol, 35 mg) was added. The vessel was capped and heated by microwave to 105° C. for 1 h then 110° C. for 3 h. The crude was extracted with EtOAc and washed with saturated aqueous $NH_4Cl$, sat aqueous $NaHCO_3$, brine and finally dried on $Na_2SO_4$. Sodium sulfate was filtered off and the solvent was evaporated in vacuo to give a crude residue, which was purified by chromatography on silica using a gradient DCM (100%)/THF (1%, 5%, 10%) to give a yellow oil (68 mg, 40%). $^1H$ NMR (300 MHz, CDCl$_3$) δ 7.37-7.27 (m, 5H), 6.86 (br s, 1H), 6.75 (br s, 1H), 6.70 (br s, 1H), 4.35 (s, 2H), 4.29 (tr, J=8.7 Hz, 2H), 3.92 (dd, J=8.7, 6.0 Hz, 1H), 3.69-3.62 (m, 1H), 1.47 (s, 9H). m/z (ES+) (M+H)+407.0; $t_R$=3.23 min. HPLC Method 1.

Step 114-3: tert-butyl 3-(3-amino-5-(trifluoromethyl)phenyl)azetidine-1-carboxylate.

To a solution of tert-butyl 3-(3-(benzylamino)-5-(trifluoromethyl)phenyl)azetidine-1-carbo-xylate (68 mg, 0.17 mmol) in MeOH (10 mL), Pd/C was added and the suspension was degassed using a cycle of vacuum/$N_2$ flush (2×) and finally placed under an $H_2$ atmosphere. The suspension was stirred at RT for 18 h. The crude was filtered through a celite pad and evaporated to dryness to give a yellow oil (47 mg, 87%). The crude was used without further purification. m/z (ES$^+$) (M+H)$^+$ 317.0; $t_R$=2.95 min. HPLC Method 1.

Step 114-4: (S)-2-(3-aminopiperidin-1-yl)-4-((3-(azetidin-3-yl)-5-(trifluoromethyl)phenyl)amino)pyri-midine-5-carboxamide. Prepared by an analogous method to example 3 using tert-butyl 3-(3-amino-5-(trifluoromethyl)phenyl)azetidine-1-carboxylate to give the di-hydrochloride salt (Step 1: $CH_3CN$, DIPEA, 75° C., 3 h). $^1H$ NMR (300 MHz, MeOD) δ 8.63 (d, J=1.1 Hz, 1H), 8.17 (br d, J=20.3 Hz, 1H), 7.82 (br d, J=16.5 Hz, 1H), 7.61 (br d, J=7.4 Hz, 1H), 4.50-4.41 (m, 2H), 4.39-4.28 (m, 2H), 4.07 (br s, 1H), 4.00-3.89 (m, 1H), 3.85-3.75 (m, 1H), 3.57-3.51 (m, 2H), 2.25-2.18 (m, 1H), 2.03-1.94 (m, 1H), 1.90-1.77 (m, 2H). m/z (ES$^+$) (M+H)$^+$ 436.1; $t_R$=0.60 min. HPLC Method 1.

Example 115: (R)-2-(3-aminopiperidin-1-yl)-4-((3-(1-hydroxycyclopropyl)-5-(trifluoromethyl)phenyl)amino)pyrimidine-5-carboxamide Step 115-1: 1-(3-(dibenzylamino)-5-(trifluoromethyl)phenyl)cyclopropan-1-ol. To a solution methyl 3-(dibenzylamino)-5-(trifluoromethyl)benzoate (prepared from methyl 3-(trifluoromethyl)-5-aminobenzoate by an analogous method to step 87-1, 1.16 g) in anhydrous THF (20 mL) at RT, under $N_2$, was added titanium tetraisopropoxide (0.45 mmol, 0.135 mL) dropwise over 10 mins. After 15 mins of stirring, ethyl magnesium bromide (THF solution, 6.62 mmol, 0.762 mL) was added dropwise over 30 mins. The reaction was stirred at RT for 3 h. The resulting mixture was quenched with $NH_4Cl$, and extracted with ethyl acetate. The combined organic layers were dried over sodium sulphate, filtered and concentrated under vacuum. The crude product was purified by silica gel chromatography (0-30% DCM/Pet. Ether) to give the title compound (39%). HPLC (Method 1): $t_R$=0.21 min, m/z (ES+) (M+H)+398.1.

Step 115-2: 1-(3-amino-5-(trifluoromethyl)phenyl)cyclopropan-1-ol. To a solution of (3-(dibenzylamino)-5-(trifluoromethyl)phenyl)cyclopropan-1-ol in methanol, Pd/C (10%) was added and the reaction was stirred under $H_2$ gas at RT for 2 h. Pd/C was filtered and methanol was removed and the crude mixture was purified using silica gel chromatography with 0-30% DCM in Pet. Ether to give the title compound (84%). HPLC (Method 1): $t_R$=2.47 min, m/z (ES+) (M+H)+218.2.

(R)-2-(3-aminopiperidin-1-yl)-4-((3-(1-hydroxycyclopropyl)-5-(trifluoromethyl)phenyl)amino)pyrimidine-5-carboxamide. Prepared by an analogous method to example 3 using 1-(3-amino-5-(trifluoromethyl)phenyl)cyclopropan-1-ol in step 1 and (R)-tert-butyl piperidin-3-ylcarbamate in step 2. $^1H$ NMR (400 MHz, DMSO-d6) δ 11.8 (s, 1H), 8.69 (S, 1H), 8.19-7.87 (m, 2H), 7.41-7.18 (m, 2H), 4.64-4.57 (br s, 1H), 3.04-3.29 (br m, 1H), 2.82-2.27 (br m, 1H), 2.27-2.26 (br m, 1H), 1.99-1.93 (br m, 1H), 1.75-1.67 (br m, 2H), 1.37-1.29 (m, 2H), 1.22-1.18 (m, 2H), 1.10-1.04 (m, 2H), 0.88-0.82 (m, 2H); HPLC (Method 1): $t_R$=2.19 min, m/z (ES+) (M+H)+437.3.

Example 116: (S)-2-(3-aminopiperidin-1-yl)-4-((3-(1-hydroxycyclopropyl)-5-(trifluoromethyl)phenyl)amino)pyrimidine-5-carboxamide Prepared by an analogous method to example 3 using 1-(3-amino-5-(trifluoromethyl)phenyl)cyclopropan-1-ol. $^1H$ NMR (400 MHz, DMSO-d6) δ 11.8 (s, 1H), 8.69 (S, 1H), 8.19-7.87 (m, 2H), 7.41-7.18 (m, 2H), 4.64-4.57 (br s, 1H), 3.04-3.29 (br m, 1H), 2.82-2.27 (br m, 1H), 2.27-2.26 (br m, 1H), 1.99-1.93 (br m, 1H), 1.75-1.67 (br m, 2H), 1.37-1.29 (m, 2H), 1.22-1.18 (m, 2H), 1.10-1.04 (m, 2H), 0.88-0.82 (m, 2H); HPLC (Method 1): $t_R$=2.20 min, m/z (ES+) (M+H)+437.2

Example 117: (S)-2-(3-aminopiperidin-1-yl)-4-((3-(tert-butyl)-5-(1-hydroxycyclopropyl)phenyl)amino) pyrimidine-5-carboxamide Step 117-1 1-(3-(tert-butyl)-5-(dibenzylamino)phenyl)cyclopropan-1-ol. To a solution of the methyl 3-(tert-butyl)-5-(dibenzylamino)benzoate (prepared from methyl 3-(tert-butyl)-5-aminobenzoate by an analogous method to step 87-1, 1.16 g, 3 mmol) in anhydrous THF (20 mL) at RT under $N_2$ was added titanium tetraisopropoxide (0.45 mmol, 0.135 mL) dropwise over 10 mins. After 15 mins of stirring, EtMgBr (THF solution, 6.62 mmol, 0.762 mL) was added dropwise over 30 mins. The reaction was stirred at RT for 3 h. The resulting mixture was quenched with $NH_4Cl$, and extracted with ethyl acetate. The crude product was purified by silica gel chromatography (0-30% DCM/Pet. Ether) to provide the title compound (52%). HPLC (Method 1): $t_R$=3.30 min, m/z (ES+) (M+H)+385.9.

Step 117-2: 1-(3-amino-5-(tert-butyl)phenyl)cyclopropan-1-ol

To a solution of 1-(3-(tert-butyl)-5-(dibenzylamino)phenyl)cyclopropan-1-ol (30 mg) in MeOH (5 mL), $Pd(OH)_2/C$ was added and degassed using a cycle of vacuum/$N_2$ flush (2×) and then placed under an $H_2$ atmosphere for 30 min. $Pd(OH)_2/C$ was filtered and methanol was removed to provide a mixture of 1-(3-amino-5-(tert-butyl)phenyl)cyclopropan-1-ol and 1-(3-amino-5-(tert-butyl)phenyl)propan-1-ol which was used without further purification.

Step 117:3: (S)-2-(3-aminopiperidin-1-yl)-4-((3-(tert-butyl)-5-(1-hydroxycyclopropyl)phenyl)amino) pyrimidine-5-carboxamide. Prepared by an analogous method to example 3 using crude 1-(3-amino-5-(tert-butyl)phenyl)cyclopropan-1-ol (Step 1: $CH_3CN$, DIPEA, 80° C., 2 h) to give a mixture of products that were purified by preparative HPLC (phenomenex 20 mm×100 mm C18 5 m column), using a slow gradient Water/MECN (5 to 40% over 10 min) to give the title compound. $^1$H NMR (300 MHz, $CD_3OD$) δ 8.57 (s, 1H), 8.31 (br s, 3H), 7.76 (br s, 1H), 7.30 (s, 1H), 7.03 (s, 1H), 4.56 (d, J=13.0 Hz, 1H), 4.24 (br d, J=15.9 Hz, 1H), 3.62-3.54 (m, 2H), 2.20-2.11 (m, 1H), 1.91-1.81 (m, 1H), 1.81-1.62 (m, 2H), 1.33 (s, 9H), 1.22-1.17

Example 118: (S)-2-(3-aminopiperidin-1-yl)-4-((3-(tert-butyl)-5-(1-methoxycyclopropyl)phenyl)amino) pyrimidine-5-carboxamide Step 118-1: N,N-dibenzyl-3-(tert-butyl)-5-(1-methoxycyclopropyl)aniline. To a solution of compound (300 mg, 1.28 mmol) in 7 mL anhydrous THF, NaH (40 mg, 1.6 mmol) and MeI (65 μl, 0.9 mmol) was added, and the reaction was stirred at RT for 16 h. THF was removed and the crude was purified using silica gel chromatography with 0-20% DCM in Pet. Ether to afford the title compound (50%). HPLC (Method 1): $t_R$=3.58 min, m/z (ES+) (M+H)+ 399.8, 401.2.

Step 118-2: 3-(tert-butyl)-5-(1-methoxycyclopropyl)aniline. Prepared by an analogous method to step 115-2 using N,N-dibenzyl-3-(tert-butyl)-5-(1-methoxycyclopropyl)aniline. HPLC (Method 1): $t_R$=2.42 min, m/z (ES+) (M+H)+ 220.1.

Step 118-3: (S)-2-(3-aminopiperidin-1-yl)-4-((3-(tert-butyl)-5-(1-methoxycyclopropyl)phenyl)amino)pyrimidine-5-carboxamide. Prepared by an analogous method to example 3 using 1-(3-amino-5-(trifluoromethyl)phenyl)cyclopropan-1-ol. HPLC (Method 1): $t_R$=2.35 min, m/z (ES+) (M+H)+ 439.4.

$^1$H NMR (400 MHz, DMSO-d6) δ12.36 (s, 1H), 9.4 (s, 1H), 8.38-8.11 (br m, 3H), 7.80-7.78 (m, 2H), 3.98 (s, 3H), 3.97 (s, 2H), 3.95 (s, 1H), 2.83-2.73 (br s, 1H), 2.57-2.49 (br m, 2H), 2.33-2.22 (br s, 2H), 2.11 (s, 9H), 2.04 (br s, 2H), 1.96-1.93 (m, 2H), 1.81-1.75 (br m, 2H), 1.67-1.62 (m, 2H).

Example 119: 2-((S)-3-aminopiperidin-1-yl)-4-((3-(tert-butyl)-5-(1-hydroxypropyl)phenyl)amino) pyrimidine-5-carboxamide Step 119-1: 1-(3-amino-5-(tert-butyl)phenyl)propan-1-ol. Prepared from 1-(3-(tert-butyl)-5-(dibenzylamino)phenyl)cyclopropan-1-ol using an analogous method to step 117-2 (Pd/C, Ethanol, RT 16 h). $^1$H NMR (300 MHz, MeOD) δ 6.77 (dd, J1=J2=1.5 Hz, 1H), 6.73 (dd, J1=J2=1.9 Hz, 1H), 6.56 (dd, J1=J2=1.7 Hz, 1H), 4.40 (tr, J=6.6 Hz, 1H), 1.80-1.62 (m, 2H), 1.28 (s, 9H), 0.88 (tr, J=7.4 Hz, 3H), m/z (ES+) (M+H)+ 207.8; $t_R$=2.27 min (HPLC Method 1).

Step 119-2: 2-((S)-3-aminopiperidin-1-yl)-4-((3-(tert-butyl)-5-(1-hydroxypropyl)phenyl)amino) pyrimidine-5-carboxamide. Prepared by an analogous method to example 3 using tert-butyl (3R)-1-(4-(3-tert-butyl-5-(1-hydroxy-propyl)phenylamino)-5-carbamoylpyrimidin-2-yl)piperidin-3-ylcarbamate (step 1) and (S)-3-aminopiperidine dihydrochloride (step 2). $^1$H NMR (300 MHz, MeOD) δ 8.54 (s, 1H), 7.77 (br s, 1H), 7.35 (s, 1H), 7.06 (s, 1H), 4.63 (tr, J=14.1 Hz, 1H), 4.53 (tr, J=6.5 Hz, 1H), 4.43 (tr, J=11.8 Hz, 1H), 3.27-3.10 (m, 2H), 3.03-2.94 (m, 1H), 2.07 (br s, 1H), 1.85-1.68 (m, 3H), 1.63-1.50 (m, 2H), 1.33 (s, 9H), 0.94-0.88 (m, 3H), m/z (ES+) (M+H)+ 427.0; $t_R$=2.24 min. HPLC Method 1.

Example 120: 2-((R)-3-aminopiperidin-1-yl)-4-((3-(tert-butyl)-5-(1-hydroxypropyl)phenyl)amino) pyrimidine-5-carboxamide Prepared by an analogous method to example 3 using tert-butyl (3R)-1-(4-(3-tert-butyl-5-(1-hydroxy-propyl)phenylamino)-5-carbamoylpyrimidin-2-yl)piperidin-3-ylcarbamate (step 1) and (R)-3-aminopiperidine dihydrochloride (step 2). $^1$H NMR (300 MHz, MeOD) δ 8.54 (s, 1H), 7.77 (br s, 1H), 7.35 (s, 1H), 7.06 (s, 1H), 4.63 (tr, J=14.1 Hz, 1H), 4.53 (tr, J=6.5 Hz, 1H), 4.43 (tr, J=11.8 Hz, 1H), 3.27-3.10 (m, 2H), 3.03-2.94 (m, 1H), 2.07 (br s, 1H), 1.85-1.68 (m, 3H), 1.63-1.50 (m, 2H), 1.33 (s, 9H), 0.94-0.88 (m, 3H), m/z (ES+) (M+H)+ 427.3; $t_R$=2.23 min. HPLC Method 1.

Example 121: 2-((S)-3-aminopiperidin-1-yl)-4-((3-(tert-butyl)-5-(1-methoxypropyl)phenyl)amino)pyrimidine-5-carboxamide Step 121-1; N,N-dibenzyl-3-(tert-butyl)-5-(1-methoxypropyl)aniline. To a solution of N,N-dibenzyl-3-(tert-butyl)-5-(1-methoxycyclopropyl)aniline (150 mg, 0.38 mmol) in methanol, Pd/C (10%) was added and the reaction was stirred under $H_2$ gas at RT for 4 h. Pd/C was filtered and methanol was removed and the crude mixture was purified using silica gel chromatography with 0-30% DCM in Pet. Ether to afford the title compound (24%). HPLC (Method 1): $t_R$=2.26 min, m/z (ES+) (M+H)+222.1.

Step 121-2: 2-((S)-3-aminopiperidin-1-yl)-4-((3-(tert-butyl)-5-(1-methoxypropyl)phenyl)amino)pyrimidine-5-carboxamide. Prepared by an analogous method to example 3 using N,N-dibenzyl-3-(tert-butyl)-5-(1-methoxypropyl)aniline. $^1$H NMR (500 MHz, MeOD-d4) δ 8.54 (s, 1H), 7.92-7.68 (br s, 1H), 7.44-7.28 (br s, 1H), 7.07 (s, 1H) 4.71-4.64 (br m, 1H), 4.54-4.49 (br m, 1H), 4.32-4.28 (t, 3H), 3.23-3.15 (m, 1H), 3.08-2.99 (m, 1H), 2.93-2.87 (m, 1H), 2.10-2.02 (br m, 1H), 1.96-1.90 (m, 1H), 1.84-1.80 (m, 1H), 1.63-1.55 (m, 1H), 1.52-1.45 (m, 1H), 1.35 (s, 9H), 1.31 (s, 2H), 1.04-1.02 (d, 3H), 0.83-0.80 (t, 3H). HPLC (Method 1): $t_R$=2.29 min, m/z (ES+) (M+H)+441.4, Example 122 (S)-2-(3-aminopiperidin-1-yl)-4-((3-(1-methoxycyclopropyl)-5-(trifluoromethyl)phenyl)amino)pyrimidine-5-carboxamide Step 122-1: N,N-dibenzyl-3-(1-methoxycyclopropyl)-5-(trifluoromethyl)aniline. To a solution of 1-(3-amino-5-(trifluoromethyl)phenyl)cyclopropan-1-ol (150 mg, 0.4 mmol) in 7 mL anhydrous THF, NaH (20 mg, 0.4 mmol) and MeI (35 μL, 0.6 mmol) was added. After 16 h the THF was removed and the crude was purified using silica gel chromatography with 0-20% DCM in Pet. Ether to afford the title compound (99 mg, 64%). HPLC (Method 1): $t_R$=3.44 min, m/z (ES+) (M+H)+412.1

Step 122-2: 3-(1-methoxycyclopropyl)-5-(trifluoromethyl)aniline. Prepared by an analogous method to step 115-2 using N,N-dibenzyl-3-(1-methoxycyclopropyl)-5-(trifluoromethyl)aniline. HPLC (Method 1): $t_R$=2.82 min, m/z (ES+) (M+H)+231.8.

Step 122-3: (S)-2-(3-aminopiperidin-1-yl)-4-((3-(1-methoxycyclopropyl)-5-(trifluoromethyl)phenyl)amino)pyrimidine-5-carboxamide. Prepared by an analogous method to example 3 using 3-(1-methoxycyclopropyl)-5-(trifluoromethyl)aniline. $^1$H NMR (400 MHz, DMSO-d6) δ 11.8 (s, 1H), 8.69 (s, 1H), 8.09-8.00 (m, 2H), 7.20 (s, 1H), 4.53-4.37 (br s, 2H), 3.18 (s, 3H), 2.35-2.33 (m, 1H), 1.92-1.85 (m, 1H), 1.74-1.69 (m, 2H), 1.69-1.51 (br s, 1H), 1.27-1.23 (m, 2H), 1.23-1.19 (m, 2H), 1.13-1.08 (m, 2H); HPLC (Method 1): $t_R$=2.31 min, m/z (ES+) (M+H)+451.3.

Example 123: (S)-2-(3-aminopiperidin-1-yl)-4-((2-isopropyl-6-(tetrahydro-2H-pyran-4-yl)pyridin-4-yl)amino)pyrimidine-5-carboxamide Step 123-1: 2-bromo-6-(prop-1-en-2-yl)pyridin-4-amine. A stirred solution of potassium carbonate (7.5 g, 53.7 mmol), 4,4,5,5-tetramethyl-2-(prop-1-en-2-yl)-1,3,2-dioxaborolane (3.88 mL, 23.3 mmol) and 2,6-dibromopyridin-4-amine (4.0 g, 17.9 mmol) in 1,4-dioxane (200 mL) and water (40 mL) was purged with nitrogen for 10 min. PdCl$_2$(PPh$_3$)$_2$ (0.78 g, 1.3 mmol) was added and purging was continued for a further 10 min. The reaction was then heated 80° C. and stirred under nitrogen for 1 h. Upon cooling, the solution was diluted with water (30 mL) and extracted with ethyl acetate (3×30 mL). The combined organic layers were dried over magnesium sulfate, filtered and concentrated under vacuum. The crude product was purified by chromatography on silica gel (50% CH$_2$Cl$_2$/hexane) to afford the title compound (1.58 g, 42%). m/z (M+H)+ (ES+) 213.09; $t_R$=02.22 min. HPLC Method 2. $^1$H NMR (400 MHz, CDCl$_3$) δ 6.61 (d, 1H, J=1.7 Hz), 6.59 (d, 1H, J=1.7 Hz), 5.86 (m, 1H), 5.23 (m, 1H), 4.19 (br s, 2H), 2.11 (s, 3H).

Step 123-2: 2-(3,6-dihydro-2H-pyran-4-yl)-6-(prop-1-en-2-yl)pyridin-4-amine. A stirred solution of potassium carbonate (1.9 g, 14.20 mmol), 2-(3,6-dihydro-2H-pyran-4-yl)-4,4,5,5-tetramethyl-1,3,2-dioxaborolane (1.3 g, 6.13 mmol) and 2-bromo-6-(prop-1-en-2-yl)pyridin-4-amine (1.0 g, 4.72 mmol) in 1,4-dioxane (40 mL) and water (10 mL) was purged with nitrogen for 10 min. PdCl$_2$(PPh$_3$)$_2$ (0.17 g, 0.24 mmol) was added and purging was continued for a further 10 min. The reaction was then heated 100° C. and stirred under nitrogen for 1 h. Upon cooling, the solution was diluted with water (20 mL) and extracted with ethyl acetate (3×20 mL). The combined organic layers were dried over magnesium sulfate, filtered and concentrated under vacuum. The crude product was purified by chromatography on silica gel (40% AcOEt in hexane) to afford the title compound (1.0 g, 98%). m/z (M+H)+ (ES+) 217.2; $t_R$=2.3 min. HPLC Method 2. $^1$H NMR (400 MHz, CDCl$_3$) δ 6.75-6.68 (m, 1H), 6.61 (d, J=1.9 Hz, 1H), 6.50 (d, J=1.9 Hz, 1H), 5.90-5.83 (m, 1H), 5.27-5.19 (m, 1H), 4.35 (app. q, J=2.8 Hz, 2H), 4.08 (s, 2H), 3.92 (t, J=5.5 Hz, 2H), 2.65-2.58 (m, 2H), 2.17 (dd, J=1.6, 0.8 Hz, 3H).

Step 123-3: 2-chloro-4-((2-(3,6-dihydro-2H-pyran-4-yl)-6-(prop-1-en-2-yl)pyridin-4-yl)amino)pyrimidine-5-carboxamide. To a stirred solution of 2,4-dichloropyrimidine-5-carboxamide (0.82 g, 4.26 mmol) in 1,4-dioxane (30 mL) was added 2-(3,6-dihydro-2H-pyran-4-yl)-6-(prop-1-en-2-yl)pyridin-4-amine (0.71 g, 0.3.27 mmol) and DIPEA (0.77 mL, 4.41 mmol). The reaction was heated to 90° C. and stirred for 18 h. The mixture was allowed to cool and concentrated under vacuum. The crude product was purified by chromatography on silica gel (50-100% EtOAc/hexane) to afford the title compound (0.65 g, 53%). m/z (M+H)+ (ES+) 372.2; $t_R$=2.85 min. HPLC Method 2.

Step 123-4: tert-butyl (S)-(1-(5-carbamoyl-4-((2-(3,6-dihydro-2H-pyran-4-yl)-6-(prop-1-en-2-yl)pyridin-4-yl)amino)pyrimidin-2-yl)piperidin-3-yl)carbamate. To a stirred solution of 2-chloro-4-((2-(3,6-dihydro-2H-pyran-4-yl)-6-(prop-1-en-2-yl)pyridin-4-yl)amino)pyrimidine-5-carboxamide (80 mg, 0.22 mmol) in 1,4-dioxane (4 mL) was added (S)-tert-butyl piperidin-3-ylcarbamate (48 mg, 0.24 mmol) and DIPEA (0.04 mL, 0.24 mmol). The reaction was heated to 90° C. and stirred for 18 h. The mixture was allowed to cool and concentrated under vacuum. The crude product was purified by chromatography on silica gel (50-100% EtOAc/hexane) to afford to afford the title compound (31 mg, 26%). m/z (M+H)+ (ES+) 535.3; $t_R$=2.28 min. HPLC Method 2.

Step 123-5: tert-butyl (S)-(1-(5-carbamoyl-4-((2-isopropyl-6-(tetrahydro-2H-pyran-4-yl)pyridin-4-yl)amino)pyrimidin-2-yl)piperidin-3-yl)carbamate. To a stirred solution of tert-butyl (S)-(1-(5-carbamoyl-4-((2-(3,6-dihydro-2H-pyran-4-yl)-6-(prop-1-en-2-yl)pyridin-4-yl)amino)pyrimidin-2-yl)piperidin-3-yl)carbamate (31 mg, 0.06 mmol) in CH$_2$Cl$_2$ (1 mL) and MeOH (2 mL) was added Pd/C (10% Pd, 9 mg). The mixture was placed under a H$_2$ atmosphere (1 atm) and stirred for 18 h. The crude mixture was filtered through a celite pad and concentrated under vacuum. The crude product was purified by chromatography on silica gel (5% MeOH/CH$_2$Cl$_2$) to afford the title compound (30 mg, 96%). m/z (M+H)+ (ES+) 540.3; $t_R$=2.25 min. HPLC Method 2.

Step 123-6: (S)-2-(3-aminopiperidin-1-yl)-4-((2-isopropyl-6-(tetrahydro-2H-pyran-4-yl)pyridin-4-yl)amino)pyrimidine-5-carboxamide. To a stirred solution of tert-butyl (S)-(1-(5-carbamoyl-4-((3-isopropyl-5-(tetrahydro-2H-pyran-4-yl)phenyl)amino)pyrimidin-2-yl)piperidin-3-yl)carbamate (30 mg, 0.058 mmol) in 1,4-dioxane (2 mL) was added 4 N HCl in dioxane (1 mL) and the mixture was stirred for 18 h. The mixture was concentrated under reduced pressure to afford the hydrochloride salt of the title compound (20 mg, 79%). m/z (M+H)+(ES+) 440.4; $t_R$=1.62 min. HPLC Method 2. ¹H NMR (500 MHz, MeOD) δ 8.80 (s, 1H), 8.04 (s, 1H), 7.92 (s, 1H), 4.58-4.48 (m, 1H), 4.19 (br. s, 1H), 4.14-4.00 (m, 2H), 3.85-3.68 (m, 2H), 3.67-3.49 (m, 3H), 3.44 (br. s, 1H), 3.21 (br. s, 1H), 2.18 (br. s, 1H), 2.03-1.70 (m, 7H), 1.49-1.35 (m, 6H).

Example 124: (S)-2-(3-aminopiperidin-1-yl)-4-((2-(1,1-dioxidotetrahydro-2H-thiopyran-4-yl)-6-isopropylpyridin-4-yl)amino)pyrimidine-5-carboxamide Step 124-1: 2-(3,6-dihydro-2H-thiopyran-4-yl)-6-(prop-1-en-2-yl)pyridin-4-amine. A stirred solution of potassium carbonate (0.76 g, 5.5 mmol), 2-(3,6-dihydro-2H-thiopyran-4-yl)-4,4,5,5-tetramethyl-1,3,2-dioxaborolane (0.54 g, 2.4 mmol) and 2-bromo-6-(prop-1-en-2-yl)pyridin-4-amine (0.40 g, 1.8 mmol) in 1,4-dioxane (15 mL) and water (3 mL) was purged with nitrogen for 10 min. PdCl$_2$(PPh$_3$)$_2$ (0.13 g, 0.2 mmol) was added and purging was continued for a further 10 min. The reaction was then heated 100° C. and stirred under nitrogen for 1 h. Upon cooling, the solution was diluted with water (20 mL) and extracted with ethyl acetate (3×20 mL). The combined organic layers were dried over magnesium sulfate, filtered and concentrated under vacuum. The crude product was purified by chromatography on silica gel (20-50% EtOAc/hexane) to afford the title compound (0.30 g, 70%). m/z (M+H)⁺ (ES+) 233.28; t$_R$=2.48 min. HPLC Method 2. ¹H NMR (400 MHz, CDCl$_3$) δ 6.78 (m, 1H), 6.61 (d, 1H, J=2.0 Hz), 6.51 (d, 1H, J=2.0 Hz), 5.86 (m, 1H), 5.21 (m, 1H), 4.05 (br s, 2H), 3.39-3.35 (m, 2H), 2.90-2.86 (m, 2H), 2.85-2.80 (m, 2H), 2.16 (s, 3H).

Step 124-2: 4-(4-amino-6-(prop-1-en-2-yl)pyridin-2-yl)-3,6-dihydro-2H-thiopyran 1,1-dioxide. To a stirred solution of 2-(3,6-dihydro-2H-thiopyran-4-yl)-6-(prop-1-en-2-yl) pyridin-4-amine (0.1 g, 0.4 mmol) in CH$_2$Cl$_2$ (10 mL) at 0° C. was added m-CPBA (0.3 g, 1.7 mmol). The mixture was stirred for 2 h at 0° C., then it was quenched by addition of aqueous Na$_2$S$_2$O3 (10 mL). The layers were separated, the organic layer was washed with aqueous NaHCO3 (10 mL) and the combined aqueous layers were extracted with CH2Cl2 (3×10 mL). The combined organic layers were dried over magnesium sulfate, filtered and concentrated under vacuum. The crude product was purified by chromatography on silica gel (40-75% EtOAc/isohexane) to afford the title compound (48 mg, 42%). m/z (M+H)⁺ (ES⁺) 265.27; t$_R$=2.02 min. HPLC Method 2. ¹H NMR (500 MHz, CDCl$_3$) δ 6.65 (d, 1H, J=1.9 Hz), 6.54 (d, 1H, J=1.9 Hz), 6.42 (m, 1H), 5.85 (m, 1H), 5.24 (m, 1H), 4.13 (br s, 2H), 3.84-3.78 (m, 2H), 3.37-3.31 (m, 2H), 3.25-3.19 (m, 2H), 2.16 (s, 3H).

Step 124-3: 2-chloro-4-((2-(1,1-dioxido-3,6-dihydro-2H-thiopyran-4-yl)-6-(prop-1-en-2-yl)pyridin-4-yl)amino)pyrimidine-5-carboxamide. To a stirred solution of 2,4-dichloropyrimidine-5-carboxamide (0.05 g, 0.25 mmol) in 1,4-dioxane (5 mL) was added 4-(4-amino-6-(prop-1-en-2-yl) pyridin-2-yl)-3,6-dihydro-2H-thiopyran 1,1-dioxide (0.05 g, 0.18 mmol) and DIPEA (3.4 µL, 0.20 mmol). The reaction was heated to 70° C. and stirred for 18 h. The mixture was allowed to cool and concentrated under vacuum. The crude product was purified by chromatography on silica gel (50-100% EtOAc/hexane) to afford the title compound (35 mg, 46%). m/z (M−H)⁻ (ES⁻) 418.18; t$_R$=2.32 min. HPLC Method 2.

Step 124-4: tert-butyl (S)-(1-(5-carbamoyl-4-((2-(1,1-dioxido-3,6-dihydro-2H-thiopyran-4-yl)-6-(prop-1-en-2-yl) pyridin-4-yl)amino)pyrimidin-2-yl)piperidin-3-yl)carbamate. To a stirred solution of 2-chloro-4-((2-(1,1-dioxido-3,6-dihydro-2H-thiopyran-4-yl)-6-(prop-1-en-2-yl)pyridin-4-yl)amino)pyrimidine-5-carboxamide (35 mg, 0.083 mmol) in 1,4-dioxane (2 mL) was added (S)-tert-butyl piperidin-3-ylcarbamate (mg, 0.083 mmol) and DIPEA (1.6 µL, 0.09 mmol). The reaction was heated to 50° C. and stirred for 18 h, then allowed to cool and concentrated under vacuum. The material was taken to the next step without further purification. m/z (M+H)⁺ (ES⁺) 584.39; t$_R$=2.55 min. HPLC Method 2.

Step 124-5: tert-butyl (S)-(1-(5-carbamoyl-4-((2-(1,1-dioxidotetrahydro-2H-thiopyran-4-yl)-6-isopropylpyridin-4-yl)amino)pyrimidin-2-yl)piperidin-3-yl)carbamate. To a stirred solution of tert-butyl (S)-(1-(5-carbamoyl-4-((2-(1,1-dioxido-3,6-dihydro-2H-thiopyran-4-yl)-6-(prop-1-en-2-yl) pyridin-4-yl)amino)pyrimidin-2-yl)piperidin-3-yl)carbamate (48 mg, 0.083 mmol) in CH2Cl2 (1 mL) and MeOH (2 mL) was added Pd/C (10% Pd, 9 mg). The mixture was placed under a H$_2$ atmosphere and stirred for 18 h. The crude mixture was filtered through a celite pad and concentrated under vacuum. The crude product was purified by chromatography on silica gel (5% MeOH/CH$_2$C$_{12}$) to afford the title compound (20 mg, 41%). m/z (M+H)⁺ (ES⁺) 588.34; t$_R$=2.46 min. HPLC Method 2.

Step 124-6: (S)-2-(3-aminopiperidin-1-yl)-4-((2-(1,1-dioxidotetrahydro-2H-thiopyran-4-yl)-6-isopropylpyridin-4-yl)amino)pyrimidine-5-carboxamide. To a stirred solution of tert-butyl (S)-(1-(5-carbamoyl-4-((2-(1,1-dioxidotetrahydro-2H-thiopyran-4-yl)-6-isopropylpyridin-4-yl)amino) pyrimidin-2-yl)piperidin-3-yl)carbamate (20 mg, 0.034 mmol) in 1,4-dioxane (2 mL) was added 4 N HCl in dioxane (1 mL) and the mixture was stirred for 18 h. The mixture was concentrated under reduced pressure to afford the hydrochloride salt of the title compound (17 mg, 99%). m/z (M+H)⁺ (ES⁺) 488.32; t$_R$=2.07 min. HPLC Method 2. ¹H NMR (500 MHz, MeOD) δ 8.84 (s, 1H), 8.38 (s, 1H), 7.77 (s, 1H), 4.57 (br, 1H), 4.22 (br, 1H), 3.90-3.74 (m, 2H), 3.55-3.37 (m, 5H), 3.29-3.24 (m, 2H), 2.52-2.37 (m, 4H), 2.23 (m, 1H), 2.05 (m, 1H), 1.92-1.80 (m, 2H), 1.47 (d, 6H, J=7.1 Hz).

Example 125: 2-((S)-3-aminopiperidin-1-yl)-4-((2-isopropyl-6-((cis)-4-methoxycyclohexyl)pyridin-4-yl)amino)pyrimidine-5-carboxamide Step 125-1: 2-bromo-4-nitro-6-(prop-1-en-2-yl)pyridine. A stirred solution of sodium bicarbonate (2.75 g, 32.8 mmol), 4,4,5,5-tetramethyl-2-(prop-1-en-2-yl)-1,3,2-dioxaborolane (2.156 mL, 11.47 mmol) and 2,6-dibromo-4-nitropyridine (3.08 g, 10.93 mmol) in 1,4-dioxane (45 mL) and water (15 mL) was purged with nitrogen for 10 min. PdCl$_2$dppf.CH$_2$Cl$_2$ (0.892 g, 1.093 mmol) was added and purging was continued for a further 10 min. The reaction was then heated to 90° C., stirred under nitrogen for 2 h and then allowed to cool to RT. The mixture was diluted with water (100 mL) and extracted with ethyl acetate (2×200 mL). The combined organic layers were dried over magnesium sulfate, filtered and concentrated under vacuum. The crude product was purified by chromatography on silica gel (80 g cartridge, 0-50% EtOAc/isohexane) to afford 2 to afford the title compound (1.958 g, 56.8% yield). m/z (M+H)⁺ (ES⁺) 243.1, 245.1; t$_R$=2.44 min. HPLC Method 2.

Step 125-2: 2-(4-methoxycyclohex-1-en-1-yl)-4-nitro-6-(prop-1-en-2-yl)pyridine. A stirred solution of sodium bicarbonate (0.265 g, 3.15 mmol), 2-(4-methoxycyclohex-1-en-1-yl)-4,4,5,5-tetramethyl-1,3,2-dioxaborolane (0.25 g, 1.050 mmol) and 2-bromo-4-nitro-6-(prop-1-en-2-yl)pyridine (0.255 g, 1.050 mmol) in 1,4-dioxane (3 mL) and water (1 mL) was purged with nitrogen for 10 min.

PdCl₂dppf.CH₂Cl₂ (0.086 g, 0.105 mmol) was added and purging was continued for a further 10 min. The reaction was then heated to 90° C. and stirred under nitrogen for 2 h. Upon cooling, the reaction mixture was diluted with water (20 mL) and extracted with ethyl acetate (3×20 mL). The combined organic layers were dried over magnesium sulfate, filtered and concentrated under vacuum. The crude product was purified by chromatography on silica gel (40 g cartridge, 0-10% (0.7 M Ammonia/MeOH)/DCM) to afford the title compound (0.19 g, 64.7% yield). m/z (M+H)⁺ (ES⁺) 275.0; $t_R$=3.00 min. HPLC method 2.

Step 125-3: 2-isopropyl-6-(4-methoxycyclohexyl)pyridin-4-amine. A solution of 2-(4-methoxycyclohex-1-en-1-yl)-4-nitro-6-(prop-1-en-2-yl)pyridine (0.19 g, 0.693 mmol) in methanol (10 mL) was hydrogenated in the H-Cube (10% Pd/C, 30×4 mm, Full hydrogen, 40° C., 1 mL/min) and then concentrated under vacuum to afford the title compound (0.135 g, 0.538 mmol, 78% yield, mixture of diastereomers). m/z (M+H)⁺ (ES⁺) 249.1; $t_R$=1.40,1.45 min. HPLC Method 4.

Step 125-4: 2-chloro-4-((2-isopropyl-6-((cis)-4-methoxycyclohexyl)pyridin-4-yl)amino)pyrimidine-5-carboxamide. To a stirred solution of 2,4-dichloropyrimidine-5-carboxamide (0.136 g, 0.707 mmol) and 2-isopropyl-6-(4-methoxycyclohexyl)pyridin-4-amine (0.135 g, 0.544 mmol) in 1,4-dioxane (4 mL) was added DIPEA (0.190 mL, 1.087 mmol). The reaction was heated to 100° C. and stirred for 4 h, then allowed to cool and concentrated under vacuum. The crude product was purified by chromatography on silica gel (12 g cartridge, 0-10% MeOH/DCM) to afford the product as a mixture of diastereomers. The residue was slurried in DCM (5 mL) and the resulting solid was collected by filtration to afford the title compound (0.067 g, 29.0% yield). 1H NMR (500 MHz, DMSO-d6) δ 11.65 (s, 1H), 8.85 (s, 1H), 8.49 (s, 1H), 8.04 (s, 1H), 7.39 (d, 1H, J=1.9 Hz), 7.37 (d, 1H, J=1.9 Hz), 3.47-3.43 (m, 1H), 3.24 (s, 3H), 2.95 (app. p, 1H, J=6.9 Hz), 2.70-2.62 (m, 1H), 1.96-1.89 (m, 2H), 1.85-1.75 (m, 2H), 1.66-1.58 (m, 2H), 1.57-1.48 (m, 2H), 1.23 (d, 6H, J=6.9 Hz). m/z (M+H)⁺ (ES⁺) 404.0; $t_R$=2.59 min. HPLC Method 4.

Step 125-5: tert-butyl ((S)-1-(5-carbamoyl-4-((2-isopropyl-6-((cis)-4-methoxycyclohexyl)pyridin-4-yl)amino)pyrimidin-2-yl)piperidin-3-yl)carbamate. To a stirred solution of 2-chloro-4-((2-isopropyl-6-((cis)-4-methoxycyclohexyl)pyridin-4-yl)amino)pyrimidine-5-carboxamide (0.032 g, 0.079 mmol) in 1,4-dioxane (1 mL) was added (S)-tert-butyl piperidin-3-ylcarbamate (0.017 g, 0.087 mmol) and DIPEA (0.028 mL, 0.158 mmol). The reaction was heated to 100° C. and stirred for 1 h, then allowed to cool and concentrated under vacuum. The crude product was purified by chromatography on silica gel (12 g cartridge, 0-5% (0.7 M Ammonia/MeOH)/DCM) to afford the title compound (0.041 g, 86% yield). m/z (M+H)⁺ (ES⁺) 568.4; $t_R$=1.73 min. HPLC Method 2.

Step 125-6: 2-((S)-3-aminopiperidin-1-yl)-4-((2-isopropyl-6-((cis)-4-methoxycyclohexyl)pyridin-4-yl)amino)pyrimidine-5-carboxamide. To a stirred solution of tert-butyl ((S)-1-(5-carbamoyl-4-((2-isopropyl-6-((cis)-4-methoxycyclohexyl)pyridin-4-yl)amino)pyrimidin-2-yl)piperidin-3-yl)carbamate (0.04 g, 0.070 mmol) in 1,4-dioxane (1 mL) was added HCl (4M in 1,4-dioxane) (0.352 mL, 1.409 mmol) and the reaction was stirred at RT for 16 h. The reaction mixture was then concentrated under vacuum and loaded onto a column of SCX (1 g) in MeOH. The column was washed with MeOH and then the product was eluted with 0.7 M ammonia in MeOH. The resultant mixture was concentrated in vacuo. The product was further purified by chromatography on silica gel (12 g cartridge, 0-10% (0.7 M Ammonia/MeOH)/DCM) to afford the title compound (0.022 g, 63.4% yield). ¹H NMR (500 MHz, CD₃OD) δ 8.60 (s, 1H), 7.64 (d, 1H, J=1.9 Hz), 7.26 (s, 1H), 4.69-4.61 (m, 1H), 4.59-4.51 (m, 1H), 3.58-3.54 (m, 1H), 3.36 (s, 3H), 3.26-3.18 (m, 1H), 3.02 (app. sept., 2H, J=6.6 Hz), 2.89-2.80 (m, 1H), 2.75 (tt, 1H, J=12.0, 3.6 Hz), 2.13-2.03 (m, 3H), 1.95-1.78 (m, 3H), 1.77-1.67 (m, 2H), 1.66-1.55 (m, 3H), 1.52-1.42 (m, 1H), 1.35-1.26 (m, 7H). 4 exchangeable protons missing. m/z (M+H)⁺ (ES⁺) 468.0; $t_R$=1.94 min. HPLC Method 4.

Example 126: (S)-2-(3-aminopiperidin-1-yl)-4-((2-isopropyl-6-(piperidin-4-yl)pyridin-4-yl)amino)pyrimidine-5-carboxamide Step 126-1: -tert butyl 4-amino-6-(prop-1-en-2-yl)-3',6'-dihydro-[2,4'-bipyridine]-1'(2'H)-carboxylate. A stirred solution of potassium carbonate (0.5 g, 3.51 mmol), N-Boc-1,2,3,6-tetrahydropyridine-4-boronic acid pinacol ester (0.5 g, 1.53 mmol) and 2-bromo-6-(prop-1-en-2-yl)pyridin-4-amine (0.25 g, 1.17 mmol) in 1,4-dioxane (8 mL) and water (2 mL) was purged with nitrogen for 10 min. PdCl₂(PPh₃)₂ (0.08 g, 0.12 mmol) was added and purging was continued for a further 10 min. The reaction was then heated 100° C. and stirred under nitrogen for 1 h. Upon cooling, the solution was diluted with water (20 mL) and extracted with ethyl acetate (3×20 mL). The combined organic layers were dried over magnesium sulfate, filtered and concentrated under vacuum. The crude product was purified by chromatography on silica gel (40% AcOEt in hexane) to afford the titled compound (0.3 g, 81%). m/z (M+H)⁺ (ES⁺) 316.3; $t_R$=2.66 min. HPLC Method 2 (Base); ¹H NMR (400 MHz, CDCl₃) δ 6.64 (br. s, 1H), 6.61 (d, J=1.9 Hz, 1H), 6.52-6.48 (m, 1H), 5.86 (d, J=2.1,Hz, 1H), 5.29-5.16 (m, 1H), 4.15-4.04 (m, 4H), 3.68-3.58 (m, 2H), 2.65-2.59 (m, 2H), 2.17 (s, 3H), 1.48 (s, 9H).

Step 126-2: tert-butyl 4-((5-carbamoyl-2-chloropyrimidin-4-yl)amino)-6-(prop-1-en-2-yl)-3',6'-dihydro-[2,4'-bipyridine]-1'(2'H)-carboxylate. To a stirred solution of 2,4-dichloropyrimidine-5-carboxamide (79 mg, 0.42 mmol) in 1,4-dioxane (4 mL) was added tert-butyl 4-amino-6-(prop-1-en-2-yl)-3',6'-dihydro-[2,4'-bipyridine]-1'(2'H)-carboxylate (100 mg, 0.32 mmol) and DIPEA (0.06 mL, 0.35 mmol). The reaction was heated to 70° C. and stirred for 48 h. The mixture was allowed to cool and concentrated under vacuum. The crude product was purified by chromatography on silica gel (gradient 50-70% EtOAc in hexane) to afford the title compound (114 mg, 76%). m/z (M+H)⁺ (ES⁺) 471.4; $t_R$=2.92 min. HPLC Method 2 (Base).

Step 126-3: tert-butyl (S)-4-(4-((2-(3-((tert-butoxycarbonyl)amino)piperidin-1-yl)-5-carbamoylpyrimidin-4-yl)amino)-6-isopropylpyridin-2-yl)piperidine-1-carboxylate.

To a stirred solution of tert-butyl 4-((5-carbamoyl-2-chloropyrimidin-4-yl)amino)-6-(prop-1-en-2-yl)-3',6'-dihydro-[2,4'-bipyridine]-1'(2'H)-carboxylate (57 mg, 0.12 mmol) in 1,4-dioxane (4 mL) was added tert-butyl (S)-piperidin-3-ylcarbamate (24 mg, 0.12 mmol) and DIPEA (0.02 mL, 0.14 mmol). The reaction was heated to 50° C. overnight. The mixture was allowed to cool and concentrated under vacuum. m/z (M+H)⁺ (ES⁺) 635.5; $t_R$=3.05 min. HPLC Method 2 (Base). The crude was dissolved in CH₂Cl₂ (2 mL) and MeOH (3 mL) under N₂ atmosphere and Pd/C (10% Pd, 30 mg) was added. The mixture was placed under a H₂ atmosphere (1 atm) and stirred for 1 h. The crude mixture was filtered through a celite pad, concentrated under vacuum and used in the next step without further purification. m/z (M+H)⁺ (ES⁺) 639; $t_R$=2.95 min. HPLC Method 2.

Step 126-4: (S)-2-(3-aminopiperidin-1-yl)-4-((2-isopropyl-6-(piperidin-4-yl)pyridin-4-yl)amino)pyrimidine-5-carboxamide. To a stirred solution of tert-butyl (S)-4-(4-((2-(3-((tert-butoxycarbonyl)amino)piperidin-1-yl)-5-carbamoylpyrimidin-4-yl)amino)-6-isopropylpyridin-2-yl)piperidine-1-carboxylate (73 mg, 0.11 mmol) in 1,4-dioxane (3 mL) was added 4 N HCl in dioxane (1 mL) and the mixture was stirred for 18 h. The mixture was concentrated under reduced pressure to afford the hydrochloride salt of the title compound (60 mg, 99%). m/z (M+H)⁺ (ES⁺) 439.5; $t_R$=2.30 min. HPLC Method 2 (Base); ¹H NMR (500 MHz, MeOD) δ 8.81 (s, 1H), 8.15-7.93 (m, 2H), 4.49 (app. dd, J=13.3, 3.5 Hz, 1H), 4.23-4.04 (m, 1H), 3.98-3.89 (m, 1H), 3.85-3.74 (m, 1H), 3.65-3.58 (m, 2H), 3.54-3.49 (m, 1H), 3.48-3.36 (m, 2H), 3.29-3.17 (m, 2H), 2.37-2.26 (m, 2H), 2.26-2.08 (m, 3H), 2.08-1.98 (m, 1H), 1.96-1.76 (m, 2H), 1.45 (d, J=6.9 Hz, 6H).

Example 127: (S)-4-((2-(1-acetylpiperidin-4-yl)-6-isopropylpyridin-4-yl)amino)-2-(3-aminopiperidin-1-yl)pyrimidine-5-carboxamide Step 127-1: 6-(prop-1-en-2-yl)-1',2',3',6'-tetrahydro-[2,4'-bipyridin]-4-amine To a stirred solution of tert-butyl 4-amino-6-(prop-1-en-2-yl)-3',6'-dihydro-[2,4'-bipyridine]-1'(2'H)-carboxylate (0.27 g, 0.87 mmol) in 1,4-dioxane (5 mL) was added 4 N HCl in dioxane (2 mL) and the mixture was stirred for 18 h. The mixture was concentrated under reduced pressure and purified by flash chromatography in silica gel (20% MeOH in DCM) affording the title compound as a white solid (0.17 g, 90%). m/z (M+H)⁺ (ES⁺) 216.3; $t_R$=2.08 min. HPLC Method 2 (Base); ¹H NMR (500 MHz, MeOD) δ 6.86-6.78 (m, 2H), 6.54-6.49 (m, 1H), 5.79 (s, 1H), 5.60 (s, 1H), 3.99-3.94 (m, 2H), 3.51 (app. t, J=5.4 Hz, 2H), 2.85 (s, 2H), 2.21 (s, 3H).

Step 127-2: 1-(4-amino-6-(prop-1-en-2-yl)-3',6'-dihydro-[2,4'-bipyridin]-1'(2'H)-yl)ethan-1-one To a stirred solution of 6-(prop-1-en-2-yl)-1',2',3',6'-tetrahydro-[2,4'-bipyridin]-4-amine (0.16 g, 0.74 mmol) in DCM (10 mL) at 0° C. was added DIPEA (0.28 mL, 1.63 mmol) and acetyl chloride (0.03 mL, 0.74 mmol). The mixture was stirred for 1 h, then diluted with DCM (10 mL) and washed with water (10 mL) and brine (10 mL). The organic phase was concentrated and the crude was purified using reversed phase chromatography (gradient 5-100% Acetonitrile in H₂O with 0.1% of formic acid) affording the title compound as a colourless oil (109 mg, 57%). m/z (M+H)⁺ (ES⁺) 253.3; $t_R$=2.11 min. HPLC Method 2 (Base).

Step 127-3: 4-((1'-acetyl-6-(prop-1-en-2-yl)-1',2',3',6'-tetrahydro-[2,4'-bipyridin]-4-yl)amino)-2-chloropyrimidine-5-carboxamide To a stirred solution of 2,4-dichloropyrimidine-5-carboxamide (46 mg, 0.24 mmol) in 1,4-dioxane (4 mL) was added 1-(4-amino-6-(prop-1-en-2-yl)-3',6'-dihydro-[2,4'-bipyridin]-1'(2'H)-yl)ethan-1-one (40 mg, 0.19 mmol) and DIPEA (0.04 mL, 0.21 mmol). The reaction was heated to 70° C. and stirred for 24 h. The mixture was allowed to cool and concentrated under vacuum. The product was used in the next step without further purification. m/z (M+H)⁺ (ES⁺) 413.3; $t_R$=2.34 min. HPLC Method 2.

Step 127-4: tert-butyl (S)-(1-(4-((2-(1-acetylpiperidin-4-yl)-6-isopropylpyridin-4-yl)amino)-5-carbamoylpyrimidin-2-yl)piperidin-3-yl)carbamate To a stirred solution of the crude from the previous step in 1,4-dioxane (4 mL) was added tert-butyl (S)-piperidin-3-ylcarbamate (33 mg, 0.16 mmol) and DIPEA (0.04 mL, 0.21 mmol). The reaction was heated to 50° C. overnight. The mixture was allowed to cool and concentrated under vacuum. m/z (M+H)⁺ (ES⁺) 577.4; $t_R$=2.56 min. HPLC Method 2.

The crude was dissolved in CH₂Cl₂ (2 mL) and MeOH (3 mL) under N₂ atmosphere and Pd/C (10% Pd, 30 mg) was added. The mixture was placed under a H₂ atmosphere and stirred for 2 h. The crude mixture was filtered through a celite pad, concentrated under vacuum and purified by flash chromatography in silica gel (5% MeOH in DCM) affording the title compound as a colourless oil (24 mg, 17% over four steps). m/z (M+H)⁺ (ES⁺) 581.4; $t_R$=2.42 min. HPLC Method 2.

Step 127-5: (S)-4-((2-(1-acetylpiperidin-4-yl)-6-isopropylpyridin-4-yl)amino)-2-(3-aminopiperidin-1-yl)pyrimidine-5-carboxamide To a stirred solution of tert-butyl (S)-(1-(4-((2-(1-acetylpiperidin-4-yl)-6-isopropylpyridin-4-yl)amino)-5-carbamoylpyrimidin-2-yl)piperidin-3-yl)carbamate (24 mg, 0.04 mmol) in 1,4-dioxane (3 mL) was added 4 N HCl in dioxane (1 mL) and the mixture was stirred for 18 h. The mixture was concentrated under reduced pressure to afford the hydrochloride salt of the title compound (20 mg, 99%). m/z (M+H)⁺ (ES⁺) 481.4; $t_R$=2.07 min. HPLC Method 2 (Base); HPLC Method 2. ¹H NMR (500 MHz, MeOD) δ 8.84 (s, 1H), 8.06 (d, J=5.4 Hz, 1H), 7.97 (app. s, 1H), 4.78 (app. d, J=13.5 Hz, 1H), 4.64-4.53 (m, 1H), 4.28-4.08 (m, 2H), 3.92-3.67 (m, 3H), 3.49-3.39 (m, 1H), 3.36-3.28 (m, 1H), 2.81 (app. t, J=12.8 Hz, 1H), 2.29-2.07 (m, 7H), 2.05-1.94 (s, 1H), 1.92-1.68 (m, 5H), 1.46 (d, J=6.9 Hz, 6H).

Example 128: (S)-2-(3-aminopiperidin-1-yl)-4-((2-(4,4-difluorocyclohexyl)-6-isopropyl pyridin-4-yl)amino)pyrimidine-5-carboxamide Step 128-1: 2-(4,4-difluorocyclohex-1-en-1-yl)-6-(prop-1-en-2-yl)pyridin-4-amine. A solution of 4-amino-2,6-dibromopyridine (0.206 g, 0.82 mmol), 2-(4,4-difluorocyclohex-1-en-1-yl)-4,4,5,5-tetramethyl-1,3,2-dioxaborolane (0.100 g, 0.41 mmol), 4,4,5,5-tetramethyl-2-(prop-1-en-2-yl)-1,3,2-dioxaborolane (0.08 mL, 0.43 mmol), dioxane (8.5 mL), water (2.0 mL) and potassium carbonate (0.189 g, 1.37 mmol) was purged with nitrogen for 10 min. Pd(PPh₃)₂C1₂ (0.032 g, 0.05 mmol) was added and the mixture was heated at 90° C.. After 1 h, additional 4,4,5,5-tetramethyl-2-(prop-1-en-2-yl)-1,3,2-dioxaborolane (0.08 mL, 0.43 mmol) was added and the mixture stirred for a further 1 h at 90° C. The crude product was purified by flash column chromatography on silica (3:1 hexane: EtOAc followed by 2.5:1 and finally 2:1) to give the title compound in around 90% purity (10% 4-amino-2,6-diisopropenylpyridine present by LCMS analysis) as a yellow solid (0.070 g, 34%). ¹H NMR (400 MHz, CDCl₃) δ 6.60 (d, J=2.0 Hz, 1H), 6.53-6.48 (m, 1H), 6.50 (d, J=2.0 Hz, 1H), 5.88-5.85 (m, 1H), 5.24-5.21 (m, 1H), 4.09 (br s, 2H), 2.83-2.67 (m, 4H), 2.22-2.09 (m, 2H), 2.17 (app s, 3H). LCMS: m/z (ES+) (M+H)⁺ 251.2; $t_R$=2.16 min. HPLC Method 1 (Acid).

Step 128-2: 2-(4,4-difluorocyclohexyl)-6-isopropylpyridin-4-amine. Using 2-(4,4-difluorocyclohex-1-en-1-yl)-6-(prop-1-en-2-yl)pyridin-4-amine (0.070 g, 0.28 mmol) from the previous step, 10% Pd on C (0.060 g, 20 mol %), MeOH (5.0 mL), DCM (1.0 mL) and H₂ (1 atmosphere) to give the title compound as a colourless oil (0.064 g, 64%). ¹H NMR (400 MHz, CDCl₃) δ 6.28 (d, J=2.0 Hz, 1H), 6.24 (d, J=2.0 Hz, 1H), 4.17 (br s, 2H), 2.91 (sept, J=6.8 Hz, 1H), 2.70 (tt, J=11.6, 3.2 Hz, 1H), 2.23-2.12 (m, 2H), 2.05-1.96 (m, 2H), 1.94-1.83 (m, 1H), 1.83-1.70 (m, 3H), 1.23 (d, J=6.8 Hz, 6H). LCMS: m/z (ES+) (M+H)⁺ 255.2; $t_R$=2.19 min. HPLC Method 1 (Acid).

Step 128-3: (S)-2-(3-aminopiperidin-1-yl)-4-((2-(4,4-difluorocyclohexyl)-6-isopropyl pyridin-4-yl)amino)pyrimidine-5-carboxamide: 2-(4,4-Difluorocyclohexyl)-6-isopropylpyridin-4-amine (0.065 g, 0.26 mmol), 2,4-dichloropyrimidine-5-carboxamide (0.074 g, 0.39 mmol), triethylamine (0.07 mL, 0.50 mmol) were dissolved in anhydrous dioxane (3.5 mL). The mixture was heated at 90° C. for 3.5 h and left to cool to RT. The reaction mixture was diluted with EtOAc (10 mL) and washed with water (5×10 mL). The organic phase was dried over MgSO₄, filtered and concentrated under reduced pressure to give the crude product from one displacement, which was purified by flash column chromatography on silica (1:1 hexane: EtOAc) to give the product from one displacement (0.030 g), which was used without further characterisation. The intermediate (0.030 g, 0.07 mmol) was dissolved in anhydrous dioxane (1.0 mL) after which triethylamine (0.02 mL, 0.14 mmol) and tert-butyl (S)-piperidin-3-ylcarbamate (0.015 g, 0.07 mmol) was added and the mixture stirred at 50° C. for 1.5 h. The reaction mixture was diluted with EtOAc (10 mL) and washed with water (5×10 mL). The organic phase was dried over MgSO₄, filtered and concentrated under reduced pressure to give the crude product from two displacements, which was purified by flash column chromatography on silica (1:2 hexane: EtOAc followed by 1:3). The intermediate was dissolved in dioxane (2.0 mL) and 4M HCl in dioxane (2.0 mL) was added drop-wise. The reaction mixture was left to stir at RT overnight and then hexane (10 mL) was added. The resulting suspension was filtered and the solid dried to give the title compound as a white powder, containing 6% Example 54 by LCMS analysis (0.023 g, 18%). ¹H NMR (400 MHz, CD₃OD) δ 8.72 (s, 1H), 8.01 (br s, 1H), 7.82 (s, 1H), 4.43-427 (m, 1H), 3.78-3.61 (m, 2H), 3.49-3.40 (m, 1H), 3.29 (sept, J=5.6 Hz, 1H), 3.14 (app t, J=9.2 Hz, 1H), 2.22-2.05 (m, 5H), 2.03-1.85 (m, 4H), 1.85-1.68 (m, 4H), 1.36 (d, J=5.6 Hz, 6H). LCMS: m/z (ES+) (M+H)⁺ 474.3; $t_R$=1.93 min. HPLC Method 1 (Acid).

Example 129: (S)-2-(3-aminopiperidin-1-yl)-4-((2-isopropyl-6-(4-(trifluoromethyl)phenyl)pyridin-4-yl)amino)pyrimidine-5-carboxamide Step 129-1: 2-(prop-1-en-2-yl)-6-(4-(trifluoromethyl)phenyl)pyridin-4-amine. Using 4-amino-2,6-dibromopyridine (0.350 g, 1.39 mmol), (4-(trifluoromethyl)phenyl)boronic acid (0.290 g, 1.53 mmol), 4,4,5,5-tetramethyl-2-(prop-1-en-2-yl)-1,3,2-dioxaborolane (0.26 mL, 1.38 mmol), dioxane (13.0 mL), water (3.0 mL) and potassium carbonate (0.576 g, 4.17 mmol) was purged with nitrogen for 10 min. Pd(PPh₃)₂Cl₂ (0.054 g, 0.07 mmol) was added and the mixture was heated at 90° C. After 3 h, additional 4,4,5,5-tetramethyl-2-(prop-1-en-2-yl)-1,3,2-dioxaborolane (0.10 mL, 0.05 mmol) was added and the mixture stirred for a further 1 h at 90° C. The crude product was purified by flash column chromatography on silica (DCM followed by 5:1 DCM: EtOAc) to give the title compound as a white solid (0.112 g, 29%). ¹H NMR (400 MHz, CDCl₃) δ 8.11 (d, J=8.0 Hz, 2H), 7.69 (d, J=8.0 Hz, 2H), 6.91-6.86 (m, 1H), 6.73-6.68 (m, 1H), 5.97 (app s, 1H), 5.30 (app s, 1H), 4.26-4.14 (br s, 2H), 2.22 (s, 3H). LCMS: m/z (ES+) (M+H)⁺ 279.1; $t_R$=2.05 min. HPLC Method 1 (Acid).

Step 129-2: 2-isopropyl-6-(4-(trifluoromethyl)phenyl) pyridin-4-amine. Using 2-(prop-1-en-2-yl)-6-(4-(trifluoromethyl)phenyl)pyridin-4-amine (0.112 g, 0.40 mmol), 10% Pd on C (0.043 g, 10 mol %), MeOH (7.5 mL), DCM (1.5 mL) and H₂ (1 atmosphere) to give the title compound as a colourless oil (0.111 g, 99%). ¹H NMR (400 MHz, CDCl₃) δ 8.07 (d, J=8.0 Hz, 2H), 7.67 (d, J=8.0 Hz, 2H), 6.80 (app s, 1H), 6.42 (app s, 1H), 4.20-4.08 (br s, 2H), 3.01 (sept, J=6.8 Hz, 1H), 1.32 (d, J=6.8 Hz, 6H). LCMS: m/z (ES+) (M+H)⁺ 281.9; $t_R$=2.00 min. HPLC Method 1 (Acid).

Step 129-3: 2-chloro-4-((2-isopropyl-6-(4-(trifluoromethyl)phenyl)pyridine-4-yl)amino) pyrimidine-5-carboxamide. 2-Isopropyl-6-(4-(trifluoromethyl)phenyl)pyridin-4-amine (0.116 g, 0.41 mmol), 2,4-dichloropyrimidine-5-carboxamide (0.119 g, 0.62 mmol), DIPEA (0.15 mL, 0.86 mmol) were dissolved in anhydrous dioxane (4.0 mL). The mixture was heated at 90° C. for 6 h and left to cool to RT. The reaction mixture was diluted with EtOAc (10 mL) and washed with water (5×10 mL). The organic phase was dried over MgSO₄, filtered and concentrated under reduced pressure to give the crude product from one displacement, which was purified by flash column chromatography on silica (1:1 hexane: EtOAc followed by EtOAc) to give the product from one displacement, 2-chloro-4-((2-isopropyl-6-(4-(trifluoromethyl)phenyl)pyridin-4-yl)amino)pyrimidine-5-carboxamide (0.116 g, 65%), which was used without further characterisation.

Step 129-4: (S)-2-(3-aminopiperidin-1-yl)-4-((2-isopropyl-6-(4-(trifluoromethyl)phenyl) pyridin-4-yl)amino)pyrimidine-5-carboxamide: 2-Chloro-4-((2-isopropyl-6-(4-(trifluoro-methyl)phenyl)pyridin-4-yl)amino)pyrimidine-5-carboxamide (0.078 g, 0.18 mmol) was dissolved in anhydrous dioxane (4.0 mL) after which triethylamine (0.05 mL, 0.14 mmol) and tert-butyl (S)-piperidin-3-ylcarbamate (0.036 g, 0.18 mmol) was added and the mixture stirred at 50° C. for 2.0 h. The reaction mixture was diluted with EtOAc (10 mL) and washed with water (5×10 mL). The organic phase was dried over MgSO₄, filtered and concentrated under reduced pressure to give the crude product from two displacements, which was purified by flash column chromatography on silica (1:2 hexane: EtOAc). The intermediate was dissolved in dioxane (2.5 mL) and 4M HCl in dioxane (2.5 mL) was added drop-wise. The reaction mixture was left to stir at RT overnight and then hexane (10 mL) was added. The resulting suspension was filtered and the solid dried to give the title compound as a white powder (0.038 g, 40%). m/z (ES⁺) (M+H)⁺ 500.3; $t_R$=2.97 min. HPLC Method 1 (Base); ¹H NMR (400 MHz, CD₃OD) δ 8.85 (s, 1H), 8.41 (app s, 1H), 8.20 (app s, 1H), 8.13 (d, J=7.2 Hz, 2H), 8.01 (d, J=7.2 Hz, 2H), 4.47 (app d, J=11.2 Hz, 1H), 4.31-3.90 (m, 2H), 3.88-3.71 (m, 1H), 3.61-3.45 (m, 2H), 2.30-2.14 (m, 1H), 2.07-1.75 (m, 3H), 1.52 (d, J=6.4 Hz, 6H).

Example 130: (S)-2-(3-aminopiperidin-1-yl)-4-((2-cyclopentyl-6-isopropylpyridin-4-yl)amino)pyrimidine-5-carboxamide Step 130-1: 2,6-Dibromo-N,N-bis(4-methoxybenzyl) pyridin-4-amine: A mixture of 2,6-dibromo-4-aminopyridine (1.00 g, 3.97 mmol) and sodium hydride (0.35 g, 8.73 mmol) in DMF (20 mL) was stirred at 0° C. for 1 h. 4-Methoxybenzyl chloride (1.18 mL, 8.73 mmol) was added and the mixture was stirred for 2 h at RT. The mixture was extracted with AcOEt (30 mL), washed with brine (5×30 mL), dried over MgSO₄ and concentrated under reduced pressure. The crude was purified by recrystallization in hot Hexane: AcOEt, affording the titled compound as a pale purple solid (1.08 g. 55%). m/z (M+H)⁺ (ES+) 491.0, 493.0, 495.0, 496.0; $t_R$=3.09 min. HPLC Method 2; ¹H NMR (400

MHz, CDCl₃) δ 7.1-7.04 (m, 4H), 6.96-6.86 (m, 4H), 6.76 (s, 2H), 4.53 (s, 4H), 3.84 (s, 6H).

Step 130-2: 2-Bromo-N,N-bis(4-methoxybenzyl)-6-(prop-1-en-2-yl)pyridin-4-amine: A stirred solution of potassium carbonate (1.60 g, 11.60 mmol), 4,4,5,5-tetramethyl-2-(prop-1-en-2-yl)-1,3,2-dioxaborolane (0.95 mL, 5.03 mmol) and 2,6-Dibromo-N,N-bis(4-methoxybenzyl)pyridin-4-amine (1.90 g, 3.87 mmol) in 1,4-dioxane (80 mL) and water (20 mL) was purged with nitrogen for 10 min. PdCl₂(PPh₃)₂ (0.09 g, 0.15 mmol) was added and purging was continued for a further 10 min. The reaction was then heated 80° C. and stirred under nitrogen for 2 h. Upon cooling, the solution was diluted with water (20 mL) and extracted with ethyl acetate (3×20 mL). The combined organic layers were dried over magnesium sulfate, filtered and concentrated under vacuum. The crude product was purified by chromatography on silica gel (0.5% AcOEt in Toluene) to afford the titled compound (0.91 g, 52%). m/z (M+H)⁺ (ES⁺) 453.2, 455.2; $t_R$=3.38 min. HPLC Method 2 (Base); ¹H NMR (400 MHz, CDCl₃) δ 7.12 (d, J=8.4 Hz, 4H), 6.90 (d, J=8.4 Hz, 4H), 6.70 (d, J=1.4 Hz, 2H), 5.81-5.73 (m, 1H), 5.26-5.15 (m, 1H), 4.57 (s, 4H), 3.83 (s, 6H), 2.05 (app. d, J=1.2 Hz, 3H).

Step 130-3: 2-(cyclopent-1-en-1-yl)-N,N-bis(4-methoxybenzyl)-6-(prop-1-en-2-yl)pyridin-4-amine. Using 2-Bromo-N,N-bis(4-methoxybenzyl)-6-(prop-1-en-2-yl)pyridin-4-amine (0.547 g, 1.21 mmol), 2-(cyclopent-1-en-1-yl)-4,4,5,5-tetramethyl-1,3,2-dioxaborolane (0.258 g, 1.33 mmol), dioxane (22.0 mL), water (5.0 mL) and potassium carbonate (0.500 g, 3.62 mmol) was purged with nitrogen for 10 min. Pd(PPh₃)₂Cl₂ (0.085 g, 0.12 mmol) was added and the mixture was heated at 90° C. for 1 h. The crude product was purified by flash column chromatography on silica (4:1 hexane: EtOAc) to give the title compound as a colourless oil (0.438 g, 82%). m/z (ES⁴) (M+H)⁺ 441.3; $t_R$=2.47 min. HPLC Method 1 (Acid); ¹H NMR (400 MHz, CDCl₃) δ 7.15 (d, J=8.4 Hz, 4H), 6.88 (d, J=8.4 Hz, 4H), 6.69 (d, J=2.0 Hz, 1H), 6.62 (d, J=2.0 Hz, 1H), 6.60-6.56 (m, 1H), 5.80 (app d, J=1.2 Hz, 1H), 5.18 (app pent, J=1.2 Hz, 1H), 4.61 (s, 4H), 3.80 (s, 6H), 2.73-2.66 (m, 2H), 2.56-2.49 (m, 2H), 2.15 (s, 3H), 2.00 (app pent, J=7.6 Hz, 2H).

Step 130-4: 2-cyclopentyl-6-isopropyl-N,N-bis(4-methoxybenzyl)pyridin-4-amine. Using 2-(cyclopent-1-en-1-yl)-N,N-bis(4-methoxybenzyl)-6-(prop-1-en-2-yl)pyridin-4-amine (0.438 g, 0.99 mmol), 10% Pd on C (0.210 g, 20 mol %), MeOH (9.0 mL), DCM (1.8 mL) and H₂ (1 atmosphere) to give the title compound as a colourless oil that solidified upon standing (0.339 g, 77%). m/z (ES⁺) (M+H)⁺ 445.3; $t_R$=2.49 min. HPLC Method 1 (Acid); ¹H NMR (400 MHz, CDCl₃) δ 7.04 (d, J=8.8 Hz, 2H), 6.82 (d, J=8.4 Hz, 2H), 6.37 (d, J=2.4 Hz, 1H), 6.35 (d, J=2.4 Hz, 1H), 4.58 (s, 4H), 3.72 (s, 4H), 3.36 (pent, J=8.8 Hz, 1H), 3.29 (sept, J=6.8 Hz, 1H), 2.11-2.01 (m, 2H), 1.68-1.45 (m, 6H), 1.17 (d, J=6.8 Hz, 6H).

Step 130-5: 2-cyclopentyl-6-isopropylpyridin-4-amine. 2-Cyclopentyl-6-isopropyl-N,N-bis(4-methoxybenzyl)pyridin-4-amine (0.339 g, 0.25 mmol) was dissolved in DCM (2.50 mL) and TFA (2.50 mL) was added drop-wise. The mixture was heated at 50° C. for 2 h and then allowed to cool to RT. The reaction mixture was neutralised by the drop-wise addition of a saturated solution of NaHCO₃ (final pH=8-9). The mixture was extracted with EtOAc (3×20 mL) and washed with water (10 mL). The organic phase was dried over MgSO₄, filtered and concentrated under reduced pressure to give the crude product, which was purified by flash column chromatography on silica (1:1 hexane: EtOAc followed by 1:2, EtOAc and finally 5% MeOH in DCM) to give the title compound as a colourless oil (0.147 g, 94%). m/z (ES⁺) (M+H)⁺ 205.3; $t_R$=1.91 min. HPLC Method 1 (Acid); ¹H NMR (400 MHz, CDCl₃) δ 6.28 (d, J=2.0 Hz, 1H), 6.25 (d, J=2.0 Hz, 1H), 3.03 (pent, J=8.0 Hz, 1H), 2.91 (sept, J=7.2 Hz, 1H), 2.08-1.94 (m, 2H), 1.81-1.70 (m, 2H), 1.70-1.55 (m, 4H), 1.21 (d, J=7.2 Hz, 6H).

Step 130-6: 2-chloro-4-((2-cyclopentyl-6-isopropylpyridin-4-yl)amino)pyrimidine-5-carboxamide. 2-Cyclopentyl-6-isopropylpyridin-4-amine (0.147 g, 0.72 mmol), 2,4-dichloropyrimidine-5-carboxamide (0.207 g, 1.08 mmol), Hünig's base (0.25 mL, 1.44 mmol) were dissolved in anhydrous dioxane (6.0 mL). The mixture was heated at 90° C. for 3 h and left to cool to RT. The reaction mixture was diluted with EtOAc (10 mL) and washed with water (5×10 mL). The organic phase was dried over MgSO₄, filtered and concentrated under reduced pressure to give the crude product from one displacement, which was purified by flash column chromatography on silica (1:2 hexane: EtOAc followed by EtOAc) to give the title compound (0.125 g, 48%), which was used without further characterisation.

Step 130-7: (S)-2-(3-aminopiperidin-1-yl)-4-((2-cyclopentyl-6-isopropylpyridin-4-yl)amino) pyrimidine-5-carboxamide: 2-Chloro-4-((2-cyclopentyl-6-isopropylpyridin-4-yl)amino) pyrimidine-5-carboxamide (0.080 g, 0.22 mmol) was dissolved in anhydrous dioxane (2.5 mL) after which triethylamine (0.06 mL, 0.43 mmol) and tert-butyl (S)-piperidin-3-ylcarbamate (0.045 g, 0.22 mmol) was added and the mixture stirred at 50° C. for 2 h. The reaction mixture was diluted with EtOAc (20 mL) and washed with water (5×10 mL). The organic phase was dried over MgSO₄, filtered and concentrated under reduced pressure to give the crude product from two displacements, which was purified by flash column chromatography on silica (EtOAc). The intermediate was dissolved in dioxane (2.5 mL) and 4M HCl in dioxane (2.5 mL) was added drop-wise. The reaction mixture was left to stir at RT for 3.5 h and then hexane (10 mL) was added. The resulting suspension was filtered and the solid dried to give the title compound as a white powder (0.075 g, 80%). m/z (ES⁺) (M+H)⁺ 424.4; $t_R$=2.51 min. HPLC Method 1 (Base). ¹H NMR (400 MHz, CD₃OD) δ 8.82 (s, 1H), 8.01 (app s, 1H), 7.96 (app s, 1H), 4.47 (app d, J=11.6 Hz, 1H), 4.33-4.04 (m, 1H), 4.04-3.70 (m, 2H), 3.58-3.49 (m, 1H), 3.43 (pent, J=8.8 Hz, 1H), 3.36 (sept, J=6.8 Hz, 1H), 2.37-2.15 (m, 3H), 2.07-1.75 (m, 9H), 1.45 (d, J=6.8 Hz, 6H).

Example 131: (S)-2-(3-aminopiperidin-1-yl)-4-((2-cyclohexyl-6-isopropylpyridin-4-yl)amino)pyrimidine-5-carboxamide Step 131-1: 2-(cyclohex-1-en-1-yl)-N,N-bis(4-methoxybenzyl)-6-(prop-1-en-2-yl)pyridin-4-amine. Heated at 90° C. for 2 h, using 2-Bromo-N,N-bis(4-methoxybenzyl)-6-(prop-1-en-2-yl)pyridin-4-amine (0.595 g, 1.31 mmol), cyclohexylboronic acid (0.182 g, 1.44 mmol), dioxane (22.0 mL), water (5.0 mL), potassium carbonate (0.543 g, 3.93 mmol) and Pd(PPh₃)₂Cl₂ (0.092 g, 0.13 mmol). The crude product was purified by flash column chromatography on silica (4:1 hexane: EtOAc) to give the title compound as a colourless oil (0.360 g, 60%). m/z (ES⁺) (M+H)⁺ 455.4; $t_R$=2.65 min. HPLC Method 1 (Acid); ¹H NMR (400 MHz, CDCl₃) δ 7.14 (d, J=8.8 Hz, 4H), 6.87 (d, J=8.8 Hz, 4H), 6.71-6.68 (m, 1H), 6.69 (d, J=2.4 Hz, 1H), 6.63 (d, J=2.4 Hz, 1H), 5.78 (app d, J=1.2 Hz, 1H), 5.17-5.14 (m, 1H), 4.59 (s, 4H), 3.79 (s, 6H), 2.47-2.41 (m, 2H), 2.50-2.17 (m, 2H), 2.13 (s, 3H), 1.79-1.70 (m, 2H), 1.69-1.60 (m, 2H).

Step 131-2: 2-cyclohexyl-6-isopropyl-N,N-bis(4-methoxybenzyl)pyridin-4-amine. Using 2-(cyclohex-1-en-1-yl)-N,N-bis(4-methoxybenzyl)-6-(prop-1-en-2-yl)pyridin-4-amine (0.358 g, 0.79 mmol), 10% Pd on C (0.170 g, 20 mol %), MeOH (9.0 mL), DCM (1.8 mL) and H$_2$ (1 atmosphere) to give the title compound as a colourless oil (0.333 g, 92%). m/z (ES$^+$) (M+H)$^+$ 459.4; t$_R$=2.41 min. HPLC Method 1 (Acid); $^1$H NMR (400 MHz, CDCl$_3$) δ 7.03 (d, J=8.8 Hz, 4H), 6.81 (d, J=8.8 Hz, 4H), 6.34 (app s, 2H), 4.55 (s, 4H), 3.71 (s, 6H), 3.23 (sept, J=6.8 Hz, 1H), 2.89 (app t, J=11.6 Hz, 1H), 1.88 (app d, J=12.0 Hz, 2H), 1.69 (app d, J=12.8 Hz, 2H), 1.61 (app d, J=12.4 Hz, 1H), 1.42-1.19 (m, 4H), 1.15 (d, J=6.8 Hz, 6H). Step 131-3: 2-cyclohexyl-6-isopropylpyridin-4-amine. Using 2-cyclohexyl-6-isopropyl-N,N-bis(4-methoxybenzyl)pyridin-4-amine (0.348 g, 0.76 mmol), DCM (2.5 mL), TFA (2.5 mL) to give the crude product which was purified by flash column chromatography on silica (1:1 hexane: EtOAc followed by 1:2, EtOAc and finally 5% MeOH in DCM) to give the title compound as a colourless oil (0.099 g, 60%). m/z (ES$^+$) (M+H)$^+$ 219.3; t$_R$=2.01 min. HPLC Method 1 (Acid); $^1$H NMR (400 MHz, CDCl$_3$) δ 6.57 (d, J=2.4 Hz, 1H), 6.56 (d, J=2.4 Hz, 1H), 5.10-4.98 (br s, 2H), 3.02 (sept, J=6.8 Hz, 1H), 2.69 (tt, J=11.6, 3.2 Hz, 1H), 1.99-1.91 (m, 2H), 1.91-1.83 (m, 2H), 1.81-1.73 (m, 1H), 1.54-1.36 (m, 5H), 1.31 (d, J=6.8 Hz).

Step 131-4: 2-chloro-4-((2-cyclohexyl-6-isopropylpyridin-4-yl)amino)pyrimidine-5-carboxamide. Using 2-cyclohexyl-6-isopropylpyridin-4-amine (0.099 g, 0.45 mmol), 2,4-dichloropyrimidine-5-carboxamide (0.130 g, 0.68 mmol), DIPEA (0.16 mL, 0.92 mmol) and anhydrous dioxane (5.0 mL), heated at 90° C. for 7 h. The crude product was purified by flash column chromatography on silica (1:2 hexane: EtOAc followed by EtOAc) to give the title compound (0.080 g, 47%), which was used without further characterisation.

Step 131-5: (S)-2-(3-aminopiperidin-1-yl)-4-((2-cyclohexyl-6-isopropylpyridin-4-yl)amino)pyrimidine-5-carboxamide. Using 2-chloro-4-((2-cyclohexyl-6-isopropylpyridin-4-yl)amino)pyrimidine-5-carboxamide (0.040 g, 0.11 mmol), anhydrous dioxane (2.0 mL), triethylamine (0.03 mL, 0.22 mmol) and tert-butyl (S)-piperidin-3-ylcarbamate (0.023 g, 0.11 mmol), reaction heated at 50° C. for 4 h. The crude product was purified by flash column chromatography on silica (1:2.5 hexane: EtOAc). The intermediate was dissolved in dioxane (2.0 mL) and 4M HCl in dioxane (2.0 mL) was added drop-wise. The reaction mixture was left to stir at RT for 2 h and then hexane (10 mL) was added. The resulting suspension was filtered and the solid dried to give the title compound as a white powder (0.018 g, 36%). m/z (ES$^+$) (M+H)$^+$ 438.4; t$_R$=2.62 min. HPLC Method 1 (Base); $^1$H NMR (400 MHz, CD$_3$OD) δ 8.82 (s, 1H), 8.04-7.92 (m, 2H), 4.43 (app d, J=12.4 Hz, 1H), 4.35-3.89 (m, 2H), 3.89-3.74 (m, 1H), 3.64-3.53 (m, 1H), 3.38 (sept, J=6.8 Hz, 1H), 3.06 (app t, J=11.2 Hz, 1H), 2.30-2.18 (m, 1H), 2.13-1.79 (m, 8H), 1.69-1.48 (m, 4H), 1.45 (d, J=6.8 Hz, 6H), 1.42-1.33 (m, 1H).

Example 132: (S)-2-(3-aminopiperidin-1-yl)-4-((2-isopropyl-6-(4-methoxyphenyl)pyridin-4-yl)amino)pyrimidine-5-carboxamide Step 132-1: 2-(4-methoxyphenyl)-6-(prop-1-en-2-yl)pyridin-4-amine. A stirred solution of sodium bicarbonate (0.483 g, 5.74 mmol), (4-methoxyphenyl)boronic acid (0.306 g, 2.011 mmol) and 2-bromo-6-(prop-1-en-2-yl)pyridin-4-amine (0.408 g, 1.915 mmol) in 1,4-dioxane (9 mL) and water (3 mL) was purged with nitrogen for 10 min. PdCl$_2$dppf.CH$_2$Cl$_2$ (0.156 g, 0.191 mmol) was added and purging was continued for a further 10 min. The reaction was heated to reflux and stirred under nitrogen for 2 h, then allowed to cool. The mixture was diluted with brine (20 mL) and extracted with ethyl acetate (3×20 mL). The combined organic layers were dried over magnesium sulfate, filtered and concentrated under vacuum. The crude product was purified by chromatography on silica gel (40 g cartridge, 0-50% EtOAc/isohexane) to afford the title compound (0.285 g, 61.3% yield). (M+H)$^+$ (ES$^+$) m/z 241.2; t$_R$=1.61 min. HPLC Method 2.

Step 132-2: 2-isopropyl-6-(4-methoxyphenyl)pyridin-4-amine. A solution of 2-(4-methoxyphenyl)-6-(prop-1-en-2-yl)pyridin-4-amine (0.285 g, 1.186 mmol) in methanol (10 mL) was hydrogenated in the H-Cube (10% Pd/C, 30×4 mm, Full hydrogen, 40° C., 1 mL/min) and concentrated under vacuum to afford to afford the title compound (0.195 g, 64.5% yield). $^1$H NMR (500 MHz, DMSO d-6) δ 7.89-7.85 (m, 2H), 7.01-7.6.96 (m, 2H), 6.76 (d, 1H, J=1.7 Hz), 6.29 (d, 1H, J=1.7 Hz), 5.89 (s, 2H), 3.79 (s, 3H), 2.81 (sept, 1H, J=6.9 Hz), 1.21 (d, 6H, J=6.9 Hz). m/z (M+H)$^+$ (ES$^+$) 243.0; t$_R$=1.94 min. HPLC Method 4.

Step 132-3: 2-chloro-4-((2-isopropyl-6-(4-methoxyphenyl)pyridin-4-yl)amino)pyrimidine-5-carboxamide. To a stirred solution of 2,4-dichloropyrimidine-5-carboxamide (0.201 g, 1.046 mmol) in 1,4-dioxane (4 mL) was added 2-isopropyl-6-(4-methoxyphenyl)pyridin-4-amine (0.195 g, 0.805 mmol) and DIPEA (0.281 mL, 1.609 mmol). The reaction was heated to 100° C. and stirred for 3 h, then allowed to cool to RT. The mixture was concentrated under vacuum and the crude product was purified by chromatography on silica gel (24 cartridge, 0-5% (0.7 M Ammonia/MeOH)/DCM to afford the title compound (0.226 g, 63.5% yield).

$^1$H NMR (500 MHz, DMSO-d6) δ 11.73 (s, 1H), 8.88 (s, 1H), 8.52 (s, 1H), 8.08-8.01 (m, 4H), 7.50 (s, 1H), 7.08-7.03 (m, 2H), 3.82 (s, 3H), 3.04 (app. p, 1H, J=6.9 Hz), 1.30 (d, 6H, J=6.9 Hz). m/z (M+H)$^+$ (ES+) 398.2, 400.2; t$_R$=1.56 min. HPLC Method 2.

Step 132-4: (S)-tert-butyl (1-(5-carbamoyl-4-((2-isopropyl-6-(4-methoxyphenyl)pyridin-4-yl)amino)pyrimidin-2-yl)piperidin-3-yl)carbamate. To a stirred solution of 2-chloro-4-((2-isopropyl-6-(4-methoxyphenyl)pyridin-4-yl)amino)pyrimidine-5-carboxamide (0.08 g, 0.201 mmol) in 1,4-dioxane (1 mL) was added DIPEA (0.070 mL, 0.402 mmol) and (S)-tert-butyl piperidin-3-ylcarbamate (0.042 g, 0.211 mmol). The reaction was heated to 90° C. for 1 h, then allowed to cool to RT. The mixture was concentrated under vacuum and the crude product was purified by chromatography on silica gel (12 g cartridge, 0-10% (0.7 M Ammonia/MeOH)/DCM) to afford the title compound (0.105 g, 92% yield). m/z (M+H)$^+$ (ES$^+$) 562.4; t$_R$=1.77 min. HPLC Method 2

Step 132-4: (S)-2-(3-aminopiperidin-1-yl)-4-((2-isopropyl-6-(4-methoxyphenyl)pyridin-4-yl)amino)pyrimidine-5-carboxamide. To a stirred solution of (S)-tert-butyl (1-(5-carbamoyl-4-((2-isopropyl-6-(4-methoxyphenyl)pyridin-4-yl)amino)pyrimidin-2-yl)piperidin-3-yl)carbamate (0.110 g, 0.196 mmol) in 1,4-dioxane (2 mL) was added hydrogen chloride (4M in 1,4-dioxane) (0.979 mL, 3.92 mmol) and the reaction was stirred at RT for 16 h. The mixture was then concentrated under vacuum and loaded onto a column of SCX (2 g) in MeOH. The column was washed with MeOH and then the product was eluted with 0.7 M ammonia in MeOH. The resultant mixture was concentrated under vacuum and further purified by chromatography on silica gel (12 g cartridge, 0-10% (0.7 M Ammonia/MeOH)/DCM) to afford (S)-2-(3-aminopiperidin-1-yl)-4-((2-isopropyl-6-(4-methoxyphenyl)pyridin-4-yl)amino)pyrimidine-5-carboxamide (0.06 g, 63.1% yield). $^1$H NMR (500 MHz, CD$_3$OD) δ 8.60 (s, 1H), 7.98 (s, 1H), 7.89-7.84 (m, 2H), 7.38 (s, 1H), 7.04-7.00 (m, 2H), 4.66-4.58 (m, 1H), 4.50 (dt, 1H, J=13.3, 4.4 Hz), 3.86 (s, 3H), 3.30-3.20 (m, 1H), 3.13-3.02 (m, 2H), 2.93-2.85 (m, 1H), 2.10-2.01 (m, 1H), 1.89-1.80 (m, 1H), 1.67-1.56 (m, 1H), 1.55-1.45 (m, 1H), 1.36 (d, 6H, J=7.0 Hz). 5 exchangeable protons missing. m/z (M+H)$^+$ (ES$^+$) 462.3; $t_R$=1.09 min. HPLC method 2.

Example 133: (S)-2-(3-aminopiperidin-1-yl)-4-((5-(2-hydroxypropan-2-yl)-4'-methoxy-[1,1'-biphenyl]-3-yl)amino)pyrimidine-5-carboxamide Step 133-1: Methyl 3-bromo-5-(dibenzylamino)benzoate. To a solution of methyl 3-amino-5 (trifluoromethyl)benzoate (4.34 mmol, 1 g) in acetonitrile (20 mL), DIPEA (10.85 mmol, 1.9 mL) and benzyl bromide (9.1 mmol, 1.11 mL) were added. The mixture was refluxed for 24 h. The resulting mixture was quenched with NH$_4$Cl, and extracted with ethyl acetate. The combined organic layers were dried over sodium sulphate, filtered and concentrated under vacuum. The crude product was purified by silica gel chromatography (0-30% DCM/Pet. Ether) to give the title compound (80%). HPLC (Method 1): $t_R$=$^3$0.41 min, m/z (ES+) (M+H)+410.2.

Step 133-2: Methyl 5-(dibenzylamino)-4'-methoxy-[1,1'-biphenyl]-3-carboxylate. To a solution of Methyl 3-bromo-5-(dibenzylamino)benzoate (0.61 mmol, 250 mg) and (4-methoxyphenyl)boronic acid (10.73 mmol, 112 mg) in 1,4 dioxane: water (8:2 mL); Pd(PPh$_3$)$_4$ (0.0305 mmol, 35 mg) and K$_2$CO$_3$ (1.83 mmol, 252 mg) were added and the reaction was stirred at 100° C. under N$_2$ for 3 h. The resulting mixture was quenched with NH$_4$Cl, and extracted with ethyl acetate. The combined organic layers were dried over sodium sulphate, filtered and concentrated under vacuum. The crude product was purified by silica gel chromatography (0-60% DCM/Pet. Ether) to give the title compound. HPLC (Method 1): $t_R$=3.44 min, m/z (ES+) (M+H)+438.3.

Step 133-3: 2-(5-(dibenzylamino)-4'-methoxy-[1,1'-biphenyl]-3-yl)propan-2-ol. The compound methyl 5-(dibenzylamino)-4'-methoxy-[1,1'-biphenyl]-3-carboxylate (390 mg, 0.9 mmol) was dissolved in THF and cooled to −78° C. under Nitrogen. Methyl lithium (1.6M in diethyl ether, 4.5 mmol, 11 mL) was then added drop wise. The mixture was left to stir at −78° C. for one hour and then quenched with saturated aqueous ammonium chloride. The organic layer was then extracted with ethyl acetate and the organic phase was washed with aq. NaHCO$_3$, brine and finally dried over anhydrous sodium sulphate. The solvent was evaporated and the crude was purified by silica gel chromatography (0-20% DCM/Pet. Ether) to give the title compound (20%). HPLC (Method 1): $t_R$=3.19 min, m/z (ES+) (M+H)+438.2.

Step 133-4: 2-(5-amino-4'-methoxy-[1,1'-biphenyl]-3-yl)propan-2-ol. To a solution of 2-(5-(dibenzylamino)-4'-methoxy-[1,1'-biphenyl]-3-yl)propan-2-ol (73 mg, 0.17 mmol) in methanol (10 mL), 10% Pd/C was added and the reaction was stirred under H$_2$ at RT for 2 h. The solution was filtered and methanol was removed. Crude compound (75%) was used in the next step without any further purification. HPLC (Method 1): $t_R$=2.28 min, m/z (ES+) (M+H)+258.3.

Step 133-5: 2-chloro-4-((5-(2-hydroxypropan-2-yl)-4'-methoxy-[1,1'-biphenyl]-3-yl)amino)pyrimidine-5-carboxamide. Prepared by an analogous method to step 3-1, using acetonitrile, 70° C., 16 h. The compound was used in the next step without any further purification. HPLC (Method 1): $t_R$=2.85 min, m/z (ES+) (M+H)+413.2.

Step 133-6: (S)-2-(3-aminopiperidin-1-yl)-4-((5-(2-hydroxypropan-2-yl)-4'-methoxy-[1,1'-biphenyl]-3-yl)amino)pyrimidine-5-carboxamide. 2-chloro-4-((5-(2-hydroxypropan-2-yl)-4'-methoxy-[1,1'-biphenyl]-3-yl)amino)pyrimidine-5-carboxamide was dissolved in acetonitrile (10 mL). To this DIPEA (0.4 mmol, 70 microlt) and (S)-3-(amino)piperidine (10.14 mmol, 25 mg) were added and the reaction was stirred at RT for 12 hours. The organic layer was then extracted with ethyl acetate and the organic phase was washed with aq. NaHCO$_3$, brine and finally dried over anhydrous sodium sulphate. The solvent was evaporated and the crude was purified by silica gel chromatography (0-20% aceotonitrile/DCM) to give the title compound. 1H NMR (400 MHz, DMSO-d$_6$) δ 8.57 (s, 1H), 7.74-7.58 (br s, 4H), 7.33 (s, 1H), 7.06 (br s, 2H), 4.56-4.47 (dd, 1H), 3.82 (s, 3H), 2.97 (br s, 1H), 2.75-2.64 (m, 2H), 1.95-1.85 (m, 2H), 1.22 (br s, 1H), 1.46 (s, 6H), 1.16 (s, H), 1.14 (br s, 3H); HPLC (Method 1): $t_R$=2.29 min, m/z (ES+) (M+H)+477.4.

Example 134: (S)-2-(3-aminopiperidin-1-yl)-4-((5-isopropyl-4'-methoxy-[1H-biphenyl]-3-yl)amino)pyrimidine-5-carboxamide Step 134-1: 1-bromo-3-nitro-5-(prop-1-en-2-yl)benzene. To a solution 2,6-dibromo-4-nitropyridine (2 g, 7.14 mmol) and 4,4,5,5-tetramethyl-2-(prop-1-en-2-yl)-1,3,2-dioxaborolane (1.4 g, 8.6 mmol) in 1,4 dioxane: water (8:2, 10 mL), Pd(PPh$_3$)$_4$ (0.142 mmol, 164 mg) and K$_2$CO$_3$ (21.4 mmol, 3 g) were added and the reaction was stirred at 100° C. under N$_2$ for 3 h. The resulting mixture was quenched with NH$_4$Cl, and extracted with ethyl acetate. The combined organic layers were dried over sodium sulphate, filtered and concentrated under vacuum. The crude product was purified by silica gel chromatography (0-60% DCM/Pet. Ether) to give the title compound.

Step 134-2: 4'-methoxy-3-nitro-5-(prop-1-en-2-yl)-1,1'-biphenyl. 1-nitro-3,5-di(prop-1-en-2-yl)benzene (0.83 mmol, 200 mg), (4-methoxyphenyl)boronic acid (0.99 mmol, 150 mg), Pd(PPh$_3$)$_4$ (0.016 mmol, 20 mg), K$_2$CO$_3$ (2.5 mmol, 345 mg). The crude product was purified by silica gel chromatography (0-40% DCM/Pet. Ether) to give the title compound (53%).

Step 134-3: 5-isopropyl-4'-methoxy-[1,1'-biphenyl]-3-amine. To a solution of 4'-methoxy-3-nitro-5-(prop-1-en-2-yl)-1,1'-biphenyl (0.44 mmol, 119 mg), in methanol (10 mL), 10% Pd/C was added and the reaction was stirred at RT under H$_2$ for 2 h. The solution was filtered and methanol was removed. Crude compound (98%) was used in the next step without any further purification. HPLC (Method 1): $t_R$=2.67 min, m/z (ES+) (M+H)+241.7.

Step 134-4: 2-chloro-4-((5-isopropyl-4'-methoxy-[1,1'-biphenyl]-3-yl)amino)pyrimidine-5-carboxamide. Prepared by an analogous method to step 3-1, using acetonitrile, 70° C., 16 h. The compound was used in the next step without any further purification. HPLC (Method 1): $t_R$=3.22 min, m/z (ES+) (M+H)+396.6.

Step 134-5: tert-butyl (S)-(1-(5-carbamoyl-4-((5-isopropyl-4'-methoxy-[1,1'-biphenyl]-3-yl)amino)pyrimidin-2-yl)piperidin-3-yl)carbamate. Prepared by an analogous method to step 3-3, using acetonitrile, 60° C., 16 h. HPLC (Method 1): $t_R$=3.08 min, m/z (ES+) (M+H)+561.7.

Step 134-6: (S)-2-(3-aminopiperidin-1-yl)-4-((5-isopropyl-4'-methoxy-[1,1'-biphenyl]-3-yl)amino)pyrimidine-5-carboxamide. Prepared by an analogous method to step 3-4, using N HCl in 1,4-dioxane, RT, 1 h. 1H NMR (400 MHz, DMSO-d$_6$) δ 8.70 (s, 1H), 7.71 (s, 1H), 7.61-7.58 (d, 2H), 7.43 (s, 1H), 7.25 (s, 1H), 7.05-7.02 (d, 2H), 4.35 (br s, 1H), 4.05 (br s, 1H), 3.79 (s, 3H), 3.31 (br.s, 1H), 3.00-2.92 (m, 1H), 2.08-2.00 (br s, 1H), 1.88-1.71 (m, 2H), 1.64-1.56 (m, 1H), 1.26-1.23 (d, 6H); HPLC (Method 1): t$_R$=2.38 min, m/z (ES+) (M+H)+460.8.

Example 135: (S)-2-(3-aminopiperidin-1-yl)-4-((5-(2-cyanopropan-2-yl)-[1,1'-biphenyl]-3-yl)amino) pyrimidine-5-carboxamide Step 135-1: 2-(5-(dibenzylamino)-[1,1'-biphenyl]-3-yl)-2-methylpropanenitrile. A stirred solution of potassium carbonate (0.20 g, 1.44 mmol), phenyl-4,4,5,5-tetramethyl-1,3,2-dioxaborolane (0.15 g, 0.71 mmol) and 2-(3-bromo-5-(dibenzylamino)phenyl)-2-methylpropanenitrile (from step 50-2, 0.20 g, 0.48 mmol) in 1,4-dioxane (8 mL) and water (2 mL) was purged with nitrogen for 10 min. PdCl$_2$(PPh$_3$)$_2$ (34 mg, 0.05 mmol) was added and purging was continued for a further 10 min. The reaction was then heated 100° C. and stirred under nitrogen for 1 h. Upon cooling, the solution was diluted with water (20 mL) and extracted with ethyl acetate (3×20 mL). The combined organic layers were dried over magnesium sulfate, filtered and concentrated under vacuum. The crude product was purified by chromatography on silica gel (20% AcOEt in hexane) to afford the titled product (0.14 g, 74%). m/z (M+H)$^+$ (ES$^+$) 417.3; t$_R$=3.14 min. HPLC Method 2 (Base). $^1$H NMR (400 MHz, Chloroform-d) δ 7.52-7.44 (m, 2H), 7.44-7.25 (m, 13H), 7.02 (d, J=1.5 Hz, 1H), 6.92 (app. t, J=1.9 Hz, 1H), 6.82 (app. t, J=2.1 Hz, 1H), 4.75 (s, 4H), 1.66 (s, 6H).

Step 135-2: 2-(5-amino-[1,1'-biphenyl]-3-yl)-2-methylpropanenitrile. 2-(5-(dibenzylamino)-[1,1'-biphenyl]-3-yl)-2-methylpropanenitrile (0.14 g, 0.34 mmol) was introduced to a flask which was flushed with N$_2$ for 10 min. Pd(OH)$_2$ (0.04 g, 10-20% Pd basis), DCM (3.0 mL) and finally MeOH (3.0 mL) were added and the flask purged with H$_2$. The mixture was left to stir vigorously at RT for 1 h after which the flask was opened to the air and the mixture filtered through a pad of Celite® under reduced pressure. The cake was washed with additional MeOH (30 mL) and DCM (30 mL), the filtrate concentrated under reduced pressure and the crude product purified by flash column chromatography on silica (20% AcOEt in hexane) to give the title compound as a colourless oil (60 mg, 88%). m/z (M+H)$^+$ (ES$^+$) 237.2; t$_R$=2.42 min. HPLC Method 2 (Base); $^1$H NMR (400 MHz, CDCl$_3$) δ 7.61-7.54 (m, 2H), 7.51-7.42 (m, 2H), 7.41-7.35 (m, 1H), 7.05 (app. t, J=1.6 Hz, 1H), 6.86 (app. t, J=1.8 Hz, 1H), 6.82 (app. t, J=2.0 Hz, 1H), 1.77 (s, 6H).

Step 135-3: (S)-2-(3-aminopiperidin-1-yl)-4-((5-(2-cyanopropan-2-yl)-[1,1'-biphenyl]-3-yl)amino)pyrimidine-5-carboxamide. 2-(5-amino-[1,1'-biphenyl]-3-yl)-2-methylpropane-nitrile (60 mg, 0.26 mmol), 2,4-dichloropyrimidine-5-carboxamide (49 mg, 0.26 mmol), DIPEA (0.05 mL, 0.29 mmol) were dissolved in anhydrous dioxane (5 mL). The mixture was heated at 50° C. overnight and then left to cool to RT. Tert-Butyl (S)-piperidin-3-ylcarbamate (52 mg, 0.26 mmol) and DIPEA (0.05 mL, 0.29 mmol) were added and the reaction mixture heated at 50° C. overnight. The mixture was concentrated under reduced pressure to give the crude product from two displacements which was purified by flash column chromatography (60% EtOAc in Hexane) to give the titled product (50 mg, 34%). m/z (M+H)$^+$ (ES$^+$) 556.3; t$_R$=2.69 min. HPLC Method 2 (Base). Dioxane (4 mL) was added followed by the dropwise addition of 4N HCl in dioxane (1 mL) and the reaction mixture was stirred at RT for 24 h. Hexane (30 mL) was added and the solid filtered and triturated with Et$_2$O to remove residual dioxane. The resulting solid was filtered and dried to give the hydrochloride salt of the title compound as a white powder (30 mg, 73%). m/z (M+H)+(ES+) 456.3; t$_R$=2.23 min. HPLC Method 2 (Base); $^1$H NMR (400 MHz, CD$_3$OD) δ 8.61 (s, 1H), 8.04 (br. s, 1H), 7.72 (br. s, 1H), 7.70-7.66 (m, 2H), 7.62 (app. t, J=1.7 Hz, 1H), 7.54-7.49 (m, 2H), 7.46-7.39 (m, 1H), 4.42 (app. dd, J=14.0, 3.7 Hz, 1H), 4.08 (br. s, 1H), 3.82 (br. s, 1H), 3.69-3.60 (m, 1H), 3.57-3.48 (m, 1H), 2.27-2.14 (m, 1H), 2.05-1.94 (m, 1H), 1.88-1.79 (m, 8H.

Example 136: (S)-2-(3-aminopiperidin-1-yl)-4-((4-cyano-3,5-diisopropylphenyl)amino) pyrimidine-5-carboxamide Step 136-1: 4-nitro-2,6-di(prop-1-en-2-yl)benzonitrile. A solution of 1,3-dibromo-2-fluoro-5-nitrobenzene (0.25 g, 0.84 mmol) in DMSO (2 mL) was cooled down to 0° C. Potassium cyanide (0.06 g, 0.88 mmol) was added and the mixture was stirred for 2 h. The crude was diluted with AcOEt (15 mL) and washed with brine (2×20 mL). The organic phase was dried, concentrated and the crude was purified by flash chromatography in silica gel (5% AcOEt in hexane) to afford the title compound as a pale pink solid (90 mg, 35%). $^1$H NMR (500 MHz, CDCl$_3$) δ 8.49 (s, 2H); $^{13}$C NMR (101 MHz, CDCl$_3$) δ 149.5, 127.8, 126.7, 124.4, 114.6.

Step 136-2: 4-nitro-2,6-di(prop-1-en-2-yl)benzonitrile. A stirred solution of potassium carbonate (0.19 g, 1.3 mmol), 4-nitro-2,6-di(prop-1-en-2-yl)benzonitrile (0.14 g, 0.5 mmol) and 4,4,5,5-tetramethyl-2-(prop-1-en-2-yl)-1,3,2-dioxaborolane (0.22 mL, 0.8 mmol) in 1,4-dioxane (5 mL) and water (1 mL) was purged with nitrogen for 10 min. PdCl$_2$(PPh$_3$)$_2$ (0.03 g, 0.05 mmol) was added and purging was continued for a further 10 min. The reaction was then heated 100° C. and stirred under nitrogen for 2 h. Upon cooling, the solution was diluted with water (20 mL) and extracted with ethyl acetate (3×20 mL). The combined organic layers were dried over magnesium sulfate, filtered and concentrated under vacuum. The crude product was purified by chromatography on silica gel (5% AcOEt in hexane) to afford the title compound (75 mg, 66%). $^1$H NMR (400 MHz, CDCl$_3$) δ 8.07 (s, 2H), 5.52-5.48 (m, 2H), 5.33-5.28 (m, 2H), 2.23 (dd, J=1.5, 0.9 Hz, 6H); $^{13}$C NMR (101 MHz, CDCl$_3$) δ 150.4, 149.3, 141.0, 121.3, 120.1, 115.9, 114.5, 23.2.

Step 136-3: 4-amino-2,6-diisopropylbenzonitrile. To a stirred solution of 4-nitro-2,6-di(prop-1-en-2-yl)benzonitrile (88 mg, 0.39 mmol) in CH$_2$Cl$_2$ (1 mL) and MeOH (3 mL) was added Pd/C (10% Pd, 50 mg). The mixture was placed under a H$_2$ atmosphere and stirred for 18 h. The crude mixture was filtered through a celite pad and concentrated under vacuum. The crude product was concentrated and taken into the next step without further purification m/z (M+H)$^+$ (ES$^+$) 203.3; t$_R$=2.44 min. HPLC Method 2 (Base).

Step 136-4: (S)-2-(3-aminopiperidin-1-yl)-4-((4-cyano-3,5-diisopropylphenyl)amino) pyrimidine-5-carboxamide. 4-amino-2,6-diisopropylbenzonitrile (71 mg, 0.35 mmol), 2,4-dichloropyrimidine-5-carboxamide (67 mg, 0.35 mmol), triethylamine (0.05 mL, 0.39 mmol) were dissolved in anhydrous dioxane (5 mL). The mixture was heated at 50° C. overnight and then left to cool to RT. Tert-Butyl (S)-piperidin-3-ylcarbamate (70 mg, 0.35 mmol) and triethylamine (0.05 mL, 0.39 mmol) were added and the reaction mixture heated at 50° C. overnight. The mixture was concentrated under reduced pressure to give the crude product from two displacements which was purified by flash column chromatography (40% EtOAc in Hexane) to give the titled product (80 mg, 44%). m/z (M+H)⁺ (ES⁺) 522.3; $t_R$=2.82 min. HPLC Method 2 (Base). Dioxane (4 mL) was added followed by the drop-wise addition of 4N HCl in dioxane (1 mL) and the reaction mixture was stirred at RT for 24 h. Hexane (30 mL) was added and the solid filtered and triturated with Et₂O to remove residual dioxane. The resulting solid was filtered and dried to give the hydrochloride salt of the title compound as a white powder (55 mg, 87%). m/z (M+H)⁺ (ES+) 422.4; $t_R$=2.30 min. HPLC Method 2 (Base); ¹H NMR (400 MHz, CD₃OD) δ 8.64 (s, 1H), 7.60 (s, 2H), 4.37 (dd, J=13.5, 3.7 Hz, 1H), 4.25-4.06 (s, 1H), 3.86-3.75 (m, 1H), 3.75-3.64 (m, 1H), 3.56-3.45 (m, 1H), 3.43 (p, J=6.8 Hz, 2H), 2.27-2.15 (m, 1H), 2.05-1.92 (m, 1H), 1.91-1.76 (m, 2H), 1.36 (app. dd, J=6.9, 2.0 Hz, 12H).

Example 137: 2-(trans-3-amino-5-hydroxypiperidin-1-yl)-4-((2,6-diisopropylpyridin-4-yl)amino)pyrimidine-5-carboxamide Step 137-1: (trans)-benzyl 3-((tert-butoxycarbonyl)amino)-5-((triethylsilyl)oxy)piperidine-1-carboxylate. To a stirred mixture of tert-butyl (5-hydroxypiperidin-3-yl)carbamate (1 g, 4.62 mmol) and N,N-dimethylpyridin-4-amine (0.056 g, 0.462 mmol) in DCM (20 mL) at RT was added triethylamine (0.968 mL, 6.94 mmol) followed by benzyl carbonochloridate (0.680 mL, 4.62 mmol). The reaction mixture was stirred at RT for 16 h, then washed with sat. ammonium chloride solution (20 mL), dried over magnesium sulfate, filtered and concentrated under vacuum. The residue was dissolved in DMF (25 mL) and cooled to 0° C. Chlorotriethylsilane (0.842 mL, 5.02 mmol) and 1H-imidazole (0.342 g, 5.02 mmol) were added, reaction mixture was allowed to warm to RT and stirred for 16 h. The mixture was then diluted with water (100 mL) and extracted with ethyl acetate (3×100 mL). The combined organic layers were dried over magnesium sulfate, filtered and concentrated under vacuum. The crude product was purified by chromatography on silica gel (80 g cartridge, 0-50% MTBE in hexane) to afford (trans)-benzyl 3-((tert-butoxycarbonyl)amino)-5-((triethylsilyl)oxy)piperidine-1-carboxylate (1.328 g, 59.5% yield). ¹H NMR (500 MHz, DMSO-d6, 90° C.) δ 7.38-7.28 (m, 5H), 6.42 (s, 1H), 5.11 (d, 1H, J=12.8 Hz), 5.03 (d, 1H, J=12.8 Hz), 4.08-4.02 (m, 1H), 3.81-3.68 (m, 2H), 3.54-3.44 (m, 1H), 3.57-3.42 (m, 1H), 3.05-2.90 (m, 1H), 1.77-1.70 (m, 1H), 1.69-1.62 (m, 1H), 1.39 (s, 9H), 0.92 (t, 9H, J=7.9 Hz), 0.57 (q, 6H, J=7.9 Hz). A second isomer, (cis)-benzyl 3-((tert-butoxycarbonyl)amino)-5-((triethylsilyl)oxy)piperidine-1-carboxylate was also isolated (0.524 g, 23.5% yield). ¹H NMR (500 MHz, DMSO-d6, 90° C.) δ 7.38-7.28 (m, 5H), 6.41 (d, 1H, J=6.4 Hz), 5.12 (d, 1H, J=12.7 Hz), 5.06 (d, 1H, J=12.7 Hz), 3.83-3.69 (m, 3H), 3.48-3.40 (m, 1H), 2.91-2.83 (m, 2H), 2.05-1.97 (m, 1H), 1.45 (dt, 1H, J=12.7, 9.2 Hz), 1.39 (s, 9H), 0.93 (t, 9H, J=7.9 Hz), 0.58 (q, 6H, J=7.9 Hz).

Step 137-2: tert-butyl ((trans)-5-((triethylsilyl)oxy)piperidin-3-yl)carbamate. A mixture of (trans)-benzyl 3-((tert-butoxycarbonyl)amino)-5-((triethylsilyl)oxy)piperidine-1-carboxylate (0.5 g, 1.076 mmol) and palladium hydroxide on carbon (0.05 g, 0.356 mmol) in methanol (5 mL) was stirred under an atmosphere of hydrogen (1 Bar) at RT for 16 h. The mixture was then filtered through Celite®, rinsed with methanol (2×20 mL) and concentrated under vacuum to afford the title compound (0.316 g, 84% yield). 1H NMR (500 MHz, DMSO-d6) δ 6.71 (d, 1H, J=7.9 Hz), 3.84-3.79 (m, 1H), 3.57 (s, 1H), 3.45-2.99 (br m, 1H), 2.67 (d, 2H, J=12.9 Hz), 2.42-2.34 (m, 2H), 1.78-1.66 (m, 1H), 1.58-1.48 (m, 1H), 1.38 (s, 9H), 0.91 (t, 9H, J=7.9 Hz), 0.54 (q, 6H, J=7.9 Hz).

Step 137-3: tert-butyl ((trans)-1-(5-carbamoyl-4-((2,6-diisopropylpyridin-4-yl)amino)pyrimidin-2-yl)-5-((triethylsilyl)oxy)piperidin-3-yl)carbamate. To a stirred solution of tert-butyl ((trans)-5-((triethylsilyl)oxy)piperidin-3-yl)carbamate (0.065 g, 0.198 mmol) and 2-chloro-4-((2,6-diisopropylpyridin-4-yl)amino)pyrimidine-5-carboxamide (0.06 g, 0.180 mmol) in 1,4-dioxane (3 mL) was added DIPEA (0.063 mL, 0.359 mmol). The reaction was heated to 50° C. and stirred for 2 h. The mixture was allowed to cool, concentrated under vacuum and purified by chromatography on silica gel (12 g cartridge, 0-10% (0.7 M Ammonia/MeOH)/DCM) to afford the title compound (0.077 g, 66.9% yield). m/z (M+H)⁺ (ES⁺) 628.5; (M–H)⁻ (ES⁻) 626.3. $t_R$=2.21 min. HPLC Method 2.

Step 137-4: 2-((trans)-3-amino-5-hydroxypiperidin-1-yl)-4-((2,6-diisopropylpyridin-4-yl)amino)pyrimidine-5-carboxamide. To a stirred solution of tert-butyl ((trans)-1-(5-carbamoyl-4-((2,6-diisopropylpyridin-4-yl)amino)pyrimidin-2-yl)-5-((triethylsilyl)oxy)piperidin-3-yl)carbamate (0.075 g, 0.119 mmol) in 1,4-dioxane (2 mL) was added hydrochloric acid (4M in 1,4-dioxane) (0.597 mL, 2.389 mmol) and the reaction was stirred at RT for 16 h. The mixture was concentrated under vacuum, dissolved in methanol (1 mL) and loaded onto SCX (ca. 2 g). The SCX was rinsed through with methanol (3×10 mL) followed by ammonia solution (0.7M in methanol, 3×10 mL). The ammoniacal fractions were combined and concentrated under vacuum to afford the title compound (0.043 g, 78% yield).
¹H NMR (500 MHz, CD₃OD) δ 8.63 (s, 1H), 7.48 (s, 2H), 4.60-4.48 (m, 1H), 4.44-4.30 (m, 1H), 4.14-4.09 (m, 1H), 3.65 (app. d, 1H, J=13.3 Hz), 3.39-3.33 (m, 1H), 3.05 (sept, 2H, J=7.0 Hz), 2.09-2.01 (m, 1H), 1.81-1.73 (m, 1H), 1.37-1.28 (m, 13H). 6 exchangeable protons missing. m/z (M+H)⁺ (ES⁺) 414.4; $t_R$=0.80 min. HPLC Method 2.

Example 138: 2-(cis-3-amino-5-hydroxypiperidin-1-yl)-4-((2,6-diisopropylpyridin-4-yl)amino)pyrimidine-5-carboxamide Step 138-1: tert-butyl ((cis)-5-((triethylsilyl)oxy)piperidin-3-yl)carbamate. A mixture of (cis)-benzyl 3-((tert-butoxycarbonyl)amino)-5-((triethylsilyl)oxy)piperidine-1-carboxylate (0.3 g, 0.646 mmol) and palladium hydroxide (0.03 g, 0.214 mmol) in methanol (5 mL) was stirred under an atmosphere of hydrogen (1 Bar) at RT for 16 h. The mixture was then filtered through Celite®, rinsed with methanol (2×20 mL) and concentrated under vacuum to afford to afford the title compound (0.194 g, 86% yield). ¹H NMR (500 MHz, DMSO-d6) δ 6.70 (d, 1H, J=8.2 Hz), 3.57-3.49 (m, 1H), 3.38-3.22 (m, 2H), 2.86-2.76 (m, 2H), 2.06 (dd, 1H, J=11.9, 9.5 Hz), 2.00 (app. t, 1H, J=11.1 Hz), 1.96-1.87 (m, 1H), 1.37 (s, 9H), 1.25-1.13 (m, 1H), 0.91 (t, 9H, J=7.9 Hz), 0.54 (q, 6H, J=7.9 Hz).

Step 138-2: tert-butyl ((cis)-1-(5-carbamoyl-4-((2,6-diisopropylpyridin-4-yl)amino)pyrimidin-2-yl)-5-((triethylsilyl)oxy)piperidin-3-yl)carbamate. To a stirred solution of tert-butyl ((cis)-5-((triethylsilyl)oxy)piperidin-3-yl)carbamate (0.065 g, 0.198 mmol) and 2-chloro-4-((2,6-diisopropylpyridin-4-yl)amino)pyrimidine-5-carboxamide (0.06 g, 0.180 mmol) in 1,4-dioxane (2 mL) was added N-ethyl-N-isopropylpropan-2-amine (0.063 mL, 0.359 mmol). The reaction was heated to 50° C. for 2 h, then allowed to cool and concentrated under vacuum. The crude product was purified by chromatography on silica gel (12 g cartridge, 0-5% (0.7 M Ammonia/MeOH)/DCM) to afford the title compound (0.08 g, 63.8% yield). m/z (M+H)$^+$ (ES$^+$) 628.5; $t_R$=2.29 min. HPLC Method 2.

Step 138-3: 2-((cis)-3-amino-5-hydroxypiperidin-1-yl)-4-((2,6-diisopropylpyridin-4-yl)amino)pyrimidine-5-carboxamide. To a stirred solution of tert-butyl ((3R,5S)-1-(5-carbamoyl-4-((2,6-diisopropylpyridin-4-yl)amino)pyrimidin-2-yl)-5-((triethylsilyl)oxy)piperidin-3-yl)carbamate (0.078 g, 0.124 mmol) in 1,4-dioxane (1 mL) was added hydrogen chloride (4M in 1,4-dioxane) (0.621 mL, 2.484 mmol) and the reaction was stirred at RT for 4 h. The mixture was then concentrated under vacuum. The crude product was loaded onto a column of SCX (2 g) in MeOH. The column was washed with MeOH and then the product was eluted with 0.7 M ammonia in MeOH. The ammonical layers were combined and concentrated under vacuum to afford the title compound (0.046 g, 85% yield). $^1$H NMR (500 MHz, CD$_3$OD) δ 8.63 (s, 1H), 7.46 (s, 2H), 4.75-4.64 (m, 2H), 3.75-3.68 (m, 1H), 3.10-2.95 (m, 4H), 2.94-2.88 (m, 1H), 2.31-2.24 (m, 1H), 1.50-1.41 (m, 1H), 1.34 (d, 12H, J=6.9 Hz). 6 exchangeable protons missing. m/z (M+H)$^+$ (ES$^+$) 414.1; $t_R$=1.65 min. HPLC Method 4.

Example 139: (S)-2-(3-aminopiperidin-1-yl)-4-((2-(tert-butyl)-6-isopropylpyridin-4-yl)amino)pyrimidine-5-carboxamide Step 139-1: 2-(prop-1-en-2-yl)pyridin-4-amine. A stirred solution of potassium carbonate (0.95 g, 6.90 mmol), 2-bromopyridin-4-amine (0.40 g, 2.30 mmol) and 4,4,5,5-tetramethyl-2-(prop-1-en-2-yl)-1,3,2-dioxaborolane (0.65 mL, 3.45 mmol) in 1,4-dioxane (16 mL) and water (4 mL) was purged with nitrogen for 10 min. XPhos Pd G3 (0.19 g, 0.23 mmol) was added and purging was continued for a further 10 min. The reaction was then heated 100° C. and stirred under nitrogen overnight. Upon cooling, the solution was diluted with water (20 mL) and extracted with ethyl acetate (3×20 mL). The combined organic layers were dried over magnesium sulfate, filtered and concentrated under vacuum. The crude product was purified by chromatography on silica gel (5% MeOH in CH$_2$Cl$_2$) to afford the titled compound (100 mg, 33%). m/z (M+H)$^+$ (ES$^+$) 135.2; $t_R$=1.68 min. HPLC Method 2 (Base).

Step 139-2: (S)-2-(3-aminopiperidin-1-yl)-4-((2-isopropylpyridin-4-yl)amino)pyrimidine-5-carboxamide. 2-(prop-1-en-2-yl)pyridin-4-amine (0.10 g, 0.76 mmol), 2,4-dichloropyrimidine-5-carboxamide (0.19 g, 0.98 mmol), DIPEA (0.15 mL, 0.84 mmol) were dissolved in anhydrous dioxane (5 mL). The mixture was heated at 70° C. overnight and then left to cool to RT. The crude was concentrated and purified by flash chromatography in silica gel (30% of Hexane in AcOEt). m/z (M+H)$^+$ (ES$^+$) 290.2; $t_R$=2.16 min. HPLC Method 2 (Base). The resulting white solid (0.12 mg, 0.40 mmol) was dissolved in dioxane (5 mL) and tert-Butyl (S)-piperidin-3-ylcarbamate (0.08 g, 0.40 mmol) and DIPEA (0.08 mL, 0.44 mmol) were added. The reaction mixture heated at 50° C. overnight. The resulting mixture was concentrated under reduced pressure to give the crude product from two displacements. m/z (M+H)$^+$ (ES$^+$) 454.4; $t_R$=2.47 min. HPLC Method 2 (Base). The crude was dissolved in CH$_2$Cl$_2$ (2 mL) and MeOH (3 mL) under N$_2$ atmosphere and Pd/C (10% Pd, 30 mg) was added. The mixture was placed under a H$_2$ atmosphere and stirred for 2 h. The crude mixture was filtered through a celite pad, concentrated under vacuum and purified by flash chromatography in silica gel (20% Hexane in AcOEt) affording the titled product as a white solid (133 mg, 39% over 3 steps). m/z (M+H)$^+$ (ES$^+$) 456.4; $t_R$=2.43 min. HPLC Method 2 (Base). The solid (40 mg, 0.09 mmol) was dissolved in dioxane (5 mL) was added followed by the drop-wise addition of 4N HCl in dioxane (2 mL) and the reaction mixture was stirred at RT for 24 h. Hexane (30 mL) was added and the solid filtered and triturated with Et$_2$O to remove residual dioxane. The resulting solid was filtered and dried to give the hydrochloride salt of the title compound as a white powder (30 mg, 94%). m/z (M+H)$^+$ (ES$^+$) 356.3; $t_R$=2.00 min. HPLC Method 2 (Base); $^1$H NMR (400 MHz, CD$_3$OD) δ 8.78 (s, 1H), 8.66 (br. s, 1H), 8.37 (br. s, 1H), 7.92 (br. s, 1H), 4.50 (dd, J=13.7, 3.7 Hz, 1H), 4.22-4.04 (m, 1H), 3.85-3.73 (m, 1H), 3.73-3.61 (m, 1H), 3.58-3.48 (m, 1H), 3.34-3.26 (m, 1H), 2.25-2.15 (m, 1H), 2.07-1.95 (m, 1H), 1.93-1.74 (m, 2H), 1.42 (d, J=7.0 Hz, 6H).

Step 139-3: (S)-2-(3-aminopiperidin-1-yl)-4-((2-(tert-butyl)-6-isopropylpyridin-4-yl)amino)pyrimidine-5-carboxamide. (S)-2-(3-aminopiperidin-1-yl)-4-((2-isopropylpyridin-4-yl)amino)pyrimidine-5-carboxamide (25 mg, 0.07 mmol), 1,3-dioxoisoindolin-2-yl pivalate (87 mg, 0.35 mmol) and TFA (54 μL, 0.70 mmol) were dissolved in DMSO (1 mL). 4-CzIPN (3 mg, 3.5 μmol) was added. The solution was degassed by bubbling a N$_2$ balloon for 20 min, then it was stirred for 3 h at room temperature under blue LED irradiation. The mixture was filtered through an SCX column washing first with MeOH (10 mL) then 7M NH$_3$ in MeOH (10 mL). The NH$_3$ fraction was concentrated under reduced pressure and the crude product was purified by reverse phase column chromatography (10 to 100% MeCN in H$_2$O gradient, containing 0.1% NH$_{40}$H modifier) to give the title compound as a white powder (5 mg, 25%). m/z (M+H)$^+$ (ES$^+$) 412.38; $t_R$=2.80 min. HPLC Method 2 (Base); $^1$H NMR (500 MHz, CD$_3$OD) δ 8.60 (1H, s), 7.51 (1H, d, J 1.60 Hz), 7.36 (1H, d, J 1.60 Hz), 4.64 (1H, dd, J 12.8, 3.8 Hz), 4.55 (1H, m), 3.25 (1H, m), 3.09-2.97 (2H, m), 2.87 (1H, m), 2.05 (1H, m), 1.85 (1H, m), 1.61 (1H, m), 1.62 (1H, m), 1.50 (1H, m), 1.37 (9H, s), 1.31 (6H, d, J 6.7 Hz).

Example 140: Tm-Shift Assay

Constructs and protein expression and purification: DNAs encoding two kinases [CAMK1D and SYK] were obtained from synthetic sources and used as templates to amplify kinase domain-containing sequences and further sub-cloned into two different expression vectors, using ligation independent cloning (Strain-Damerell et al., 2014).

Expression in *Escherichia coli*: CAMK1D (aa 1-333) was cloned into pNIC28-Bsa4 [pET expression vector with His6 tag in a 22 aa-N-terminal fusion peptide, with TEV protease cleavage site, (Kan$^+$)] and co-expressed with λ-phosphatase in *Escherichia coli* BL21 (DE3)-R$^3$ cells. Transformed cells were initially cultured (from an overnight pre-culture) in Luria-Bertami (LB) supplemented with 50 μg/mL of appropriate antibiotic) medium to OD$_{600}$ of ~ 0.4 at 37° C., 180 rpm, followed by additional growth while cooling to 18° C. to an OD$_{600}$ of ~ 0.7 before induction with 0.5 mM IPTG, overnight. 8L were grown/batch. Cells were harvested by centrifugation (JLA 8,100 rotor Beckman Coulter, Avanti J-20 XP centrifuge) and were frozen at −20° C. Cells expressing His6-tagged proteins were re-suspended in lysis buffer: 15 mL of buffer/pellet of 1L cultured cells (50 mM HEPES pH 7.5, 500 mM NaCl, 10 mM Imidazole, 5% glycerol and 0.5 mM TCEP (Tris(2-carboxyethyl)phosphine hydrochloride) in the presence of protease inhibitors cocktail (1 μl/mL) and lysed by sonication using a 750 W Sonics Vibra-Cell sonicator, with amplitude set to 35%, with bursts of 5 sec on-10 sec off, for 5 minutes, on ice. PEI (polyethyleneimine) was added to a final concentration of 0.15% and lysates were transferred to centrifuge tubes and centrifuged at 53,000×g using a JA-25.50 rotor, for at least 45 minutes, at 4° C. After centrifugation, the clarified supernatant was passed through a gravity column of 5 mL Ni-Sepharose resin, IMAC (GE Healthcare), previously equilibrated in lysis buffer. The resin was first washed with 50 mL of lysis buffer containing 1 M NaCl and 30 mM imidazole, then with 25 mL of Lysis Buffer containing 100 mM imidazole and finally the protein was eluted with 25 mL of Lysis Buffer containing 300 mM imidazole. The eluted proteins were collected and treated overnight with TEV (Tobacco Etch Virus) protease at 4° C. to remove the N-terminal tag. Digested protein was loaded onto a nickel column again to remove the cleaved hexa-histidine expression tag protease used. The flow-through containing the cleaved protein was collected and concentrated to a 5 mL volume using concentrators (Amicon) and injected onto a Superdex 75 (16/60) gel filtration column on an AKTA system (GE Healthcare) pre-equilibrated into GF Buffer (50 mM HEPES pH7.5, 300 mM NaCl, 5% glycerol, and 0.5 mM TCEP). The resulting pure protein was quantified and stored at −80° C. in 50 mM HEPES, pH 7.5, 300 mM NaCl, 0.5 mM TCEP and 5% glycerol.

Expression in *Spodoptera frugiperda* (Sf9): SYK (aa 356-635) was cloned into PFB-LIC-Bse [Baculovirus transfer vector with His6 tag in a 22 aa-N-terminal fusion peptide, with TEV protease cleavage site, (Amp$^+$)] and the construct DNA was transformed into the DH10Bac *Escherichia coli* strain (Invitrogen). After transposition the recombinant bacmid DNA was then purified and used directly to transfect insect cells (Sf9), using the baculovirus expression vector system. Recombinant baculoviruses were produced following an established protocol (Pravin et al., 2014) based on the Bac-to-Bac® system (Invitrogen). Sf9 cells were routinely grown as a suspension in Sf-900™ II SFM (1×) (Invitrogen) at 27° C., with shaking set at 100 rpm. For large scale expression, cells were infected at a density of 2×10$^6$/mL with recombinant baculovirus (10 mL of virus stock/1L of cultured cells). Seventy-two hours after infection, the cultures were collected and centrifuged at 900×g for 20 minutes, 4° C., using a JLA 8.1000 rotor on an Avanti J-20XP. The cell pellets were resuspended in cold lysis buffer (25 mL/pellet from 1L of culture) consisting of 50 mM HEPES [pH 7.5], 500 mM NaCl, 5 mM imidazole, 5% glycerol, 0.5 mM TCEP tris(2-carboxyethyl)phosphine) and a protease inhibitor cocktail III (1:1000 dilution, Calbiochem). Cell suspensions were lysed and protein was purified following the same IMAC-resin method described above for the purification of CAMK1, with the exception that the His-tag was not cleaved. His tagged-SYK protein fractions were collected and concentrated to a 5 mL volume and injected onto a Superdex 75 (16/60) gel filtration column as a final polishing step before quantification and storage at −80° C. in 50 mM HEPES, pH 7.5, 300 mM NaCl, 0.5 mM TCEP and 5% glycerol.

The correct mass and purity for all protein constructs was confirmed by an Agilent 1100 Series LC/MSD TOF (Agilent Technologies Inc.—Palo Alto, Calif.).

Tm-Shift assay: Thermal melting experiments were carried out using a Stratagene M×3005p Real Time PCR machine (Agilent Technologies). Proteins were buffered in 10 mM HEPES, pH 7.5, 500 mM NaCl and assayed in a 96-well plate at a final concentration of 2 µM in a 20-µl volume. Compounds were added at a final concentration of 10 µM (final DMSO concentration was 0.025%). SYPRO Orange (Molecular Probes) was added as a fluorescence probe at a dilution of 1:1,000 (v/v). Excitation and emission filters for the SYPRO-Orange dye were set to 465 nm and 590 nm, respectively. The temperature was raised with a step of 3° C. per minute from 25° C. to 96° C., and fluorescence readings were taken at each interval. The observed temperature shifts, $\Delta Tm^{obs}$, were recorded as the difference between the transition midpoints of sample and reference wells containing protein without ligand in the same plate and determined by non-linear least squares fit, reported in ° C. Experiments were performed in triplicate and data were analysed as previously described [Fedorov et al. (2011), (2012)].

REFERENCES

Strain-Damerell C, Mahajan P, Gileadi O, Burgess-Brown N A. (2014) Medium-throughput production of recombinant human proteins: ligation-independent cloning. Methods Mol Biol. 1091: 55-72.

Mahajan P, Strain-Damerell C, Gileadi O, Burgess-Brown N A. (2014) Medium-throughput production of recombinant human proteins: protein production in insect cells. Methods Mol Biol. 1091: 95-121.

Fedorov O, Huber K, Eisenreich A, Filippakopoulos P, King O, Bullock A N, Szklarczyk D, Jensen L J, Fabbro D, Trappe J, Rauch U, Bracher F, Knapp S. (2011) Specific CLK inhibitors from a novel chemotype for regulation of alternative splicing. Chem Biol. 18(1): 67-76.

Fedorov O, Niesen F H, Knapp S. (2012) Kinase inhibitor selectivity profiling using differential scanning fluorimetry. Methods Mol Biol. 795:109-18.

Example 141: Biochemical CaMK1D Enzymatic Activity Assay

The following describes an ADP-Glo Kinase™ Assay, which measures the ADP formed from a kinase reaction; the ADP generated is converted into ATP and is used to generate light in a luciferase reaction. The assay is used to assess the effect of compounds on the activity of purified CaMK1 D.

Materials and Solutions:

All reagents are from Sigma-Aldrich unless otherwise specified. ADP-Glo Kinase Assay (Promega, V9102). His-tagged CaMK1D_1-385 (Fisher Scientific, PR6770A). Autocamtide-2 (SignalChem, A15-58). Calmodulin (Merck, 208694). 1M Tris-HCl pH7.5 (Fisher Scientific, 10123722). 1M DTT (Fisher Scientific, 10674545). Calcium chloride ($C_{1016}$). Magnesium Chloride (M8266). DMSO (D8418). Autocamtide-2 provided as a lyophilised powder and prepared as a 10 mM stock in MilliQ water. RB: 50 mM Tris-HCl pH 7.5, 10 mM MgCl$_2$, 0.1 CaCl$_2$), just prior to use 1M DTT was added to a final concentration of 2 mM.

Assay Protocol: 7.88 µL reaction mixture (including: calmodulin, Autocamtide-2, CaMK1 D in RB) was incubated with 12 µL test compound in 100% DMSO. To start the reaction 4 µL of ATP mixture were added. Final assay concentrations: 3 nM CaMK1D, 1 µM Calmodulin, 125 µM Autocamtide-2 and 10 µM ATP. Plates were incubated at 25C for 2 hours prior to the 1:1 addition of ADP-Glo reagent. Plates were incubated for a further 1 hour prior to the 1:1 addition of ADP-Glo substrate. After 30 minutes plates read with the EnVision® Multilabel Plate Reader, using Luminescence 700. Compound IC$_{50}$ was determined using a 4-parameter equation and are reported in nM.

Example 142: Biological Data on Examles

The following data was generated using the assays described in examples 140 and 141.

| Example | Structure | CAMK1d Tm-Shift | SYK Tm-Shift | CamK1D IC$_{50}$ | CamK1D IC$_{50}$ n measurements |
|---|---|---|---|---|---|
| 1 | 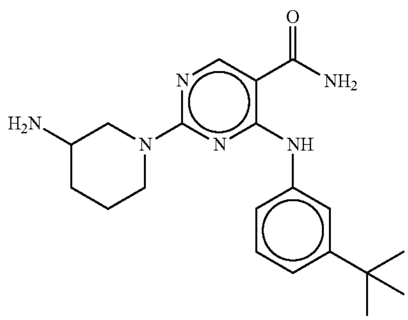 | 10.6 | 4.6 | 429 | 1 |
| 2 | 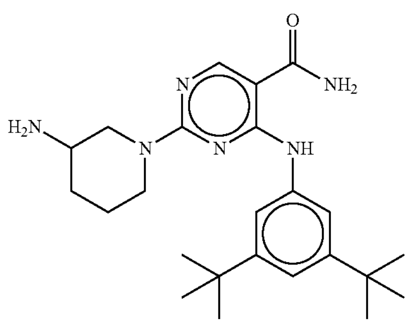 | 14.0 | 0.7 | | |
| 3 | 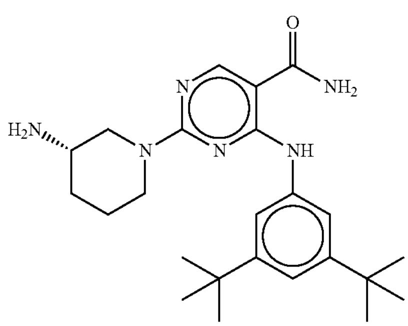 | 13.4 | 0.3 | 429 | 2 |
| 4 | 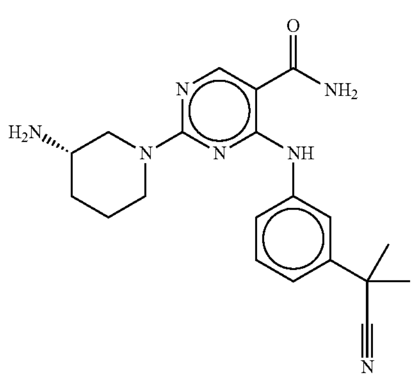 | 9.0 | 5.0 | 96 | 3 |

-continued
| Example | Structure | CAMK1d Tm-Shift | SYK Tm-Shift | CamK1D IC$_{50}$ | CamK1D IC$_{50}$ n measurements |
|---|---|---|---|---|---|
| 5 | 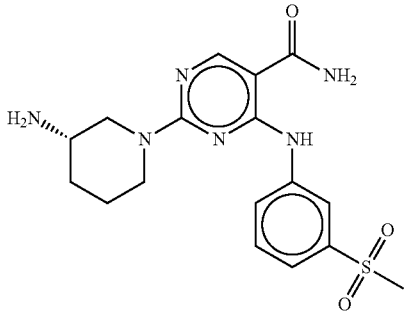 | 7.9 | 5.2 | 101 | 3 |
| 6 | 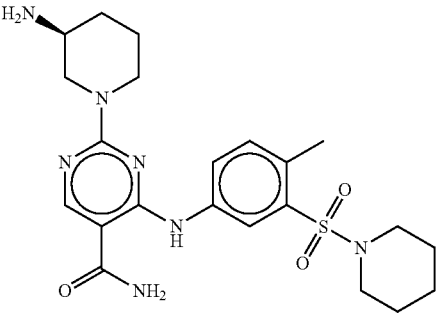 | 9.9 | 3.3 | | |
| 7 | 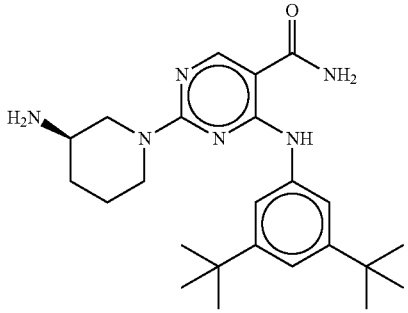 | 10.6 | 0.7 | 114 | 1 |
| 8 | 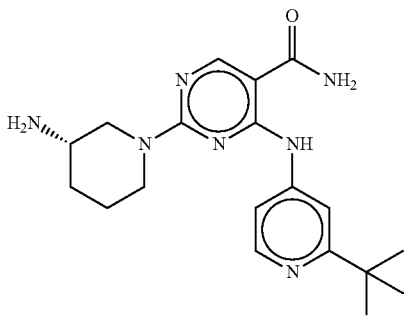 | 9.5 | 3.2 | 38 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 9 | 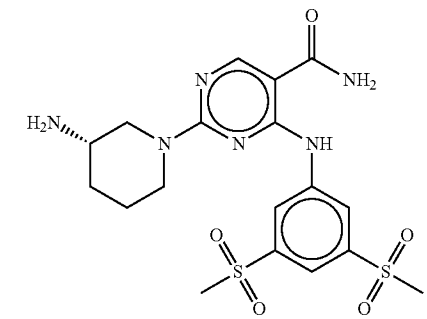 | 10.1 | 0.2 | | |
| 10 | 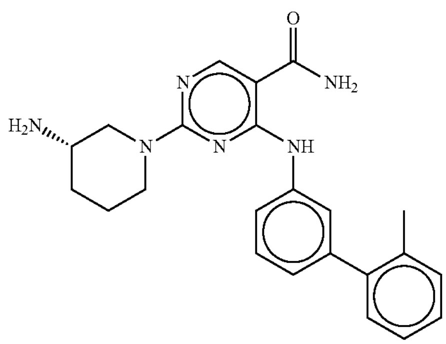 | 11.3 | 6.5 | 122 | 1 |
| 11 | 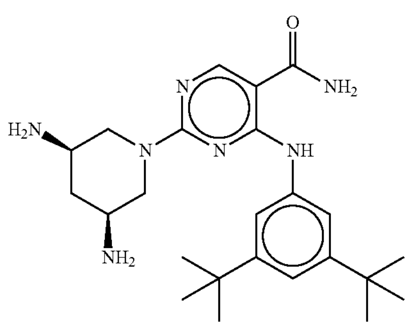 | 12.8 | −0.5 | 283 | 1 |
| 12 | 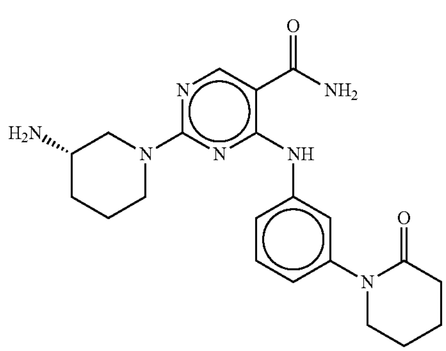 | 7.6 | | 523 | 1 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 13 | 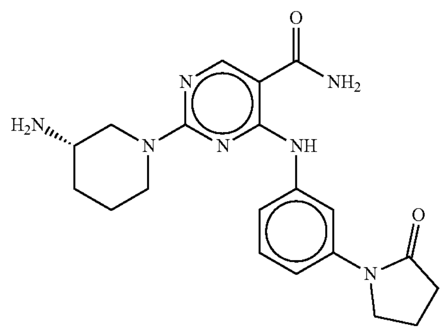 | 11.2 | | 633 | 1 |
| 14 | 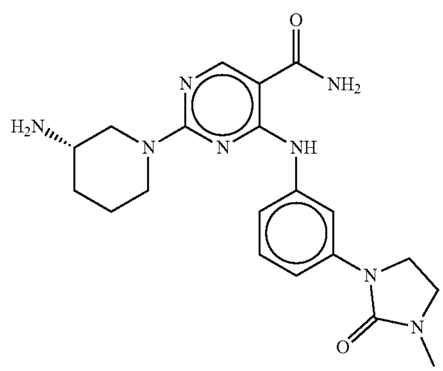 | 6.8 | | 419 | 1 |
| 15 | 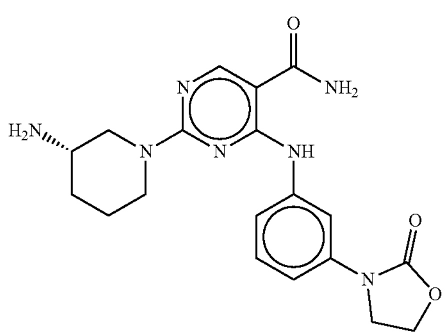 | 6.7 | | 255 | 1 |
| 16 | 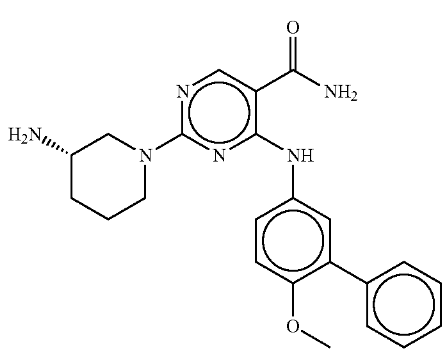 | 11.8 | | 42 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 17 | 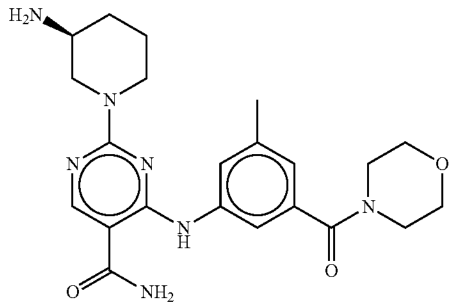 | 9.5 | | 132 | 1 |
| 18 | 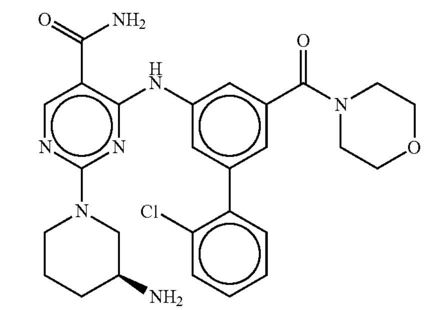 | 12.9 | | 28 | 2 |
| 19 | 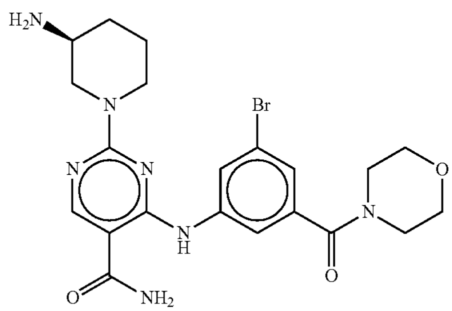 | 10.2 | | 137 | 1 |
| 20 | 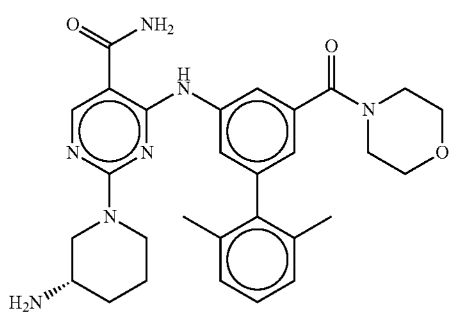 | 12.5 | 0.3 | 137 | 2 |
| 21 | 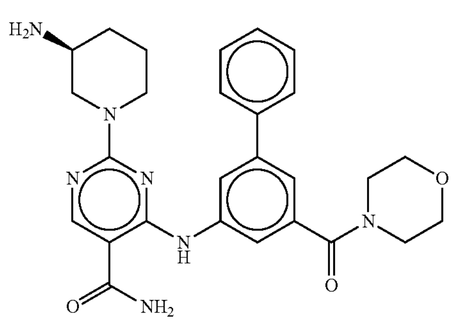 | 13.0 | 0.3 | 45 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 22 | 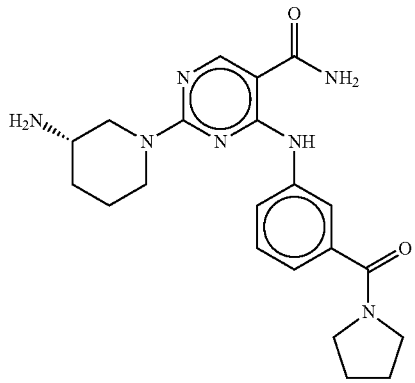 | 8.4 | 2.4 | 424 | 1 |
| 23 | 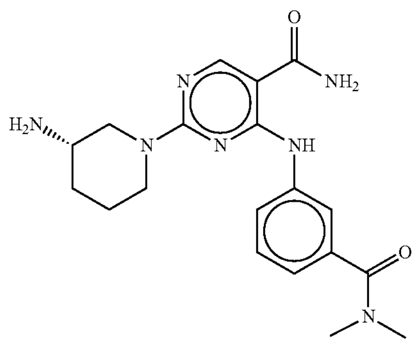 | 6.9 | 1.6 | 269 | 1 |
| 24 | 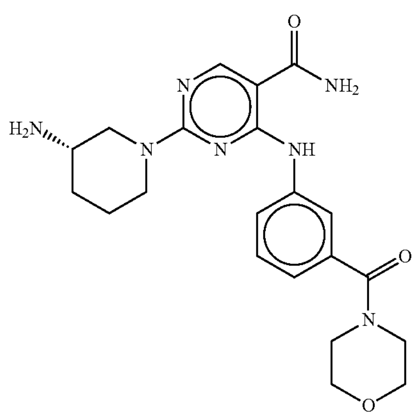 | 8.2 | 1.4 | 391 | 2 |
| 25 | 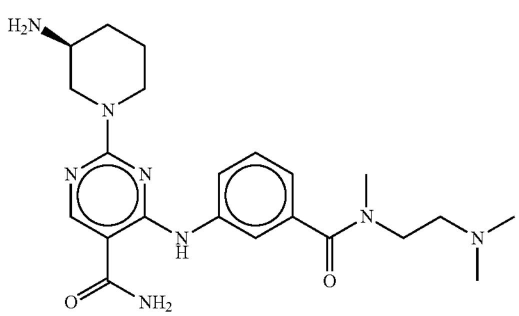 | 8.1 | 0.7 | | |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 26 | 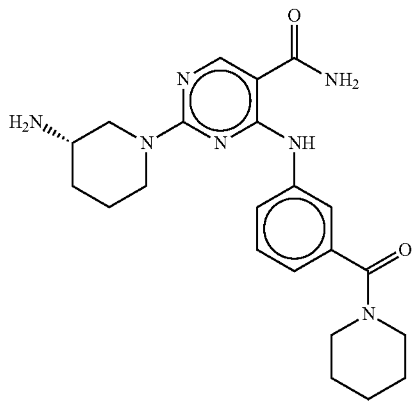 | 9.4 | 1.8 | 149 | 1 |
| 27 | 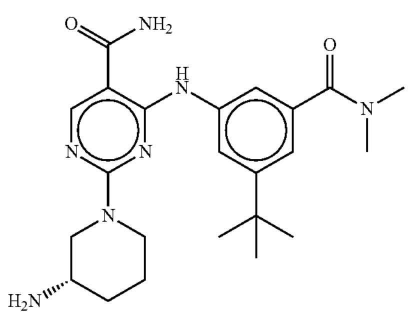 | 12.5 | 0.4 | | |
| 28 | 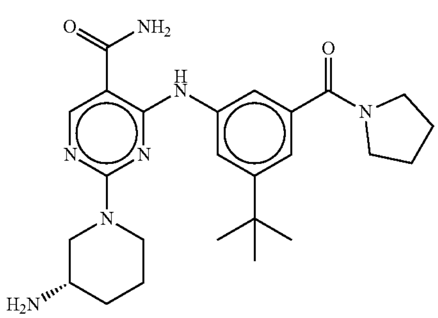 | 11.8 | 0.5 | | |
| 29 | 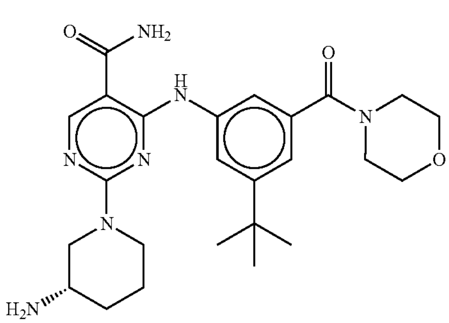 | 12.4 | 0.3 | | |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 30 | 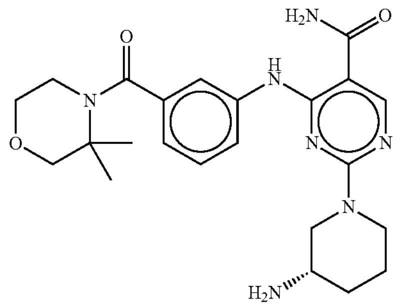 | 9.5 | 2.0 | | |
| 31 | 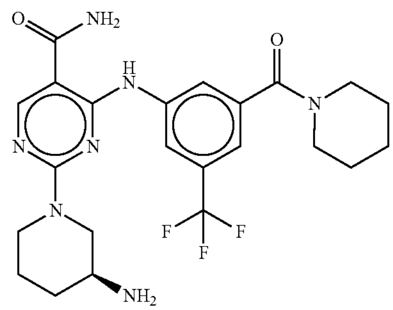 | 12.8 | 0.5 | 52 | 2 |
| 32 | 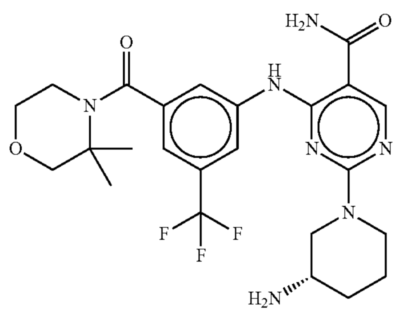 | 11.2 | 2.1 | | |
| 33 | 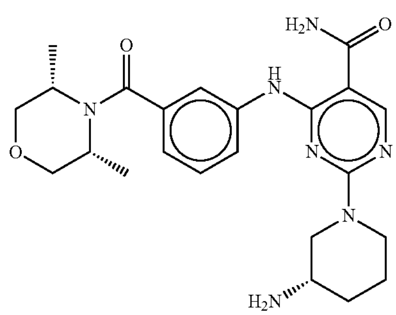 | 7.4 | 0.5 | 233 | 2 |
| 34 | 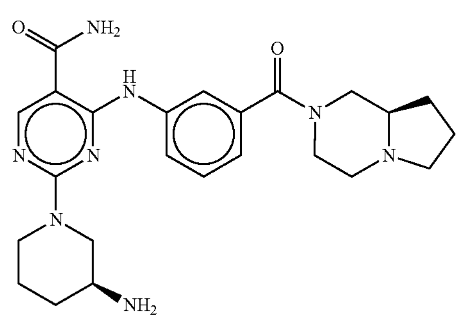 | 9.1 | 2.3 | 122 | 1 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 35 | 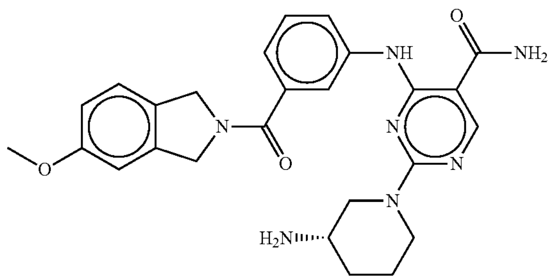 | 9.7 | 4.3 | 234 | 1 |
| 36 | 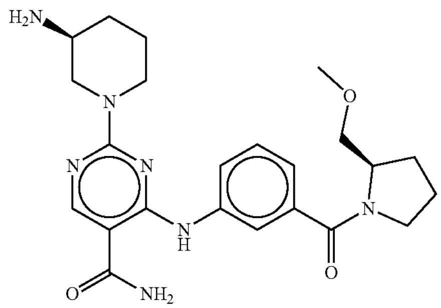 | 5.7 | 1.4 | 414 | 1 |
| 37 | 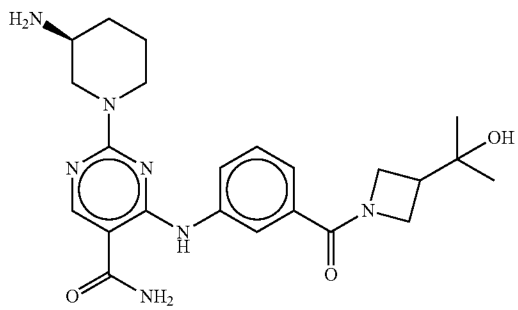 | 6.5 | 5.0 | 312 | 1 |
| 38 | 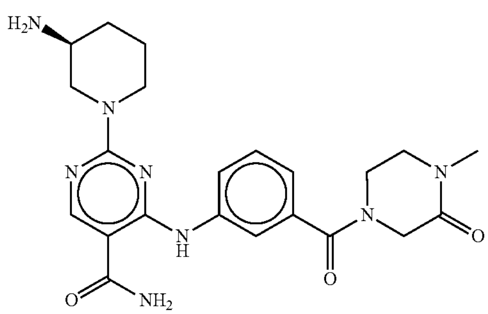 | 6.5 | 3.4 | 345 | 2 |
| 39 | 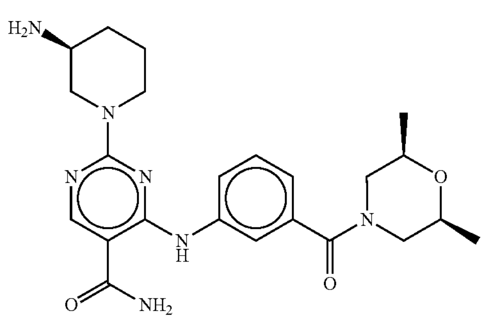 | 9.1 | 3.1 | 227 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 40 | 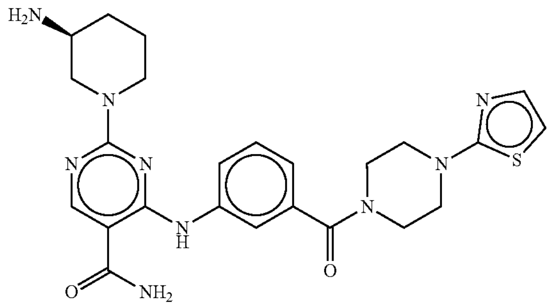 | 8.6 | | 874 | 1 |
| 41 | 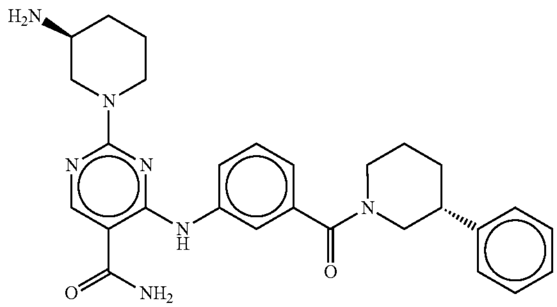 | 10.7 | | 241 | 1 |
| 42 | 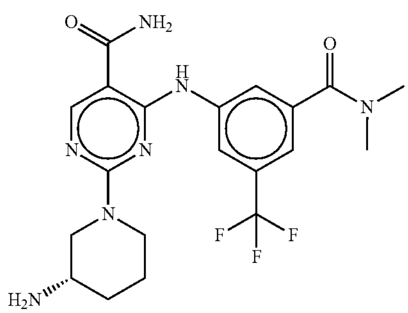 | 11.2 | 1.5 | 106 | 3 |
| 43 | 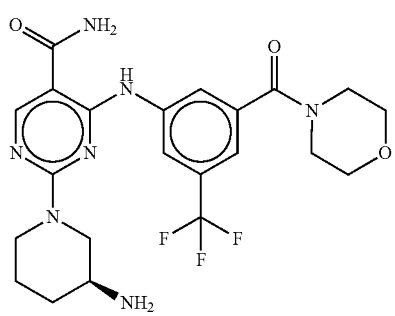 | 11.7 | 1.2 | 43 | 3 |
| 44 | 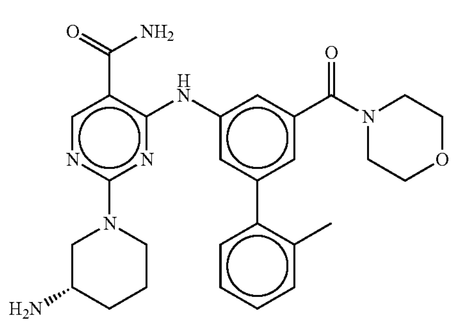 | 10.9 | −0.3 | | |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 45 | 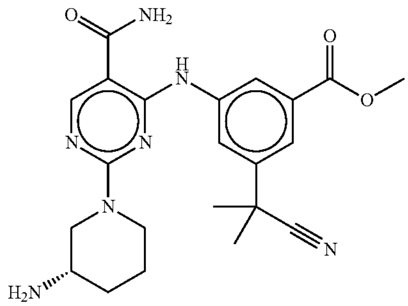 | 12.6 | 4.6 | | |
| 46 | 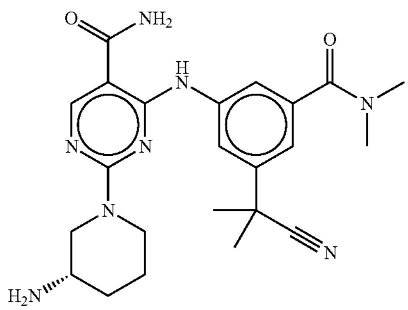 | 10.9 | 0.5 | 39 | 2 |
| 47 | 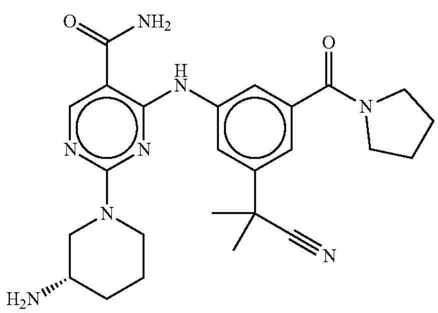 | 10.8 | 0.7 | 89 | 1 |
| 48 | 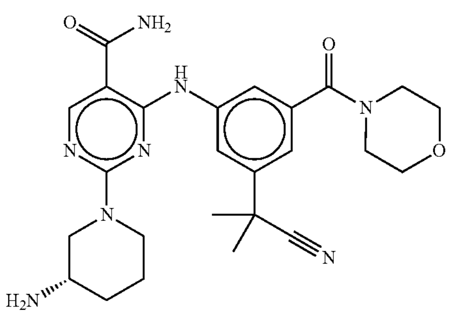 | 11.1 | 0.5 | 47 | 3 |
| 49 | 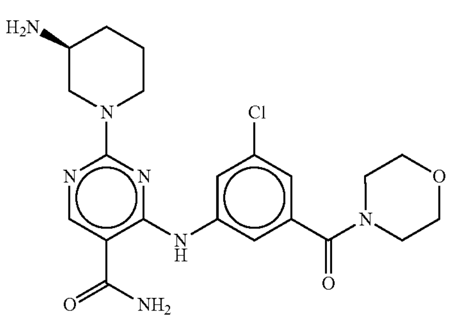 | 9.9 | | 50 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 50 | 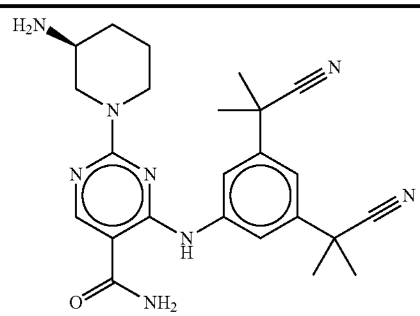 | 11.5 | | 31 | 3 |
| 51 | 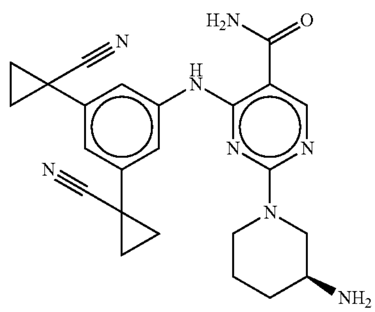 | 12.0 | | 37 | 2 |
| 52 | 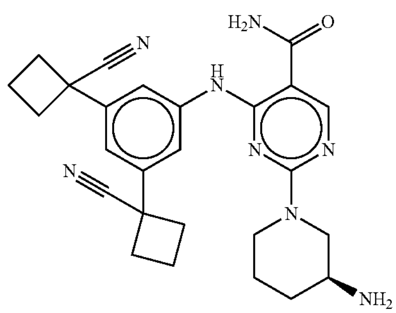 | 13.5 | | 28 | 2 |
| 53 | 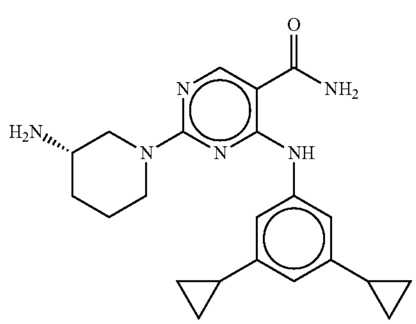 | 12.3 | 8.2 | 115 | 3 |
| 54 | 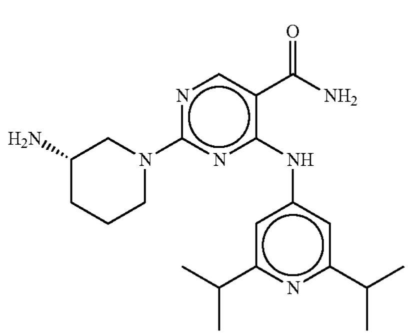 | 16.0 | | 8 | 3 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 55 | 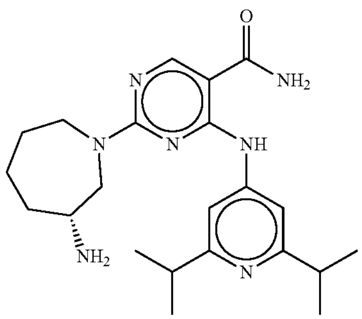 | 10.6 | | 147 | 1 |
| 56 | 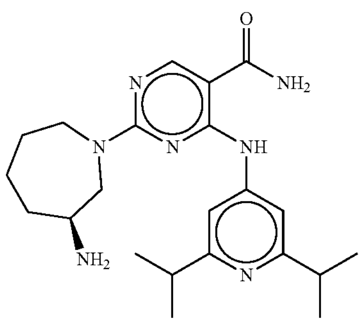 | 12.7 | | 34 | 2 |
| 57 | 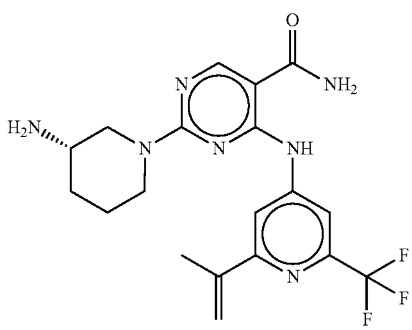 | 14.3 | | 22 | 2 |
| 58 | 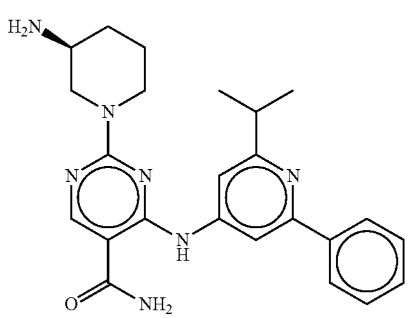 | 15.4 | | 27 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 59 | 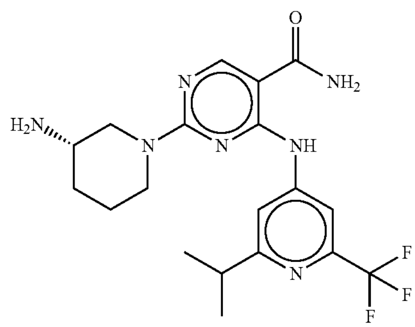 | 14.4 | | 35 | 3 |
| 60 | 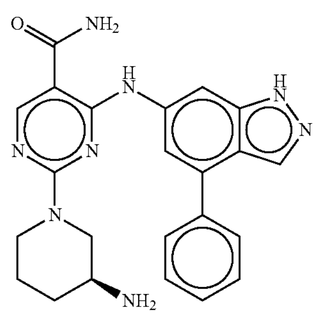 | 9.9 | | 10 | 2 |
| 61 | 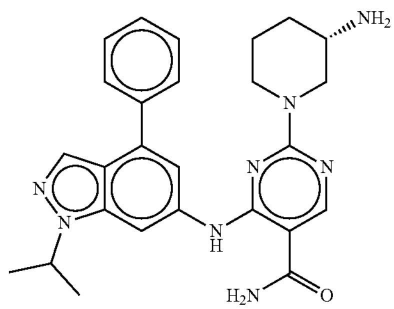 | 8.1 | | 4506 | 1 |
| 62 | 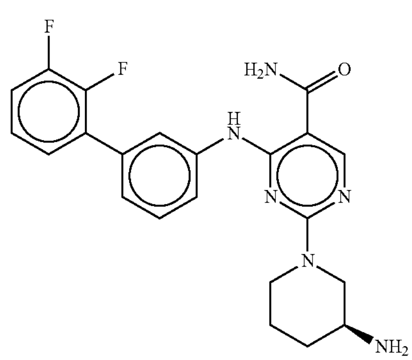 | 12.6 | | 125 | 1 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 63 | 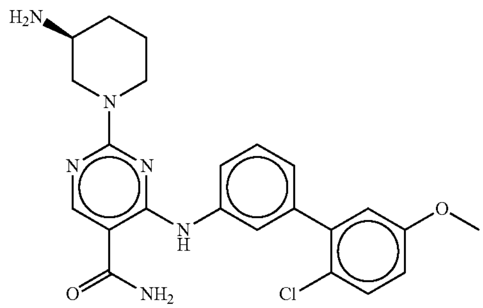 | 12.9 | | 183 | 1 |
| 64 | 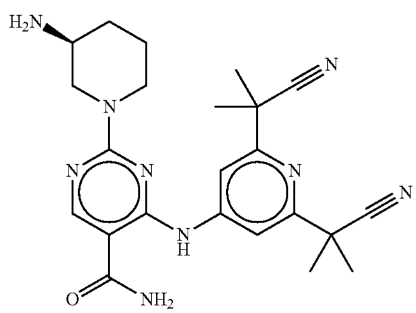 | 13.9 | | 24 | 3 |
| 65 | 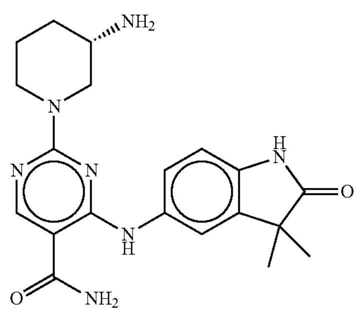 | 10.0 | 0.3 | 167 | 2 |
| 66 | 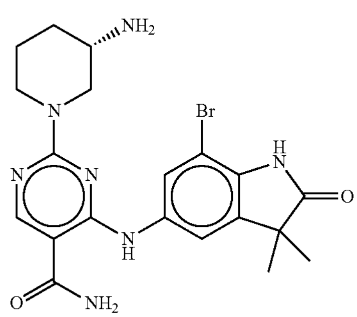 | 11.5 | | 33 | 2 |
| 67 | 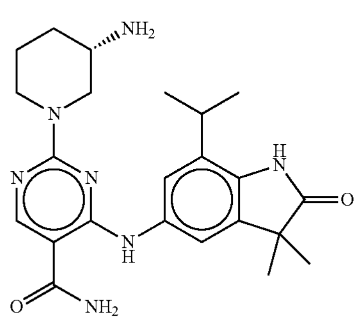 | 12.5 | | 21 | 3 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 68 | 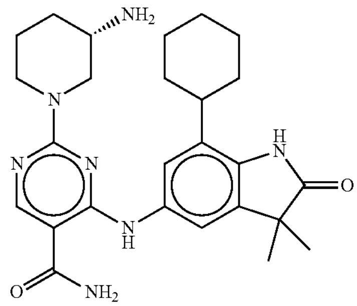 | 13.3 | | 10 | 2 |
| 69 | 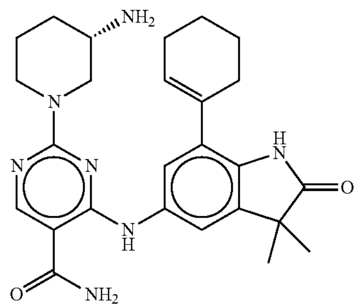 | 14.6 | | 6 | 2 |
| 70 | 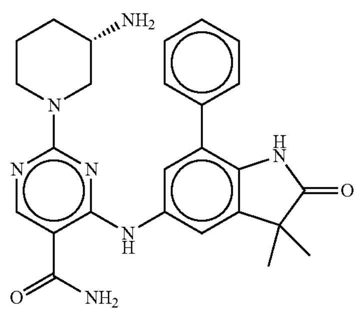 | 15.1 | | 6 | 2 |
| 71 | 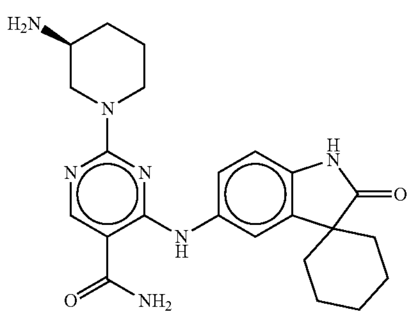 | 11.0 | | 55 | 2 |
| 72 | 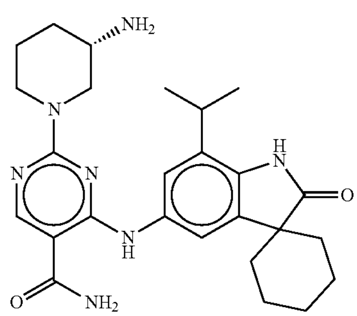 | 16.3 | | 15 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 73 | 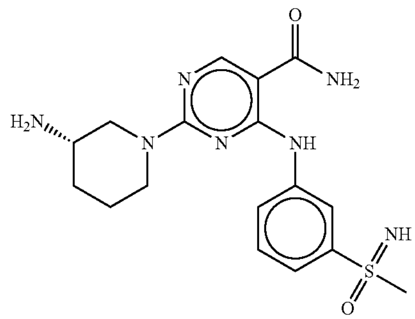 | 6.7 | | 516 | 1 |
| 74 | 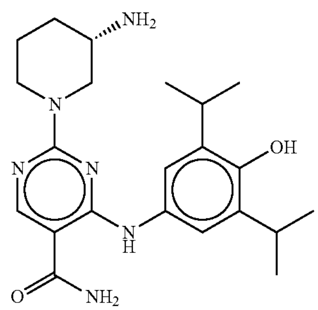 | 11.7 | | 22 | 3 |
| 75 | 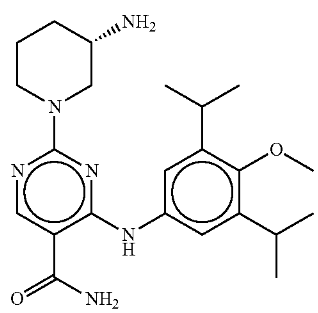 | 11.3 | | 126 | 1 |
| 76 | 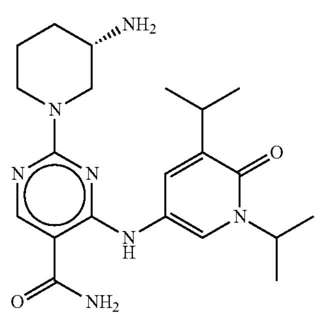 | 11.0 | | 36 | 3 |
| 77 | 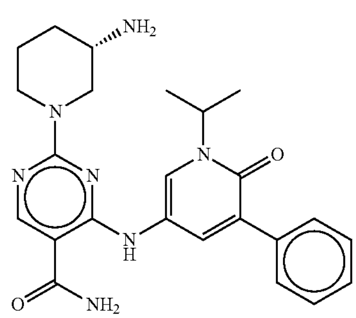 | 13.1 | | 10 | 3 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 78 | 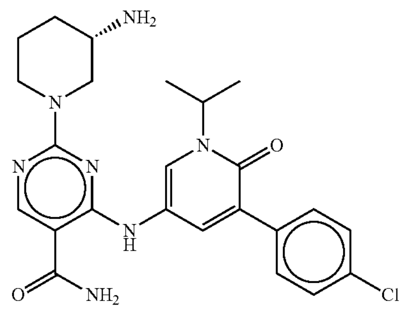 | 16.1 | | 6 | 2 |
| 79 | 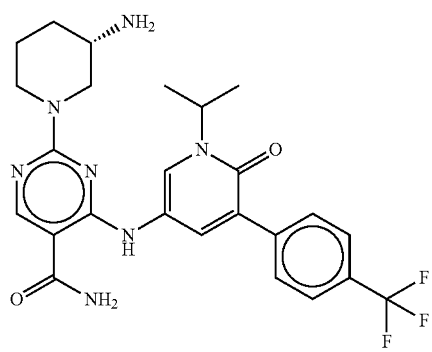 | 17.1 | | 4 | 2 |
| 80 | 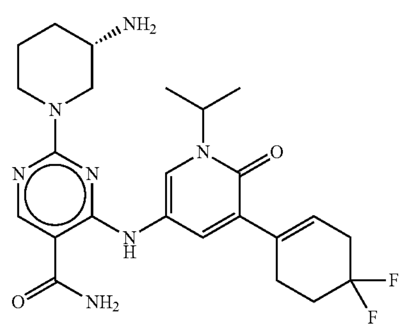 | 13.6 | | 11 | 2 |
| 81 | 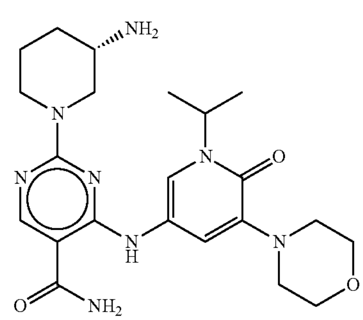 | 11.8 | | 78 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 82 | 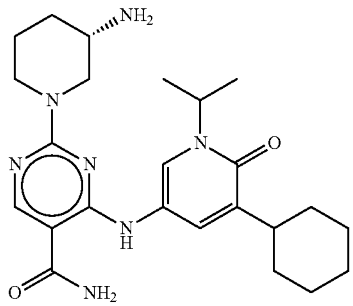 | 13.0 | | 12 | 2 |
| 83 | 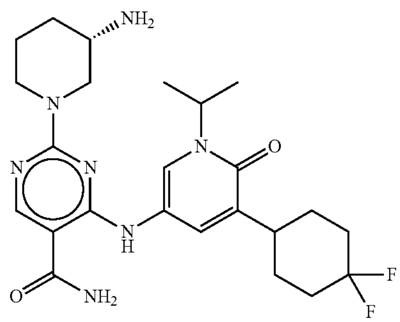 | 15.0 | | 7 | 2 |
| 84 | 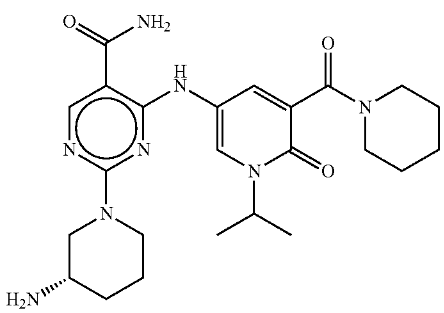 | 13.6 | | 19 | 3 |
| 85 | 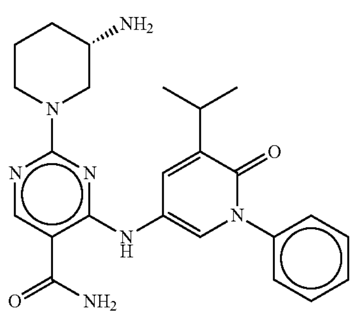 | 13.9 | | 19 | 2 |
| 86 | 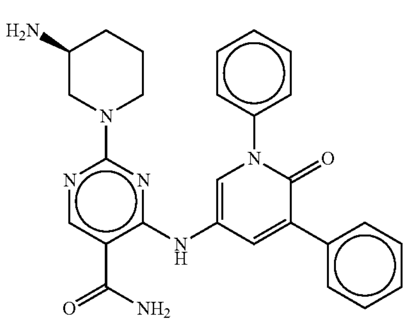 | 13.3 | | 23 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 87 | 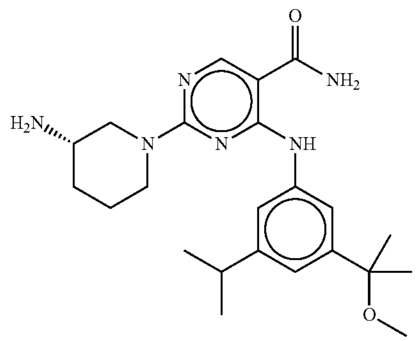 | 11.2 | | 57 | 2 |
| 88 | 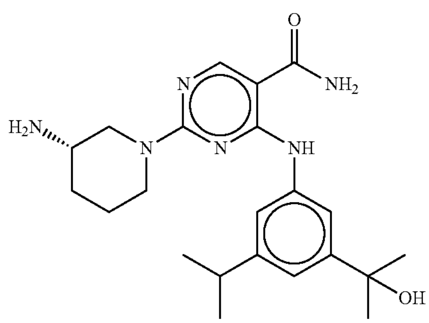 | 11.5 | | 39 | 2 |
| 89 | 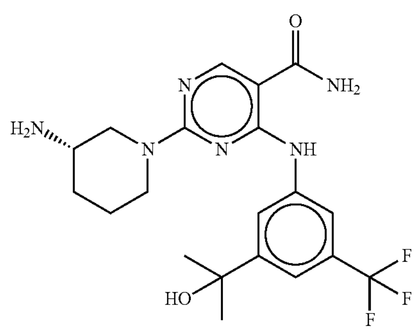 | 12.4 | 3.4 | 31 | 2 |
| 90 | 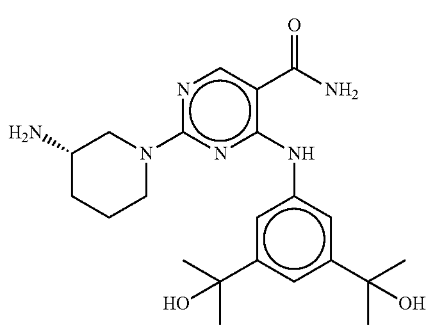 | 11.2 | 0.9 | 37 | 3 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 91 | 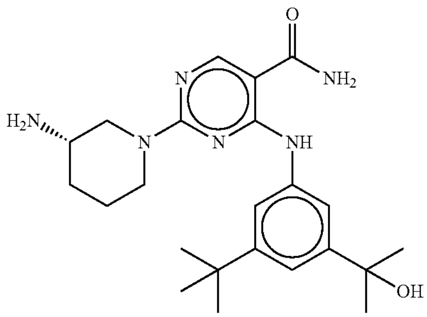 | 12.6 | | 33 | 2 |
| 92 | 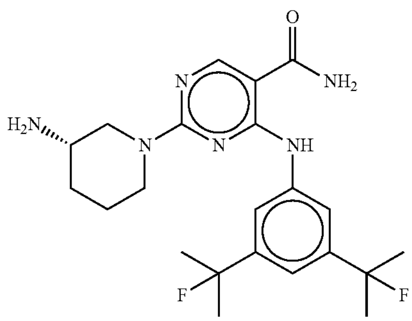 | 14.8 | | 24 | 2 |
| 93 | 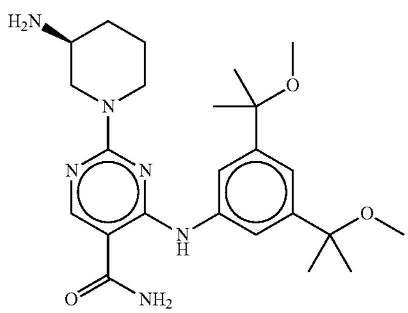 | 10.2 | | 110 | 2 |
| 94 | 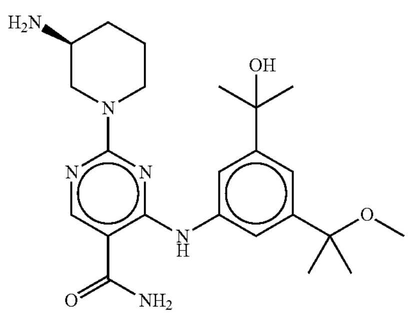 | 14.0 | | 32 | 2 |
| 95 | 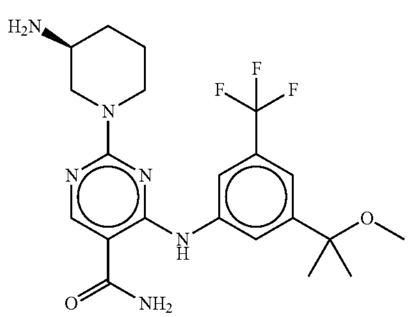 | 15.8 | | 120 | 1 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 96 | 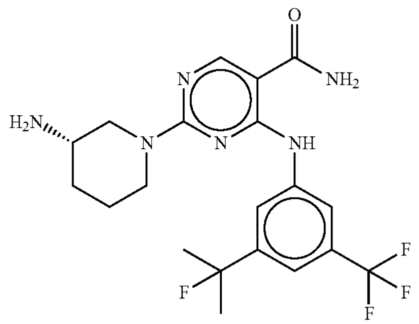 | 15.1 | | 202 | 1 |
| 97 | 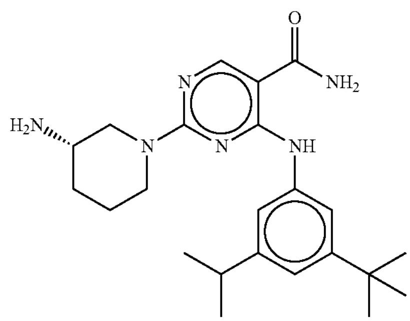 | 16.1 | | 743 | 1 |
| 98 | 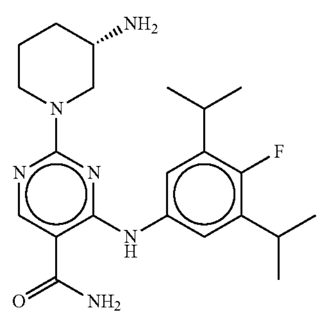 | 14.3 | | 401 | 3 |
| 99 | 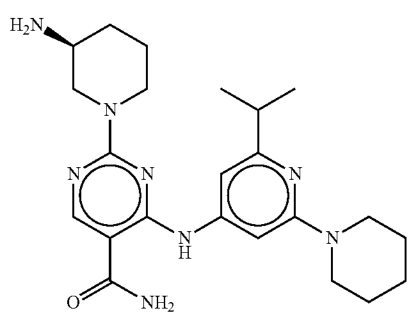 | 13.4 | | 30 | 2 |
| 100 | 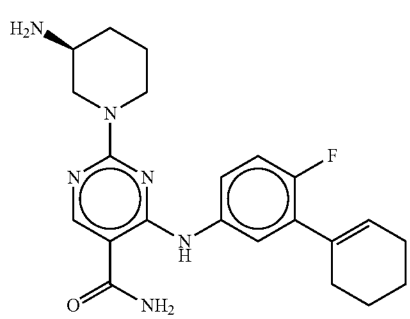 | 11.1 | | 253 | 1 |

-continued
| Example | Structure | CAMK1d Tm-Shift | SYK Tm-Shift | CamK1D IC$_{50}$ | CamK1D IC$_{50}$ n measurements |
|---|---|---|---|---|---|
| 101 | 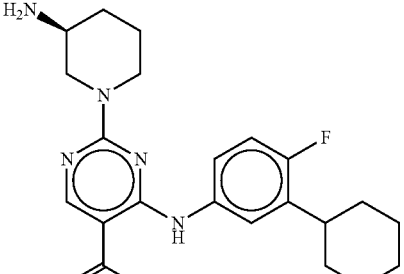 | 10.8 | | 440 | 1 |
| 102 | 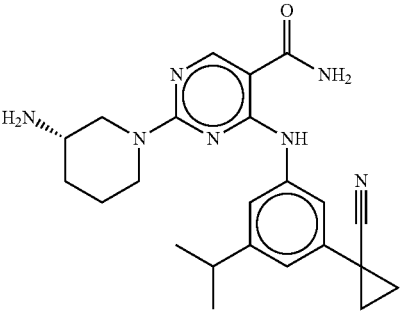 | 10.6 | | 53 | 2 |
| 103 | 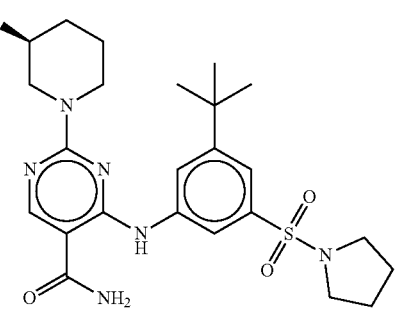 | 12.2 | 0.7 | | |
| 104 | 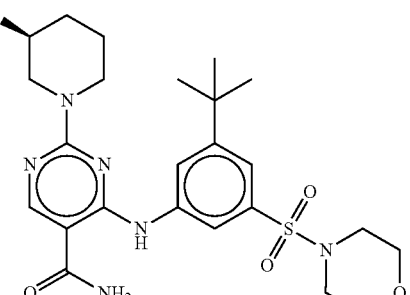 | 11.5 | 0.9 | | |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 105 | 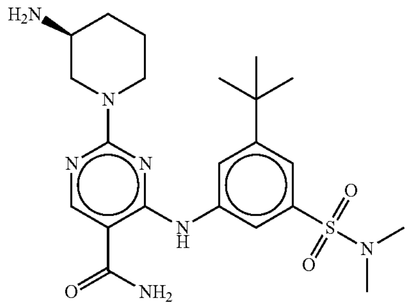 | 12.9 | 1.3 | | |
| 106 | 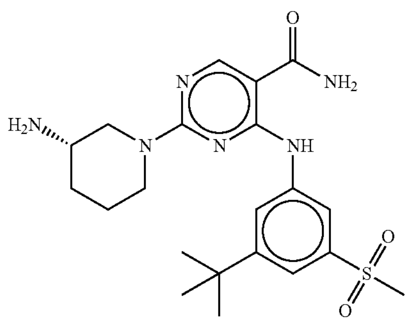 | 12.4 | 0.9 | 27 | 4 |
| 107 | 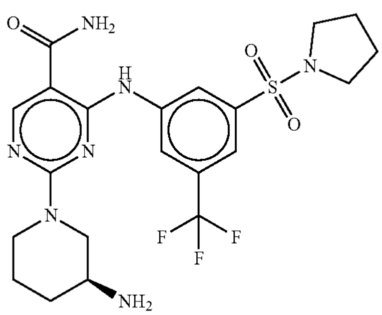 | 11.1 | 0.4 | 140 | 1 |
| 108 | 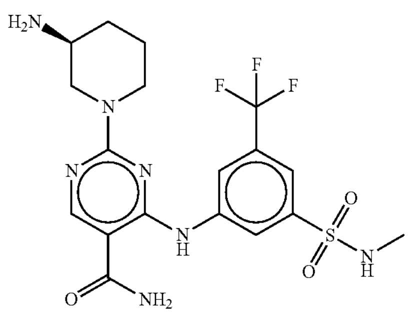 | 10.7 | 0.3 | | |
| 109 | 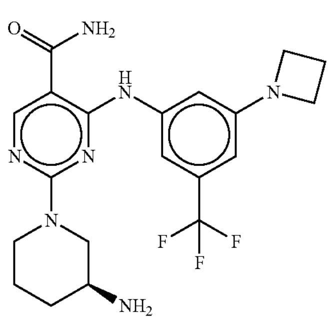 | 10.1 | 5.8 | 567 | 1 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 110 | 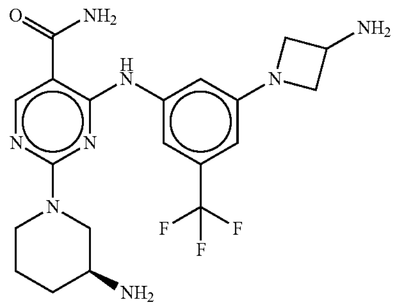 | 8.0 | | 100 | 1 |
| 111 | 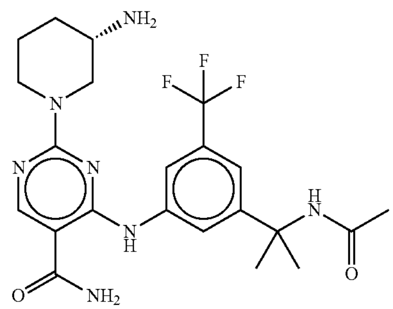 | 11.9 | | 97 | 1 |
| 112 | 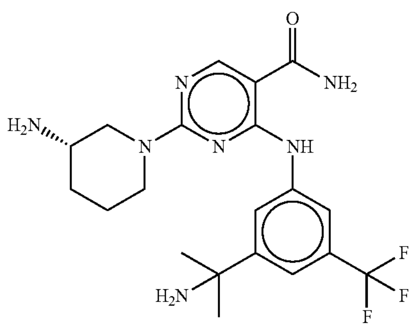 | 12.1 | | 31 | 2 |
| 113 | 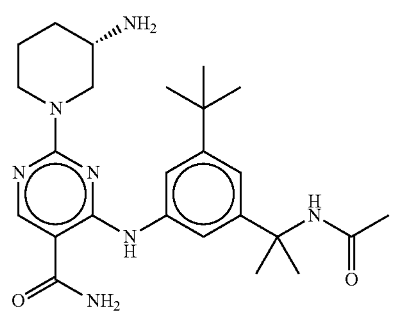 | 9.7 | | 72 | 2 |
| 114 | 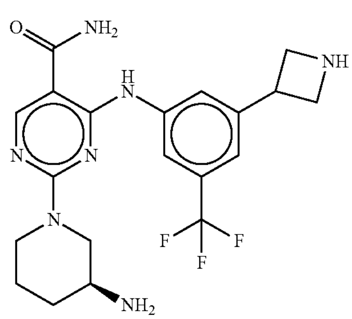 | 9.7 | | 48 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 115 | 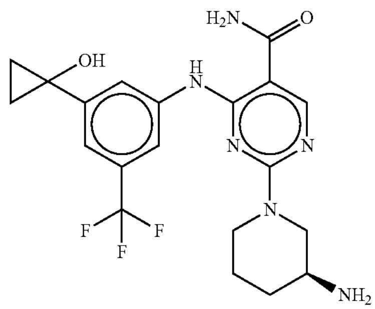 | 10.1 | | 84 | 1 |
| 116 | 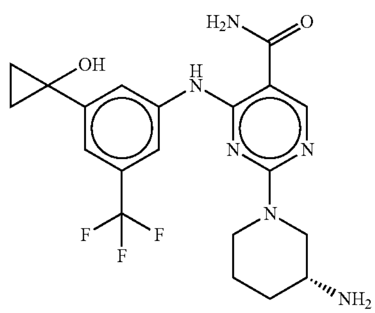 | 1.5 | | 2182 | 1 |
| 117 | 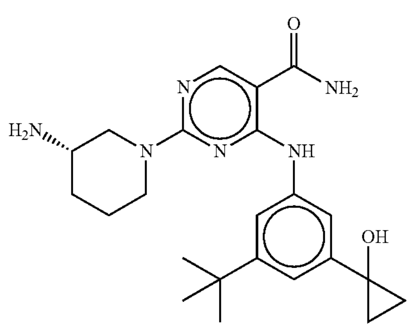 | 14.0 | | 30 | 2 |
| 118 | 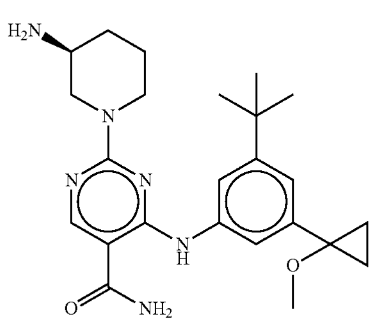 | 11.2 | | 133 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 119 | 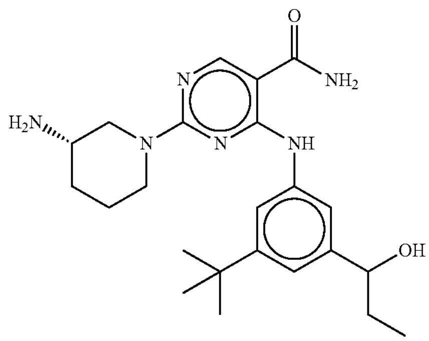 | 9.3 | | 112 | 1 |
| 120 | 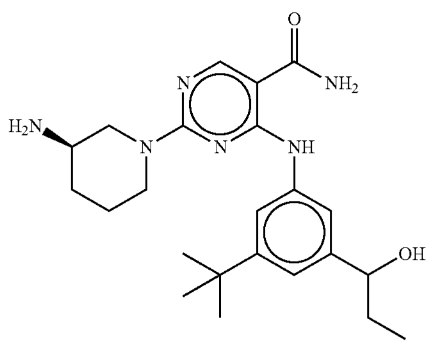 | 4.5 | | 2287 | 1 |
| 121 | 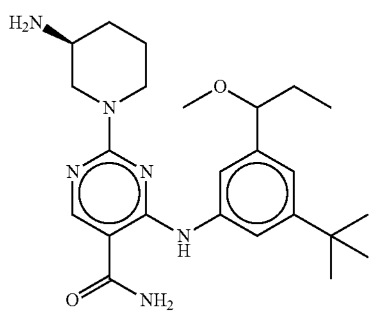 | 10.7 | | 155 | 1 |
| 122 | 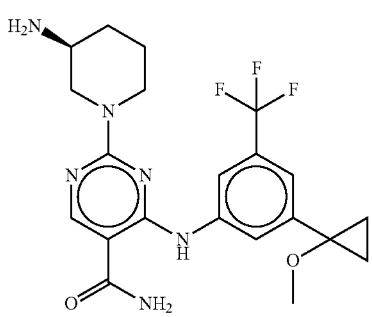 | −0.8 | | | |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 123 | 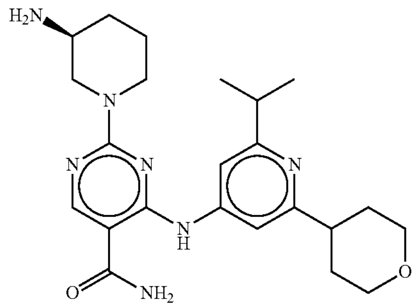 | 17.5 | | 5 | 3 |
| 124 | 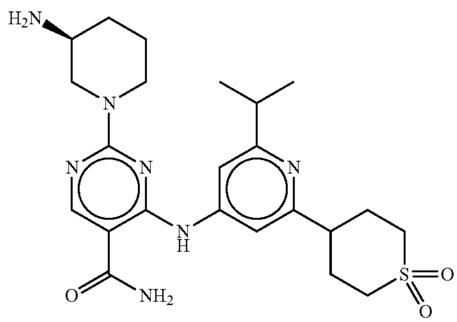 | 16.5 | | 8 | 2 |
| 125 | 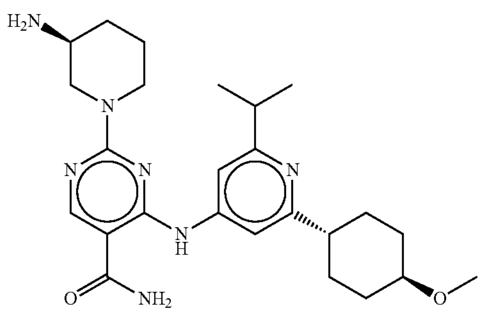 | 16.3 | | 10 | 2 |
| 126 | 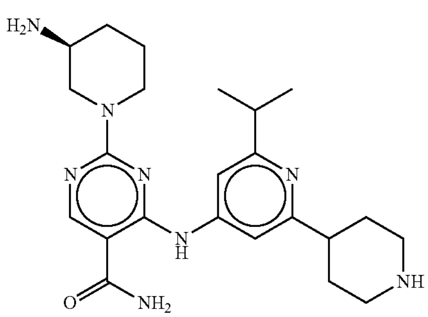 | 15.9 | | 5 | 2 |

-continued

| Example | Structure | CAMK1d Tm-Shift | SYK Tm-Shift | CamK1D IC$_{50}$ | CamK1D IC$_{50}$ n measurements |
|---|---|---|---|---|---|
| 127 | 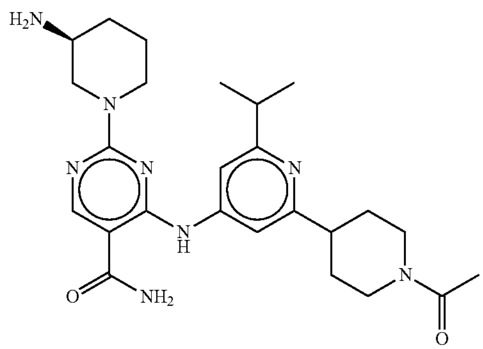 | 15.6 | | 4 | 2 |
| 128 | 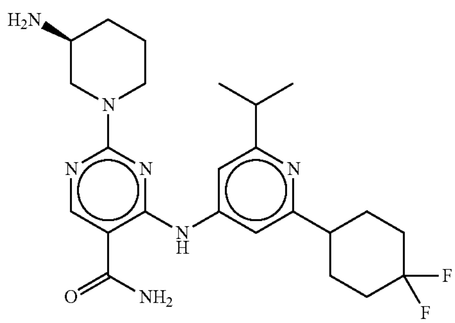 | 13.7 | | 10 | 2 |
| 129 | 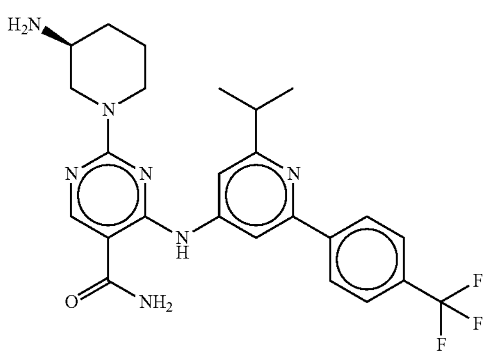 | 18.7 | | 56 | 2 |
| 130 | 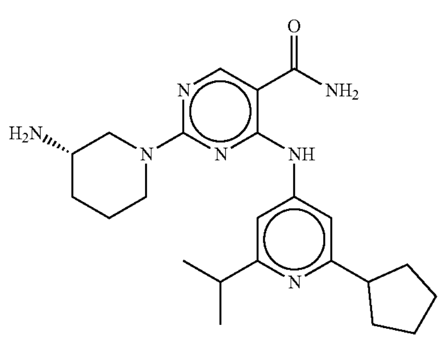 | 15.1 | | 8 | 2 |

-continued
| Example | Structure | CAMK1d Tm-Shift | SYK Tm-Shift | CamK1D IC$_{50}$ | CamK1D IC$_{50}$ n measurements |
|---|---|---|---|---|---|
| 131 | 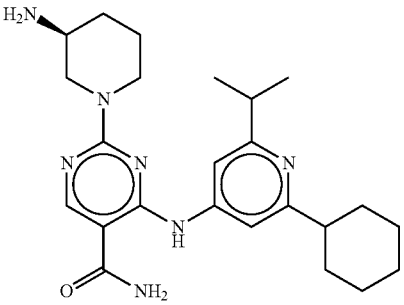 | 16.0 | | 8 | 2 |
| 132 | 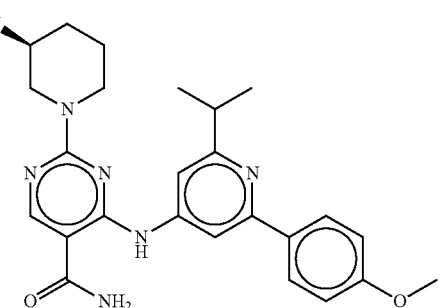 | 16.9 | | 7 | 2 |
| 133 | 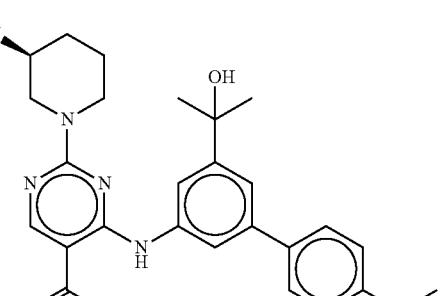 | 17.8 | | 7 | 2 |
| 134 | 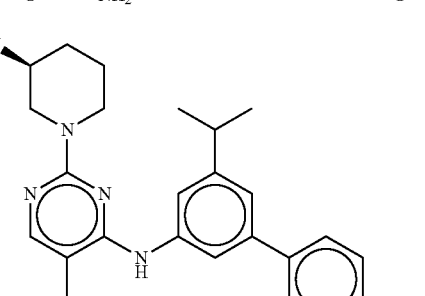 | 17.4 | | 27 | 1 |
| 135 | 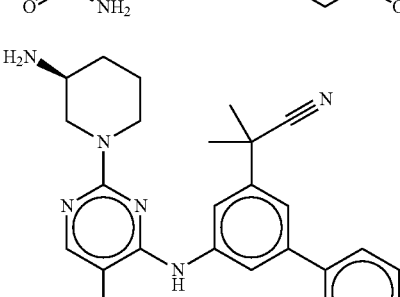 | 15.8 | | 22 | 4 |

| Example | Structure | CAMK1d Tm-Shift | SYK Tm-Shift | CamK1D IC$_{50}$ | CamK1D IC$_{50}$ n measurements |
|---|---|---|---|---|---|
| 136 | 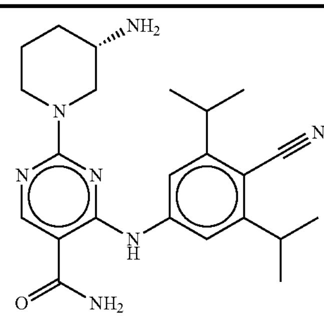 | 14.7 | | 59 | 1 |
| 137 | (racemic) | 13.4 | | 25 | 2 |
| 138 | (racemic) | 12.8 | | 24 | 2 |
| 139 | 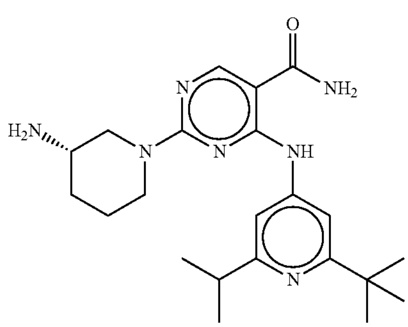 | 15.8 | | 23 | 1 |

Example 143: Oral Glucose Tolerance Test (OGTT) after Acute and Chronic (14 Day) Dosing Male C$_{57}$Bl/6J mice obtained from Charles River UK (Margate, Kent, UK) at 7-8 weeks of age were group housed for 16 weeks (n=3 in each cage) on a normal light/dark cycle (lights on: 07:00-19:00 h) with ad libitum access to a high fat diet (D12451 diet, 45% kcal as fat, 35% as carbohydrate; Research Diets, New Jersey, USA) and filtered water. Animals were allocated to dosing groups such that groups were balanced as closely as possible for mean body weight.

The day prior to the OGTT, all animals were deprived of food (but not water) beginning approximately 16.45. The following morning the mice were dosed with vehicle or either 10 mg/kg, 25 kg/kg or 50 mg/kg (S)-2-(3-aminopiperidin-1-yl)-4-((3,5-bis(2-cyanopropan-2-yl)phenyl)amino)

pyrimidine-5-carboxamide (Example 50), formulated in a vehicle of DMSO (10% final volume) and 20% (2-Hydroxypropyl)-o-cyclodextrin (90% final volume) by the oral route (beginning at 08.45). Four hours after dosing, a blood sample was taken (B1) and 3 minutes later glucose administered (2 g/kg orally). Further blood samples were taken 10, 30, 60 and 90 minutes post glucose administration. Between blood sampling, animals were returned to the home cage with free access to water (but not food). Blood samples (approx. 30 μL) were collected into lithium heparinised tubes (Sarstedt Microvette CB300LH) and plasma separated by centrifugation to produce a single aliquot of plasma which was frozen (approx. −80° C.) and subsequently assayed for glucose (in duplicate; Thermoelectron Infinity glucose reagent TR15498) and insulin (single replicate; Alpco mouse ultrasensitive insulin kit 80-INSMSU-E10).

Upon completion of the OGTT, all animals were singly housed with food provided as above for two weeks prior to the onset of the baseline phase of the chronic study. Upon single housing after the OGTT, mice were placed on a reverse-phase light dark cycle (lights off: 09:30-17:30). Following this period the animals underwent a 5-day baseline phase where they were dosed twice daily with vehicle at approximately 08:45 and 16:45 each day. Towards the end of the baseline phase mice were allocated to dosing groups such that groups within the study were balanced as closely as possible for body weight and food and water intake and previous treatment.

From Day 1 of the second stage onwards, all mice were be dosed orally twice daily with 25 kg/kg (S)-2-(3-aminopiperidin-1-yl)-4-((3,5-bis(2-cyanopropan-2-yl)phenyl)amino)pyrimidine-5-carboxamide (Example 50) formulated in a vehicle of DMSO (10% final volume) and 20% (2-Hydroxypropyl)-3-cyclodextrin (90% final volume) on days 1-6 and 1% methyl cellulose at 5 ml/kg on subsequent days, or twice daily orally with vehicle alone, or 0.1 mg/kg liraglutide (Bachem) formulated in pH 7.4 phosphate buffer solution by the sub cutaneous route. Oral dosing began at approximately 08:45 and 16.45, with subcutaneous dosing at 08:45 only.

Dosing continued until the morning of Day 14, when food was removed beginning at approximately 16:45. Approximately 16 h post fast the animals were moved to a separate room maintained under normal lighting and dosed with vehicle or test compounds in the normal manner to a timed schedule 4 hours prior to the administration of the glucose challenge (2.0 g/kg orally). Blood samples were taken immediately prior to dosing (B1), immediately prior to glucose administration (B2) and 15, 30, 60 and 90 minutes after glucose administration. All blood samples (approx. 30 μl) were taken in lithium heparin-coated tubes (Sarstedt CB300LH) and spun as soon as possible in a centrifuge. Plasma samples were stored frozen (approx. −80° C.) until determination of plasma glucose (in duplicate; Thermoelectron Infinity glucose reagent TR15498) and insulin (single replicate; Alpco mouse ultrasensitive insulin kit 80-INSMSU-E10).

Plasma glucose and insulin data from the OGTTs were analysed by robust regression with treatment as a factor and bleeding order and Day 1 body weight as covariates. AUCs for 0 to 60 and 0 to 90 minutes were calculated (as total AUC and AUC from baseline) by trapezoidal rule and analysed by the same methodology. In all cases, this analysis was followed by appropriate comparisons (two-tailed) to determine significant differences from the vehicle group.

The results for this example are provided in FIG. 1, wherein A: Glucose and Insulin AUC (baseline) from OGTT following single dose, B: Glucose and Insulin AUC (baseline from B2) from OGTT following 14 days dosing. Significant differences between compound-dosed and vehicle-dosed groups are denoted by *p<0.05, *p<0.01 and ***p<0.001.

The invention claimed is:

1. A compound of Formula I or a pharmaceutically acceptable salt thereof:

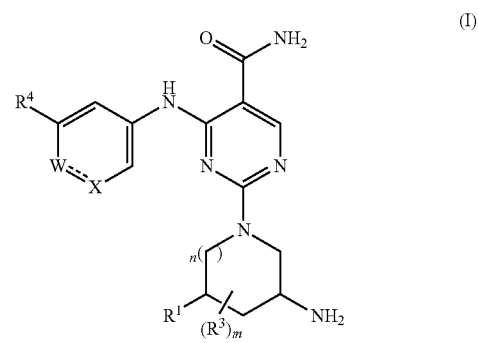

wherein:

$R^1$ is selected from the group consisting of: H, $C_{1-3}$ alkyl, $C_{1-3}$ haloalkyl, halo, —$OR^2$, —$NR^2R^2$, $C_3$ cycloalkyl and $C_3$ halocycloalkyl;

each $R^2$ is independently selected from the group consisting of: H, $C_{1-3}$ alkyl and $C_{1-3}$ haloalkyl;

each $R^3$ is independently selected from the group consisting of: $C_{1-3}$ alkyl, $C_{1-3}$ haloalkyl, halo, —$OR^2$, —$NR^2R^2$, $C_3$ cycloalkyl and $C_3$ halocycloalkyl;

n is 1 or 2;

m is 0 to 3;

W is

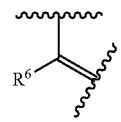

and X is

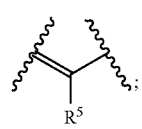

or W is

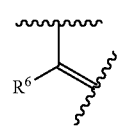

and X is

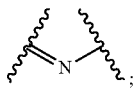 [SMILES: *N=*]

or W is

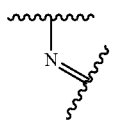

and X is

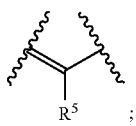

or W is

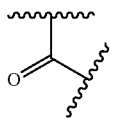 [SMILES: *C(*)=O]

and X is

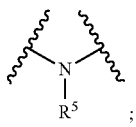

$R^4$ is selected from the group consisting of: $C_{3-6}$ alkyl, $C_{3-6}$ heteroalkyl, $C_{3-6}$ haloalkyl, $C_{3-6}$ heterohaloalkyl, $C_{3-6}$ alkenyl wherein (i) the carbon atom beta to the ring to which the alkene is bonded is cis-substituted with carbon; and (ii) the carbon atom alpha to the ring to which the alkene is bonded substituted with carbon, $C_{3-6}$ cycloalkyl, $C_{4-6}$ cycloalkenyl, 4- to 6-membered heterocycloalkyl including 1, 2 or 3 heteroatoms selected from N, O or S, 4- to 6-membered heterocycloalkenyl including 1, 2 or 3 heteroatoms selected from N, O or S, aryl, heteroaryl including 1, 2 or 3 heteroatoms selected from N, O or S, $-NR^{B1a}R^{B2a}$, $-NR^{B3a}C(O)R^{B2a}$, $-C(O)NR^{B2a}R^{B2a}$, $-C(O)$-(4- to 12-membered non-aromatic saturated or partially saturated monocyclic or fused, bridged, or spiro bicyclic heterocyclic ring system including 1, 2 or 3 heteroatoms selected from N, O or S), $-NR^{B3a}C(O)OR^{B2a}$, $-NR^{B3a}C(O)NR^{B3a}R^{B3a}$, $-NR^{B3a}SO_2R^{B2a}$, $-SO_2NR^{B3a}R^{B3a}$, $-SO_2R^{B2a}$ and $-S(O)(=NR^{B3a})R^{B2a}$;

$R^5$ is selected from the group consisting of: H, $C_{1-6}$ alkyl, $C_{1-6}$ heteroalkyl, $C_{1-6}$ haloalkyl, $C_{1-6}$ heterohaloalkyl, $C_{2-6}$ alkenyl, $C_{2-6}$ alkynyl, $C_{3-6}$ cycloalkyl, $C_{4-6}$ cycloalkenyl, 4- to 6-membered heterocycloalkyl including 1, 2 or 3 heteroatoms selected from N, O or S, 4- to 6-membered heterocycloalkenyl including 1, 2 or 3 heteroatoms selected from N, O or S, aryl, heteroaryl including 1, 2 or 3 heteroatoms selected from N, O or S, —O-aryl, —O-heteroaryl, halo, $-OR^{B2a}$, $-NR^{B3a}R^{B3a}$, $-SR^{B2a}$, $-CN$, $-NR^{B3a}C(O)R^{B2a}$, $-C(O)NR^{B2a}R^{B2a}$, $-CR^{B3a}(=NR^{B3a})$, $-NR^{B3a}C(O)OR^{B2a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NR^{B3a}R^{B3a}$, $-SO_2R^{B2a}$, $-S(O)(=NR^{B3a})R^{B2a}$ and $-C(O)OR^{B2a}$;

$R^6$ is selected from the group consisting of: H, $C_{1-6}$ alkyl, $C_{1-6}$ heteroalkyl, $C_{1-6}$ haloalkyl, $C_{1-6}$ heterohaloalkyl, $C_{2-6}$ alkenyl, $C_{2-6}$ alkynyl, $C_{3-6}$ cycloalkyl, $C_{4-6}$ cycloalkenyl, 4- to 6-membered heterocycloalkyl including 1, 2 or 3 heteroatoms selected from N, O or S, 4- to 6-membered heterocycloalkenyl including 1, 2 or 3 heteroatoms selected from N, O or S, aryl, heteroaryl including 1, 2 or 3 heteroatoms selected from N, O or S, —O-aryl, —O-heteroaryl, halo, $-OR^{B3a}$, $-NR^{B3a}R^{B3a}$, $-CR^{B3a}(=NR^{B3a})$, $-SR^{B3a}$, $-CN$, $-NR^{B3a}C(O)R^{B2a}$, $-C(O)NR^{B2a}R^{B2a}$, $-NR^{B3a}C(O)OR^{B2a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NR^{B3a}R^{B3a}$, $-SO_2R^{B2a}$, $-S(O)(=NR^{B3a})R^{B2a}$ and $-C(O)OR^{B2a}$ wherein $R^{B1a}$ is selected from the group consisting of: $C_{3-4}$ alkyl, $C_{3-4}$ heteroalkyl, $C_{3-4}$ haloalkyl, $C_{3-4}$ haloheteroalkyl, $C_{3-6}$ cycloalkyl, $C_{1-4}$ alkyl $C_{3-6}$ cycloalkyl, 4- to 12-membered non-aromatic saturated or partially saturated monocyclic or fused, bridged, or spiro bicyclic heterocyclic ring system including 1, 2 or 3 heteroatoms selected from N, O or S;

wherein $R^{B2a}$ is selected from the group consisting of: $C_{1-4}$ alkyl, $C_{1-4}$ heteroalkyl, $C_{1-4}$ haloalkyl, $C_{1-4}$ haloheteroalkyl, $C_{3-6}$ cycloalkyl, $C_{1-4}$ alkyl $C_{3-6}$ cycloalkyl, 4- to 12-membered non-aromatic saturated or partially saturated monocyclic or fused, bridged, or spiro bicyclic heterocyclic ring system including 1, 2 or 3 heteroatoms selected from N, O or S;

wherein $R^{B3a}$ is selected from the group consisting of: H, $C_{1-4}$ alkyl, $C_{1-4}$ heteroalkyl, $C_{1-4}$ haloalkyl, $C_{1-4}$ haloheteroalkyl, $C_{3-6}$ cycloalkyl, $C_{1-4}$ alkyl $C_{3-6}$ cycloalkyl, 4- to 12-membered non-aromatic saturated or partially saturated monocyclic or fused, bridged, or spiro bicyclic heterocyclic ring system including 1, 2 or 3 heteroatoms selected from N, O or S;

wherein the $C_{3-4}$ alkyl, $C_{3-4}$ heteroalkyl, $C_{3-4}$ haloalkyl, $C_{3-4}$ haloheteroalkyl, $C_{1-4}$ alkyl, $C_{1-4}$ heteroalkyl, $C_{1-4}$ haloalkyl, $C_{1-4}$ haloheteroalkyl, $C_{3-6}$ cycloalkyl, $C_{1-4}$ alkyl $C_{3-6}$ cycloalkyl and 4- to 12-membered non-aromatic saturated or partially saturated monocyclic or fused, bridged, or spiro bicyclic heterocyclic ring system including 1, 2 or 3 heteroatoms selected from N, O or S can be optionally substituted with $C_{1-4}$ alkyl, $C_{1-4}$ heteroalkyl, C$_{1-4}$ haloalkyl, C$_{1-4}$ haloheteroalkyl, C$_{3-6}$ cycloalkyl, C$_{1-4}$ alkyl C$_{3-6}$ cycloalkyl, aryl, heteroaryl including 1, 2 or 3 heteroatoms selected from N, O or S, —OH, —O(C$_{1-3}$ alkyl), —(C$_{1-3}$ alkyl)-OH, —(C$_{1-3}$ alkyl)-O(C$_{1-3}$ alkyl), =O, —NH$_2$, —NH(C$_{1-3}$ alkyl), —N(C$_{1-3}$ alkyl)$_2$ or (C$_{1-3}$ alkyl)-NH$_2$, —(C$_{1-3}$ alkyl)-NH(C$_{1-3}$ alkyl) or —(C$_{1-3}$ alkyl)-N(C$_{1-3}$ alkyl)$_2$;

wherein in the specific groups —NR$^{B1a}$R$^{B2a}$, —NR$^{B3a}$R$^{B3a}$, —C(O)NR$^{B2a}$R$^{B2a}$, —OC(O)NR$^{B3a}$R$^{B3a}$, —NR$^{B3a}$C(O)NR$^{B3a}$R$^{B3a}$, —NR$^{B3a}$C(NR$^{B3a}$)NR$^{B3a}$R$^{B3a}$ and —SO$_2$NR$^{B3a}$R$^{B3a}$, the pairs R$^{B1a}$/R$^{B2a}$, R$^{B3a}$/R$^{B3a}$ and R$^{B2a}$/R$^{B2a}$, together with the nitrogen atom to which they are bonded, can form a 4- to 12-membered monocyclic or fused, bridged, or spiro bicyclic ring system optionally including 1, 2 or 3 heteroatoms selected from N, O or S;

or wherein R$^4$ is C$_{1-6}$ alkyl or C$_{3-6}$ cycloalkyl and R$^6$ is —NR$^{B3a}$C(O)R$^{B2a}$, wherein the terminal R$^{B2a}$ is absent and R$^4$ and R$^6$ are joined via the carbonyl carbon, so that, together with the carbon atoms to which they are bonded, R$^4$ and R$^6$ form a 5- or 6-membered ring;

or wherein R$^5$ is —NR$^{B3a}$R$^{B3a}$ and R$^6$ is —CR$^{B3a}$(=NR$^{B3a}$), wherein the terminal R$^{B3a}$ of —CR$^{B3a}$(=NR$^{B3a}$) is absent and one R$^{B3a}$ of —NR$^{B3a}$R$^{B3a}$ is absent and R$^5$ and R$^6$ are joined via the imine nitrogen atom, so that, together with the carbon atoms to which they are bonded, R$^5$ and R$^6$ form a 5-membered ring;

provided that, when R$^4$ is aryl or heteroaryl including 1, 2 or 3 heteroatoms selected from N, O or S and R$^5$ is absent or H, one or both of the following is true: (i) the aryl or heteroaryl including 1, 2 or 3 heteroatoms selected from N, O or S is ortho-substituted with an R$^{sub}$ moiety; or (ii) R$^6$ is not H;

wherein each of the aforementioned C$_{3-6}$ alkyl, C$_{1-6}$ alkyl, C$_{3-6}$ heteroalkyl, C$_{3-6}$ haloalkyl, C$_{1-6}$ haloalkyl, C$_{3-6}$ heterohaloalkyl, C$_{1-6}$ heterohaloalkyl, C$_{3-6}$ alkenyl, C$_{2-6}$ alkenyl, C$_{3-6}$ cycloalkyl, C$_{4-6}$ cycloalkenyl, 4- to 6-membered heterocycloalkyl including 1, 2 or 3 heteroatoms selected from N, O or S, 4- to 6-membered heterocycloalkenyl including 1, 2 or 3 heteroatoms selected from N, O or S, aryl, heteroaryl, 4- to 12-membered non-aromatic saturated or partially saturated monocyclic or fused, bridged, or spiro bicyclic heterocyclic ring system including 1, 2 or 3 heteroatoms selected from N, O or S and C$_{2-6}$ alkynyl can be optionally substituted with 1, 2 or 3 R$^{sub}$ moieties, wherein each R$^{sub}$ moiety is independently selected from the group consisting of: C$_{1-6}$ alkyl, C$_{1-6}$ heteroalkyl, C$_{1-6}$ haloalkyl, C$_{1-6}$ heterohaloalkyl, C$_{2-6}$ alkenyl, C$_{2-6}$ alkynyl, C$_{3-6}$ cycloalkyl, 4- to 6-membered heterocycloalkyl including 1, 2 or 3 heteroatoms selected from N, O or S, aryl, heteroaryl including 1, 2 or 3 heteroatoms selected from N, O or S, halo, —OR$^{B3a}$, =O, —NR$^{B3a}$R$^{B3a}$, —SR$^{B3a}$, —CN, —NO$_2$, —NR$^{B3a}$C(O)R$^{B3a}$, —C(O)NR$^{B3a}$R$^{B3a}$, —NR$^{B3a}$C(O)OR$^{B3a}$, —OC(O)NR$^{B3a}$R$^{B3a}$, —NR$^{B3a}$C(O)NR$^{B3a}$R$^{B3a}$, —NR$^{B3a}$C(NR$^{B3a}$)NR$^{B3a}$R$^{B3a}$, —NR$^{B3a}$SO$_2$R$^{B3a}$, —SO$_2$NR$^{B3a}$R$^{B3a}$, —SO$_2$R$^{B3a}$, —C(O)R$^{B3a}$ and —C(O)OR$^{B3a}$.

2. The compound of claim 1, wherein the compound of Formula I has a structure of Formula IIA:

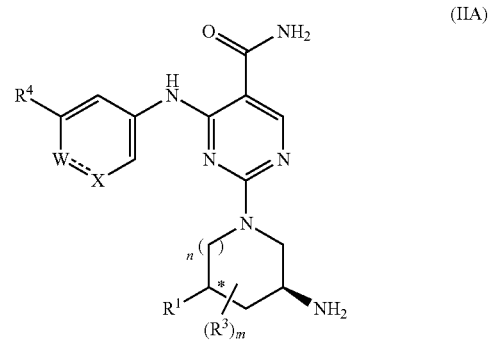

in which the carbon atom depicted by the * is in the R-configuration or the S-configuration.

3. The compound of claim 1, wherein R$^1$ is H.

4. The compound of claim 1, wherein R$^1$ is selected from the group consisting of: C$_{1-3}$ alkyl, halo, —OR$^2$ and —NR$^2$R$^2$.

5. The compound of claim 4, wherein R$^2$ is selected from the group consisting of H and C$_{1-3}$ alkyl.

6. The compound of claim 1, wherein m is 0.

7. The compound of claim 1, wherein n is 1.

8. The compound of claim 1, wherein W is

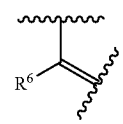

and X is

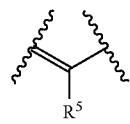

such that the compound has the Formula IIIA:

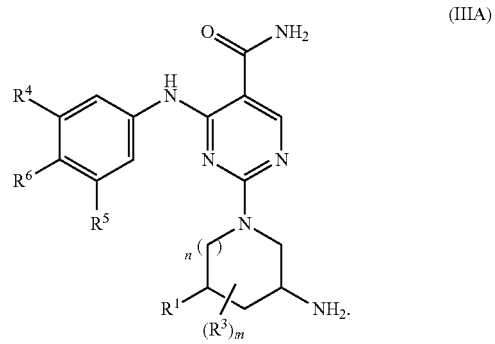

9. The compound of claim 1, wherein W is

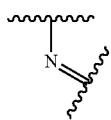 [SMILES: *N=*]

and X is

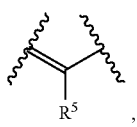

such that the compound has the Formula IIIC:

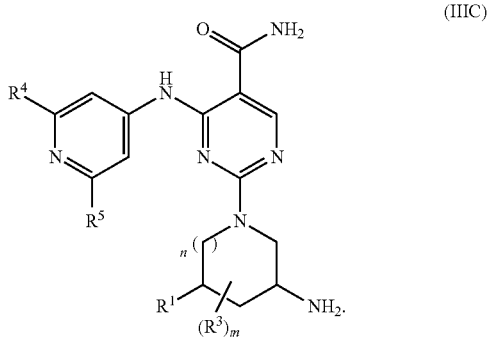

(IIIC)

10. The compound of claim 1, wherein $R^4$ is selected from the group consisting of: $C_{3-6}$ alkyl, $C_{3-6}$ haloalkyl, $C_{3-6}$ alkenyl wherein (i) the carbon atom beta to the ring to which the alkene is bonded is cis-substituted with carbon; and (ii) the carbon atom alpha to the ring to which the alkene is bonded substituted with carbon, $C_{3-6}$ cycloalkyl, $C_{4-6}$ cycloalkenyl, 4- to 6-membered heterocycloalkyl including 1, 2 or 3 heteroatoms selected from N, O or S, aryl, heteroaryl including 1, 2 or 3 heteroatoms selected from N, O or S, $-NR^{B3a}C(O)R^{B2a}$, $-C(O)NR^{B2a}R^{B2a}$, $-C(O)-(4-$ to 12-membered non-aromatic saturated or partially saturated monocyclic or fused, bridged, or spiro bicyclic heterocyclic ring system including 1, 2 or 3 heteroatoms selected from N, O or S), $-SO_2NR^{B3a}R^{B3a}$, $-SO_2R^{B2a}$ and $-S(O)(=NR^{B3a})R^{B2a}$; wherein the $R^{B2a}$ and $R^{B3a}$ groups are as defined in claim 1; and wherein each of the aforementioned $C_{3-6}$ alkyl, $C_{3-6}$ haloalkyl, $C_{3-6}$ alkenyl, $C_{3-6}$ cycloalkyl, $C_{4-6}$ cycloalkenyl, 4- to 6-membered heterocycloalkyl including 1, 2 or 3 heteroatoms selected from N, O or S, aryl, heteroaryl and 4- to 12-membered non-aromatic saturated or partially saturated monocyclic or fused, bridged, or spiro bicyclic heterocyclic ring system including 1, 2 or 3 heteroatoms selected from N, O or S can be optionally substituted as per claim 1.

11. The compound of claim 10, wherein $R^4$ is $C_{3-6}$ alkyl.

12. The compound of claim 11, wherein the substitutents for the $C_{3-6}$ alkyl group are selected from the group consisting of: $-OR^{B3a}$, $=O$, $-NR^{B3a}R^{B3a}$, $-SR^{B3a}$, $-CN$, $-NO_2$, $-NR^{B3a}C(O)R^{B3a}$, $-C(O)NR^{B3a}R^{B3a}$, $-NR^{B3a}C(O)OR^{B3a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NR^{B3a}R^{B3a}$, $-SO_2R^{B3a}$, $-C(O)R^{B3a}$ and $-C(O)OR^{B3a}$.

13. The compound of claim 12, wherein the substitutents for the $C_{3-6}$ alkyl group are selected from the group consisting of: $-OR^{B3a}$, $-NR^{B3a}R^{B3a}$, $-SR^{B3a}$, $-CN$ and $-NR^{B3a}C(O)R^{B3a}$.

14. The compound of claim 12, wherein $R^{B3a}$ is selected from the group consisting of H, $C_{1-4}$ alkyl, $C_{1-4}$ haloalkyl and $C_{3-6}$ cycloalkyl.

15. The compound of claim 11, wherein $R^4$ is selected from the group consisting of iso-propyl and t-butyl.

16. The compound of claim 10, wherein $R^4$ is $C_{3-6}$ haloalkyl.

17. The compound of claim 16, wherein $R^4$ is selected from the group consisting of $C_3$ and $C_4$ haloalkyl.

18. The compound of claim 1, wherein $R^5$ is selected from the group consisting of: $C_{3-6}$ alkyl, $C_{3-6}$ haloalkyl, $C_{3-6}$ alkenyl wherein (i) the carbon atom beta to the ring to which the alkene is bonded is cis-substituted with carbon; and (ii) the carbon atom alpha to the ring to which the alkene is bonded substituted with carbon, $C_{3-6}$ cycloalkyl, $C_{4-6}$ cycloalkenyl, 4- to 6-membered heterocycloalkyl including 1, 2 or 3 heteroatoms selected from N, O or S, aryl, heteroaryl including 1, 2 or 3 heteroatoms selected from N, O or S, $-NR^{B3a}C(O)R^{B2a}$, $-C(O)NR^{B2a}R^{B2a}$, $-C(O)-(4-$ to 12-membered non-aromatic saturated or partially saturated monocyclic or fused, bridged, or spiro bicyclic heterocyclic ring system including 1, 2 or 3 heteroatoms selected from N, O or S), $-SO_2NR^{B3a}R^{B3a}$, $-SO_2R^{B2a}$ and $-S(O)(=NR^{B3a})R^{B2a}$; wherein the $R^{B2a}$ and $R^{B3a}$ groups are as defined in claim 1; and wherein each of the aforementioned $C_{3-6}$ alkyl, $C_{3-6}$ haloalkyl, $C_{3-6}$ alkenyl, $C_{3-6}$ cycloalkyl, $C_{4-6}$ cycloalkenyl, 4- to 6-membered heterocycloalkyl including 1, 2 or 3 heteroatoms selected from N, O or S, aryl, heteroaryl and 4- to 12-membered non-aromatic saturated or partially saturated monocyclic or fused, bridged, or spiro bicyclic heterocyclic ring system including 1, 2 or 3 heteroatoms selected from N, O or S can be optionally substituted as per claim 1.

19. The compound of claim 18, wherein $R^5$ is $C_{3-6}$ alkyl.

20. The compound of claim 19, wherein the substitutents for the $C_{3-6}$ alkyl group are selected from the group consisting of: $-OR^{B3a}$, $=O$, $-NR^{B3a}R^{B3a}$, $-SR^{B3a}$, $-CN$, $-NO_2$, $-NR^{B3a}C(O)R^{B3a}$, $-C(O)NR^{B3a}R^{B3a}$, $-NR^{B3a}C(O)OR^{B3a}$, $-OC(O)NR^{B3a}R^{B3a}$, $-NR^{B3a}C(O)NR^{B3a}R^{B3a}$, $-NR^{B3a}C(NR^{B3a})NR^{B3a}R^{B3a}$, $-NR^{B3a}SO_2R^{B3a}$, $-SO_2NR^{B3a}R^{B3a}$, $-SO_2R^{B3a}$, $-C(O)R^{B3a}$ and $-C(O)OR^{B3a}$.

21. The compound of claim 20, wherein the substitutents for the $C_{3-6}$ alkyl group are selected from the group consisting of: $-OR^{B3a}$, $-NR^{B3a}R^{B3a}$, $-SR^{B3a}$, $-CN$ and $-NR^{B3a}C(O)R^{B3a}$.

22. The compound of claim 20, wherein $R^{B3a}$ is selected from the group consisting of H, $C_{1-4}$ alkyl, $C_{1-4}$ haloalkyl and $C_{3-6}$ cycloalkyl.

23. The compound of claim 18, wherein $R^5$ is selected from the group consisting of iso-propyl and t-butyl.

24. The compound of claim 18, wherein $R^5$ is $C_{3-6}$ haloalkyl.

25. The compound of claim 24, wherein $R^5$ is selected from the group consisting of $C_3$ and $C_4$ haloalkyl.

26. The compound of claim 18, wherein $R^5$ is a 4- to 6-membered heterocycloalkyl including 1, 2 or 3 heteroatoms selected from N, O or S, which can be optionally substituted with a group selected from the group consisting of: aryl, $=O$, $-NR^{B3a}R^{B3a}$ and $-C(O)R^{B3a}$.

27. The compound of claim 26, wherein the 4- to 6-membered heterocycloalkyl is selected from the group consisting of:

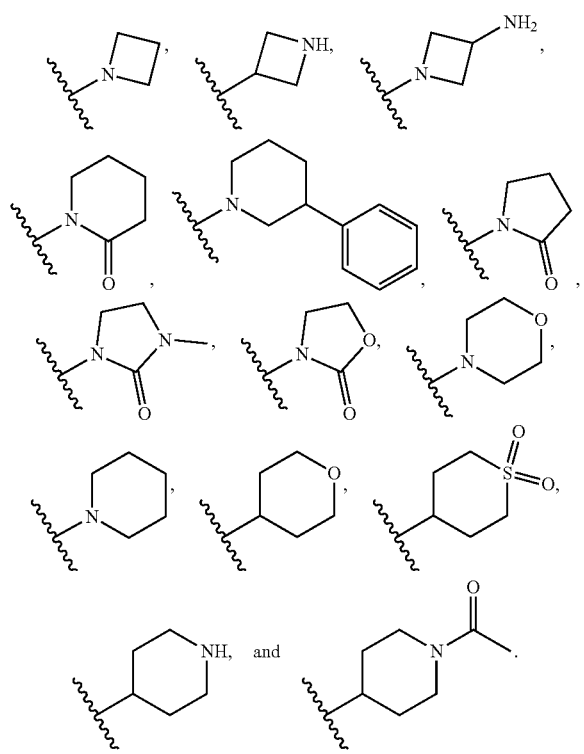

28. The compound of claim 18, wherein $R^5$ is $C_{3-6}$ cycloalkyl, which can be optionally substituted with a group selected from the group consisting of: halo, —$OR^{B3a}$ and —CN, optionally wherein $R^{B3a}$ is selected from the group consisting of: H, $C_{1-4}$ alkyl and $C_{1-4}$ haloalkyl.

29. The compound of claim 28, wherein the $C_{3-6}$ cycloalkyl are selected from the group consisting of:

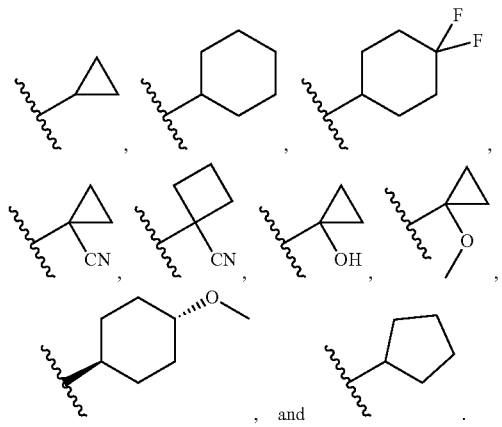

30. The compound of claim 18, wherein $R^5$ is aryl or heteroaryl including 1, 2 or 3 heteroatoms selected from N, O or S, which can be optionally substituted with a group selected from the group consisting of: $C_{1-6}$ alkyl, $C_{1-6}$ haloalkyl, halo and —$OR^{B3a}$.

31. The compound of claim 1, wherein $R^6$ is H.

32. The compound of claim 1, wherein $R^6$ is CN.

33. A pharmaceutical formulation comprising a compound of claim 1, or a pharmaceutically acceptable salt thereof, and a pharmaceutically acceptable excipient.

34. A method to treat a condition in a subject in need thereof, the method comprising administering to the subject a therapeutically effective amount of a compound of claim 1, wherein the condition is selected from the group consisting of: sarcoma, carcinoma, blastoma, lymphoma and leukemia.

35. A method to treat a condition in a subject in need thereof, the method comprising administering to the subject a therapeutically effective amount of a compound of claim 1, wherein the condition is selected from the group consisting of rheumatoid arthritis, chronic obstructive pulmonary disease, acute respiratory distress syndrome, hepatic cirrhosis, lung fibrosis, glomerulonephritis, multiple sclerosis, psoriasis, benign prostatic hypertrophy (BPH), hypersensitivity reactions of the skin, atherosclerosis and restenosis, allergic asthma, diabetic retinopathy, diabetic nephropathy, insulin-dependent/type-1 diabetes, insulin-independent/type-2 diabetes, and stress-induced hyperglycemia.

36. A method to treat a condition in a subject in need thereof, the method comprising administering to the subject a therapeutically effective amount of a compound of claim 1, wherein the condition is selected from the group consisting of: basal cell carcinoma, medulloblastoma, rhabdomyosarcoma, chondrosarcoma, melanoma, small-cell lung cancer, non-small-cell lung cancer, B-cell lymphoma, multiple myeloma, brain cancer, esophagus cancer, breast cancer, ovarian cancer, stomach cancer, colorectal cancer, liver cancer, kidney cancer, head and neck cancer, mesothelioma, soft tissue sarcomas, bone sarcomas, testicular cancer, prostate cancer, pancreatic cancer, bone cancer, bone metastasis, acute leukemia, chronic leukemia, glioma, Hodgkin's disease, cutaneous melanoma, bladder cancer, endocrine system cancer, parathyroid gland cancer, thyroid gland cancer, cervical cancer, endometrium cancer, ovarian cancer, skin cancer, renal cell carcinoma, pituitary adenoma, spinal axis tumours, uterine cancer, gastric cancer and biliary tract cancer.

37. The compound of claim 30, wherein the $C_{1-6}$ alkyl is selected from $C_1$, $C_2$, $C_3$ and $C_4$ alkyl; the $C_{1-6}$ haloalkyl is selected from $C_1$, $C_2$, $C_3$ or $C_4$ haloalkyl; and the —$OR^{B3a}$ is selected from —O—$C_{1-4}$ alkyl and —O—$C_{1-4}$ haloalkyl.

38. The compound of claim 37, wherein the $C_{1-6}$ haloalkyl is $CF_3$; the —O—$C_{1-4}$ alkyl is —O—$CH_3$; and the —O—$C_{1-4}$ haloalkyl is —O—$CF_3$.

* * * * *